(12) United States Patent
Batt et al.

(10) Patent No.: US 10,968,177 B2
(45) Date of Patent: Apr. 6, 2021

(54) TRICYCLIC SULFONES AS $ROR_\gamma$ MODULATORS

(71) Applicant: BRISTOL-MYERS SQUIBB COMPANY, Princeton, NJ (US)

(72) Inventors: Douglas G. Batt, Wilmington, DE (US); T. G. Murali Dhar, Newtown, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 16/340,447

(22) PCT Filed: Oct. 9, 2017

(86) PCT No.: PCT/US2017/055687
§ 371 (c)(1),
(2) Date: Apr. 9, 2019

(87) PCT Pub. No.: WO2018/071314
PCT Pub. Date: Apr. 19, 2018

(65) Prior Publication Data
US 2019/0233374 A1 Aug. 1, 2019

Related U.S. Application Data

(60) Provisional application No. 62/406,085, filed on Oct. 10, 2016.

(51) Int. Cl.
| | |
|---|---|
| C07D 209/60 | (2006.01) |
| C07D 471/04 | (2006.01) |
| C07D 409/06 | (2006.01) |
| C07D 491/052 | (2006.01) |
| A61P 37/02 | (2006.01) |
| A61P 3/00 | (2006.01) |
| A61P 11/06 | (2006.01) |
| A61P 37/08 | (2006.01) |
| A61P 35/00 | (2006.01) |

(52) U.S. Cl.
CPC .............. *C07D 209/60* (2013.01); *A61P 3/00* (2018.01); *A61P 11/06* (2018.01); *A61P 35/00* (2018.01); *A61P 37/02* (2018.01); *A61P 37/08* (2018.01); *C07D 409/06* (2013.01); *C07D 471/04* (2013.01); *C07D 491/052* (2013.01)

(58) Field of Classification Search
CPC .. C07D 209/60; C07D 409/06; C07D 471/04; C07D 491/052
See application file for complete search history.

(56) References Cited

FOREIGN PATENT DOCUMENTS

| | | |
|---|---|---|
| WO | WO2007084595 A2 | 7/2007 |
| WO | WO2015103509 A1 | 7/2015 |
| WO | WO2016179460 A1 | 11/2016 |

OTHER PUBLICATIONS

Cancer and Metastasis Reviews (1998), 17(1), 91-106.*
Science (1999), vol. 286, 531-537.*

* cited by examiner

*Primary Examiner* — Rebecca L Anderson
(74) *Attorney, Agent, or Firm* — Elliott Korsen; Shrikant Kulkarni

(57) ABSTRACT

There are described $ROR_\gamma$ modulators of the formula (I), and formula (II) or stereoisomers, tautomers, pharmaceutically acceptable salts, solvates, or prodrugs thereof, wherein all substituents are defined herein. Also provided are pharmaceutical compositions comprising the same. Such compounds and compositions are useful in methods for modulating $ROR_\gamma$ activity in a cell and methods for treating a subject suffering from a disease or disorder in which the subject would therapeutically benefit from modulation of $ROR_\gamma$ activity, for example, autoimmune and/or inflammatory disorders.

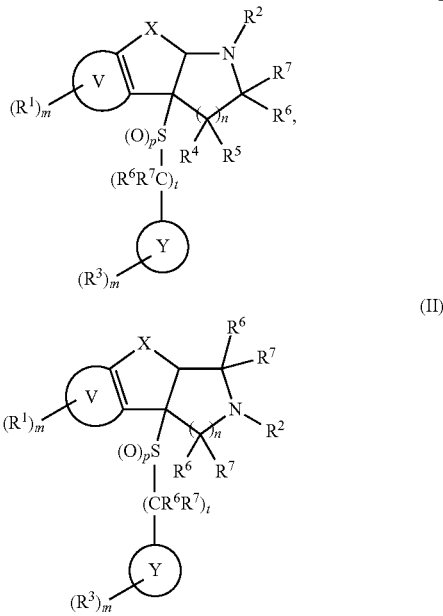

20 Claims, No Drawings

TRICYCLIC SULFONES AS ROR$_\gamma$ MODULATORS

CROSS-REFERENCE TO RELATED APPLICATIONS

This application claims the benefit of U.S. Provisional Application No. 62/406,085, filed Oct. 10, 2016, the disclosure of which is incorporated herein by reference in its entirety.

FIELD OF THE INVENTION

This invention relates to modulators of the retinoid-related orphan receptor ROR$\gamma$ and methods for using said modulators. The compounds described herein can be particularly useful for treating a variety of diseases and disorders in humans and animals. Exemplary disorders include, but are not limited to, psoriasis, rheumatoid arthritis, inflammatory bowel disease, Crohn's disease, ulcerative colitis, acute graft-versus-host disease, psoriatic arthritis, ankylosing spondylitis and multiple sclerosis.

BACKGROUND OF THE INVENTION

The retinoid-related orphan receptors, ROR$\alpha$, ROR$\beta$, and ROR$\gamma$, play an important role in numerous biological processes including organ development, immunity, metabolism, and circadian rhythms. See, for example, Dussault et al. in Mech. Dev. (1998) vol. 70, 147-153; Andre et al. in EMBO J. (1998) vol. 17, 3867-3877; Sun et al. in Science (2000) vol. 288, 2369-2373; and Jetten in Nucl. Recept. Signal. (2009) vol. 7, 1-32.

ROR$\gamma$ is expressed in several tissues including the thymus, kidney, liver, and muscle. Two isoforms of ROR$\gamma$ have been identified: ROR$\gamma$1 and ROR$\gamma$2 (also known, respectively, as ROR$\gamma$ and ROR$\gamma$t). See, for example, Hirose et al. in Biochem. Biophys. Res. Commun. (1994) vol. 205, 1976-1983; Oritz et al. in Mol. Endocrinol. (1995) vol. 9, 1679-1691; and He et al. in Immunity (1998) vol. 9, 797-806. Expression of ROR$\gamma$t is restricted to lymphoid cell types including CD4+CD8+ thymocytes, IL-17 producing T helper (Th17) cells, lymphoid tissue inducer (LTi) cells, and $\gamma\delta$ cells. ROR$\gamma$t is essential for the development of lymph nodes and Peyer's patches and for the normal differentiation of Th17, $\gamma\delta$, and LTi cells. See, for example, Sun et al. in Science (2000) vol. 288, 2369-2373; Ivanov et al. in Cell (2006) vol. 126, 1121-1133; Eberl et al. in Nat. Immunol. (2004) vol. 5, 64-73; Ivanov et al. in Semin. Immunol. (2007) vol. 19, 409-417; and Cua and Tato in Nat. Rev. Immunol. (2010) vol. 10, 479-489.

Proinflammatory cytokines such as IL-17A (also referred to as IL-17), IL-17F, and IL-22 produced by Th17 cells and other ROR$\gamma$+ lymphocytes activate and direct the immune response to extracellular pathogens. See, for example, Ivanov et al. in Semin. Immunol. (2007) vol. 19: 409-417; and Marks and Craft in Semin. Immunol. (2009) vol. 21, 164-171. ROR$\gamma$ directly regulates IL-17 transcription and disruption of ROR$\gamma$ in mice attenuates IL-17 production. See, for example, Ivanov et al. in Cell (2006) vol. 126, 1121-1133.

Dysregulated production of IL-17 has been implicated in several human autoimmune and inflammatory diseases including multiple sclerosis, rheumatoid arthritis, psoriasis, inflammatory bowel disease (IBD), and asthma. See, for example, Lock et al. in Nat. Med. (2002) vol. 8, 500-508; Tzartos et al. in Am. J. Pathol. (2008) vol. 172, 146-155; Kotake et al. in J. Clin. Invest. (1999) vol. 103, 1345-1352; Kirkham et al. in Arthritis Rheum. (2006) vol. 54, 1122-1131; Lowes et al. in J. Invest. Dermatol. (2008) vol. 128, 1207-1211; Leonardi et al. in N. Engl. J. Med. (2012) vol. 366, 1190-1199; Fujino et al. in Gut (2003) vol. 52, 65-70; Seiderer et al. in Inflamm. Bowel Dis. (2008) vol. 14, 437-445; Wong et al. in Clin. Exp. Immunol. (2001) vol. 125, 177-183; and Agache et al. in Respir. Med. (2010) 104: 1131-1137. In murine models of these diseases, inhibition of IL-17 function by neutralizing antibodies or genetic disruption of IL-17 or IL-17 receptor ameliorates the disease course or clinical symptoms. See, for example, Hu et al. in Ann. N.Y. Acad. Sci. (2011) vol. 1217, 60-76.

Disruption of ROR$\gamma$ in mice also attenuates disease progression or severity in animal models of autoimmunity and inflammation including experimental autoimmune encephalomyelitis (EAE), imiquimod induced psoriasis, colitis, and allergic airway disease. See, for example, Ivanov et al. in Cell (2006) vol. 126, 1121-1133; Yang et al. in Immunity (2008) vol. 28, 29-39; Pantelyushin et al. in J. Clin. Invest. (2012) vol. 122, 2252-2256; Leppkes et al. in Gastroenterology (2009) vol. 136, 257-267; and Tilley et al. in J. Immunol. (2007) vol. 178, 3208-3218.

Each of the references in this Background section is incorporated herein by reference in its entirety for all purposes.

Therapeutic agents exist to treat a variety of inflammatory and autoimmune diseases, but there still remains a significant unmet medical need in these therapeutic areas. Given the role of IL-17 in human disease and the validation of IL-17 and ROR$\gamma$ as targets in murine disease models, compounds capable of modulating ROR$\gamma$t activity are contemplated to provide a therapeutic benefit in the treatment of multiple immune and inflammatory disorders.

SUMMARY OF THE INVENTION

In one aspect, the invention comprises compounds of the formula (I),

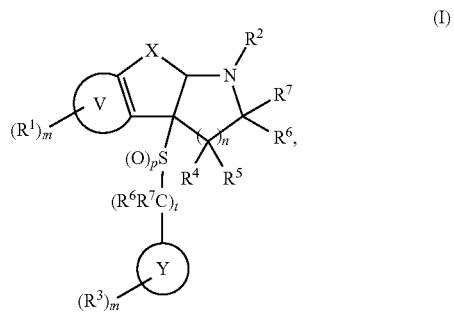

or pharmaceutically acceptable salts thereof, wherein all substituents are defined herein. The invention includes stereoisomers, tautomers, solvates, or prodrugs thereof.

In another aspect, the invention comprises compounds of the formula (II),

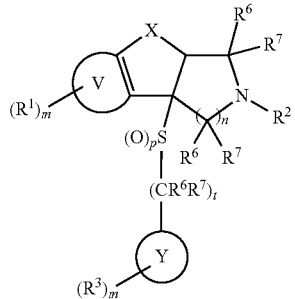
(II)

or pharmaceutically acceptable salts thereof, wherein all substituents are defined herein. The invention includes stereoisomers, tautomers, solvates, or prodrugs thereof.

In another aspect, the invention comprises pharmaceutical compositions comprising a compound according to formula (I), stereoisomeric form or pharmaceutically acceptable salt, as described herein, and a pharmaceutically acceptable carrier, excipient, or diluent.

In another aspect, the invention comprises methods for modulating RORγ in a cell comprising contacting the cell with an effective amount of a compound according to formula (I), stereoisomeric form or pharmaceutically acceptable salt, as described herein. This aspect may be conducted in vitro or in vivo.

In another aspect, the invention comprises methods for treating a subject suffering from a disease or disorder modulated by RORγ, the method comprising administering to a subject a therapeutically effective amount of a compound according to formula (I), stereoisomeric form, pharmaceutically acceptable salt or pharmaceutical composition as described herein.

In another aspect, the invention comprises a method for treating a disease or disorder selected from an inflammatory disease or disorder, an autoimmune disease or disorder, an allergic disease or disorder, a metabolic disease or disorder, and/or cancer in a subject, the method comprising administering to the subject a therapeutically effective amount of a compound according to formula (I), or a stereoisomeric form, pharmaceutically acceptable salt or pharmaceutical composition as described herein.

DETAILED DESCRIPTION OF THE INVENTION

In one aspect, the invention comprises compounds of formula (I),

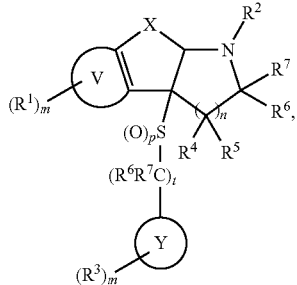
I or a stereoisomer or pharmaceutically acceptable salt thereof, wherein X is —CR$^4$R$^5$—, —(CR$^4$R$^5$)$_2$, —OCR$^6$R$^7$—, —S(O)$_p$CR$^6$R$^7$— or —NR$^6$CR$^6$R$^7$—; wherein when X is —OCR$^6$R$^7$—, —S(O)$_p$CR$^6$R$^7$— or —NR$^6$CR$^6$R$^7$—; the structure contemplated, for example when X is —OCR$^6$R$^7$—, would be

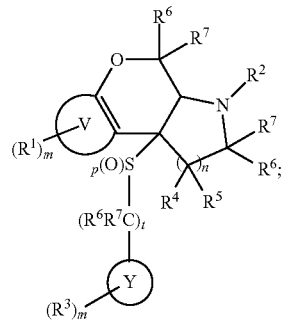

V and Y are independently 5 or 6-membered aromatic or heteroaromatic rings;

R$^1$ is, independently at each occurrence, selected from hydrogen, CD$_3$, halo, OCF$_3$, CN, —O(C$_1$-C$_6$)alkyl, —O(C$_1$-C$_6$)alkyl-OH, -alkoxyalkoxy (e.g. —O—CH$_2$CH$_2$OCH$_3$), S(O)$_p$(C$_1$-C$_6$)alkyl, —S(O)$_p$(C$_1$-C$_6$)alkyl-OH, -thioalkoxyalkoxy (e.g. —SCH$_2$CH$_2$OCH$_3$), NR$^{11}$R$^{11}$, C$_{1-6}$ alkyl substituted with 0-3 R$^{1a}$, —(CR$^{1b}$R$^{1c}$)$_r$-3-14 membered carbocycle substituted with 0-3 R$^{1a}$ and —(CR$^{1b}$R$^{1c}$)$_r$-5-10 membered heterocycle comprising carbon atoms and 1-4 heteroatoms selected from N, O, and S(O)$_p$ substituted with 0-3 R$^{1a}$;

R$^{1a}$ is, independently at each occurrence, hydrogen, =O, halo, CF$_3$, OCF$_3$, CN, NO$_2$, —(CR$^{1b}$R$^{1c}$)$_r$—OR$^b$, —(CR$^{1b}$R$^{1c}$)$_r$—S(O)$_p$R$^b$, —(CR$^{1b}$R$^{1c}$)$_r$—C(O)R$^b$, —(CR$^{1b}$R$^{1c}$)$_r$—C(O)OR$^b$, —(CR$^{1b}$R$^{1c}$)$_r$—OC(O)R$^b$, —(CR$^{1b}$R$^{1c}$)$_r$—NR$^{11}$R$^{11}$, —(CR$^{1b}$R$^{1c}$)$_r$—C(O)NR$^{11}$R$^{11}$, —(CR$^{1b}$R$^{1c}$)$_r$—NR$^b$C(O)R$^c$, —(CR$^{1b}$R$^{1c}$)$_r$—NR$^b$C(O)OR$^c$, —NR$^b$C(O)NR$^{11}$R$^{11}$, —S(O)$_p$NR$^{11}$R$^{11}$, —NR$^b$S(O)$_p$R$^c$, C$_{1-6}$ alkyl substituted with 0-3 R$^a$, C$_{1-6}$ haloalkyl, C$_{2-6}$ alkenyl substituted with 0-3 R$^a$, C$_{2-6}$ alkynyl substituted with 0-3 R$^a$, —(CR$^{1b}$R$^{1c}$)$_r$-3-14 membered carbocycle substituted with 0-3 R$^a$, or —(CR$^{1b}$R$^{1c}$)$_r$-5-7 membered heterocycle comprising carbon atoms and 1-4 heteroatoms selected from N, O, and S(O)$_p$ substituted with 0-3 R$^a$;

R$^{1b}$ and R$^{1c}$ are, independently at each occurrence, hydrogen, halogen or C$_{1-6}$ alkyl;

R$^2$ is

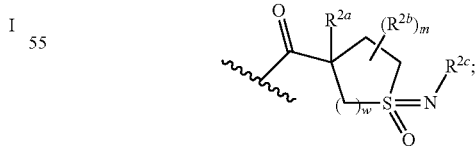

R$^{2a}$ and R$^{2b}$ are, independently at each occurrence, hydrogen, halo, OCF$_3$, CF$_3$, CHF$_2$, CN, NO$_2$, —(CR$^{1b}$R$^{1c}$)$_r$—OR$^b$, —(CR$^{1b}$R$^{1c}$)$_r$—S(O)$_p$R$^b$, —(CR$^{1b}$R$^{1c}$)$_r$—C(O)R$^b$, —(CR$^{1b}$R$^{1c}$)$_r$—C(O)OR$^b$, —(CR$^{1b}$R$^{1c}$)$_r$—OC(O)R$^b$, —(CR$^{1b}$R$^{1c}$)$_r$—NR$^{11}$R$^{11}$, —(CR$^{1b}$R$^{1c}$)$_r$—C(O)NR$^{11}$R$^{11}$, —(CR$^{1b}$R$^{1c}$)$_r$—NR$^b$C(O)R$^c$, —(CR$^{1b}$R$^{1c}$)$_r$—NR$^b$C(O)OR$^c$, —NR$^b$C(O)NR$^{11}$R$^{11}$, —S(O)$_p$NR$^{11}$R$^{11}$, —NR$^b$ $S(O)_pR^c$, $C_{1-6}$ alkyl substituted with 0-3 $R^f$, $C_{1-6}$ haloalkyl, $C_{2-6}$ alkenyl substituted with 0-3 $R^e$, $C_{2-6}$ alkynyl substituted with 0-3 $R^e$, —$(CR^{1b}R^{1c})_r$-3-14 membered carbocycle, or —$(CR^{1b}R^{1c})_r$-5-7 membered heterocycle comprising carbon atoms and 1-4 heteroatoms selected from N, O, P(=O) and $S(O)_p$ substituted with 0-4 $R^f$;

$R^{2c}$ is hydrogen, $C_{1-6}$ alkyl substituted with 0-3 $R^f$, $C_{1-6}$ haloalkyl, —$(CR^{1b}R^{1c})_r$—C(O)$R^b$, —$(CR^{1b}R^{1c})_r$—C(O)O$R^b$, —$(CR^{1b}R^{1c})_r$—C(O)NR$^{11}$R$^{11}$, —$(CR^{1b}R^{1c})_r$-3-14 membered carbocycle, or —$(CR^{1b}R^{1c})_r$-5-7 membered heterocycle comprising carbon atoms and 1-4 heteroatoms selected from N, O, P(=O) and $S(O)_p$ substituted with 0-4 $R^f$;

$R^3$ is, independently at each occurrence, selected from hydrogen, halo, $N_3$, CN, —$(CR^{1b}R^{1c})_r$—OR$^{3b}$, —$(CR^{1b}R^{1c})_r$—NR$^{11}$R$^{11}$, $C_{1-6}$ alkyl substituted with 0-3 $R^{3a}$, $C_{3-10}$ cycloalkyl substituted with 0-3 $R^{3a}$; and phenyl substituted with 0-3 $R^{3a}$, or 4-10 membered heterocycle containing 1-4 heteroatoms selected from N, O, and $S(O)_p$, substituted with 0-3 $R^{3a}$, or two $R^3$ located on adjacent carbon atoms link to form a 5-7 membered carbocycle or a 5-7 membered heterocycle comprising carbon atoms and 1-4 heteroatom selected from N, O and $S(O)_p$, both optionally substituted with 0-3 $R^{3a}$;

$R^{3a}$ is, independently at each occurrence, hydrogen, =O, halo, OCF$_3$, OCHF$_2$, CF$_3$, CHF$_2$, CN, NO$_2$, —$(CR^{1b}R^{1c})_r$—OR$^b$, —$(CR^{1b}R^{1c})_r$—$S(O)_pR^b$, —$(CR^{1b}R^{1c})_r$—C(O)$R^b$, —$(CR^{1b}R^{1c})_r$—C(O)O$R^b$, —$(CR^{1b}R^{1c})_r$—OC(O)$R^b$, —$(CR^{1b}R^{1c})_r$—NR$^{11}$R$^{11}$, —$(CR^{1b}R^{1c})_r$—C(O)NR$^{11}$R$^{11}$, —$(CR^{1b}R^{1c})_r$—NR$^b$C(O)$R^c$, —$(CR^{1b}R^{1c})_r$—NR$^b$C(O)O$R^c$, —NR$^b$C(O)NR$^{11}$R$^{11}$, —$S(O)_p$NR$^{11}$R$^{11}$, —NR$^b$S(O)$_pR^c$, $C_{1-6}$ alkyl substituted with 0-3 $R^a$, $C_{2-6}$ alkenyl substituted with 0-3 $R^a$, $C_{2-6}$ alkynyl substituted with 0-3 $R^a$, $C_{1-6}$ haloalkyl, —$(CR^{1b}R^{1c})_r$-3-14 membered carbocycle substituted with 0-3 $R^a$, or —$(CR^{1b}R^{1c})_r$-5-10 membered heterocycle comprising carbon atoms and 1-4 heteroatoms selected from N, O, and $S(O)_p$ substituted with 0-3 $R^a$;

$R^{3b}$ is, independently at each occurrence, hydrogen, CF$_3$, —$(CR^{1b}R^{1c})_q$OR$^b$, —$(CR^{1b}R^{1c})_q$$S(O)_pR^b$, —$(CR^{1b}R^{1c})_r$—C(O)$R^{3d}$, —$(CR^{1b}R^{1c})_r$—C(O)O$R^b$, —$(CR^{1b}R^{1c})_q$OC(O)$R^b$, —$(CR^{1b}R^{1c})_q$NR$^{11}$R$^{11}$, —$(CR^{1b}R^{1c})_r$—C(O)NR$^{11}$R$^{11}$, —$(CR^{1b}R^{1c})_q$NR$^b$C(O)$R^{3c}$, —$(CR^{1b}R^{1c})_q$NR$^b$C(O)OR$^c$, —$(CR^{1b}R^{1c})_q$NR$^b$C(O)N R$^{11}$R$^{11}$, —$(CR^{1b}R^{1c})_q$S(O)$_2$N R$^{11}$R$^{11}$, —$(CR^{1b}R^{1c})_q$NR$^b$S(O)$_2R^c$, $C_{1-6}$ alkyl substituted with 0-3 $R^a$, $C_{1-6}$ haloalkyl, —$(CR^{1b}R^{1c})_r$-3-14 membered carbocycle substituted with 0-3 $R^a$, or —$(CR^{1b}R^{1c})_r$-5-7 membered heterocycle comprising carbon atoms and 1-4 heteroatoms selected from N, O, and S(O), substituted with 0-3 $R^a$;

$R^{3c}$ and $R^{3d}$ are, independently at each occurrence, hydrogen or $C_{1-6}$ alkyl;

$R^4$ and $R^5$ are independently hydrogen, halo, $C_{1-6}$ alkyl or $C_{1-6}$ haloalkyl, or $R^4$ and $R^5$ together with the carbon atom to which they are attached form a 3- to 6-membered spirocarbocyclyl ring or a spiroheterocyclyl ring;

$R^6$ and $R^7$ are independently hydrogen, C(=O)$C_{1-4}$ alkyl, C(=O)O$C_{1-4}$ alkyl, $C_{1-6}$ alkyl or $C_{1-6}$ haloalkyl; or $R^6$ and $R^7$ taken together are =O;

$R^{11}$ is, independently at each occurrence, hydrogen, $C_{1-6}$ alkyl substituted with 0-3 $R^f$, CF$_3$, $C_{3-10}$ cycloalkyl substituted with 0-3 $R^d$, —$(CR^{1b}R^{1c})_r$-phenyl substituted with 0-3 $R^d$, or —$(CR^{1b}R^{1c})_r$-5-7 membered heterocycle comprising carbon atoms and 1-4 heteroatoms selected from N, O, P(=O) and $S(O)_p$ substituted with 0-4 $R^d$;

or one $R^{11}$ and a second $R^{11}$, both attached to the same nitrogen atom, combine to form a heterocycle comprising carbon atoms and 1-4 heteroatoms selected from N, O, P(=O) and $S(O)_p$ substituted with 0-4 $R^d$;

$R^a$ is, independently at each occurrence, hydrogen, =O, halo, OCF$_3$, CF$_3$, CHF$_2$, CN, NO$_2$, —$(CR^{1b}R^{1c})_r$—OR$^b$, —$(CR^{1b}R^{1c})_r$—$S(O)_pR^b$, —$(CR^{1b}R^{1c})_r$—C(O)$R^b$, —$(CR^{1b}R^{1c})_r$—C(O)O$R^b$, —$(CR^{1b}R^{1c})_r$—OC(O)$R^b$, —$(CR^{1b}R^{1c})_r$—NR$^{11}$R$^{11}$, —$(CR^{1b}R^{1c})_r$—C(O)NR$^{11}$R$^{11}$, —$(CR^{1b}R^{1c})_r$—NR$^b$C(O)$R^c$, —$(CR^{1b}R^{1c})_r$—NR$^b$C(O)OR$^c$, —NR$^b$C(O)NR$^{11}$R$^{11}$, —$S(O)_p$NR$^{11}$R$^{11}$, —NR$^b$$S(O)_pR^c$, $C_{1-6}$ alkyl substituted with 0-3 $R^f$, $C_{1-6}$ haloalkyl, $C_{2-6}$ alkenyl substituted with 0-3 $R^e$, $C_{2-6}$ alkynyl substituted with 0-3 $R^e$, —$(CR^{1b}R^{1c})_r$-3-14 membered carbocycle, or —$(CR^{1b}R^{1c})_r$-5-7 membered heterocycle comprising carbon atoms and 1-4 heteroatoms selected from N, O, P(=O) and $S(O)_p$ substituted with 0-4 $R^f$;

$R^b$ is, independently at each occurrence, hydrogen, $C_{1-6}$ alkyl substituted with 0-3 $R^d$, $C_{1-6}$ haloalkyl, $C_{3-6}$ cycloalkyl substituted with 0-3 $R^d$, —$(CR^{1b}R^{1c})_r$-5-7 membered heterocycle comprising carbon atoms and 1-4 heteroatoms selected from N, O, P(=O) and $S(O)_p$ substituted with 0-4 $R^f$, or —$(CR^{1b}R^{1c})_r$-6-10 membered carbocycle substituted with 0-3 $R^d$;

$R^c$ is, independently at each occurrence, $C_{1-6}$ alkyl substituted with 0-3 $R^f$, —$(CR^{1b}R^{1c})_r$—$C_{3-6}$ cycloalkyl substituted with 0-3 $R^f$, or —$(CR^{1b}R^{1c})_r$-phenyl substituted with 0-3 $R^f$;

$R^d$ is, independently at each occurrence, hydrogen, =O, halo, OCF$_3$, CF$_3$, CN, NO$_2$, —OR$^e$, —$(CR^{1b}R^{1c})_r$—C(O)$R^e$, —NR$^e$R$^e$, —NR$^e$C(O)OR$^c$, C(O)NR$^e$R$^e$, —NR$^e$C(O)$R^c$, CO$_2$H, CO$_2R^c$, —NR$^e$SO$_2R^c$, SO$_2R^c$, $C_{1-6}$ alkyl substituted with 0-3 $R^f$, $C_{3-6}$ cycloalkyl substituted with 0-3 $R^f$, —$(CR^{1b}R^{1c})_r$-phenyl substituted with 0-3 $R^f$ or —$(CR^{1b}R^{1c})_r$-5-7 membered heterocycle comprising carbon atoms and 1-4 heteroatoms selected from N, O, P(=O) and $S(O)_p$ substituted with 0-4 $R^f$;

$R^e$ is, independently at each occurrence, selected from hydrogen, C(O)NR$^f$R$^f$, $C_{1-6}$ alkyl, $C_{3-6}$ cycloalkyl, -5-7 membered heterocycle or —$(CR^{1b}R^{1c})_r$-phenyl substituted with 0-3 $R^f$;

$R^f$ is, independently at each occurrence, hydrogen, =O, halo, CN, NH$_2$, NH($C_{1-6}$ alkyl), N($C_{1-6}$ alkyl)$_2$, SO$_2$($C_{1-6}$ alkyl), CO$_2$H, CO$_2$($C_{1-6}$ alkyl), OH, $C_{3-6}$ cycloalkyl, CF$_3$; O($C_{1-6}$ alkyl); or an optionally substituted —$(CR^{1b}R^{1c})_r$-5-10 membered heterocycle comprising carbon atoms and 1-4 heteroatoms selected from N, O, P(=O) and $S(O)_p$, phenyl or $C_{3-6}$ cycloalkyl, each group optionally substituted with halo, CN, CF$_3$, $C_{1-6}$ alkyl or O($C_{1-6}$ alkyl);

m is 0, 1, 2 or 3 n is 0, 1 or 2;

p and q are, independently at each occurrence, 0, 1, or 2;

r is 0, 1, 2, 3, or 4;

t is 0 or 1; and w is 1, 2 or 3.

In a second aspect, the invention comprises compounds of formula Ia

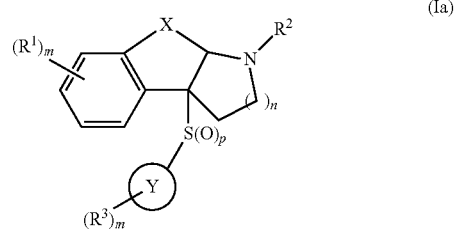

(Ia)

wherein

X is —CR$^4$R$^5$—, —(CR$^4$R$^5$)$_2$—, —OCR$^6$R$^7$—, —S(O)$_p$CR$^6$R$^7$— or —NR$^6$CR$^6$R$^7$—;

Y is a 5 or 6-membered aromatic or heteroaromatic ring;

R$^1$ is, independently at each occurrence, selected from hydrogen, CD$_3$, halo, C$_{1-6}$ alkyl substituted with 0-3 R$^{1a}$, —(CR$^{1b}$R$^{1c}$)$_r$-3-14 membered carbocycle substituted with 0-3 R$^{1a}$ and —(CR$^{1b}$R$^{1c}$)$_r$-5-10 membered heterocycle comprising carbon atoms and 1-4 heteroatoms selected from N, O, and S(O)$_p$ substituted with 0-3 R$^{1a}$;

R$^{1a}$ is, independently at each occurrence, hydrogen, =O, halo, CF$_3$, OCF$_3$, CN, NO$_2$, —(CR$^{1b}$R$^{1c}$)$_r$—OR$^b$, —(CR$^{1b}$R$^{1c}$)$_r$—S(O)$_p$R$^b$, —(CR$^{1b}$R$^{1c}$)$_r$—C(O)R$^b$, —(CR$^{1b}$R$^{1c}$)$_r$—C(O)OR$^b$, —(CR$^{1b}$R$^{1c}$)$_r$—OC(O)R$^b$, —(CR$^{1b}$R$^{1c}$)$_r$—NR$^{11}$R$^{11}$, —(CR$^{1b}$R$^{1c}$)$_r$—C(O)NR$^{11}$R$^{11}$, —(CR$^{1b}$R$^{1c}$)$_r$—NR$^b$C(O)R$^c$, —(CR$^{1b}$R$^{1c}$)$_r$—NR$^b$C(O)OR$^c$, —NR$^b$C(O)NR$^{11}$R$^{11}$, —S(O)$_p$NR$^{11}$R$^{11}$, —NR$^b$S(O)$_p$R$^c$, C$_{1-6}$ alkyl substituted with 0-3 R$^a$, C$_{1-6}$ haloalkyl, C$_{2-6}$ alkenyl substituted with 0-3 R$^a$, C$_{2-6}$ alkynyl substituted with 0-3 R$^a$, —(CR$^{1b}$R$^{1c}$)$_r$-3-14 membered carbocycle substituted with 0-3 R$^a$, or —(CR$^{1b}$R$^{1c}$)$_r$-5-7 membered heterocycle comprising carbon atoms and 1-4 heteroatoms selected from N, O, and S(O)$_p$ substituted with 0-3 R$^a$;

R$^{1b}$ and R$^{1c}$ are, independently at each occurrence, hydrogen, halogen or C$_{1-6}$ alkyl;

R$^2$ is

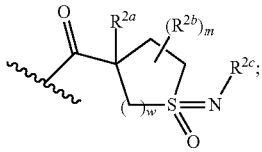

R$^{2a}$ and R$^{2b}$ are, independently at each occurrence, hydrogen, halo, OCF$_3$, CF$_3$, CHF$_2$, CN, NO$_2$, —(CR$^{1b}$R$^{1c}$)$_r$—OR$^b$, —(CR$^{1b}$R$^{1c}$)$_r$—S(O)$_p$R$^b$, —(CR$^{1b}$R$^{1c}$)$_r$—C(O)R$^b$, —(CR$^{1b}$R$^{1c}$)$_r$—C(O)OR$^b$, —(CR$^{1b}$R$^{1c}$)$_r$—OC(O)R$^b$, —(CR$^{1b}$R$^{1c}$)$_r$—NR$^{11}$R$^{11}$, —(CR$^{1b}$R$^{1c}$)$_r$—C(O)NR$^{11}$R$^{11}$, —(CR$^{1b}$R$^{1c}$)$_r$—NR$^b$C(O)R$^c$, —(CR$^{1b}$R$^{1c}$)$_r$—NR$^b$C(O)OR$^c$, —NR$^b$C(O)NR$^{11}$R$^{11}$, —S(O)$_p$NR$^{11}$R$^{11}$, —NR$^b$S(O)$_p$R$^c$, C$_{1-6}$ alkyl substituted with 0-3 R$^f$, C$_{1-6}$ haloalkyl, C$_{2-6}$ alkenyl substituted with 0-3 R$^e$, C$_{2-6}$ alkynyl substituted with 0-3 R$^e$, —(CR$^{1b}$R$^{1c}$)$_r$-3-14 membered carbocycle, or —(CR$^{1b}$R$^{1c}$)$_r$-5-7 membered heterocycle comprising carbon atoms and 1-4 heteroatoms selected from N, O, P(=O) and S(O)$_p$ substituted with 0-4 R$^f$;

R$^{2c}$ is hydrogen, C$_{1-6}$ alkyl substituted with 0-3 R$^f$, C$_{1-6}$ haloalkyl, —(CR$^{1b}$R$^{1c}$)$_r$—C(O)R$^b$, —(CR$^{1b}$R$^{1c}$)$_r$—C(O)OR$^b$, —(CR$^{1b}$R$^{1c}$)$_r$—C(O)NR$^{11}$R$^{11}$, —(CR$^{1b}$R$^{1c}$)$_r$-3-14 membered carbocycle, or —(CR$^{1b}$R$^{1c}$)$_r$-5-7 membered heterocycle comprising carbon atoms and 1-4 heteroatoms selected from N, O, P(=O) and S(O)$_p$ substituted with 0-4 R$^f$;

R$^3$ is, independently at each occurrence, selected from hydrogen, halo, N$_3$, CN, —(CR$^{1b}$R$^{1c}$)$_r$—OR$^{3b}$, —(CR$^{1b}$R$^{1c}$)$_r$—NR$^{11}$R$^{11}$, C$_{1-6}$ alkyl substituted with 0-3 R$^{3a}$, C$_{3-10}$ cycloalkyl substituted with 0-3 R$^{3a}$; and phenyl substituted with 0-3 R$^{3a}$, or 4-10 membered heterocycle containing 1-4 heteroatoms selected from N, O, and S(O)$_p$, substituted with 0-3 R$^{3a}$, or two R$^3$ located on adjacent carbon atoms link to form a 5-7 membered carbocycle or a 5-7 membered heterocycle comprising carbon atoms and 1-4 heteroatom selected from N, O and S(O)$_p$, both optionally substituted with 0-3 R$^{3a}$;

R$^{3a}$ is, independently at each occurrence, hydrogen, =O, halo, OCF$_3$, OCHF$_2$, CF$_3$, CHF$_2$, CN, NO$_2$, —(CR$^{1b}$R$^{1c}$)$_r$—OR$^b$, —(CR$^{1b}$R$^{1c}$)$_r$—S(O)$_p$R$^b$, —(CR$^{1b}$R$^{1c}$)$_r$—C(O)R$^b$, —(CR$^{1b}$R$^{1c}$)$_r$—C(O)OR$^b$, —(CR$^{1b}$R$^{1c}$)$_r$—OC(O)R$^b$, —(CR$^{1b}$R$^{1c}$)$_r$—NR$^{11}$R$^{11}$, —(CR$^{1b}$R$^{1c}$)$_r$—C(O)NR$^{11}$R$^{11}$, —(CR$^{1b}$R$^{1c}$)$_r$—NR$^b$C(O)R$^c$, —(CR$^{1b}$R$^{1c}$)$_r$—NR$^b$C(O)OR$^c$, —NR$^b$C(O)NR$^{11}$R$^{11}$, —S(O)$_p$NR$^{11}$R$^{11}$, —NR$^b$S(O)$_p$R$^c$, C$_{1-6}$ alkyl substituted with 0-3 R$^a$, C$_{2-6}$ alkenyl substituted with 0-3 R$^a$, C$_{2-6}$ alkynyl substituted with 0-3 R$^a$, C$_{1-6}$ haloalkyl, —(CR$^{1b}$R$^{1c}$)$_r$-3-14 membered carbocycle substituted with 0-3 R$^a$, or —(CR$^{1b}$R$^{1c}$)$_r$-5-10 membered heterocycle comprising carbon atoms and 1-4 heteroatoms selected from N, O, and S(O)$_p$ substituted with 0-3 R$^a$;

R$^{3b}$ is, independently at each occurrence, hydrogen, CF$_3$, —(CR$^{1b}$R$^{1c}$)$_q$OR$^b$, —(CR$^{1b}$R$^{1c}$)$_q$S(O)$_p$R$^b$, —(CR$^{1b}$R$^{1c}$)$_r$—C(O)R$^{3d}$, —(CR$^{1b}$R$^{1c}$)$_r$—C(O)OR$^b$, —(CR$^{1b}$R$^{1c}$)$_q$OC(O)R$^b$, —(CR$^{1b}$R$^{1c}$)$_q$NR$^{11}$R$^{11}$, —(CR$^{1b}$R$^{1c}$)$_r$—C(O)NR$^{11}$R$^{11}$, —(CR$^{1b}$R$^{1c}$)$_q$NR$^b$C(O)R$^{3c}$, —(CR$^{1b}$R$^{1c}$)$_q$NR$^b$C(O)OR$^c$, —(CR$^{1b}$R$^{1c}$)$_q$NR$^b$C(O)N R$^{11}$R$^{11}$, —(CR$^{1b}$R$^{1c}$)$_q$S(O)$_2$N R$^{11}$R$^{11}$, —(CR$^{1b}$R$^{1c}$)$_q$NR$^b$S(O)$_2$R$^c$, C$_{1-6}$ alkyl substituted with 0-3 R$^a$, C$_{1-6}$ haloalkyl, —(CR$^{1b}$R$^{1c}$)$_r$-3-14 membered carbocycle substituted with 0-3 R$^a$, or —(CR$^{1b}$R$^{1c}$)$_r$-5-7 membered heterocycle comprising carbon atoms and 1-4 heteroatoms selected from N, O, and S(O)$_p$ substituted with 0-3 R$^a$;

R$^{3c}$ and R$^{3d}$ are, independently at each occurrence, hydrogen or C$_{1-6}$ alkyl;

R$^4$ and R$^5$ are independently hydrogen, halo, C$_{1-6}$ alkyl or C$_{1-6}$ haloalkyl, or R$^4$ and R$^5$ together with the carbon atom to which they are attached form a 3- to 6-membered spirocarbocyclyl ring or a spiroheterocyclyl ring;

R$^6$ and R$^7$ are independently hydrogen, C$_{1-6}$ alkyl or C$_{1-6}$ haloalkyl;

R$^{11}$ is, independently at each occurrence, hydrogen, C$_{1-6}$ alkyl substituted with 0-3 R$^f$, CF$_3$, C$_{3-10}$ cycloalkyl substituted with 0-3 R$^f$, —(CR$^{1b}$R$^{1c}$)$_r$-phenyl substituted with 0-3 R$^d$, or —(CR$^{1b}$R$^{1c}$)$_r$-5-7 membered heterocycle comprising carbon atoms and 1-4 heteroatoms selected from N, O, P(=O) and S(O)$_p$ substituted with 0-4 R$^d$;

or one R$^{11}$ and a second R$^{11}$, both attached to the same nitrogen atom, combine to form a heterocycle comprising carbon atoms and 1-4 heteroatoms selected from N, O, P(=O) and S(O)$_p$ substituted with 0-4 R$^d$;

R$^a$ is, independently at each occurrence, hydrogen, =O, halo, OCF$_3$, CF$_3$, CHF$_2$, CN, NO$_2$, —(CR$^{1b}$R$^{1c}$)$_r$—OR$^b$, —(CR$^{1b}$R$^{1c}$)$_r$—S(O)$_p$R$^b$, —(CR$^{1b}$R$^{1c}$)$_r$—C(O)R$^b$, —(CR$^{1b}$R$^{1c}$)$_r$—C(O)OR$^b$, —(CR$^{1b}$R$^{1c}$)$_r$—OC(O)R$^b$, —(CR$^{1b}$R$^{1c}$)$_r$—NR$^{11}$R$^{11}$, —(CR$^{1b}$R$^{1c}$)$_r$—C(O)NR$^{11}$R$^{11}$, —(CR$^{1b}$R$^{1c}$)$_r$—NR$^b$C(O)R$^c$, —(CR$^{1b}$R$^{1c}$)$_r$—NR$^b$C(O)OR$^c$, —NR$^b$C(O)NR$^{11}$R$^{11}$, —S(O)$_p$NR$^{11}$R$^{11}$, —NR$^b$S(O)$_p$R$^c$, C$_{1-6}$ alkyl substituted with 0-3 R$^f$, C$_{1-6}$ haloalkyl, C$_{2-6}$ alkenyl substituted with 0-3 R$^e$, C$_{2-6}$ alkynyl substituted with 0-3 R$^e$, —(CR$^{1b}$R$^{1c}$)$_r$-3-14 membered carbocycle, or —(CR$^{1b}$R$^{1c}$)$_r$-5-7 membered heterocycle comprising carbon atoms and 1-4 heteroatoms selected from N, O, P(=O) and S(O)$_p$ substituted with 0-4 R$^f$;

R$^b$ is, independently at each occurrence, hydrogen, C$_{1-6}$ alkyl substituted with 0-3 R$^d$, C$_{1-6}$ haloalkyl, C$_{3-6}$ cycloalkyl substituted with 0-3 R$^d$, —(CR$^{1b}$R$^{1c}$)$_r$-5-7 membered heterocycle comprising carbon atoms and 1-4 heteroatoms selected from N, O, P(=O) and S(O)$_p$ substituted with 0-4 R$^f$, or —(CR$^{1b}$R$^{1c}$)$_r$-6-10 membered carbocycle substituted with 0-3 R$^d$;

$R^c$ is, independently at each occurrence, $C_{1-6}$ alkyl substituted with 0-3 $R^f$, —$(CR^{1b}R^{1c})_r$—$C_{3-6}$ cycloalkyl substituted with 0-3 $R^f$, or —$(CR^{1b}R^{1c})_r$-phenyl substituted with 0-3 $R^f$;

$R^d$ is, independently at each occurrence, hydrogen, =O, halo, $OCF_3$, $CF_3$, CN, $NO_2$, —$OR^e$, —$(CR^{1b}R^{1c})_r$—C(O)$R^c$, —$NR^eR^e$, —$NR^eC(O)OR^c$, $C(O)NR^eR^e$, —$NR^eC(O)R^c$, $CO_2H$, $CO_2R^c$, —$NR^eSO_2R^c$, $SO_2R^c$, $C_{1-6}$ alkyl substituted with 0-3 $R^f$, $C_{3-6}$ cycloalkyl substituted with 0-3 $R^f$, —$(CR^{1b}R^{1c})_r$-phenyl substituted with 0-3 $R^f$ or —$(CR^{1b}R^{1c})_r$-5-7 membered heterocycle comprising carbon atoms and 1-4 heteroatoms selected from N, O, P(=O) and S(O)$_p$ substituted with 0-4 $R^f$;

$R^e$ is, independently at each occurrence, selected from hydrogen, $C(O)NR^fR^f$, $C_{1-6}$ alkyl, $C_{3-6}$ cycloalkyl, -5-7 membered heterocycle or —$(CR^{1b}R^{1c})_r$-phenyl substituted with 0-3 $R^f$;

$R^f$ is, independently at each occurrence, hydrogen, =O, halo, CN, $NH_2$, $NH(C_{1-6}$ alkyl), $N(C_{1-6}$ alkyl)$_2$, $SO_2(C_{1-6}$ alkyl), $CO_2H$, $CO_2(C_{1-6}$ alkyl), OH, $C_{3-6}$ cycloalkyl, $CF_3$; $O(C_{1-6}$ alkyl); or an optionally substituted —$(CR^{1b}R^{1c})_r$-5-10 membered heterocycle comprising carbon atoms and 1-4 heteroatoms selected from N, O, P(=O) and S(O)$_p$, phenyl or $C_{3-6}$ cycloalkyl, each group optionally substituted with halo, CN, $CF_3$, $C_{1-6}$ alkyl or $O(C_{1-6}$ alkyl);

m is 0, 1, 2 or 3 n is 0, 1 or 2;

p and q are, independently at each occurrence, 0, 1, or 2;

r is 0, 1, 2, 3, or 4; and w is 1, 2 or 3;

or a stereoisomer or pharmaceutically-acceptable salt thereof.

In a third aspect, the invention comprises compounds of the formula

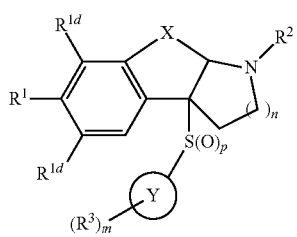

wherein

X is —$CR^4R^5$—, —$(CR^4R^5)_2$—, —$OCR^6R^7$—, —$S(O)_pCR^6R^7$— or —$NR^6CR^6R^7$—;

Y is a 5 or 6-membered aromatic or heteroaromatic ring;

$R^1$ is selected from halo, $C_{1-6}$ alkyl substituted with 0-3 $R^{1a}$, —$(CR^{1b}R^{1c})_r$-3-14 membered carbocycle substituted with 0-3 $R^{1a}$ and —$(CR^{1b}R^{1c})_r$-5-10 membered heterocycle comprising carbon atoms and 1-4 heteroatoms selected from N, O, and S(O)$_p$ substituted with 0-3 $R^{1a}$;

$R^{1a}$ is, independently at each occurrence, hydrogen, =O, halo, $CF_3$, $OCF_3$, CN, $NO_2$, —$(CR^{1b}R^{1c})_r$—$OR^b$, —$(CR^{1b}R^{1c})_r$—S(O)$_pR^b$, —$(CR^{1b}R^{1c})_r$—C(O)$R^b$, —$(CR^{1b}R^{1c})_r$—C(O)O$R^b$, —$(CR^{1b}R^{1c})_r$—OC(O)$R^b$, —$(CR^{1b}R^{1c})_r$—$NR^{11}R^{11}$, —$(CR^{1b}R^{1c})_r$—C(O)$NR^{11}R^{11}$, —$(CR^{1b}R^{1c})_r$—$NR^bC(O)R^c$, —$(CR^{1b}R^{1c})_r$—$NR^bC(O)OR^c$, —$NR^bC(O)NR^{11}R^{11}$, —S(O)$_pNR^{11}R^{11}$, —$NR^bS(O)_pR^c$, $C_{1-6}$ alkyl substituted with 0-3 $R^a$, $C_{1-6}$ haloalkyl, $C_{2-6}$ alkenyl substituted with 0-3 $R^a$, $C_{2-6}$ alkynyl substituted with 0-3 $R^a$, —$(CR^{1b}R^{1c})_r$-3-14 membered carbocycle substituted with 0-3 $R^a$, or —$(CR^{1b}R^{1c})_r$-5-7 membered heterocycle comprising carbon atoms and 1-4 heteroatoms selected from N, O, and S(O)$_p$ substituted with 0-3 $R^a$;

$R^{1b}$ and $R^{1c}$ are, independently at each occurrence, hydrogen, halogen or $C_{1-6}$ alkyl;

$R^{1d}$ is, independently at each occurrence, hydrogen, $CD_3$, halo, $CF_3$, and $C_1$-$C_4$ alkyl;

$R^2$ is

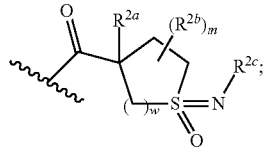

$R^{2a}$ and $R^{2b}$ are, independently at each occurrence, hydrogen, halo, $OCF_3$, $CF_3$, $CHF_2$, CN, $NO_2$, —$(CR^{1b}R^{1c})_r$—$OR^b$, —$(CR^{1b}R^{1c})_r$—S(O)$_pR^b$, —$(CR^{1b}R^{1c})_r$—C(O)$R^b$, —$(CR^{1b}R^{1c})_r$—C(O)O$R^b$, —$(CR^{1b}R^{1c})_r$—OC(O)$R^b$, —$(CR^{1b}R^{1c})_r$—$NR^{11}R^{11}$, —$(CR^{1b}R^{1c})_r$—C(O)$NR^{11}R^{11}$, —$(CR^{1b}R^{1c})_r$—$NR^bC(O)R^c$, —$(CR^{1b}R^{1c})_r$—$NR^bC(O)OR^c$, —$NR^bC(O)NR^{11}R^{11}$, —S(O)$_pNR^{11}R^{11}$, —$NR^bS(O)_pR^c$, $C_{1-6}$ alkyl substituted with 0-3 $R^f$, $C_{1-6}$ haloalkyl, $C_{2-6}$ alkenyl substituted with 0-3 $R^e$, $C_{2-6}$ alkynyl substituted with 0-3 $R^e$, —$(CR^{1b}R^{1c})_r$-3-14 membered carbocycle, or —$(CR^{1b}R^{1c})_r$-5-7 membered heterocycle comprising carbon atoms and 1-4 heteroatoms selected from N, O, P(=O) and S(O)$_p$ substituted with 0-4 $R^f$;

$R^{2c}$ is hydrogen, $C_{1-6}$ alkyl substituted with 0-3 $R^f$, $C_{1-6}$ haloalkyl, —$(CR^{1b}R^{1c})_r$—C(O)$R^b$, —$(CR^{1b}R^{1c})_r$—C(O)O$R^b$, —$(CR^{1b}R^{1c})_r$—C(O)$NR^{11}R^{11}$, —$(CR^{1b}R^{1c})_r$-3-14 membered carbocycle, or —$(CR^{1b}R^{1c})_r$-5-7 membered heterocycle comprising carbon atoms and 1-4 heteroatoms selected from N, O, P(=O) and S(O)$_p$ substituted with 0-4 $R^f$;

$R^3$ is, independently at each occurrence, selected from hydrogen, halo, $N_3$, CN, —$(CR^{1b}R^{1c})_r$—$OR^{3b}$, —$(CR^{1b}R^{1c})_r$—$NR^{11}R^{11}$, $C_{1-6}$ alkyl substituted with 0-3 $R^{3a}$, $C_{3-10}$ cycloalkyl substituted with 0-3 $R^{3a}$; and phenyl substituted with 0-3 $R^{3a}$, or 4-10 membered heterocycle containing 1-4 heteroatoms selected from N, O, and S(O)$_p$, substituted with 0-3 $R^{3a}$, or two $R^3$ located on adjacent carbon atoms link to form a 5-7 membered carbocycle or a 5-7 membered heterocycle comprising carbon atoms and 1-4 heteroatom selected from N, O and S(O)$_p$, both optionally substituted with 0-3 $R^{3a}$;

$R^{3a}$ is, independently at each occurrence, hydrogen, =O, halo, $OCF_3$, $OCHF_2$, $CF_3$, $CHF_2$, CN, $NO_2$, —$(CR^{1b}R^{1c})_r$—$OR^b$, —$(CR^{1b}R^{1c})_r$—S(O)$_pR^b$, —$(CR^{1b}R^{1c})_r$—C(O)$R^b$, —$(CR^{1b}R^{1c})_r$—C(O)O$R^b$, —$(CR^{1b}R^{1c})_r$—OC(O)$R^b$, —$(CR^{1b}R^{1c})_r$—$NR^{11}R^{11}$, —$(CR^{1b}R^{1c})_r$—C(O)$NR^{11}R^{11}$, —$(CR^{1b}R^{1c})_r$—$NR^bC(O)R^c$, —$(CR^{1b}R^{1c})_r$—$NR^bC(O)OR^c$, —$NR^bC(O)NR^{11}R^{11}$, —S(O)$_pNR^{11}R^{11}$, —$NR^bS(O)_pR^c$, $C_{1-6}$ alkyl substituted with 0-3 $R^a$, $C_{2-6}$ alkenyl substituted with 0-3 $R^a$, $C_{2-6}$ alkynyl substituted with 0-3 $R^a$, $C_{1-6}$ haloalkyl, —$(CR^{1b}R^{1c})_r$-3-14 membered carbocycle substituted with 0-3 $R^a$, or —$(CR^{1b}R^{1c})_r$-5-10 membered heterocycle comprising carbon atoms and 1-4 heteroatoms selected from N, O, and S(O)$_p$ substituted with 0-3 $R^a$;

$R^{3b}$ is, independently at each occurrence, hydrogen, $CF_3$, —$(CR^{1b}R^{1c})_qOR^b$, —$(CR^{1b}R^{1c})_qS(O)_pR^b$, —$(CR^{1b}R^{1c})_r$—C(O)$R^{3d}$, —$(CR^{1b}R^{1c})_r$—C(O)O$R^b$, —$(CR^{1b}R^{1c})_qOC(O)R^b$, —$(CR^{1b}R^{1c})_r$—$NR^{11}R^{11}$, —$(CR^{1b}R^{1c})_r$—C(O)$NR^{11}R^{11}$, —$(CR^{1b}R^{1c})_qNR^bC(O)R^{3c}$, —$(CR^{1b}R^{1c})_qNR^bC(O)OR^c$, —$(CR^{1b}R^{1c})_qNR^bC(O)N R^{11}R^{11}$, —$(CR^{1b}R^{1c})_qS(O)_2NR^{11}R^{11}$, —$(CR^{1b}R^{1c})_qNR^bS(O)R^c$, $C_{1-6}$ alkyl substituted with 0-3 $R^a$, $C_{1-6}$ haloalkyl, —$(CR^{1b}R^{1c})_r$-3-14 membered carbocycle substituted with 0-3 $R^a$, or —$(CR^{1b}R^{1c})_r$-5-7 membered heterocycle comprising carbon atoms and 1-4 heteroatoms selected from N, O, and S(O)$_p$ substituted with 0-3 $R^a$;

$R^{3c}$ and $R^{3d}$ are, independently at each occurrence, hydrogen or $C_{1-6}$ alkyl;

$R^4$ and $R^5$ are independently hydrogen, halo, $C_{1-6}$ alkyl or $C_{1-6}$ haloalkyl, or $R^4$ and $R^5$ together with the carbon atom to which they are attached form a 3- to 6-membered spirocarbocyclyl ring or a spiroheterocyclyl ring;

$R^6$ and $R^7$ are independently hydrogen, $C_{1-6}$ alkyl or $C_{1-6}$ haloalkyl;

$R^{11}$ is, independently at each occurrence, hydrogen, $C_{1-6}$ alkyl substituted with 0-3 $R^f$, $CF_3$, $C_{3-10}$ cycloalkyl substituted with 0-3 $R^f$, —$(CR^{1b}R^{1c})_r$-phenyl substituted with 0-3 $R^d$, or —$(CR^{1b}R^{1c})_r$-5-7 membered heterocycle comprising carbon atoms and 1-4 heteroatoms selected from N, O, P(=O) and S(O)$_p$ substituted with 0-4 $R^d$;

or one $R^{11}$ and a second $R^{11}$, both attached to the same nitrogen atom, combine to form a heterocycle comprising carbon atoms and 1-4 heteroatoms selected from N, O, P(=O) and S(O)$_p$ substituted with 0-4 $R^d$;

$R^a$ is, independently at each occurrence, hydrogen, =O, halo, $OCF_3$, $CF_3$, $CHF_2$, CN, $NO_2$, —$(CR^{1b}R^{1c})_r$—$OR^b$, —$(CR^{1b}R^{1c})_r$—$S(O)_pR^b$, —$(CR^{1b}R^{1c})_r$—$C(O)R^b$, —$(CR^{1b}R^{1c})_r$—$C(O)OR^b$, —$(CR^{1b}R^{1c})_r$—$OC(O)R^b$, —$(CR^{1b}R^{1c})_r$—$NR^{11}R^{11}$, —$(CR^{1b}R^{1c})_r$—$C(O)NR^{11}R^{11}$, —$(CR^{1b}R^{1c})_r$—$NR^bC(O)R^c$, —$(CR^{1b}R^{1c})_r$—$NR^bC(O)OR^c$, —$NR^bC(O)NR^{11}R^{11}$, —$S(O)_pNR^{11}R^{11}$, —$NR^bS(O)_pR^c$, $C_{1-6}$ alkyl substituted with 0-3 $R^f$, $C_{1-6}$ haloalkyl, $C_{2-6}$ alkenyl substituted with 0-3 $R^e$, $C_{2-6}$ alkynyl substituted with 0-3 $R^e$, —$(CR^{1b}R^{1c})_r$-3-14 membered carbocycle, or —$(CR^{1b}R^{1c})_r$-5-7 membered heterocycle comprising carbon atoms and 1-4 heteroatoms selected from N, O, P(=O) and S(O)$_p$ substituted with 0-4 $R^f$;

$R^b$ is, independently at each occurrence, hydrogen, $C_{1-6}$ alkyl substituted with 0-3 $R^d$, $C_{1-6}$ haloalkyl, $C_{3-6}$ cycloalkyl substituted with 0-3 $R^d$, —$(CR^{1b}R^{1c})_r$-5-7 membered heterocycle comprising carbon atoms and 1-4 heteroatoms selected from N, O, P(=O) and S(O)$_p$ substituted with 0-4 $R^f$, or —$(CR^{1b}R^{1c})_r$-6-10 membered carbocycle substituted with 0-3 $R^d$;

$R^c$ is, independently at each occurrence, $C_{1-6}$ alkyl substituted with 0-3 $R^f$, —$(CR^{1b}R^{1c})_r$—$C_{3-6}$ cycloalkyl substituted with 0-3 $R^f$, or —$(CR^{1b}R^{1c})_r$-phenyl substituted with 0-3 $R^f$;

$R^d$ is, independently at each occurrence, hydrogen, =O, halo, $OCF_3$, $CF_3$, CN, $NO_2$, —$OR^e$, —$(CR^{1b}R^{1c})_r$—$C(O)R^c$, —$NR^eR^e$, —$NR^eC(O)OR^c$, $C(O)NR^eR^e$, —$NR^eC(O)R^c$, $CO_2H$, $CO_2R^c$, —$NR^eSO_2R^c$, $SO_2R^c$, $C_{1-6}$ alkyl substituted with 0-3 $R^f$, $C_{3-6}$ cycloalkyl substituted with 0-3 $R^f$, —$(CR^{1b}R^{1c})_r$-phenyl substituted with 0-3 $R^f$ or —$(CR^{1b}R^{1c})_r$-5-7 membered heterocycle comprising carbon atoms and 1-4 heteroatoms selected from N, O, P(=O) and S(O)$_p$ substituted with 0-4 $R^f$;

$R^e$ is, independently at each occurrence, selected from hydrogen, $C(O)NR^fR^f$, $C_{1-6}$ alkyl, $C_{3-6}$ cycloalkyl, -5-7 membered heterocycle or —$(CR^{1b}R^{1c})_r$-phenyl substituted with 0-3 $R^f$;

$R^f$ is, independently at each occurrence, hydrogen, =O, halo, CN, $NH_2$, $NH(C_{1-6}$ alkyl), $N(C_{1-6}$ alkyl)$_2$, $SO_2(C_{1-6}$ alkyl), $CO_2H$, $CO_2(C_{1-6}$ alkyl), OH, $C_{3-6}$ cycloalkyl, $CF_3$; $O(C_{1-6}$ alkyl); or an optionally substituted —$(CR^{1b}R^{1c})_r$-5-10 membered heterocycle comprising carbon atoms and 1-4 heteroatoms selected from N, O, P(=O) and S(O)$_p$, phenyl or $C_{3-6}$ cycloalkyl, each group optionally substituted with halo, CN, $CF_3$, $C_{1-6}$ alkyl or $O(C_{1-6}$ alkyl);

m is 0, 1, 2 or 3 n is 0, 1 or 2;

p and q are, independently at each occurrence, 0, 1, or 2;

r is 0, 1, 2, 3, or 4; and w is 1, 2 or 3;

or a stereoisomer or pharmaceutically-acceptable salt thereof.

In a 4$^{th}$ aspect, the invention comprises compounds of the formula

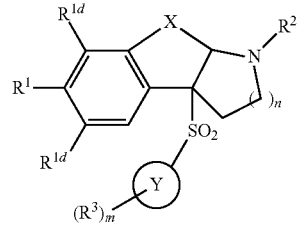

wherein

X is —$CR^4R^5$—, —$(CR^4R^5)_2$—, —$OCR^6R^7$—, —$S(O)_pCR^6R^7$— or —$NR^6CR^6R^7$—;

Y is a 5 or 6-membered aromatic or heteroaromatic ring;

$R^1$ is selected from halo, $C_{1-6}$ alkyl substituted with 0-3 $R^{1a}$, —$(CR^{1b}R^{1c})_r$-3-14 membered carbocycle substituted with 0-3 $R^{1a}$ and —$(CR^{1b}R^{1c})_r$-5-10 membered heterocycle comprising carbon atoms and 1-4 heteroatoms selected from N, O, and S(O)$_p$ substituted with 0-3 $R^{1a}$;

$R^{1a}$ is, independently at each occurrence, hydrogen, =O, halo, $CF_3$, $OCF_3$, CN, $NO_2$, —$(CR^{1b}R^{1c})_r$—$OR^b$, —$(CR^{1b}R^{1c})_r$—$S(O)_pR^b$, —$(CR^{1b}R^{1c})_r$—$C(O)R^b$, —$(CR^{1b}R^{1c})_r$—$C(O)OR^b$, —$(CR^{1b}R^{1c})_r$—$OC(O)R^b$, —$(CR^{1b}R^{1c})_r$—$NR^{11}R^{11}$, —$(CR^{1b}R^{1c})_r$—$C(O)NR^{11}R^{11}$, —$(CR^{1b}R^{1c})_r$—$NR^bC(O)R^c$, —$(CR^{1b}R^{1c})_r$—$NR^bC(O)OR^c$, —$NR^bC(O)NR^{11}R^{11}$, —$S(O)_pNR^{11}R^{11}$, —$NR^bS(O)_pR^c$, $C_{1-6}$ alkyl substituted with 0-3 $R^a$, $C_{1-6}$ haloalkyl, $C_{2-6}$ alkenyl substituted with 0-3 $R^a$, $C_{2-6}$ alkynyl substituted with 0-3 $R^a$, —$(CR^{1b}R^{1c})_r$-3-14 membered carbocycle substituted with 0-3 $R^a$, or —$(CR^{1b}R^{1c})_r$-5-7 membered heterocycle comprising carbon atoms and 1-4 heteroatoms selected from N, O, and S(O)$_p$ substituted with 0-3 $R^a$;

$R^{1b}$ and $R^{1c}$ are, independently at each occurrence, hydrogen, halogen or $C_{1-6}$ alkyl;

$R^{1d}$ is, independently at each occurrence, hydrogen, $CD_3$, halo, $CF_3$, and $C_1$-$C_4$ alkyl;

$R^2$ is

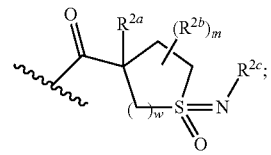

$R^{2a}$ and $R^{2b}$ are, independently at each occurrence, hydrogen, halo, $OCF_3$, $CF_3$, $CHF_2$, CN, $NO_2$, —$(CR^{1b}R^{1c})_r$—$OR^b$, —$(CR^{1b}R^{1c})_r$—$S(O)_pR^b$, —$(CR^{1b}R^{1c})_r$—$C(O)R^b$, —$(CR^{1b}R^{1c})_r$—$C(O)OR^b$, —$(CR^{1b}R^{1c})_r$—$OC(O)R^b$, —$(CR^{1b}R^{1c})_r$—$NR^{11}R^{11}$, —$(CR^{1b}R^{1c})_r$—$C(O)NR^{11}R^{11}$, —$(CR^{1b}R^{1c})_r$—$NR^bC(O)R^c$, —$(CR^{1b}R^{1c})_r$—$NR^bC(O)OR^c$, —$NR^bC(O)NR^{11}R^{11}$, —$S(O)_pNR^{11}R^{11}$, —$NR^bS(O)_pR^c$, $C_{1-6}$ alkyl substituted with 0-3 $R^f$, $C_{1-6}$ haloalkyl, $C_{2-6}$ alkenyl substituted with 0-3 $R^e$, $C_{2-6}$ alkynyl substituted with 0-3 $R^e$, —$(CR^{1b}R^{1c})_r$-3-14 membered carbocycle, or —$(CR^{1b}R^{1c})_r$-5-7 membered heterocycle comprising carbon atoms and 1-4 heteroatoms selected from N, O, P(=O) and $S(O)_p$ substituted with 0-4 $R^f$;

$R^{2c}$ is hydrogen, $C_{1-6}$ alkyl substituted with 0-3 $R^f$, $C_{1-6}$ haloalkyl, —$(CR^{1b}R^{1c})_r$—C(O)$R^b$, —$(CR^{1b}R^{1c})_r$—C(O)OR$^b$, —$(CR^{1b}R^{1c})_r$—C(O)NR$^{11}R^{11}$, —$(CR^{1b}R^{1c})_r$-3-14 membered carbocycle, or —$(CR^{1b}R^{1c})_r$-5-7 membered heterocycle comprising carbon atoms and 1-4 heteroatoms selected from N, O, P(=O) and $S(O)_p$ substituted with 0-4 $R^f$;

$R^3$ is, independently at each occurrence, selected from hydrogen, halo, $N_3$, CN, —$(CR^{1b}R^{1c})_r$—OR$^{3b}$, —$(CR^{1b}R^{1c})_r$—NR$^{11}R^{11}$, $C_{1-6}$ alkyl substituted with 0-3 $R^{3a}$, $C_{3-10}$ cycloalkyl substituted with 0-3 $R^{3a}$; and phenyl substituted with 0-3 $R^{3a}$, or 4-10 membered heterocycle containing 1-4 heteroatoms selected from N, O, and $S(O)_p$, substituted with 0-3 $R^{3a}$, or two $R^3$ located on adjacent carbon atoms link to form a 5-7 membered carbocycle or a 5-7 membered heterocycle comprising carbon atoms and 1-4 heteroatom selected from N, O and $S(O)_p$, both optionally substituted with 0-3 $R^{3a}$;

$R^{3a}$ is, independently at each occurrence, hydrogen, =O, halo, $OCF_3$, $OCHF_2$, $CF_3$, $CHF_2$, CN, $NO_2$, —$(CR^{1b}R^{1c})_r$—OR$^b$, —$(CR^{1b}R^{1c})_r$—S(O)$_pR^b$, —$(CR^{1b}R^{1c})_r$—C(O)$R^b$, —$(CR^{1b}R^{1c})_r$—C(O)OR$^b$, —$(CR^{1b}R^{1c})_r$—OC(O)$R^b$, —$(CR^{1b}R^{1c})_r$—NR$^{11}R^{11}$, —$(CR^{1b}R^{1c})_r$—C(O)NR$^{11}R^{11}$, —$(CR^{1b}R^{1c})_r$—NR$^bC(O)R^c$, —$(CR^{1b}R^{1c})_r$—NR$^bC(O)OR^c$, —NR$^bC(O)NR^{11}R^{11}$, —S(O)$_p$NR$^{11}R^{11}$, —NR$^bS(O)_pR^c$, $C_{1-6}$ alkyl substituted with 0-3 $R^a$, $C_{2-6}$ alkenyl substituted with 0-3 $R^a$, $C_{2-6}$ alkynyl substituted with 0-3 $R^a$, $C_{1-6}$ haloalkyl, —$(CR^{1b}R^{1c})_r$-3-14 membered carbocycle substituted with 0-3 $R^a$, or —$(CR^{1b}R^{1c})_r$-5-10 membered heterocycle comprising carbon atoms and 1-4 heteroatoms selected from N, O, and $S(O)_p$ substituted with 0-3 $R^a$;

$R^{3b}$ is, independently at each occurrence, hydrogen, $CF_3$, —$(CR^{1b}R^{1c})_q$OR$^b$, —$(CR^{1b}R^{1c})_q$S(O)$_pR^b$, —$(CR^{1b}R^{1c})_r$—C(O)$R^{3d}$, —$(CR^{1b}R^{1c})_r$—C(O)OR$^b$, —$(CR^{1b}R^{1c})_q$OC(O)$R^b$, —$(CR^{1b}R^{1c})_q$NR$^{11}R^{11}$, —$(CR^{1b}R^{1c})_r$—C(O)NR$^{11}R^{11}$, —$(CR^{1b}R^{1c})_q$NR$^bC(O)R^{3c}$, —$(CR^{1b}R^{1c})_q$NR$^bC(O)OR^c$, —$(CR^{1b}R^{1c})_q$NR$^bC(O)N$ $R^{11}R^{11}$, —$(CR^{1b}R^{1c})_q$S(O)$_2$N$R^{11}R^{11}$, —$(CR^{1b}R^{1c})_q$NR$^bS(O)_2R^c$, $C_{1-6}$ alkyl substituted with 0-3 $R^a$, $C_{1-6}$ haloalkyl, —$(CR^{1b}R^{1c})_r$-3-14 membered carbocycle substituted with 0-3 $R^a$, or —$(CR^{1b}R^{1c})_r$-5-7 membered heterocycle comprising carbon atoms and 1-4 heteroatoms selected from N, O, and S(O), substituted with 0-3 $R^a$;

$R^{3c}$ and $R^{3d}$ are, independently at each occurrence, hydrogen or $C_{1-6}$ alkyl;

$R^4$ and $R^5$ are independently hydrogen, halo, $C_{1-6}$ alkyl or $C_{1-6}$ haloalkyl, or $R^4$ and $R^5$ together with the carbon atom to which they are attached form a 3- to 6-membered spirocarbocyclyl ring or a spiroheterocyclyl ring;

$R^6$ and $R^7$ are independently hydrogen, $C_{1-6}$ alkyl or $C_{1-6}$ haloalkyl;

$R^{11}$ is, independently at each occurrence, hydrogen, $C_{1-6}$ alkyl substituted with 0-3 $R^f$, $CF_3$, $C_{3-10}$ cycloalkyl substituted with 0-3 $R^f$, —$(CR^{1b}R^{1c})_r$-phenyl substituted with 0-3 $R^d$, or —$(CR^{1b}R^{1c})_r$-5-7 membered heterocycle comprising carbon atoms and 1-4 heteroatoms selected from N, O, P(=O) and $S(O)_p$ substituted with 0-4 $R^d$;

or one $R^{11}$ and a second $R^{11}$, both attached to the same nitrogen atom, combine to form a heterocycle comprising carbon atoms and 1-4 heteroatoms selected from N, O, P(=O) and $S(O)_p$ substituted with 0-4 $R^d$;

$R^a$ is, independently at each occurrence, hydrogen, =O, halo, $OCF_3$, $CF_3$, $CHF_2$, CN, $NO_2$, —$(CR^{1b}R^{1c})_r$—OR$^b$, —$(CR^{1b}R^{1c})_r$—S(O)$_pR^b$, —$(CR^{1b}R^{1c})_r$—C(O)$R^b$, —$(CR^{1b}R^{1c})_r$—C(O)OR$^b$, —$(CR^{1b}R^{1c})_r$—OC(O)$R^b$, —$(CR^{1b}R^{1c})_r$—NR$^{11}R^{11}$, —$(CR^{1b}R^{1c})_r$—C(O)NR$^{11}R^{11}$, —$(CR^{1b}R^{1c})_r$—NR$^bC(O)R^c$, —$(CR^{1b}R^{1c})_r$—NR$^bC(O)OR^c$, —NR$^bC(O)NR^{11}R^{11}$, —S(O)$_p$NR$^{11}R^{11}$, —NR$^bS(O)_pR^c$, $C_{1-6}$ alkyl substituted with 0-3 $R^f$, $C_{1-6}$ haloalkyl, $C_{2-6}$ alkenyl substituted with 0-3 $R^e$, $C_{2-6}$ alkynyl substituted with 0-3 $R^e$, —$(CR^{1b}R^{1c})_r$-3-14 membered carbocycle, or —$(CR^{1b}R^{1c})_r$-5-7 membered heterocycle comprising carbon atoms and 1-4 heteroatoms selected from N, O, P(=O) and $S(O)_p$ substituted with 0-4 $R^f$;

$R^b$ is, independently at each occurrence, hydrogen, $C_{1-6}$ alkyl substituted with 0-3 $R^d$, $C_{1-6}$ haloalkyl, $C_{3-6}$ cycloalkyl substituted with 0-3 $R^d$, —$(CR^{1b}R^{1c})_r$-5-7 membered heterocycle comprising carbon atoms and 1-4 heteroatoms selected from N, O, P(=O) and $S(O)_p$ substituted with 0-4 $R^f$, or —$(CR^{1b}R^{1c})_r$-6-10 membered carbocycle substituted with 0-3 $R^d$;

$R^c$ is, independently at each occurrence, $C_{1-6}$ alkyl substituted with 0-3 $R^f$, —$(CR^{1b}R^{1c})_r$—$C_{3-6}$ cycloalkyl substituted with 0-3 $R^f$, or —$(CR^{1b}R^{1c})_r$-phenyl substituted with 0-3 $R^f$;

$R^d$ is, independently at each occurrence, hydrogen, =O, halo, $OCF_3$, $CF_3$, CN, $NO_2$, —OR$^e$, —$(CR^{1b}R^{1c})_r$—C(O)$R^e$, —NR$^eR^e$, —NR$^eC(O)OR^c$, C(O)NR$^eR^e$, —NR$^eC(O)R^c$, $CO_2H$, $CO_2R^c$, —NR$^eSO_2R^c$, $SO_2R^c$, $C_{1-6}$ alkyl substituted with 0-3 $R^f$, $C_{3-6}$ cycloalkyl substituted with 0-3 $R^f$, —$(CR^{1b}R^{1c})_r$-phenyl substituted with 0-3 $R^f$ or —$(CR^{1b}R^{1c})_r$-5-7 membered heterocycle comprising carbon atoms and 1-4 heteroatoms selected from N, O, P(=O) and $S(O)_p$ substituted with 0-4 $R^f$;

$R^e$ is, independently at each occurrence, selected from hydrogen, C(O)NR$^fR^f$, $C_{1-6}$ alkyl, $C_{3-6}$ cycloalkyl, -5-7 membered heterocycle or —$(CR^{1b}R^{1c})_r$-phenyl substituted with 0-3 $R^f$;

$R^f$ is, independently at each occurrence, hydrogen, =O, halo, CN, $NH_2$, $NH(C_{1-6}$ alkyl), $N(C_{1-6}$ alkyl)$_2$, $SO_2(C_{1-6}$ alkyl), $CO_2H$, $CO_2(C_{1-6}$ alkyl), OH, $C_{3-6}$ cycloalkyl, $CF_3$; $O(C_{1-6}$ alkyl) or an optionally substituted —$(CR^{1b}R^{1c})_r$-5-10 membered heterocycle comprising carbon atoms and 1-4 heteroatoms selected from N, O, P(=O) and $S(O)_p$, phenyl or $C_{3-6}$ cycloalkyl, each group optionally substituted with halo, CN, $CF_3$, $C_{1-6}$ alkyl or $O(C_{1-6}$ alkyl);

m is 0, 1, 2 or 3 n is 0, 1 or 2;

p and q are, independently at each occurrence, 0, 1, or 2;

r is 0, 1, 2, 3, or 4; and w is 1, 2 or 3;

or a stereoisomer or pharmaceutically-acceptable salt thereof.

In a 5$^{th}$ aspect, the invention comprises compounds of the formula

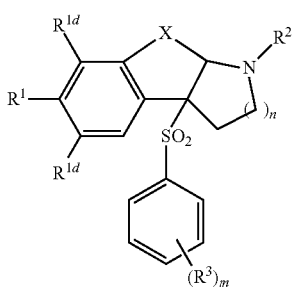

wherein

X is —CR⁴R⁵—, —(CR⁴R⁵)₂, —OCR⁶R⁷—, —S(O)$_p$CR⁶R⁷— or —NR⁶CR⁶R⁷—;

$R^1$ is selected from halo, $C_{1-6}$ alkyl substituted with 0-3 $R^{1a}$, —(CR$^{1b}$R$^{1c}$)$_r$-3-14 membered carbocycle substituted with 0-3 $R^{1a}$ and —(CR$^{1b}$R$^{1c}$)$_r$-5-10 membered heterocycle comprising carbon atoms and 1-4 heteroatoms selected from N, O, and S(O)$_p$ substituted with 0-3 $R^{1a}$;

$R^{1a}$ is, independently at each occurrence, hydrogen, =O, halo, CF₃, OCF₃, CN, NO₂, —(CR$^{1b}$R$^{1c}$)$_r$—OR$^b$, —(CR$^{1b}$R$^{1c}$)$_r$—S(O)$_p$R$^b$, —(CR$^{1b}$R$^{1c}$)$_r$—C(O)R$^b$, —(CR$^{1b}$R$^{1c}$)$_r$—C(O)OR$^b$, —(CR$^{1b}$R$^{1c}$)$_r$—OC(O)R$^b$, —(CR$^{1b}$R$^{1c}$)$_r$—NR$^{11}$R$^{11}$, —(CR$^{1b}$R$^{1c}$)$_r$—C(O)NR$^{11}$R$^{11}$, —(CR$^{1b}$R$^{1c}$)$_r$—NR$^b$C(O)R$^c$, —(CR$^{1b}$R$^{1c}$)$_r$—NR$^b$C(O)OR$^c$, —NR$^b$C(O)NR$^{11}$R$^{11}$, —S(O)$_p$NR$^{11}$R$^{11}$, —NR$^b$S(O)$_p$R$^c$, $C_{1-6}$ alkyl substituted with 0-3 $R^a$, $C_{1-6}$ haloalkyl, $C_{2-6}$ alkenyl substituted with 0-3 $R^a$, $C_{2-6}$ alkynyl substituted with 0-3 $R^a$, —(CR$^{1b}$R$^{1c}$)$_r$-3-14 membered carbocycle substituted with 0-3 $R^a$, or —(CR$^{1b}$R$^{1c}$)$_r$-5-7 membered heterocycle comprising carbon atoms and 1-4 heteroatoms selected from N, O, and S(O)$_p$ substituted with 0-3 $R^a$;

$R^{1b}$ and $R^{1c}$ are, independently at each occurrence, hydrogen, halogen or $C_{1-6}$ alkyl;

$R^{1d}$ is, independently at each occurrence, hydrogen, CD₃, halo, CF₃, and $C_1$-$C_4$ alkyl;

$R^2$ is

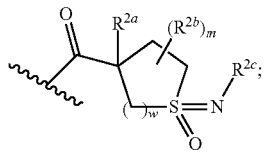

$R^{2a}$ and $R^{2b}$ are, independently at each occurrence, hydrogen, halo, OCF₃, CF₃, CHF₂, CN, NO₂, —(CR$^{1b}$R$^{1c}$)$_r$—OR$^b$, —(CR$^{1b}$R$^{1c}$)$_r$—S(O)$_p$R$^b$, —(CR$^{1b}$R$^{1c}$)$_r$—C(O)R$^b$, —(CR$^{1b}$R$^{1c}$)$_r$—C(O)OR$^b$, —(CR$^{1b}$R$^{1c}$)$_r$—OC(O)R$^b$, —(CR$^{1b}$R$^{1c}$)$_r$—NR$^{11}$R$^{11}$, —(CR$^{1b}$R$^{1c}$)$_r$—C(O)NR$^{11}$R$^{11}$, —(CR$^{1b}$R$^{1c}$)$_r$—NR$^b$C(O)R$^c$, —(CR$^{1b}$R$^{1c}$)$_r$—NR$^b$C(O)OR$^c$, —NR$^b$C(O)NR$^{11}$R$^{11}$, —S(O)$_p$NR$^{11}$R$^{11}$, —NR$^b$S(O)$_p$R$^c$, $C_{1-6}$ alkyl substituted with 0-3 $R^f$, $C_{1-6}$ haloalkyl, $C_{2-6}$ alkenyl substituted with 0-3 $R^e$, $C_{2-6}$ alkynyl substituted with 0-3 $R^e$, —(CR$^{1b}$R$^{1c}$)$_r$-3-14 membered carbocycle, or —(CR$^{1b}$R$^{1c}$)$_r$-5-7 membered heterocycle comprising carbon atoms and 1-4 heteroatoms selected from N, O, P(=O) and S(O)$_p$ substituted with 0-4 $R^f$;

$R^{2c}$ is hydrogen, $C_{1-6}$ alkyl substituted with 0-3 $R^f$, $C_{1-6}$ haloalkyl, —(CR$^{1b}$R$^{1c}$)$_r$—C(O)R$^b$, —(CR$^{1b}$R$^{1c}$)$_r$—C(O)OR$^b$, —(CR$^{1b}$R$^{1c}$)$_r$—C(O)NR$^{11}$R$^{11}$, —(CR$^{1b}$R$^{1c}$)$_r$-3-14 membered carbocycle, or —(CR$^{1b}$R$^{1c}$)$_r$-5-7 membered heterocycle comprising carbon atoms and 1-4 heteroatoms selected from N, O, P(=O) and S(O)$_p$ substituted with 0-4 $R^f$;

$R^3$ is, independently at each occurrence, selected from hydrogen, halo, N₃, CN, —(CR$^{1b}$R$^{1c}$)$_r$—OR$^{3b}$, —(CR$^{1b}$R$^{1c}$)$_r$—NR$^{11}$R$^{11}$, $C_{1-6}$ alkyl substituted with 0-3 $R^{3a}$, $C_{3-10}$ cycloalkyl substituted with 0-3 $R^{3a}$; and phenyl substituted with 0-3 $R^{3a}$, or 4-10 membered heterocycle containing 1-4 heteroatoms selected from N, O, and S(O)$_p$, substituted with 0-3 $R^{3a}$, or two $R^3$ located on adjacent carbon atoms link to form a 5-7 membered carbocycle or a 5-7 membered heterocycle comprising carbon atoms and 1-4 heteroatom selected from N, O and S(O)$_p$, both optionally substituted with 0-3 $R^{3a}$;

$R^{3a}$ is, independently at each occurrence, hydrogen, =O, halo, OCF₃, OCHF₂, CF₃, CHF₂, CN, NO₂, —(CR$^{1b}$R$^{1c}$)$_r$—OR$^b$, —(CR$^{1b}$R$^{1c}$)$_r$—S(O)$_p$R$^b$, —(CR$^{1b}$R$^{1c}$)$_r$—C(O)R$^b$, —(CR$^{1b}$R$^{1c}$)$_r$—C(O)OR$^b$, —(CR$^{1b}$R$^{1c}$)$_r$—OC(O)R$^b$, —(CR$^{1b}$R$^{1c}$)$_r$—NR$^{11}$R$^{11}$, —(CR$^{1b}$R$^{1c}$)$_r$—C(O)NR$^{11}$R$^{11}$, —(CR$^{1b}$R$^{1c}$)$_r$—NR$^b$C(O)R$^c$, —(CR$^{1b}$R$^{1c}$)$_r$—NR$^b$C(O)OR$^c$, —NR$^b$C(O)NR$^{11}$R$^{11}$, —S(O)$_p$NR$^{11}$R$^{11}$, —NR$^b$S(O)$_p$R$^c$, $C_{1-6}$ alkyl substituted with 0-3 $R^a$, $C_{2-6}$ alkenyl substituted with 0-3 $R^a$, $C_{2-6}$ alkynyl substituted with 0-3 $R^a$, $C_{1-6}$ haloalkyl, —(CR$^{1b}$R$^{1c}$)$_r$-3-14 membered carbocycle substituted with 0-3 $R^a$, or —(CR$^{1b}$R$^{1c}$)$_r$-5-10 membered heterocycle comprising carbon atoms and 1-4 heteroatoms selected from N, O, and S(O)$_p$ substituted with 0-3 $R^a$;

$R^{3b}$ is, independently at each occurrence, hydrogen, CF₃, —(CR$^{1b}$R$^{1c}$)$_q$OR$^b$, —(CR$^{1b}$R$^{1c}$)$_q$S(O)$_p$R$^b$, —(CR$^{1b}$R$^{1c}$)$_r$—C(O)R$^{3d}$, —(CR$^{1b}$R$^{1c}$)$_r$—C(O)OR$^b$, —(CR$^{1b}$R$^{1c}$)$_q$OC(O)R$^b$, —(CR$^{1b}$R$^{1c}$)$_q$NR$^{11}$R$^{11}$, —(CR$^{1b}$R$^{1c}$)$_r$—C(O)NR$^{11}$R$^{11}$, —(CR$^{1b}$R$^{1c}$)$_q$NR$^b$C(O)R$^{3c}$, —(CR$^{1b}$R$^{1c}$)$_q$NR$^b$C(O)OR$^c$, —(CR$^{1b}$R$^{1c}$)$_q$NR$^b$C(O)N R$^{11}$R$^{11}$, —(CR$^{1b}$R$^{1c}$)$_q$S(O)$_2$N R$^{11}$R$^{11}$, —(CR$^{1b}$R$^{1c}$)$_q$NR$^b$S(O)$_2$R$^c$, $C_{1-6}$ alkyl substituted with 0-3 $R^a$, $C_{1-6}$ haloalkyl, —(CR$^{1b}$R$^{1c}$)$_r$-3-14 membered carbocycle substituted with 0-3 $R^a$, or —(CR$^{1b}$R$^{1c}$)$_r$-5-7 membered heterocycle comprising carbon atoms and 1-4 heteroatoms selected from N, O, and S(O)$_p$ substituted with 0-3 $R^a$;

$R^{3c}$ and $R^{3d}$ are, independently at each occurrence, hydrogen or $C_{1-6}$ alkyl;

$R^4$ and $R^5$ are independently hydrogen, halo, $C_{1-6}$ alkyl or $C_{1-6}$ haloalkyl, or $R^4$ and $R^5$ together with the carbon atom to which they are attached form a 3- to 6-membered spirocarbocyclyl ring or a spiroheterocyclyl ring;

$R^6$ and $R^7$ are independently hydrogen, $C_{1-6}$ alkyl or $C_{1-6}$ haloalkyl;

$R^{11}$ is, independently at each occurrence, hydrogen, $C_{1-6}$ alkyl substituted with 0-3 $R^f$, CF₃, $C_{3-10}$ cycloalkyl substituted with 0-3 $R^f$, —(CR$^{1b}$R$^{1c}$)$_r$-phenyl substituted with 0-3 $R^d$, or —(CR$^{1b}$R$^{1c}$)$_r$-5-7 membered heterocycle comprising carbon atoms and 1-4 heteroatoms selected from N, O, P(=O) and S(O)$_p$ substituted with 0-4 $R^d$;

or one $R^{11}$ and a second $R^{11}$, both attached to the same nitrogen atom, combine to form a heterocycle comprising carbon atoms and 1-4 heteroatoms selected from N, O, P(=O) and S(O)$_p$ substituted with 0-4 $R^d$;

$R^a$ is, independently at each occurrence, hydrogen, =O, halo, OCF₃, CF₃, CHF₂, CN, NO₂, —(CR$^{1b}$R$^{1c}$)$_r$—OR$^b$, —(CR$^{1b}$R$^{1c}$)$_r$—S(O)$_p$R$^b$, —(CR$^{1b}$R$^{1c}$)$_r$—C(O)R$^b$, —(CR$^{1b}$R$^{1c}$)$_r$—C(O)OR$^b$, —(CR$^{1b}$R$^{1c}$)$_r$—OC(O)R$^b$, —(CR$^{1b}$R$^{1c}$)$_r$—NR$^{11}$R$^{11}$, —(CR$^{1b}$R$^{1c}$)$_r$—C(O)NR$^{11}$R$^{11}$, —(CR$^{1b}$R$^{1c}$)$_r$—NR$^b$C(O)R$^c$, —(CR$^{1b}$R$^{1c}$)$_r$—NR$^b$C(O)OR$^c$, —NR$^b$C(O)NR$^{11}$R$^{11}$, —S(O)$_p$NR$^{11}$R$^{11}$, —NR$^b$S(O)$_p$R$^c$, $C_{1-6}$ alkyl substituted with 0-3 $R^f$, $C_{1-6}$ haloalkyl, $C_{2-6}$ alkenyl substituted with 0-3 $R^e$, $C_{2-6}$ alkynyl substituted with 0-3 $R^e$, —(CR$^{1b}$R$^{1c}$)$_r$-3-14 membered carbocycle, or —(CR$^{1b}$R$^{1c}$)$_r$-5-7 membered heterocycle comprising carbon atoms and 1-4 heteroatoms selected from N, O, P(=O) and S(O)$_p$ substituted with 0-4 $R^f$;

$R^b$ is, independently at each occurrence, hydrogen, $C_{1-6}$ alkyl substituted with 0-3 $R^d$, $C_{1-6}$ haloalkyl, $C_{3-6}$ cycloalkyl substituted with 0-3 $R^d$, —(CR$^{1b}$R$^{1c}$)$_r$-5-7 membered heterocycle comprising carbon atoms and 1-4 heteroatoms selected from N, O, P(=O) and S(O)$_p$ substituted with 0-4 $R^f$, or —(CR$^{1b}$R$^{1c}$)$_r$-6-10 membered carbocycle substituted with 0-3 $R^d$;

$R^c$ is, independently at each occurrence, $C_{1-6}$ alkyl substituted with 0-3 $R^f$, —$(CR^{1b}R^{1c})_r$—$C_{3-6}$ cycloalkyl substituted with 0-3 $R^f$, or —$(CR^{1b}R^{1c})_r$-phenyl substituted with 0-3 $R^f$;

$R^d$ is, independently at each occurrence, hydrogen, =O, halo, $OCF_3$, $CF_3$, CN, $NO_2$, —$OR^e$, —$(CR^{1b}R^{1c})_r$—C(O)$R^e$, —$NR^eR^e$, —$NR^eC(O)OR^c$, $C(O)NR^eR^e$, —$NR^eC(O)R^c$, $CO_2H$, $CO_2R^c$, —$NR^eSO_2R^c$, $SO_2R^c$, $C_{1-6}$ alkyl substituted with 0-3 $R^f$, $C_{3-6}$ cycloalkyl substituted with 0-3 $R^f$, —$(CR^{1b}R^{1c})_r$-phenyl substituted with 0-3 $R^f$ or —$(CR^{1b}R^{1c})_r$-5-7 membered heterocycle comprising carbon atoms and 1-4 heteroatoms selected from N, O, P(=O) and $S(O)_p$ substituted with 0-4 $R^f$;

$R^e$ is, independently at each occurrence, selected from hydrogen, $C(O)NR^fR^f$, $C_{1-6}$ alkyl, $C_{3-6}$ cycloalkyl, -5-7 membered heterocycle or —$(CR^{1b}R^{1c})_r$-phenyl substituted with 0-3 $R^f$;

$R^f$ is, independently at each occurrence, hydrogen, =O, halo, CN, $NH_2$, $NH(C_{1-6}$ alkyl), $N(C_{1-6}$ alkyl$)_2$, $SO_2(C_{1-6}$ alkyl), $CO_2H$, $CO_2(C_{1-6}$ alkyl), OH, $C_{3-6}$ cycloalkyl, $CF_3$; $O(C_{1-6}$ alkyl) or an optionally substituted —$(CR^{1b}R^{1c})_r$-5-10 membered heterocycle comprising carbon atoms and 1-4 heteroatoms selected from N, O, P(=O) and $S(O)_p$, phenyl or $C_{3-6}$ cycloalkyl, each group optionally substituted with halo, CN, $CF_3$, $C_{1-6}$ alkyl or $O(C_{1-6}$ alkyl);

m is 0, 1, 2 or 3
n is 0, 1 or 2;
p and q are, independently at each occurrence, 0, 1, or 2;
r is 0, 1, 2, 3, or 4; and
w is 1, 2 or 3;

or a stereoisomer or pharmaceutically-acceptable salt thereof.

In a 6th aspect, the invention comprises compounds of the formula

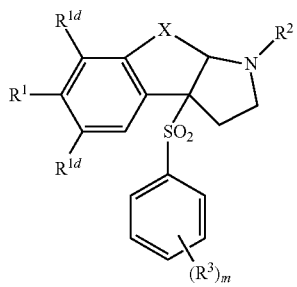

or a stereoisomer or pharmaceutically-acceptable salt thereof.

In a 7th aspect, the invention comprises compounds of the formula

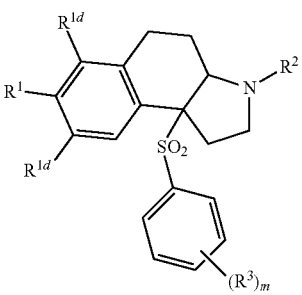

or a stereoisomer or pharmaceutically-acceptable salt thereof.

In an 8th aspect, the invention comprises compounds of the formula

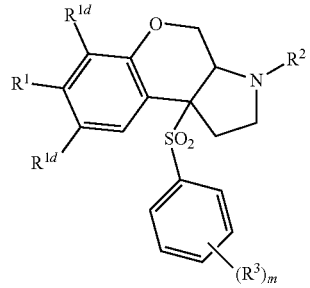

or a stereoisomer or pharmaceutically-acceptable salt thereof.

In an 9th aspect, the invention comprises compounds of the formula

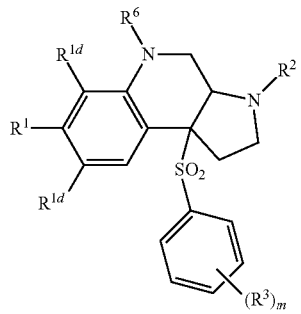

or a stereoisomer or pharmaceutically-acceptable salt thereof.

In a 10th aspect, the invention comprises compounds within the 7th aspect, wherein $R^1$ is halo, phenyl substituted with 0-3 $R^{1a}$, or $C_{1-6}$ alkyl substituted with 0-3 $R^{1a}$;

$R^{1a}$ is, independently at each occurrence, hydrogen, $CF_3$, halo, $C_{1-6}$ alkyl substituted with 0-3 $R^a$, —$(CR^{1b}R^{1c})_r$—$OR^b$, and —$(CR^{1b}R^{1c})_r$-phenyl substituted with 0-3 $R^a$, $R^3$ is, independently at each occurrence, hydrogen, halo, $N_3$, CN, $OR^{3b}$, —$NH_2$, $NH(C_{1-6}$ alkyl), $N(C_{1-6}$ alkyl$)_2$, $C_{1-6}$ alkyl substituted with 0-3 $R^{3a}$ or $C_{3-10}$ cycloalkyl substituted with 0-3 $R^{3a}$;

$R^{3a}$ is, independently at each occurrence, hydrogen, =O, halo, $OCF_3$, $OCHF_2$, $CF_3$, $CHF_2$, CN, $NO_2$, —$(CR^{1b}R^{1c})_r$—$OR^b$, —$(CR^{1b}R^{1c})_r$—$S(O)_pR^b$, —$(CR^{1b}R^{1c})_r$—C(O)$R^b$, —$(CR^{1b}R^{1c})_r$—C(O)$OR^b$, —$(CR^{1b}R^{1c})_r$—OC(O)$R^b$, —$(CR^{1b}R^{1c})_r$—$NR^{11}R^{11}$, —$(CR^{1b}R^{1c})_r$—C(O)$NR^{11}R^{11}$, —$(CR^{1b}R^{1c})_r$—$NR^bC(O)R^c$, —$(CR^{1b}R^{1c})_r$—$NR^bC(O)OR^c$, —$NR^bC(O)NR^{11}R^{11}$, —$S(O)_pNR^{11}R^{11}$, —$NR^bS(O)_pR^c$, $C_{1-6}$ alkyl substituted with 0-3 $R^a$, $C_{2-6}$ alkenyl substituted with 0-3 $R^a$, $C_{2-6}$ alkynyl substituted with 0-3 $R^a$, $C_{1-6}$ haloalkyl, —$(CR^{1b}R^{1c})_r$-3-14 membered carbocycle substituted with 0-3 $R^a$, or —$(CR^{1b}R^{1c})_r$-5-10 membered heterocycle comprising carbon atoms and 1-4 heteroatoms selected from N, O, and $S(O)_p$ substituted with 0-3 $R^a$; and $R^{3b}$ is, independently at each occurrence, hydrogen, $C_{1-6}$ alkyl substituted with 0-3 $R^a$ or phenyl substituted with 0-3 $R^a$;

or a stereoisomer or pharmaceutically-acceptable salt thereof.

In an 11th aspect, the invention comprises compounds within the 8th aspect, wherein $R^1$ is halo, phenyl substituted with 0-3 $R^{1a}$, or $C_{1-6}$ alkyl substituted with 0-3 $R^{1a}$;

$R^{1a}$ is, independently at each occurrence, hydrogen, $CF_3$, halo, $C_{1-6}$ alkyl substituted with 0-3 $R^a$, —$(CR^{1b}R^{1c})_r$—$OR^b$, and —$(CR^{1b}R^{1c})_r$-phenyl substituted with 0-3 $R^a$, $R^3$ is, independently at each occurrence, hydrogen, halo, $N_3$, CN, $OR^{3b}$, —$NH_2$, $NH(C_{1-6}$ alkyl), $N(C_{1-6}$ alkyl)$_2$, $C_{1-6}$ alkyl substituted with 0-3 $R^{3a}$ or $C_{3-10}$ cycloalkyl substituted with 0-3 $R^{3a}$;

$R^{3a}$ is, independently at each occurrence, hydrogen, =O, halo, $OCF_3$, $OCHF_2$, $CF_3$, $CHF_2$, CN, $NO_2$, —$(CR^{1b}R^{1c})_r$—$OR^b$, —$(CR^{1b}R^{1c})_r$—$S(O)_pR^b$, —$(CR^{1b}R^{1c})_r$—$C(O)R^b$, —$(CR^{1b}R^{1c})_r$—$C(O)OR^b$, —$(CR^{1b}R^{1c})_r$—$OC(O)R^b$, —$(CR^{1b}R^{1c})_r$—$NR^{11}R^{11}$, —$(CR^{1b}R^{1c})_r$—$C(O)NR^{11}R^{11}$, —$(CR^{1b}R^{1c})_r$—$NR^bC(O)R^c$, —$(CR^{1b}R^{1c})_r$—$NR^bC(O)OR^c$, —$NR^bC(O)NR^{11}R^{11}$, —$S(O)_pNR^{11}R^{11}$, —$NR^bS(O)_pR^c$, $C_{1-6}$ alkyl substituted with 0-3 $R^a$, $C_{2-6}$ alkenyl substituted with 0-3 $R^a$, $C_{2-6}$ alkynyl substituted with 0-3 $R^a$, $C_{1-6}$ haloalkyl, —$(CR^{1b}R^{1c})_r$-3-14 membered carbocycle substituted with 0-3 $R^a$, or —$(CR^{1b}R^{1c})_r$-5-10 membered heterocycle comprising carbon atoms and 1-4 heteroatoms selected from N, O, and $S(O)_p$ substituted with 0-3 $R^a$; and $R^{3b}$ is, independently at each occurrence, hydrogen, $C_{1-6}$ alkyl substituted with 0-3 $R^a$ or phenyl substituted with 0-3 $R^a$;

or a stereoisomer or pharmaceutically-acceptable salt thereof.

In a 12th aspect, the invention comprises compounds within the 10th aspect, wherein $R^1$ is $C_{1-6}$ alkyl substituted with 0-3 $R^{1a}$;

$R^{1a}$ is, independently at each occurrence, hydrogen, $CF_3$, halo or $C_{1-6}$ alkyl substituted with 0-3 $R^{1a}$;

$R^3$ is hydrogen, halo, cyclopropyl or $C_{1-6}$ alkyl;

or a stereoisomer or pharmaceutically-acceptable salt thereof.

In a 13th aspect, the invention comprises compounds within the 11th aspect, wherein $R^1$ is $C_{1-6}$ alkyl substituted with 0-3 $R^{1a}$;

$R^{1a}$ is, independently at each occurrence, hydrogen, $CF_3$, halo or $C_{1-6}$ alkyl substituted with 0-3 $R^a$;

$R^3$ is hydrogen, halo, cyclopropyl or $C_{1-6}$ alkyl;

or a stereoisomer or pharmaceutically-acceptable salt thereof.

In a further aspect, the invention comprises compounds according to the 12th aspect, wherein $R^1$ is

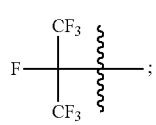

$R^3$ is F, Cl, cyclopropyl or methyl;

or a stereoisomer or pharmaceutically-acceptable salt thereof.

In a further aspect, the invention comprises compounds according to the 13th aspect, wherein $R^1$ is

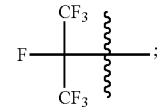

$R^3$ is F, Cl, cyclopropyl or methyl;

or a stereoisomer or pharmaceutically-acceptable salt thereof.

In another aspect, there is provided a compound of Formula (II), or stereoisomers, tautomers, pharmaceutically acceptable salts, solvates, or prodrugs thereof, wherein:

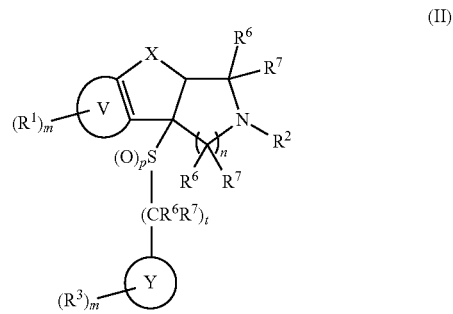

(II)

X is —$CR^4R^5$—, —O—, —$NR^6$—, —$S(O)_p$—, —$(CR^4R^5)_2$—, —$OCR^6R^7$—, —$CR^6R^7O$—, —$S(O)_pCR^6R^7$—, —$CR^6R^7S(O)_p$—, —$NR^6CR^6R^7$— or —$CR^6R^7NR^6$—;

V and Y are independently 5 or 6-membered aromatic or heteroaromatic rings;

$R^1$ is, independently at each occurrence, selected from halo, $C_{1-6}$ alkyl substituted with 0-3 $R^{1a}$, —$(CR^{1b}R^{1c})_r$-3-14 membered carbocycle substituted with 0-3 $R^{1a}$ and —$(CR^{1b}R^{1c})_r$-5-10 membered heterocycle comprising carbon atoms and 1-4 heteroatoms selected from N, O, and $S(O)_p$ substituted with 0-3 $R^{1a}$;

$R^{1a}$ is, independently at each occurrence, hydrogen, =O, halo, $CF_3$, $OCF_3$, CN, $NO_2$, —$(CR^{1b}R^{1c})_r$—$OR^b$, —$(CR^{1b}R^{1c})_r$—$S(O)_pR^b$, —$(CR^{1b}R^{1c})_r$—$C(O)R^b$, —$(CR^{1b}R^{1c})_r$—$C(O)OR^b$, —$(CR^{1b}R^{1c})_r$—$OC(O)R^b$, —$(CR^{1b}R^{1c})_r$—$NR^{11}R^{11}$, —$(CR^{1b}R^{1c})_r$—$C(O)NR^{11}R^{11}$, —$(CR^{1b}R^{1c})_r$—$NR^bC(O)R^c$, —$(CR^{1b}R^{1c})_r$—$NR^bC(O)OR^c$, —$NR^bC(O)NR^{11}R^{11}$, —$S(O)_pNR^{11}R^{11}$, —$NR^bS(O)_pR^c$, $C_{1-6}$ alkyl substituted with 0-3 $R^a$, $C_{1-6}$ haloalkyl, $C_{2-6}$ alkenyl substituted with 0-3 $R^a$, $C_{2-6}$ alkynyl substituted with 0-3 $R^a$, —$(CR^{1b}R^{1c})_r$-3-14 membered carbocycle substituted with 0-3 $R^a$, or —$(CR^{1b}R^{1c})_r$-5-7 membered heterocycle comprising carbon atoms and 1-4 heteroatoms selected from N, O, and $S(O)_p$ substituted with 0-3 $R^a$;

$R^2$ is

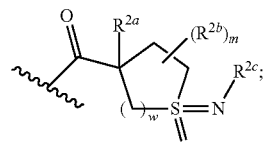

$R^{2a}$ and $R^{2b}$ are, independently at each occurrence, hydrogen, halo, $OCF_3$, $CF_3$, $CHF_2$, CN, $NO_2$, —$(CR^{1b}R^{1c})_r$—$OR^b$, —$(CR^{1b}R^{1c})_r$—$S(O)_pR^b$, —$(CR^{1b}R^{1c})_r$—$C(O)R^b$, —$(CR^{1b}R^{1c})_r$—$C(O)OR^b$, —$(CR^{1b}R^{1c})_r$—$OC(O)R^b$, —$(CR^{1b}R^{1c})_r$—$NR^{11}R^{11}$, —$(CR^{1b}R^{1c})_r$—$C(O)NR^{11}R^{11}$, —$(CR^{1b}R^{1c})_r$—$NR^bC(O)R^c$, —$(CR^{1b}R^{1c})_r$—$NR^bC(O)OR^c$, —$NR^bC(O)NR^{11}R^{11}$, —$S(O)_pNR^{11}R^{11}$, —$NR^bS(O)_pR^c$, $C_{1-6}$ alkyl substituted with 0-3 $R^f$, $C_{1-6}$ haloalkyl, $C_{2-6}$ alkenyl substituted with 0-3 $R^e$, $C_{2-6}$ alkynyl substituted with 0-3 $R^e$, —$(CR^{1b}R^{1c})_r$-3-14 membered carbocycle, or —$(CR^{1b}R^{1c})_r$-5-7 membered heterocycle comprising carbon atoms and 1-4 heteroatoms selected from N, O, P(═O) and $S(O)_p$ substituted with 0-4 $R^f$;

$R^{2c}$ is hydrogen, $C_{1-6}$ alkyl substituted with 0-3 $R^f$, $C_{1-6}$ haloalkyl, —$(CR^{1b}R^{1c})_r$—$C(O)R^b$, —$(CR^{1b}R^{1c})_r$—$C(O)OR^b$, —$(CR^{1b}R^{1c})_r$—$C(O)NR^{11}R^{11}$, —$(CR^{1b}R^{1c})_r$-3-14 membered carbocycle, or —$(CR^{1b}R^{1c})_r$-5-7 membered heterocycle comprising carbon atoms and 1-4 heteroatoms selected from N, O, P(═O) and $S(O)_p$ substituted with 0-4 $R^f$;

$R^3$ is, independently at each occurrence, selected from hydrogen, halo, $N_3$, CN, —$(CR^{1b}R^{1c})_r$—$OR^{3b}$, —$(CR^{1b}R^{1c})_r$—$NR^{11}R^{11}$, $C_{1-6}$ alkyl substituted with 0-3 $R^{3a}$, $C_{3-10}$ cycloalkyl substituted with 0-3 $R^{3a}$; and phenyl substituted with 0-3 $R^{3a}$, or 4-10 membered heterocycle containing 1-4 heteroatoms selected from N, O, and $S(O)_p$, substituted with 0-3 $R^{3a}$, or two $R^3$ located on adjacent carbon atoms link to form a 5-7 membered carbocycle or a 5-7 membered heterocycle comprising carbon atoms and 1-4 heteroatom selected from N, O and $S(O)_p$, both optionally substituted with 0-3 $R^{3a}$;

$R^{3a}$ is, independently at each occurrence, hydrogen, ═O, halo, $OCF_3$, $OCHF_2$, $CF_3$, $CHF_2$, CN, $NO_2$, —$(CR^{1b}R^{1c})_r$—$OR^b$, —$(CR^{1b}R^{1c})_r$—$S(O)_pR^b$, —$(CR^{1b}R^{1c})_r$—$C(O)R^b$, —$(CR^{1b}R^{1c})_r$—$C(O)OR^b$, —$(CR^{1b}R^{1c})_r$—$OC(O)R^b$, —$(CR^{1b}R^{1c})_r$—$NR^{11}R^{11}$, —$(CR^{1b}R^{1c})_r$—$C(O)NR^{11}R^{11}$, —$(CR^{1b}R^{1c})_r$—$NR^bC(O)R^c$, —$(CR^{1b}R^{1c})_r$—$NR^bC(O)OR^c$, —$NR^bC(O)NR^{11}R^{11}$, —$S(O)_pNR^{11}R^{11}$, —$NR^bS(O)_pR^c$, $C_{1-6}$ alkyl substituted with 0-3 $R^a$, $C_{2-6}$ alkenyl substituted with 0-3 $R^a$, $C_{2-6}$ alkynyl substituted with 0-3 $R^a$, $C_{1-6}$ haloalkyl, —$(CR^{1b}R^{1c})_r$-3-14 membered carbocycle substituted with 0-3 $R^a$, or —$(CR^{1b}R^{1c})_r$-5-10 membered heterocycle comprising carbon atoms and 1-4 heteroatoms selected from N, O, and $S(O)_p$ substituted with 0-3 $R^a$;

$R^{3b}$ is, independently at each occurrence, hydrogen, $CF_3$, —$(CR^{1b}R^{1c})_qOR^b$, —$(CR^{1b}R^{1c})_qS(O)_pR^b$, —$(CR^{1b}R^{1c})_r$—$C(O)R^{3d}$, —$(CR^{1b}R^{1c})_r$—$C(O)OR^b$, —$(CR^{1b}R^{1c})_qOC(O)R^b$, —$(CR^{1b}R^{1c})_qNR^{11}R^{11}$, —$(CR^{1b}R^{1c})_r$—$C(O)NR^{11}R^{11}$, —$(CR^{1b}R^{1c})_qNR^bC(O)R^{3c}$, —$(CR^{1b}R^{1c})_qNR^bC(O)OR^c$, —$(CR^{1b}R^{1c})_qNR^bC(O)N$ $R^{11}R^{11}$, —$(CR^{1b}R^{1c})_qS(O)_2NR_{11}R^{11}$, —$(CR^{1b}R^{1c})_qNR^bS(O)_2R^c$, $C_{1-6}$ alkyl substituted with 0-3 $R^a$, $C_{1-6}$ haloalkyl, —$(CR^{1b}R^{1c})_r$-3-14 membered carbocycle substituted with 0-3 $R^a$, or —$(CR^{1b}R^{1c})_r$-5-7 membered heterocycle comprising carbon atoms and 1-4 heteroatoms selected from N, O, and $S(O)_p$ substituted with 0-3 $R^a$;

$R^{3c}$ and $R^{3d}$ are, independently at each occurrence, hydrogen or $C_{1-6}$ alkyl;

$R^4$ and $R^5$ are independently hydrogen, halo, $C_{1-6}$ alkyl or $C_{1-6}$ haloalkyl, or $R^4$ and $R^5$ together with the carbon atom to which they are attached form a 3- to 6-membered spirocarbocyclyl ring or a spiroheterocyclyl ring;

$R^6$ and $R^7$ are independently hydrogen, $C_{1-6}$ alkyl or $C_{1-6}$ haloalkyl;

$R^{11}$ is, independently at each occurrence, hydrogen, $C_{1-6}$ alkyl substituted with 0-3 $R^f$, $CF_3$, $C_{3-10}$ cycloalkyl substituted with 0-3 $R^f$, —$(CR^{1b}R^{1c})_r$-phenyl substituted with 0-3 $R^d$, or —$(CR^{1b}R^{1c})_r$-5-7 membered heterocycle comprising carbon atoms and 1-4 heteroatoms selected from N, O, P(═O) and $S(O)_p$ substituted with 0-4 $R^d$;

or one $R^{11}$ and a second $R^{11}$, both attached to the same nitrogen atom, combine to form a heterocycle comprising carbon atoms and 1-4 heteroatoms selected from N, O, P(═O) and $S(O)_p$ substituted with 0-4 $R^d$;

$R^a$ is, independently at each occurrence, hydrogen, ═O, halo, $OCF_3$, $CF_3$, $CHF_2$, CN, $NO_2$, —$(CR^{1b}R^{1c})_r$—$OR^b$, —$(CR^{1b}R^{1c})_r$—$S(O)_pR^b$, —$(CR^{1b}R^{1c})_r$—$C(O)R^b$, —$(CR^{1b}R^{1c})_r$—$C(O)OR^b$, —$(CR^{1b}R^{1c})_r$—$OC(O)R^b$, —$(CR^{1b}R^{1c})_r$—$NR^{11}R^{11}$, —$(CR^{1b}R^{1c})_r$—$C(O)NR^{11}R^{11}$, —$(CR^{1b}R^{1c})_r$—$NR^bC(O)R^c$, —$(CR^{1b}R^{1c})_r$—$NR^bC(O)OR^c$, —$NR^bC(O)NR^{11}R^{11}$, —$S(O)_pNR^{11}R^{11}$, —$NR^bS(O)_pR^c$, $C_{1-6}$ alkyl substituted with 0-3 $R^f$, $C_{1-6}$ haloalkyl, $C_{2-6}$ alkenyl substituted with 0-3 $R^e$, $C_{2-6}$ alkynyl substituted with 0-3 $R^e$, —$(CR^{1b}R^{1c})_r$-3-14 membered carbocycle, or —$(CR^{1b}R^{1c})_r$-5-7 membered heterocycle comprising carbon atoms and 1-4 heteroatoms selected from N, O, P(═O) and $S(O)_p$ substituted with 0-4 $R^f$;

$R^b$ is, independently at each occurrence, hydrogen, $C_{1-6}$ alkyl substituted with 0-3 $R^d$, $C_{1-6}$ haloalkyl, $C_{3-6}$ cycloalkyl substituted with 0-3 $R^d$, —$(CR^{1b}R^{1c})_r$-5-7 membered heterocycle comprising carbon atoms and 1-4 heteroatoms selected from N, O, P(═O) and $S(O)_p$ substituted with 0-4 $R^f$, or —$(CR^{1b}R^{1c})_r$-6-10 membered carbocycle substituted with 0-3 $R^d$;

$R^c$ is, independently at each occurrence, $C_{1-6}$ alkyl substituted with 0-3 $R^f$, —$(CR^{1b}R^{1c})_r$—$C_{3-6}$ cycloalkyl substituted with 0-3 $R^f$, or —$(CR^{1b}R^{1c})_r$-phenyl substituted with 0-3 $R^f$;

$R^d$ is, independently at each occurrence, hydrogen, ═O, halo, $OCF_3$, $CF_3$, CN, $NO_2$, —$OR^e$, —$(CR^{1b}R^{1c})_r$—$C(O)R^e$, —$NR^eR^e$, —$NR^eC(O)OR^e$, $C(O)NR^eR^e$, —$NR^eC(O)R^e$, $CO_2H$, $CO_2R^e$, —$NR^eSO_2R^e$, $SO_2R^e$, $C_{1-6}$ alkyl substituted with 0-3 $R^f$, $C_{3-6}$ cycloalkyl substituted with 0-3 $R^f$, —$(CR^{1b}R^{1c})_r$-phenyl substituted with 0-3 $R^f$ or —$(CR^{1b}R^{1c})_r$-5-7 membered heterocycle comprising carbon atoms and 1-4 heteroatoms selected from N, O, P(═O) and $S(O)_p$ substituted with 0-3 $R^f$;

$R^e$ is, independently at each occurrence, selected from hydrogen, $C(O)NR^fR^f$, $C_{1-6}$ alkyl, $C_{3-6}$ cycloalkyl, -5-7 membered heterocycle or —$(CR^{1b}R^{1c})_r$-phenyl substituted with 0-3 $R^f$;

$R^f$ is, independently at each occurrence, hydrogen, ═O, halo, CN, $NH_2$, $NH(C_{1-6}$ alkyl), $N(C_{1-6}$ alkyl$)_2$, $SO_2(C_{1-6}$ alkyl), $CO_2H$, $CO_2(C_{1-6}$ alkyl), OH, $C_{3-6}$ cycloalkyl, $CF_3$; $O(C_{1-6}$ alkyl) or an optionally substituted —$(CR^{1b}R^{1c})_r$-5-10 membered heterocycle comprising carbon atoms and 1-4 heteroatoms selected from N, O, P(═O) and $S(O)_p$, phenyl or $C_{3-6}$ cycloalkyl, each group optionally substituted with halo, CN, $CF_3$, $C_{1-6}$ alkyl or $O(C_{1-6}$ alkyl);

m is 0, 1, 2 or 3 n is 1 or 2;

p and q are, independently at each occurrence, 0, 1, or 2;

r is 0, 1, 2, 3, or 4;

t is 0 or 1; and w is 1, 2 or 3.

In another aspect, the invention comprises compounds of formula IIa

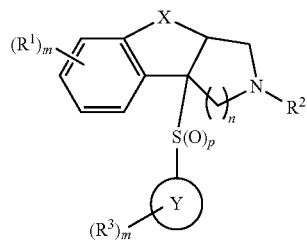
(IIa)

wherein

X is —CR$^4$R$^5$—, —O—, —NR$^6$—, —S(O)$_p$—, —(CR$^4$R$^5$)$_2$—, —OCR$^6$R$^7$—, —CR$^6$R$^7$O—, —S(O)$_p$CR$^6$R$^7$—, —CR$^6$R$^7$S(O)$_p$—, —NR$^6$CR$^6$R$^7$— or —CR$^6$R$^7$NR$^6$—;

Y is a 5 or 6-membered aromatic or heteroaromatic ring;

R$^1$ is, independently at each occurrence, selected from halo, C$_{1-6}$ alkyl substituted with 0-3 R$^{1a}$, —(CR$^{1b}$R$^{1c}$)$_r$-3-14 membered carbocycle substituted with 0-3 R$^{1a}$ and —(CR$^{1b}$R$^{1c}$)$_r$-5-10 membered heterocycle comprising carbon atoms and 1-4 heteroatoms selected from N, O, and S(O)$_p$ substituted with 0-3 R$^{1a}$;

R$^{1a}$ is, independently at each occurrence, hydrogen, =O, halo, CF$_3$, OCF$_3$, CN, NO$_2$, —(CR$^{1b}$R$^{1c}$)$_r$—OR$^b$, —(CR$^{1b}$R$^{1c}$)$_r$—S(O)$_p$R$^b$, —(CR$^{1b}$R$^{1c}$)$_r$—C(O)R$^b$, —(CR$^{1b}$R$^{1c}$)$_r$—C(O)OR$^b$, —(CR$^{1b}$R$^{1c}$)$_r$—OC(O)R$^b$, —(CR$^{1b}$R$^{1c}$)$_r$—NR$^{11}$R$^{11}$, —(CR$^{1b}$R$^{1c}$)$_r$—C(O)NR$^{11}$R$^{11}$, —(CR$^{1b}$R$^{1c}$)$_r$—NR$^b$C(O)R$^c$, —(CR$^{1b}$R$^{1c}$)$_r$—NR$^b$C(O)OR$^c$, —NR$^b$C(O)NR$^{11}$R$^{11}$, —S(O)$_p$NR$^{11}$R$^{11}$, —NR$^b$S(O)$_p$R$^c$, C$_{1-6}$ alkyl substituted with 0-3 R$^a$, C$_{1-6}$ haloalkyl, C$_{2-6}$ alkenyl substituted with 0-3 R$^a$, C$_{2-6}$ alkynyl substituted with 0-3 R$^a$, —(CR$^{1b}$R$^{1c}$)$_r$-3-14 membered carbocycle substituted with 0-3 R$^a$, or —(CR$^{1b}$R$^{1c}$)$_r$-5-7 membered heterocycle comprising carbon atoms and 1-4 heteroatoms selected from N, O, and S(O)$_p$ substituted with 0-3 R$^a$;

R$^2$ is

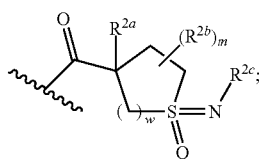

R$^{2a}$ and R$^{2b}$ are, independently at each occurrence, hydrogen, halo, OCF$_3$, CF$_3$, CHF$_2$, CN, NO$_2$, —(CR$^{1b}$R$^{1c}$)$_r$—OR$^b$, —(CR$^{1b}$R$^{1c}$)$_r$—S(O)$_p$R$^b$, —(CR$^{1b}$R$^{1c}$)$_r$—C(O)R$^b$, —(CR$^{1b}$R$^{1c}$)$_r$—C(O)OR$^b$, —(CR$^{1b}$R$^{1c}$)$_r$—OC(O)R$^b$, —(CR$^{1b}$R$^{1c}$)$_r$—NR$^{11}$R$^{11}$, —(CR$^{1b}$R$^{1c}$)$_r$—C(O)NR$^{11}$R$^{11}$, —(CR$^{1b}$R$^{1c}$)$_r$—NR$^b$C(O)R$^c$, —(CR$^{1b}$R$^{1c}$)$_r$—NR$^b$C(O)OR$^c$, —NR$^b$C(O)NR$^{11}$R$^{11}$, —S(O)$_p$NR$^{11}$R$^{11}$, —NR$^b$S(O)$_p$R$^c$, C$_{1-6}$ alkyl substituted with 0-3 R$^f$, C$_{1-6}$ haloalkyl, C$_{2-6}$ alkenyl substituted with 0-3 R$^e$, C$_{2-6}$ alkynyl substituted with 0-3 R$^e$, —(CR$^{1b}$R$^{1c}$)$_r$-3-14 membered carbocycle, or —(CR$^{1b}$R$^{1c}$)$_r$-5-7 membered heterocycle comprising carbon atoms and 1-4 heteroatoms selected from N, O, P(=O) and S(O)$_p$ substituted with 0-4 R$^f$;

R$^{2c}$ is hydrogen, C$_{1-6}$ alkyl substituted with 0-3 R$^f$, C$_{1-6}$ haloalkyl, —(CR$^{1b}$R$^{1c}$)$_r$—C(O)R$^b$, —(CR$^{1b}$R$^{1c}$)$_r$—C(O)OR$^b$, —(CR$^{1b}$R$^{1c}$)$_r$—C(O)NR$^{11}$R$^{11}$, —(CR$^{1b}$R$^{1c}$)$_r$-3-14 membered carbocycle, or —(CR$^{1b}$R$^{1c}$)$_r$-5-7 membered heterocycle comprising carbon atoms and 1-4 heteroatoms selected from N, O, P(=O) and S(O)$_p$ substituted with 0-4 R$^f$;

R$^3$ is, independently at each occurrence, selected from hydrogen, halo, N$_3$, CN, —(CR$^{1b}$R$^{1c}$)$_r$—OR$^{3b}$, —(CR$^{1b}$R$^{1c}$)$_r$—NR$^{11}$R$^{11}$, C$_{1-6}$ alkyl substituted with 0-3 R$^{3a}$, C$_{3-10}$ cycloalkyl substituted with 0-3 R$^{3a}$; and phenyl substituted with 0-3 R$^{3a}$, or 4-10 membered heterocycle containing 1-4 heteroatoms selected from N, O, and S(O)$_p$, substituted with 0-3 R$^{3a}$, or two R$^3$ located on adjacent carbon atoms link to form a 5-7 membered carbocycle or a 5-7 membered heterocycle comprising carbon atoms and 1-4 heteroatom selected from N, O and S(O)$_p$, both optionally substituted with 0-3 R$^{3a}$;

R$^{3a}$ is, independently at each occurrence, hydrogen, =O, halo, OCF$_3$, OCHF$_2$, CF$_3$, CHF$_2$, CN, NO$_2$, —(CR$^{1b}$R$^{1c}$)$_r$—OR$^b$, —(CR$^{1b}$R$^{1c}$)$_r$—S(O)$_p$R$^b$, —(CR$^{1b}$R$^{1c}$)$_r$—C(O)R$^b$, —(CR$^{1b}$R$^{1c}$)$_r$—C(O)OR$^b$, —(CR$^{1b}$R$^{1c}$)$_r$—OC(O)R$^b$, —(CR$^{1b}$R$^{1c}$)$_r$—NR$^{11}$R$^{11}$, —(CR$^{1b}$R$^{1c}$)$_r$—C(O)NR$^{11}$R$^{11}$, —(CR$^{1b}$R$^{1c}$)$_r$—NR$^b$C(O)R$^c$, —(CR$^{1b}$R$^{1c}$)$_r$—NR$^b$C(O)OR$^c$, —NR$^b$C(O)NR$^{11}$R$^{11}$, —S(O)$_p$NR$^{11}$R$^{11}$, —NR$^b$S(O)$_p$R$^c$, C$_{1-6}$ alkyl substituted with 0-3 R$^a$, C$_{2-6}$ alkenyl substituted with 0-3 R$^a$, C$_{2-6}$ alkynyl substituted with 0-3 R$^a$, C$_{1-6}$ haloalkyl, —(CR$^{1b}$R$^{1c}$)$_r$-3-14 membered carbocycle substituted with 0-3 R$^a$, or —(CR$^{1b}$R$^{1c}$)$_r$-5-10 membered heterocycle comprising carbon atoms and 1-4 heteroatoms selected from N, O, and S(O)$_p$ substituted with 0-3 R$^a$;

R$^{3b}$ is, independently at each occurrence, hydrogen, CF$_3$, —(CR$^{1b}$R$^{1c}$)$_q$OR$^b$, —(CR$^{1b}$R$^{1c}$)$_q$S(O)$_p$R$^b$, —(CR$^{1b}$R$^{1c}$)$_q$—C(O)R$^{3d}$, —(CR$^{1b}$R$^{1c}$)$_q$—C(O)OR$^b$, —(CR$^{1b}$R$^{1c}$)$_q$OC(O)R$^b$, —(CR$^{1b}$R$^{1c}$)$_q$NR$^{11}$R$^{11}$, —(CR$^{1b}$R$^{1c}$)$_q$—C(O)NR$^{11}$R$^{11}$, —(CR$^{1b}$R$^{1c}$)$_q$NR$^b$C(O)R$^{3c}$, —(CR$^{1b}$R$^{1c}$)$_q$NR$^b$C(O)OR$^c$, —(CR$^{1b}$R$^{1c}$)$_q$NR$^b$C(O)N R$^{11}$R$^{11}$, —(CR$^{1b}$R$^{1c}$)$_q$S(O)$_2$N R$^{11}$R$^{11}$, —(CR$^{1b}$R$^{1c}$)$_q$NR$^b$S(O)R$^c$, C$_{1-6}$ alkyl substituted with 0-3 R$^a$, C$_{1-6}$ haloalkyl, —(CR$^{1b}$R$^{1c}$)$_r$-3-14 membered carbocycle substituted with 0-3 R$^a$, or —(CR$^{1b}$R$^{1c}$)$_r$-5-7 membered heterocycle comprising carbon atoms and 1-4 heteroatoms selected from N, O, and S(O)$_p$ substituted with 0-3 R$^a$;

R$^{3c}$ and R$^{3d}$ are, independently at each occurrence, hydrogen or C$_{1-6}$ alkyl;

R$^4$ and R$^5$ are independently hydrogen, halo, C$_{1-6}$ alkyl or C$_{1-6}$ haloalkyl, or R$^4$ and R$^5$ together with the carbon atom to which they are attached form a 3- to 6-membered spirocarbocyclyl ring or a spiroheterocyclyl ring;

R$^6$ and R$^7$ are independently hydrogen, C$_{1-6}$ alkyl or C$_{1-6}$ haloalkyl;

R$^{11}$ is, independently at each occurrence, hydrogen, C$_{1-6}$ alkyl substituted with 0-3 R$^f$, CF$_3$, C$_{3-10}$ cycloalkyl substituted with 0-3 R$^f$, —(CR$^{1b}$R$^{1c}$)$_r$-phenyl substituted with 0-3 R$^d$, or —(CR$^{1b}$R$^{1c}$)$_r$-5-7 membered heterocycle comprising carbon atoms and 1-4 heteroatoms selected from N, O, P(=O) and S(O)$_p$ substituted with 0-4 R$^d$;

or one R$^{11}$ and a second R$^{11}$, both attached to the same nitrogen atom, combine to form a heterocycle comprising carbon atoms and 1-4 heteroatoms selected from N, O, P(=O) and S(O)$_p$ substituted with 0-4 R$^d$;

R$^a$ is, independently at each occurrence, hydrogen, =O, halo, OCF$_3$, CF$_3$, CHF$_2$, CN, NO$_2$, —(CR$^{1b}$R$^{1c}$)$_r$—OR$^b$, —(CR$^{1b}$R$^{1c}$)$_r$—S(O)$_p$R$^b$, —(CR$^{1b}$R$^{1c}$)$_r$—C(O)R$^b$, —(CR$^{1b}$R$^{1c}$)$_r$—C(O)OR$^b$, —(CR$^{1b}$R$^{1c}$)$_r$—OC(O)R$^b$, —(CR$^{1b}$R$^{1c}$)$_r$—NR$^{11}$R$^{11}$, —(CR$^{1b}$R$^{1c}$)$_r$—C(O)NR$^{11}$R$^{11}$, —(CR$^{1b}$R$^{1c}$)$_r$—NR$^b$C(O)R$^c$, —(CR$^{1b}$R$^{1c}$)$_r$—NR$^b$C(O)OR$^c$, —NR$^b$C(O)NR$^{11}$R$^{11}$, —S(O)$_p$NR$^{11}$R$^{11}$, —NR$^b$ S(O)$_p$R$^c$, C$_{1-6}$ alkyl substituted with 0-3 R$^f$, C$_{1-6}$ haloalkyl, C$_{2-6}$ alkenyl substituted with 0-3 R$^e$, C$_{2-6}$ alkynyl substituted with 0-3 R$^e$, —(CR$^{1b}$R$^{1c}$)$_r$-3-14 membered carbocycle, or —(CR$^{1b}$R$^{1c}$)$_r$-5-7 membered heterocycle comprising carbon atoms and 1-4 heteroatoms selected from N, O, and S(O)$_p$ substituted with 0-3 R$^f$;

R$^b$ is, independently at each occurrence, hydrogen, C$_{1-6}$ alkyl substituted with 0-3 R$^d$, C$_{1-6}$ haloalkyl, C$_{3-6}$ cycloalkyl substituted with 0-3 R$^d$, —(CR$^{1b}$R$^{1c}$)$_r$-5-7 membered heterocycle comprising carbon atoms and 1-4 heteroatoms selected from N, O, P(═O) and S(O)$_p$ substituted with 0-4 R$^f$, or —(CR$^{1b}$R$^{1c}$)$_r$-6-10 membered carbocycle substituted with 0-3 R$^d$;

R$^c$ is, independently at each occurrence, C$_{1-6}$ alkyl substituted with 0-3 R$^f$, —(CR$^{1b}$R$^{1c}$)$_r$—C$_{3-6}$ cycloalkyl substituted with 0-3 R$^f$, or —(CR$^{1b}$R$^{1c}$)$_r$-phenyl substituted with 0-3 R$^f$;

R$^d$ is, independently at each occurrence, hydrogen, ═O, halo, OCF$_3$, CF$_3$, CN, NO$_2$, —OR$^e$, —(CR$^{1b}$R$^{1c}$)$_r$—C(O) R$^c$, —NR$^e$R$^e$, —NR$^e$C(O)OR$^c$, C(O)NR$^e$R$^e$, —NR$^e$C(O)R$^c$, CO$_2$H, CO$_2$R$^c$, —NR$^e$SO$_2$R$^c$, SO$_2$R$^c$, C$_{1-6}$ alkyl substituted with 0-3 R$^f$, C$_{3-6}$ cycloalkyl substituted with 0-3 R$^f$, —(CR$^{1b}$R$^{1c}$)$_r$-phenyl substituted with 0-3 R$^f$ or —(CR$^{1b}$R$^{1c}$)$_r$-5-7 membered heterocycle comprising carbon atoms and 1-4 heteroatoms selected from N, O, P(═O) and S(O)$_p$ substituted with 0-4 R$^f$;

R$^e$ is, independently at each occurrence, selected from hydrogen, C(O)NR$^f$R$^f$, C$_{1-6}$ alkyl, C$_{3-6}$ cycloalkyl, -5-7 membered heterocycle or —(CR$^{1b}$R$^{1c}$)$_r$-phenyl substituted with 0-3 R$^f$;

R$^f$ is, independently at each occurrence, hydrogen, ═O, halo, CN, NH$_2$, NH(C$_{1-6}$ alkyl), N(C$_{1-6}$ alkyl)$_2$, SO$_2$(C$_{1-6}$ alkyl), CO$_2$H, CO$_2$(C$_{1-6}$ alkyl), OH, C$_{3-6}$ cycloalkyl, CF$_3$; O(C$_{1-6}$ alkyl) or an optionally substituted —(CR$^{1b}$R$^{1c}$)$_r$-5-10 membered heterocycle comprising carbon atoms and 1-4 heteroatoms selected from N, O, P(═O) and S(O)$_p$, phenyl or C$_{3-6}$ cycloalkyl, each group optionally substituted with halo, CN, CF$_3$, C$_{1-6}$ alkyl or O(C$_{1-6}$ alkyl);

m is 0, 1, 2 or 3
n is 1 or 2;
p and q are, independently at each occurrence, 0, 1, or 2;
r is 0, 1, 2, 3, or 4; and
w is 1, 2 or 3;
or a stereoisomer or pharmaceutically-acceptable salt thereof.

In another aspect, the invention comprises compounds of the formula

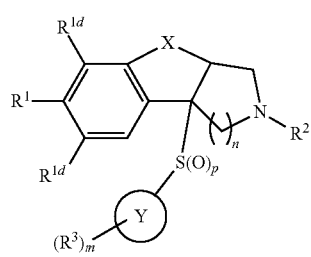

wherein
X is —CR$^4$R$^5$—, —O—, —NR$^6$—, —S(O)$_p$—, —(CR$^4$R$^5$)$_2$—, —OCR$^6$R$^7$—, —CR$^6$R$^7$O—, —S(O)$_p$CR$^6$R$^7$—, —CR$^6$R$^7$S(O)$_p$—, —NR$^6$CR$^6$R$^7$— or —CR$^6$R$^7$NR$^6$—;

Y is a 5 or 6-membered aromatic or heteroaromatic ring;
R$^1$ is selected from halo, C$_{1-6}$ alkyl substituted with 0-3 R$^{1a}$, —(CR$^{1b}$R$^{1c}$)$_r$-3-14 membered carbocycle substituted with 0-3 R$^{1a}$ and —(CR$^{1b}$R$^{1c}$)$_r$-5-10 membered heterocycle comprising carbon atoms, and 1-4 heteroatoms selected from N, O, and S(O)$_p$ substituted with 0-3 R$^{1a}$;

R$^{1a}$ is, independently at each occurrence, hydrogen, ═O, halo, CF$_3$, OCF$_3$, CN, NO$_2$, —(CR$^{1b}$R$^{1c}$)$_r$—OR$^b$, —(CR$^{1b}$R$^{1c}$)$_r$—S(O)$_p$R$^b$, —(CR$^{1b}$R$^{1c}$)$_r$—C(O)R$^b$, —(CR$^{1b}$R$^{1c}$)$_r$—C(O)OR$^b$, —(CR$^{1b}$R$^{1c}$)$_r$—OC(O)R$^b$, —(CR$^{1b}$R$^{1c}$)$_r$—NR$^{11}$R$^{11}$, —(CR$^{1b}$R$^{1c}$)$_r$—C(O)NR$^{11}$R$^{11}$, —(CR$^{1b}$R$^{1c}$)$_r$—NR$^b$C(O)R$^c$, —(CR$^{1b}$R$^{1c}$)$_r$—NR$^b$C(O) OR$^c$, —NR$^b$C(O)NR$^{11}$R$^{11}$, —S(O)$_p$NR$^{11}$R$^{11}$, —NR$^b$S(O)$_p$R$^c$, C$_{1-6}$ alkyl substituted with 0-3 R$^a$, C$_{1-6}$ haloalkyl, C$_{2-6}$ alkenyl substituted with 0-3 R$^a$, C$_{2-6}$ alkynyl substituted with 0-3 R$^a$, —(CR$^{1b}$R$^{1c}$)$_r$-3-14 membered carbocycle substituted with 0-3 R$^a$, or —(CR$^{1b}$R$^{1c}$)$_r$-5-7 membered heterocycle comprising carbon atoms, and 1-4 heteroatoms selected from N, O, and S(O)$_p$ substituted with 0-3 R$^a$;

R$^{1b}$ and R$^{1c}$ are, independently at each occurrence, hydrogen, halogen or C$_{1-6}$ alkyl;

R$^{1d}$ is, independently at each occurrence, hydrogen, CD$_3$, halo, CF$_3$, and C$_1$-C$_4$ alkyl;

R$^2$ is

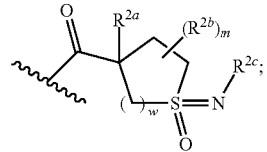

R$^{2a}$ and R$^{2b}$ are, independently at each occurrence, hydrogen, halo, OCF$_3$, CF$_3$, CHF$_2$, CN, NO$_2$, —(CR$^{1b}$R$^{1c}$)$_r$—OR$^b$, —(CR$^{1b}$R$^{1c}$)$_r$—S(O)$_p$R$^b$, —(CR$^{1b}$R$^{1c}$)$_r$—C(O)R$^b$, —(CR$^{1b}$R$^{1c}$)$_r$—C(O)OR$^b$, —(CR$^{1b}$R$^{1c}$)$_r$—OC(O)R$^b$, —(CR$^{1b}$R$^{1c}$)$_r$—NR$^{11}$R$^{11}$, —(CR$^{1b}$R$^{1c}$)$_r$—C(O)NR$^{11}$R$^{11}$, —(CR$^{1b}$R$^{1c}$)$_r$—NR$^b$C(O)R$^c$, —(CR$^{1b}$R$^{1c}$)$_r$—NR$^b$C(O) OR$^c$, —NR$^b$C(O)NR$^{11}$R$^{11}$, —S(O)$_p$NR$^{11}$R$^{11}$, —NR$^b$S(O)$_p$R$^c$, C$_{1-6}$ alkyl substituted with 0-3 R$^f$, C$_{1-6}$ haloalkyl, C$_{2-6}$ alkenyl substituted with 0-3 R$^e$, C$_{2-6}$ alkynyl substituted with 0-3 R$^e$, —(CR$^{1b}$R$^{1c}$)$_r$-3-14 membered carbocycle, or —(CR$^{1b}$R$^{1c}$)$_r$-5-7 membered heterocycle comprising carbon atoms and 1-4 heteroatoms selected from N, O, P(═O) and S(O)$_p$ substituted with 0-4 R$^f$;

R$^{2c}$ is hydrogen, C$_{1-6}$ alkyl substituted with 0-3 R$^f$, C$_{1-6}$ haloalkyl, —(CR$^{1b}$R$^{1c}$)$_r$—C(O)R$^b$, —(CR$^{1b}$R$^{1c}$)$_r$—C(O) OR$^b$, —(CR$^{1b}$R$^{1c}$)$_r$—C(O)NR$^{11}$R$^{11}$, —(CR$^{1b}$R$^{1c}$)$_r$-3-14 membered carbocycle, or —(CR$^{1b}$R$^{1c}$)$_r$-5-7 membered heterocycle comprising carbon atoms and 1-4 heteroatoms selected from N, O, P(═O) and S(O)$_p$ substituted with 0-4 R$^f$;

R$^3$ is, independently at each occurrence, selected from hydrogen, halo, N$_3$, CN, —(CR$^{1b}$R$^{1c}$)$_r$—OR$^{3b}$, —(CR$^{1b}$R$^{1c}$)$_r$—NR$^{11}$R$^{11}$, C$_{1-6}$ alkyl substituted with 0-3 R$^{3a}$, C$_{3-10}$ cycloalkyl substituted with 0-3 R$^{3a}$; and phenyl substituted with 0-3 R$^{3a}$, or 4-10 membered heterocycle containing 1-4 heteroatoms selected from N, O, and S(O)$_p$, substituted with 0-3 R$^{3a}$, or two R$^3$ located on adjacent carbon atoms link to form a 5-7 membered carbocycle or a 5-7 membered heterocycle comprising carbon atoms and 1-4 heteroatom selected from N, O and S(O)$_p$, both optionally substituted with 0-3 R$^{3a}$;

R$^{3a}$ is, independently at each occurrence, hydrogen, ═O, halo, OCF$_3$, OCHF$_2$, CF$_3$, CHF$_2$, CN, NO$_2$, —(CR$^{1b}$ $R^{1c})_r$—$OR^b$, —$(CR^{1b}R^{1c})_r$—$S(O)_pR^b$, —$(CR^{1b}R^{1c})_r$—C(O)$R^b$, —$(CR^{1b}R^{1c})_r$—C(O)O$R^b$, —$(CR^{1b}R^{1c})_r$—OC(O)$R^b$, —$(CR^{1b}R^{1c})_r$—NR$^{11}$R$^{11}$, —$(CR^{1b}R^{1c})_r$C(O)NR$^{11}$R$^{11}$, —$(CR^{1b}R^{1c})_r$—NR$^b$C(O)$R^c$, —$(CR^{1b}R^{1c})_r$—NR$^b$C(O)OR$^c$, —NR$^b$C(O)NR$^{11}$R$^{11}$, —S(O)$_p$NR$^{11}$R$^{11}$, —NR$^b$S(O)$_p$R$^c$, $C_{1-6}$ alkyl substituted with 0-3 R$^a$, $C_{2-6}$ alkenyl substituted with 0-3 R$^a$, $C_{2-6}$ alkynyl substituted with 0-3 R$^a$, $C_{1-6}$ haloalkyl, —$(CR^{1b}R^{1c})_r$-3-14 membered carbocycle substituted with 0-3 R$^a$, or —$(CR^{1b}R^{1c})_r$-5-10 membered heterocycle comprising carbon atoms and 1-4 heteroatoms selected from N, O, and S(O)$_p$ substituted with 0-3 R$^a$;

R$^{3b}$ is, independently at each occurrence, hydrogen, CF$_3$, —$(CR^{1b}R^{1c})_q$OR$^b$, —$(CR^{1b}R^{1c})_q$S(O)$_p$R$^b$, —$(CR^{1b}R^{1c})_r$—C(O)R$^{3d}$, —$(CR^{1b}R^{1c})_r$—C(O)OR$^b$, —$(CR^{1b}R^{1c})_q$OC(O)$R^b$, —$(CR^{1b}R^{1c})_q$NR$^{11}$R$^{11}$, —$(CR^{1b}R^{1c})_r$—C(O)NR$^{11}$R$^{11}$, —$(CR^{1b}R^{1c})_q$NR$^b$C(O)R$^{3c}$, —$(CR^{1b}R^{1c})_q$NR$^b$C(O)OR$^c$, —$(CR^{1b}R^{1c})_q$NR$^b$C(O)N R$^{11}$R$^{11}$, —$(CR^{1b}R^{1c})_q$S(O)$_2$N R$^{11}$R$^{11}$, —$(CR^{1b}R^{1c})_q$NR$^b$S(O)R$^c$, $C_{1-6}$ alkyl substituted with 0-3 R$^a$, $C_{1-6}$ haloalkyl, —$(CR^{1b}R^{1c})_r$-3-14 membered carbocycle substituted with 0-3 R$^a$, or —$(CR^{1b}R^{1c})_r$-5-7 membered heterocycle comprising carbon atoms and 1-4 heteroatoms selected from N, O, and S(O), substituted with 0-3 R$^a$;

R$^{3c}$ and R$^{3d}$ are, independently at each occurrence, hydrogen or $C_{1-6}$ alkyl;

R$^4$ and R$^5$ are independently hydrogen, halo, $C_{1-6}$ alkyl or $C_{1-6}$ haloalkyl, or R$^4$ and R$^5$ together with the carbon atom to which they are attached form a 3- to 6-membered spirocarbocyclyl ring or a spiroheterocyclyl ring;

R$^6$ and R$^7$ are independently H, $C_{1-6}$ alkyl or $C_{1-6}$ haloalkyl;

R$^{11}$ is, independently at each occurrence, hydrogen, $C_{1-6}$ alkyl substituted with 0-3 R$^f$, CF$_3$, $C_{3-10}$ cycloalkyl substituted with 0-3 R$^f$, —$(CR^{1b}R^{1c})_r$-phenyl substituted with 0-3 R$^d$, or —$(CR^{1b}R^{1c})_r$-5-7 membered heterocycle comprising carbon atoms and 1-4 heteroatoms selected from N, O, P(=O) and S(O)$_p$ substituted with 0-4 R$^d$;

or one R$^{11}$ and a second R$^{11}$, both attached to the same nitrogen atom, combine to form a heterocycle comprising carbon atoms and 1-4 heteroatoms selected from N, O, P(=O) and S(O)$_p$ substituted with 0-4 R$^d$;

R$^a$ is, independently at each occurrence, hydrogen, =O, halo, OCF$_3$, CF$_3$, CHF$_2$, CN, NO$_2$, —$(CR^{1b}R^{1c})_r$—OR$^b$, —$(CR^{1b}R^{1c})_r$—S(O)$_p$R$^b$, —$(CR^{1b}R^{1c})_r$—C(O)R$^b$, —$(CR^{1b}R^{1c})_r$—C(O)OR$^b$, —$(CR^{1b}R^{1c})_r$—OC(O)R$^b$, —$(CR^{1b}R^{1c})_r$—NR$^{11}$R$^{11}$, —$(CR^{1b}R^{1c})_r$—C(O)NR$^{11}$R$^{11}$, —$(CR^{1b}R^{1c})_r$—NR$^b$C(O)R$^c$, —$(CR^{1b}R^{1c})_r$—NR$^b$C(O)OR$^c$, —NR$^b$C(O)NR$^{11}$R$^{11}$, —S(O)$_p$NR$^{11}$R$^{11}$, —NR$^b$S(O)$_p$R$^c$, $C_{1-6}$ alkyl substituted with 0-3 R$^f$, $C_{1-6}$ haloalkyl, $C_{2-6}$ alkenyl substituted with 0-3 R$^e$, $C_{2-6}$ alkynyl substituted with 0-3 R$^e$, —$(CR^{1b}R^{1c})_r$-3-14 membered carbocycle, or —$(CR^{1b}R^{1c})_r$-5-7 membered heterocycle comprising carbon atoms and 1-4 heteroatoms selected from N, O, P(=O) and S(O)$_p$ substituted with 0-4 R$^f$;

R$^b$ is, independently at each occurrence, hydrogen, $C_{1-6}$ alkyl substituted with 0-3 R$^d$, $C_{1-6}$ haloalkyl, $C_{3-6}$ cycloalkyl substituted with 0-3 R$^d$, —$(CR^{1b}R^{1c})_r$-5-7 membered heterocycle comprising carbon atoms and 1-4 heteroatoms selected from N, O, P(=O) and S(O)$_p$ substituted with 0-4 R$^f$, or —$(CR^{1b}R^{1c})_r$-6-10 membered carbocycle substituted with 0-3 R$^d$;

R$^c$ is, independently at each occurrence, $C_{1-6}$ alkyl substituted with 0-3 R$^f$, —$(CR^{1b}R^{1c})_r$—$C_{3-6}$ cycloalkyl substituted with 0-3 R$^f$, or —$(CR^{1b}R^{1c})_r$-phenyl substituted with 0-3 R$^f$;

R$^d$ is, independently at each occurrence, hydrogen, =O, halo, OCF$_3$, CF$_3$, CN, NO$_2$, —OR$^e$, —$(CR^{1b}R^{1c})_r$—C(O)R$^e$, —NR$^eR^e$, —NR$^e$C(O)OR$^e$, C(O)NR$^eR^e$, —NR$^e$C(O)R$^e$, CO$_2$H, CO$_2$R$^e$, —NR$^e$SO$_2$R$^e$, SO$_2$R$^e$, $C_{1-6}$ alkyl substituted with 0-3 R$^f$, $C_{3-6}$ cycloalkyl substituted with 0-3 R$^f$, —$(CR^{1b}R^{1c})_r$-phenyl substituted with 0-3 R$^f$ or —$(CR^{1b}R^{1c})_r$-5-7 membered heterocycle comprising carbon atoms and 1-4 heteroatoms selected from N, O, P(=O) and S(O)$_p$ substituted with 0-4 R$^f$;

R$^e$ is, independently at each occurrence, selected from hydrogen, C(O)NR$^fR^f$, $C_{1-6}$ alkyl, $C_{3-6}$ cycloalkyl, -5-7 membered heterocycle or —$(CR^{1b}R^{1c})_r$-phenyl substituted with 0-3 R$^f$;

R$^f$ is, independently at each occurrence, hydrogen, =O, halo, CN, NH$_2$, NH($C_{1-6}$ alkyl), N($C_{1-6}$ alkyl)$_2$, SO$_2$($C_{1-6}$ alkyl), CO$_2$H, CO$_2$($C_{1-6}$ alkyl), OH, $C_{3-6}$ cycloalkyl, CF$_3$; O($C_{1-6}$ alkyl) or an optionally substituted —$(CR^{1b}R^{1c})_r$-5-10 membered heterocycle comprising carbon atoms and 1-4 heteroatoms selected from N, O, P(=O) and S(O)$_p$, phenyl or $C_{3-6}$ cycloalkyl, each group optionally substituted with halo, CN, CF$_3$, $C_{1-6}$ alkyl or O($C_{1-6}$ alkyl);

m is 0, 1, 2 or 3 n is 1 or 2;

p and q are, independently at each occurrence, 0, 1, or 2;

r is 0, 1, 2, 3, or 4; and w is 1, 2 or 3;

or a stereoisomer or pharmaceutically-acceptable salt thereof.

In another aspect, the invention comprises compounds of the formula

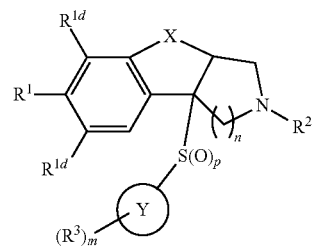

or a stereoisomer or pharmaceutically-acceptable salt thereof.

In another aspect, the invention comprises compounds of the formula

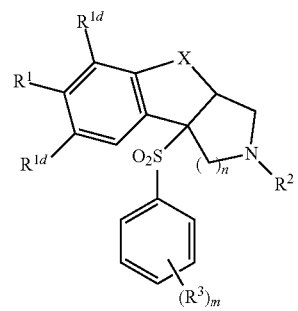

or a stereoisomer or pharmaceutically acceptable salt thereof.

In another aspect, the invention comprises compounds of the formula

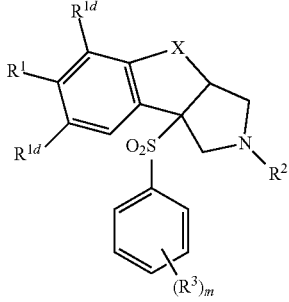

or a stereoisomer or pharmaceutically acceptable salt thereof.

In another aspect, the invention comprises compounds of the formula

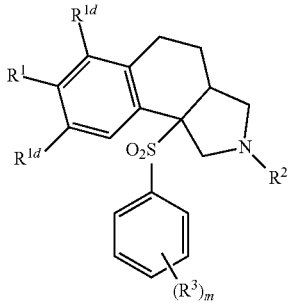

or a stereoisomer or pharmaceutically-acceptable salt thereof.

In another aspect, the invention comprises compounds of the formula

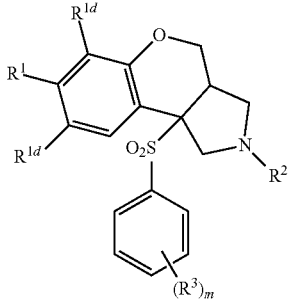

or a stereoisomer or pharmaceutically-acceptable salt thereof.

In another aspect, the invention comprises compounds of the formula

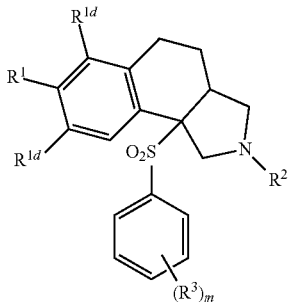

wherein $R^1$ is halo, phenyl substituted with 0-3 $R^{1a}$, or $C_{1-6}$ alkyl substituted with 0-3 $R^{1a}$;

$R^{1a}$ is, independently at each occurrence, hydrogen, $CF_3$, halo, $C_{1-6}$ alkyl substituted with 0-3 $R^a$, —$(CR^{1b}R^{1c})_r$—$OR^b$, and —$(CR^{1b}R^{1c})_r$-phenyl substituted with 0-3 $R^a$, $R^{1b}$ and $R^{1c}$ are, independently at each occurrence, hydrogen, halogen or $C_{1-6}$ alkyl;

$R^{1d}$ is, independently at each occurrence, hydrogen, $CD_3$, halo, $CF_3$, and $C_1$-$C_4$ alkyl;

$R^3$ is, independently at each occurrence, hydrogen, halo, $N_3$, CN, $OR^{3b}$, —$NH_2$, $NH(C_{1-6}$ alkyl), $N(C_{1-6}$ alkyl$)_2$, $C_{1-6}$ alkyl substituted with 0-3 $R^{3a}$ or $C_{3-10}$ cycloalkyl substituted with 0-3 $R^{3a}$;

$R^{3a}$ is, independently at each occurrence, hydrogen, =O, halo, $OCF_3$, $OCHF_2$, $CF_3$, $CHF_2$, CN, $NO_2$, —$(CR^{1b}R^{1c})_r$—$OR^b$, —$(CR^{1b}R^{1c})_r$—$S(O)_pR^b$, —$(CR^{1b}R^{1c})_r$—C(O)$R^b$, —$(CR^{1b}R^{1c})_r$—C(O)$OR^b$, —$(CR^{1b}R^{1c})_r$—OC(O)$R^b$, —$(CR^{1b}R^{1c})_r$—$NR^{11}R^{11}$, —$(CR^{1b}R^{1c})_r$—C(O)$NR^{11}R^{11}$, —$(CR^{1b}R^{1c})_r$—$NR^bC(O)R^c$, —$(CR^{1b}R^{1c})_r$—$NR^bC(O)OR^c$, —$NR^bC(O)NR^{11}R^{11}$, —$S(O)_pNR^{11}R^{11}$, —$NR^bS(O)_pR^c$, $C_{1-6}$ alkyl substituted with 0-3 $R^a$, $C_{2-6}$ alkenyl substituted with 0-3 $R^a$, $C_{2-6}$ alkynyl substituted with 0-3 $R^a$, $C_{1-6}$ haloalkyl, —$(CR^{1b}R^{1c})_r$-3-14 membered carbocycle substituted with 0-3 $R^a$, or —$(CR^{1b}R^{1c})_r$-5-10 membered heterocycle comprising carbon atoms and 1-4 heteroatoms selected from N, O, and $S(O)_p$ substituted with 0-3 $R^a$; and $R^{3b}$ is, independently at each occurrence, hydrogen, $C_{1-6}$ alkyl substituted with 0-3 $R^a$ or phenyl substituted with 0-3 $R^a$;

or a stereoisomer or pharmaceutically-acceptable salt thereof.

In another aspect, the invention comprises compounds of the formula

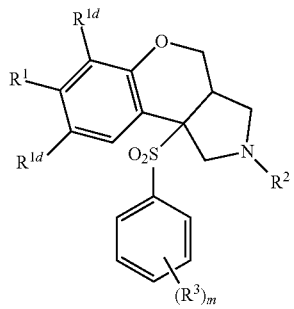

wherein $R^1$ is halo, phenyl substituted with 0-3 $R^{1a}$, or $C_{1-6}$ alkyl substituted with 0-3 $R^{1a}$;

$R^{1a}$ is, independently at each occurrence, hydrogen, $CF_3$, halo, $C_{1-6}$ alkyl substituted with 0-3 $R^a$, —$(CR^{1b}R^{1c})_r$—$OR^b$, and —$(CR^{1b}R^{1c})_r$-phenyl substituted with 0-3 $R^a$, $R^{1b}$ and $R^{1c}$ are, independently at each occurrence, hydrogen, halogen or $C_{1-6}$ alkyl;

$R^{1d}$ is, independently at each occurrence, hydrogen, $CD_3$, halo, $CF_3$, and $C_1$-$C_4$ alkyl;

$R^3$ is, independently at each occurrence, hydrogen, halo, $N_3$, CN, $OR^{3b}$, —$NH_2$, $NH(C_{1-6}$ alkyl), $N(C_{1-6}$ alkyl$)_2$, $C_{1-6}$ alkyl substituted with 0-3 $R^{3a}$ or $C_{3-10}$ cycloalkyl substituted with 0-3 $R^{3a}$;

$R^{3a}$ is, independently at each occurrence, hydrogen, =O, halo, $OCF_3$, $OCHF_2$, $CF_3$, $CHF_2$, CN, $NO_2$, —$(CR^{1b}R^{1c})_r$—$OR^b$, —$(CR^{1b}R^{1c})_r$—$S(O)_pR^b$, —$(CR^{1b}R^{1c})_r$—C (O)R$^b$, —(CR$^{1b}$R$^{1c}$)$_r$—C(O)OR$^b$, —(CR$^{1b}$R$^{1c}$)$_r$—OC(O)R$^b$, —(CR$^{1b}$R$^{1c}$)$_r$—NR$^{11}$R$^{11}$, —(CR$^{1b}$R$^{1c}$)$_r$—C(O)NR$^{11}$R$^{11}$, —(CR$^{1b}$R$^{1c}$)$_r$—NR$^b$C(O)R$^c$, —(CR$^{1b}$R$^{1c}$)$_r$—NR$^b$C(O)OR$^c$, —NR$^b$C(O)NR$^{11}$R$^{11}$, —S(O)$_p$NR$^{11}$R$^{11}$, —NR$^b$S(O)$_p$R$^c$, C$_{1-6}$ alkyl substituted with 0-3 R$^a$, C$_{2-6}$ alkenyl substituted with 0-3 R$^a$, C$_{2-6}$ alkynyl substituted with 0-3 R$^a$, C$_{1-6}$ haloalkyl, —(CR$^{1b}$R$^{1c}$)$_r$-3-14 membered carbocycle substituted with 0-3 R$^a$, or —(CR$^{1b}$R$^{1c}$)$_r$-5-10 membered heterocycle comprising carbon atoms and 1-4 heteroatoms selected from N, O, and S(O)$_p$ substituted with 0-3 R$^a$; and R$^{3b}$ is, independently at each occurrence, hydrogen, C$_{1-6}$ alkyl substituted with 0-3 R$^a$ or phenyl substituted with 0-3 R$^a$;

or a stereoisomer or pharmaceutically-acceptable salt thereof.

In another aspect, the invention comprises compounds of the formula

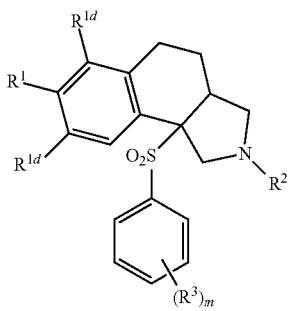

wherein
R$^1$ is C$_{1-6}$ alkyl substituted with 0-3 R$^{1a}$;
R$^{1a}$ is, independently at each occurrence, hydrogen, CF$_3$, halo or C$_{1-6}$ alkyl substituted with 0-3 R$^a$;
R$^{1d}$ is, independently at each occurrence, hydrogen, CD$_3$, halo, CF$_3$, and C$_1$-C$_4$ alkyl;
R$^3$ is hydrogen, halo or C$_{1-6}$ alkyl;
or a stereoisomer or pharmaceutically-acceptable salt thereof.

In another aspect, the invention comprises compounds of the formula

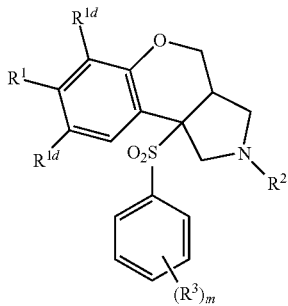

wherein
R$^1$ is C$_{1-6}$ alkyl substituted with 0-3 R$^{1a}$;
R$^{1a}$ is, independently at each occurrence, hydrogen, CF$_3$, halo or C$_{1-6}$ alkyl substituted with 0-3 R$^a$;
R$^{1d}$ is, independently at each occurrence, hydrogen, CD$_3$, halo, CF$_3$, and C$_1$-C$_4$ alkyl;
R$^3$ is hydrogen, halo or C$_{1-6}$ alkyl;
or a stereoisomer or pharmaceutically-acceptable salt thereof.

In another aspect, the invention comprises compounds of the formula

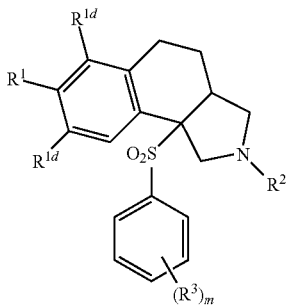

wherein
R$^1$ is

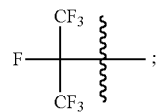

R$^{1d}$ is, independently at each occurrence, hydrogen, CD$_3$, halo, CF$_3$, and C$_1$-C$_4$ alkyl;
R$^3$ is F, Cl or methyl;
or a stereoisomer or pharmaceutically-acceptable salt thereof.

In another aspect, the invention comprises compounds of the formula

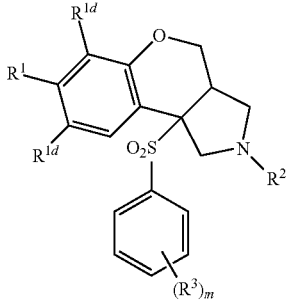

wherein
R$^1$ is

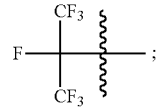

R$^{1d}$ is, independently at each occurrence, hydrogen, CD$_3$, halo, CF$_3$, and C$_1$-C$_4$ alkyl;
R$^3$ is F, Cl or methyl;
or a stereoisomer or pharmaceutically-acceptable salt thereof.

In another aspect, there is provided a compound of Formula (I), or stereoisomers, tautomers, pharmaceutically acceptable salts, solvates, or prodrugs thereof, wherein R² is:

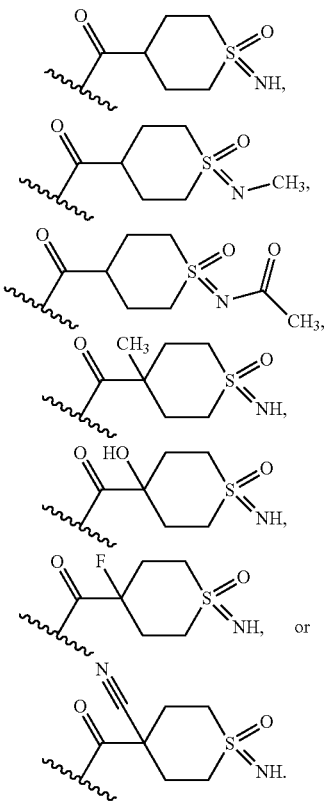

In another aspect, there is provided a compound selected from the exemplified examples within the scope of the first aspect, or a pharmaceutically acceptable salt, tautomer or stereoisomer thereof.

In another aspect, there is provided a compound selected from the exemplified examples within the scope of formula II, or a pharmaceutically acceptable salt, tautomer or stereoisomer thereof.

In another aspect, there is provided a compound selected from any subset list of compounds within the scope of any of the above aspects.

In another embodiment, the invention provides a pharmaceutical composition, comprising a pharmaceutically acceptable carrier and a therapeutically effective amount of at least one of the compounds of the invention or a stereoisomer, a tautomer, a pharmaceutically acceptable salt, or a solvate thereof.

In another embodiment, the invention provides a process for making a compound of the invention or a stereoisomer, a tautomer, a pharmaceutically acceptable salt, or a solvate thereof.

In another embodiment, the invention provides a compound of the present invention for use in therapy.

In another embodiment, the invention provides a combined preparation of a compound of the present invention and additional therapeutic agent(s) for simultaneous, separate or sequential use in therapy.

In another embodiment, the invention provides a compound of the present invention for use in treating diseases (or a method of treating diseases) in which inflammation is a component including, without limitation, diseases such as psoriasis, rheumatoid arthritis, inflammatory bowel disease, Crohn's disease, ulcerative colitis, acute graft-versus-host disease, psoriatic arthritis, ankylosing spondylitis and multiple sclerosis.

The following are definitions of terms used in this specification and appended claims. The initial definition provided for a group or term herein applies to that group or term throughout the specification and claims, individually or as part of another group, unless otherwise indicated.

Compounds of this invention may have one or more asymmetric centers. Unless otherwise indicated, all chiral (enantiomeric and diastereomeric) and racemic forms of compounds of the present invention are included in the present invention. Many geometric isomers of olefins, C=N double bonds, and the like can also be present in the compounds, and all such stable isomers are contemplated in the present invention. Cis and trans geometric isomers of the compounds of the present invention are described and may be isolated as a mixture of isomers or as separated isomeric forms. The present compounds can be isolated in optically active or racemic forms. It is well known in the art how to prepare optically active forms, such as by resolution of racemic forms or by synthesis from optically active starting materials. All chiral (enantiomeric and diastereomeric) and racemic forms and all geometric isomeric forms of a structure are intended, unless the specific stereochemistry or isomer form is specifically indicated.

When any variable (e.g., R³) occurs more than one time in any constituent or formula for a compound, its definition at each occurrence is independent of its definition at every other occurrence. Thus, for example, if a group is shown to be substituted with 0-2 R³, then said group may optionally be substituted with up to two R³ groups and R³ at each occurrence is selected independently from the definition of R³. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

In cases wherein there are nitrogen atoms (e.g., amines) on compounds of the present invention, these can be converted to N-oxides by treatment with an oxidizing agent (e.g., MCPBA and/or hydrogen peroxides) to afford other compounds of this invention. Thus, all shown and claimed nitrogen atoms are considered to cover both the shown nitrogen and its N-oxide (N→O) derivative.

In accordance with a convention used in the art,

is used in structural formulas herein to depict the bond that is the point of attachment of the moiety or substituent to the core or backbone structure.

A dash "-" that is not between two letters or symbols is used to indicate a point of attachment for a substituent. For example, —CONH$_2$ is attached through the carbon atom.

The term "optionally substituted" in reference to a particular moiety of the compound of Formula I (e.g., an optionally substituted heteroaryl group) refers to a moiety having 0, 1, 2, or more substituents. For example, "optionally substituted alkyl" encompasses both "alkyl" and "substituted alkyl" as defined below. It will be understood by those skilled in the art, with respect to any group containing one or more substituents, that such groups are not intended to introduce any substitution or substitution patterns that are sterically impractical, synthetically non-feasible and/or inherently unstable.

As used herein, the term "at least one chemical entity" is interchangeable with the term "a compound."

As used herein, the term "alkyl" or "alkylene" is intended to include both branched and straight-chain saturated aliphatic hydrocarbon groups having the specified number of carbon atoms. For example, "$C_{1-10}$ alkyl" (or alkylene), is intended to include $C_1$, $C_2$, $C_3$, $C_4$, $C_5$, $C_6$, $C_7$, $C_8$, $C_9$, and $C_{10}$ alkyl groups. Additionally, for example, "$C_1$-$C_6$ alkyl" denotes alkyl having 1 to 6 carbon atoms. Alkyl groups can be unsubstituted or substituted so that one or more of its hydrogens are replaced by another chemical group, for example, aryl or heteroaryl groups which are optionally substituted, for example, with alkyl, halo or haloalkyl. Examples of alkyl groups include, but are not limited to, methyl (Me), ethyl (Et), propyl (e.g., n-propyl and isopropyl), butyl (e.g., n-butyl, isobutyl, t-butyl), pentyl (e.g., n-pentyl, isopentyl, neopentyl), and the like.

"Alkenyl" or "alkenylene" is intended to include hydrocarbon chains of either straight or branched configuration and having one or more double carbon-carbon bonds that may occur in any stable point along the chain. For example, "$C_{2-6}$ alkenyl" (or alkenylene), is intended to include $C_2$, $C_3$, $C_4$, $C_5$, and $C_6$ alkenyl groups. Examples of alkenyl include, but are not limited to, ethenyl, 1-propenyl, 2-propenyl, 2-butenyl, 3-butenyl, 2-pentenyl, 3-pentenyl, 4-pentenyl, 2-hexenyl, 3-hexenyl, 4-hexenyl, 5-hexenyl, 2-methyl-2-propenyl, 4-methyl-3-pentenyl, and the like.

"Alkynyl" or "alkynylene" is intended to include hydrocarbon chains of either straight or branched configuration and having one or more triple carbon-carbon bonds that may occur in any stable point along the chain. For example, "$C_{2-6}$ alkynyl" (or alkynylene), is intended to include $C_2$, $C_3$, $C_4$, $C_5$, and $C_6$ alkynyl groups; such as ethynyl, propynyl, butynyl, pentynyl, hexynyl and the like.

One skilled in the field will understand that, when the designation "$CO_2$" is used herein, this is intended to refer to the group

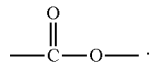

When the term "alkyl" is used together with another group, such as in "arylalkyl", this conjunction defines with more specificity at least one of the substituents that the substituted alkyl will contain. For example, "arylalkyl" refers to a substituted alkyl group as defined above where at least one of the substituents is an aryl, such as benzyl. Thus, the term aryl($C_{0-4}$)alkyl includes a substituted lower alkyl having at least one aryl substituent and also includes an aryl directly bonded to another group, i.e., aryl($C_0$)alkyl. The term "heteroarylalkyl" refers to a substituted alkyl group as defined above where at least one of the substituents is a heteroaryl.

When reference is made to a substituted alkenyl, alkynyl, alkylene, alkenylene, or alkynylene group, these groups are substituted with one to three substituents as defined above for substituted alkyl groups.

The term "alkoxy" refers to an oxygen atom substituted by alkyl or substituted alkyl, as defined herein. For example, the term "alkoxy" includes the group —O—$C_{1-6}$alkyl such as methoxy, ethoxy, propoxy, isopropoxy, n-butoxy, sec-butoxy, tert-butoxy, pentoxy, 2-pentyloxy, isopentoxy, neopentoxy, hexoxy, 2-hexoxy, 3-hexoxy, 3-methylpentoxy, and the like. "Lower alkoxy" refers to alkoxy groups having one to four carbons.

It should be understood that the selections for all groups, including for example, alkoxy, thioalkyl, and aminoalkyl, will be made by one skilled in the field to provide stable compounds.

The term "substituted", as used herein, means that any one or more hydrogens on the designated atom or group is replaced with a selection from the indicated group, provided that the designated atom's normal valence is not exceeded. When a substituent is oxo, or keto, (i.e., =O) then 2 hydrogens on the atom are replaced. Keto substituents are not present on aromatic moieties. Unless otherwise specified, substituents are named into the core structure. For example, it is to be understood that when (cycloalkyl)alkyl is listed as a possible substituent, the point of attachment of this substituent to the core structure is in the alkyl portion. Ring double bonds, as used herein, are double bonds that are formed between two adjacent ring atoms (e.g., C=C, C=N, or N=N).

Combinations of substituents and/or variables are permissible only if such combinations result in stable compounds or useful synthetic intermediates. A stable compound or stable structure is meant to imply a compound that is sufficiently robust to survive isolation from a reaction mixture to a useful degree of purity, and subsequent formulation into an efficacious therapeutic agent. It is preferred that the presently recited compounds do not contain a N-halo, S(O)$_2$H, or S(O)H group.

The term "cycloalkyl" refers to cyclized alkyl groups, including mono-, bi- or poly-cyclic ring systems. $C_{3-7}$ cycloalkyl is intended to include $C_3$, $C_4$, $C_5$, $C_6$, and $C_7$ cycloalkyl groups. Example cycloalkyl groups include, but are not limited to, cyclopropyl, cyclobutyl, cyclopentyl, cyclohexyl, norbornyl, and the like. As used herein, "carbocycle" or "carbocyclic residue" is intended to mean any stable 3, 4, 5, 6, or 7-membered monocyclic or bicyclic or 7-, 8-, 9-, 10-, 11-, 12-, or 13-membered bicyclic or tricyclic ring, any of which may be saturated, partially unsaturated, unsaturated or aromatic. Examples of such carbocycles include, but are not limited to, cyclopropyl, cyclobutyl, cyclobutenyl, cyclopentyl, cyclopentenyl, cyclohexyl, cycloheptyl, cycloheptenyl, adamantyl, cyclooctyl, cyclooctenyl, cyclooctadienyl, [3.3.0]bicyclooctane, [4.3.0]bicyclononane, [4.4.0]bicyclodecane, [2.2.2]bicyclooctane, fluorenyl, phenyl, naphthyl, indanyl, adamantyl, anthracenyl, and tetrahydronaphthyl (tetralin). As shown above, bridged rings are also included in the definition of carbocycle (e.g., [2.2.2]bicyclooctane). Preferred carbocycles, unless otherwise specified, are cyclopropyl, cyclobutyl, cyclopentyl, cyclohexyl, and phenyl. When the term "carbocycle" is used, it is intended to include "aryl". A bridged ring occurs when one or more carbon atoms link two non-adjacent carbon atoms. Preferred bridges are one or two carbon atoms. It is noted that a bridge always converts a monocyclic ring into a bicyclic ring. When a ring is bridged, the substituents recited for the ring may also be present on the bridge.

The term "aryl" refers to monocyclic or bicyclic aromatic hydrocarbon groups having 6 to 12 carbon atoms in the ring portion, such as phenyl, and naphthyl groups, each of which may be substituted.

Thus, examples of aryl groups include:

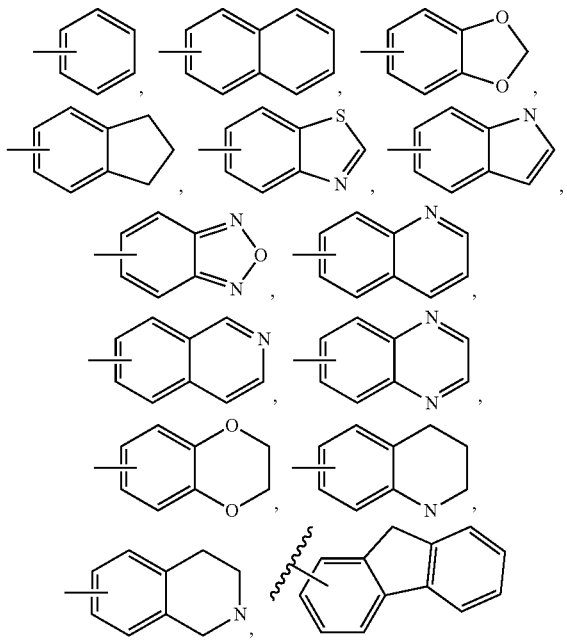

(fluorenyl) and the like, which optionally may be substituted at any available carbon or nitrogen atom. A preferred aryl group is optionally-substituted phenyl.

Accordingly, in compounds of formula I, the term "cycloalkyl" includes cyclopropyl, cyclobutyl, cyclopentyl, cyclohexyl, cycloheptyl, bicyclooctyl, etc., as well as the following ring systems:

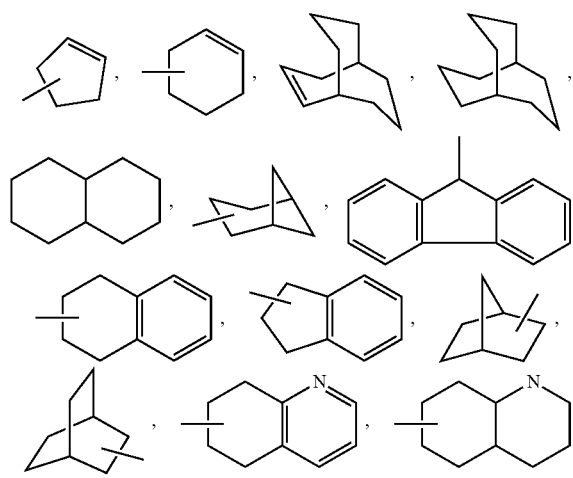

and the like, which optionally may be substituted at any available atoms of the ring(s). Preferred cycloalkyl groups include cyclopropyl, cyclopentyl, cyclohexyl, and

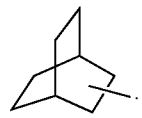

The term "halo" or "halogen" refers to chloro, bromo, fluoro and iodo.

The term "haloalkyl" means a substituted alkyl having one or more halo substituents. For example, "haloalkyl" includes mono, di, and trifluoromethyl.

The term "haloalkoxy" means an alkoxy group having one or more halo substituents. For example, "haloalkoxy" includes $OCF_3$.

The terms "heterocycle", "heterocycloalkyl", "heterocyclo", "heterocyclic", or "heterocyclyl" may be used interchangeably and refer to substituted and unsubstituted 3- to 7-membered monocyclic groups, 7- to 11-membered bicyclic groups, and 10- to 15-membered tricyclic groups, in which at least one of the rings has at least one heteroatom (O, S or N), said heteroatom containing ring preferably having 1, 2, or 3 heteroatoms selected from O, S, and N. Each ring of such a group containing a heteroatom can contain one or two oxygen or sulfur atoms and/or from one to four nitrogen atoms provided that the total number of heteroatoms in each ring is four or less, and further provided that the ring contains at least one carbon atom. The nitrogen and sulfur atoms may optionally be oxidized and the nitrogen atoms may optionally be quaternized. The fused rings completing the bicyclic and tricyclic groups may contain only carbon atoms and may be saturated, partially saturated, or fully unsaturated. The heterocyclo group may be attached at any available nitrogen or carbon atom. As used herein the terms "heterocycle", "heterocycloalkyl", "heterocyclo", "heterocyclic", and "heterocyclyl" include "heteroaryl" groups, as defined below.

In addition to the heteroaryl groups described below, exemplary monocyclic heterocycle groups include azetidinyl, pyrrolidinyl, oxetanyl, imidazolinyl, oxazolidinyl, isoxazolinyl, thiazolidinyl, isothiazolidinyl, tetrahydrofuranyl, piperidyl, piperazinyl, 2-oxopiperazinyl, 2-oxopiperidyl, 2-oxopyrrolodinyl, 2-oxoazepinyl, azepinyl, 1-pyridonyl, 4-piperidonyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl and the like. Exemplary bicyclic heterocyclo groups include quinuclidinyl. Additional monocyclic heterocyclyl groups include

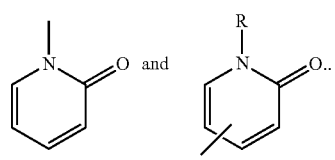

The term "heteroaryl" refers to substituted and unsubstituted aromatic 5- or 6-membered monocyclic groups, 9- or 10-membered bicyclic groups, and 11- to 14-membered tricyclic groups which have at least one heteroatom (O, S or N) in at least one of the rings, said heteroatom-containing ring preferably having 1, 2, or 3 heteroatoms selected from O, S, and N. Each ring of the heteroaryl group containing a heteroatom can contain one or two oxygen or sulfur atoms and/or from one to four nitrogen atoms provided that the total number of heteroatoms in each ring is four or less and each ring has at least one carbon atom. The fused rings completing the bicyclic and tricyclic groups may contain only carbon atoms and may be saturated, partially saturated, or unsaturated. The nitrogen and sulfur atoms may optionally be oxidized and the nitrogen atoms may optionally be quaternized. Heteroaryl groups which are bicyclic or tricyclic must include at least one fully aromatic ring but the other fused ring or rings may be aromatic or non-aromatic. The heteroaryl group may be attached at any available nitrogen or carbon atom of any ring. As valence allows, if said further ring is cycloalkyl or heterocyclo it is additionally optionally substituted with =O (oxo).

Exemplary monocyclic heteroaryl groups include pyrrolyl, pyrazolyl, pyrazolinyl, imidazolyl, oxazolyl, isoxazolyl, thiazolyl, thiadiazolyl, isothiazolyl, furanyl, thienyl, oxadiazolyl, pyridyl, pyrazinyl, pyrimidinyl, pyridazinyl, triazinyl and the like.

Exemplary bicyclic heteroaryl groups include indolyl, benzothiazolyl, benzodioxolyl, benzoxazolyl, benzothienyl, quinolinyl, tetrahydroisoquinolinyl, isoquinolinyl, benzimidazolyl, benzopyranyl, indolizinyl, benzofuranyl, chromonyl, coumarinyl, benzopyranyl, cinnolinyl, quinoxalinyl, indazolyl, pyrrolopyridyl, furopyridyl, dihydroisoindolyl, tetrahydroquinolinyl and the like.

Exemplary tricyclic heteroaryl groups include carbazolyl, benzindolyl, phenanthrolinyl, acridinyl, phenanthridinyl, xanthenyl and the like.

Unless otherwise indicated, when reference is made to a specifically-named aryl (e.g., phenyl), cycloalkyl (e.g., cyclohexyl), heterocyclo (e.g., pyrrolidinyl, piperidinyl, and morpholinyl) or heteroaryl (e.g., tetrazolyl, imidazolyl, pyrazolyl, triazolyl, thiazolyl, and furyl) the reference is intended to include rings having 0 to 3, preferably 0 to 2, substituents selected from those recited above for the aryl, cycloalkyl, heterocyclo and/or heteroaryl groups, as appropriate.

The terms "carbocycle, carbocyclyl or "carbocyclic" refers to a saturated or unsaturated monocyclic or bicyclic ring in which all atoms of all rings are carbon. Thus, the term includes cycloalkyl and aryl rings. Monocyclic carbocycles have 3 to 6 ring atoms, still more typically 5 or 6 ring atoms. Bicyclic carbocycles have 7 to 12 ring atoms, e.g., arranged as a bicyclo [4,5], [5,5], [5,6] or [6,6] system, or 9 or 10 ring atoms arranged as a bicyclo [5,6] or [6,6] system. Examples of mono- and bicyclic carbocycles include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, phenyl and naphthyl. The carbocyclic ring may be substituted in which case the substituents are selected from those recited above for cycloalkyl and aryl groups.

The term "heteroatoms" shall include oxygen, sulfur and nitrogen.

When the term "unsaturated" is used herein to refer to a ring or group, the ring or group may be fully unsaturated or partially unsaturated.

Throughout the specification, groups and substituents thereof may be chosen by one skilled in the field to provide stable moieties and compounds and compounds useful as pharmaceutically-acceptable compounds and/or intermediate compounds useful in making pharmaceutically-acceptable compounds.

The compounds of formula I may exist in a free form (with no ionization) or can form salts which are also within the scope of this invention. Unless otherwise indicated, reference to an inventive compound is understood to include reference to the free form and to salts thereof. The term "salt(s)" denotes acidic and/or basic salts formed with inorganic and/or organic acids and bases. In addition, the term "salt(s) may include zwitterions (inner salts), e.g., when a compound of formula I, contains both a basic moiety, such as an amine or a pyridine or imidazole ring, and an acidic moiety, such as a carboxylic acid. Pharmaceutically acceptable (i.e., non-toxic, physiologically acceptable) salts are preferred, such as, for example, acceptable metal and amine salts in which the cation does not contribute significantly to the toxicity or biological activity of the salt. However, other salts may be useful, e.g., in isolation or purification steps which may be employed during preparation, and thus, are contemplated within the scope of the invention. Salts of the compounds of the formula I may be formed, for example, by reacting a compound of the formula I with an amount of acid or base, such as an equivalent amount, in a medium such as one in which the salt precipitates or in an aqueous medium followed by lyophilization.

Exemplary acid addition salts include acetates (such as those formed with acetic acid or trihaloacetic acid, for example, trifluoroacetic acid), adipates, alginates, ascorbates, aspartates, benzoates, benzenesulfonates, hydrogen sulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, 2-hydroxyethanesulfonates, lactates, maleates (formed with maleic acid), methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

Exemplary basic salts include ammonium salts, alkali metal salts such as sodium, lithium, and potassium salts; alkaline earth metal salts such as calcium and magnesium salts; barium, zinc, and aluminum salts; salts with organic bases (for example, organic amines) such as trialkylamines such as triethylamine, procaine, dibenzylamine, N-benzyl-β-phenethylamine, 1-ephenamine, N,N'-dibenzylethylenediamine, dehydroabietylamine, N-ethylpiperidine, benzylamine, dicyclohexylamine or similar pharmaceutically acceptable amines and salts with amino acids such as arginine, lysine and the like. Basic nitrogen-containing groups may be quaternized with agents such as lower alkyl halides (e.g., methyl, ethyl, propyl, and butyl chlorides, bromides and iodides), dialkyl sulfates (e.g., dimethyl, diethyl, dibutyl, and diamyl sulfates), long chain halides (e.g., decyl, lauryl, myristyl and stearyl chlorides, bromides and iodides), aralkyl halides (e.g., benzyl and phenethyl bromides), and others. Preferred salts include monohydrochloride, hydrogen sulfate, methanesulfonate, phosphate or nitrate salts.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic, and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences*, 18th Edition, Mack Publishing Company, Easton, Pa. (1990), the disclosure of which is hereby incorporated by reference.

All stereoisomers of the compounds of the instant invention are contemplated, either in admixture or in pure or substantially pure form. Stereoisomers may include compounds which are optical isomers through possession of one or more chiral atoms, as well as compounds which are optical isomers by virtue of limited rotation about one or more bonds (atropisomers). The definition of compounds according to the invention embraces all the possible stereoisomers and their mixtures. It very particularly embraces the racemic forms and the isolated optical isomers having the specified activity. The racemic forms can be resolved by physical methods, such as, for example, fractional crystallization, separation or crystallization of diastereomeric derivatives or separation by chiral column chromatography. The individual optical isomers can be obtained from the racemates from the conventional methods, such as, for example, salt formation with an optically active acid followed by crystallization. One enantiomer of a compound of Formulas I and II may display superior activity compared with the other.

The present invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}$C and $^{14}$C. Isotopically-labeled compounds of the invention can generally be prepared by conventional techniques known to those skilled in the art or by processes analogous to those described herein, using an appropriate isotopically-labeled reagent in place of the non-labeled reagent otherwise employed.

Prodrugs and solvates of the inventive compounds are also contemplated. The term "prodrug" denotes a compound which, upon administration to a subject, undergoes chemical conversion by metabolic or chemical processes to yield a compound of the formula I, and/or a salt and/or solvate thereof. Any compound that will be converted in vivo to provide the bioactive agent (i.e., the compound for formula I) is a prodrug within the scope and spirit of the invention. For example, compounds containing a carboxy group can form physiologically hydrolyzable esters which serve as prodrugs by being hydrolyzed in the body to yield formula I compounds per se. Such prodrugs are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of formula I include $C_{1-6}$alkylbenzyl, 4-methoxybenzyl, indanyl, phthalyl, methoxymethyl, $C_{1-6}$alkanoyloxy-$C_{1-6}$alkyl, e.g., acetoxymethyl, pivaloyloxymethyl or propionyloxymethyl, $C_{1-6}$alkoxycarbonyloxy-$C_{1-6}$alkyl, e.g., methoxycarbonyl-oxymethyl or ethoxycarbonyloxymethyl, glycyloxymethyl, phenylglycyloxymethyl, (5-methyl-2-oxo-1,3-dioxolen-4-yl)-methyl and other well known physiologically hydrolyzable esters used, for example, in the penicillin and cephalosporin arts. Such esters may be prepared by conventional techniques known in the art.

Various forms of prodrugs are well known in the art. For examples of such prodrug derivatives, see:
a) Bundgaard, H., ed., *Design of Prodrugs*, Elsevier (1985), and Widder, K. et al., eds., *Methods in Enzymology*, 112:309-396, Academic Press (1985);
b) Bundgaard, H., Chapter 5, "Design and Application of Prodrugs", Krosgaard-Larsen, P. et al., eds., *A Textbook of Drug Design and Development*, pp. 113-191, Harwood Academic Publishers (1991); and
c) Bundgaard, H., *Adv. Drug Deliv. Rev.*, 8:1-38 (1992), each of which is incorporated herein by reference.

Compounds of the formula I and salts thereof may exist in their tautomeric form, in which hydrogen atoms are transposed to other parts of the molecules and the chemical bonds between the atoms of the molecules are consequently rearranged. It should be understood that the all tautomeric forms, insofar as they may exist, are included within the invention. Additionally, inventive compounds may have trans and cis isomers.

It should further be understood that solvates (e.g., hydrates) of the compounds of Formula I are also with the scope of the present invention. Methods of solvation are generally known in the art.

Another aspect of the invention is a pharmaceutical composition including a compound, stereoisomeric form, pharmaceutical salt, solvate or hydrate as described herein. The pharmaceutical compositions described herein generally comprise a combination of a compound described herein and a pharmaceutically acceptable carrier, diluent, or excipient. Such compositions are substantially free of non-pharmaceutically acceptable components, i.e., contain amounts of non-pharmaceutically acceptable components lower than permitted by U.S. regulatory requirements at the time of filing this application. In some embodiments of this aspect, if the compound is dissolved or suspended in water, the composition further optionally comprises an additional pharmaceutically acceptable carrier, diluent, or excipient. In other embodiments, the pharmaceutical compositions described herein are solid pharmaceutical compositions (e.g., tablet, capsules, etc.).

These compositions can be prepared in a manner well known in the pharmaceutical art, and can be administered by a variety of routes, depending upon whether local or systemic treatment is desired and upon the area to be treated. Administration may be topical (including ophthalmic and to mucous membranes including intranasal, vaginal and rectal delivery), pulmonary (e.g., by inhalation or insufflation of powders or aerosols, including by nebulizer; intratracheal, intranasal, epidermal and transdermal), ocular, oral or parenteral. Methods for ocular delivery can include topical administration (eye drops), subconjunctival, periocular or intravitreal injection or introduction by balloon catheter or ophthalmic inserts surgically placed in the conjunctival sac. Parenteral administration includes intravenous, intraarterial, subcutaneous, intraperitoneal or intramuscular injection or infusion; or intracranial, e.g., intrathecal or intraventricular, administration. Parenteral administration can be in the form of a single bolus dose, or may be, for example, by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

Also, pharmaceutical compositions can contain, as the active ingredient, one or more of the compounds described herein above in combination with one or more pharmaceutically acceptable carriers. In making the compositions described herein, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g. about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions described herein can be formulated so as to provide quick, sustained or delayed release of the active ingredient after administration to the subject by employing procedures known in the art.

The active compound can be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual subject, the severity of the subject's symptoms, and the like.

For preparing solid compositions such as tablets, the principal active ingredient is mixed with a pharmaceutical excipient to form a solid preformulation composition containing a homogeneous mixture of a compound described herein. When referring to these preformulation compositions as homogeneous, the active ingredient is typically dispersed evenly throughout the composition so that the composition can be readily subdivided into equally effective unit dosage forms such as tablets, pills and capsules. This solid preformulation is then subdivided into unit dosage forms of the type described above containing from, for example, 0.1 to about 500 mg of the active ingredient of a compound described herein.

The tablets or pills can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compounds and compositions can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions in can be nebulized by use of inert gases. Nebulized solutions may be breathed directly from the nebulizing device or the nebulizing device can be attached to a face masks tent, or intermittent positive pressure breathing machine. Solution, suspension, or powder compositions can be administered orally or nasally from devices which deliver the formulation in an appropriate manner.

The amount of compound or composition administered to a subject will vary depending upon what is being administered, the purpose of the administration, such as prophylaxis or therapy, the state of the subject, the manner of administration, and the like. In therapeutic applications, compositions can be administered to a subject already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the subject, and the like.

The compositions administered to a subject can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers, or stabilizers will result in the formation of pharmaceutical salts.

The therapeutic dosage of the compounds can vary according to, for example, the particular use for which the treatment is made, the manner of administration of the compound, the health and condition of the subject, and the judgment of the prescribing physician. The proportion or concentration of a compound described herein in a pharmaceutical composition can vary depending upon a number of factors including dosage, chemical characteristics (e.g., hydrophobicity), and the route of administration. For example, the compounds described herein can be provided in an aqueous physiological buffer solution containing about 0.1 to about 10% w/v of the compound for parenteral administration. Some typical dose ranges are from about 1 μg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular subject, the relative biological efficacy of the compound selected, formulation of the excipient, and its route of administration. Effective doses can be extrapolated from dose-response curves derived from in vitro or animal model test systems.

The compounds of the present invention are useful to treat various medical disorders in humans or animals. The compounds are used to inhibit or reduce one or more activities associated with RORγ receptors, relative to RORγ receptors in the absence of the same compounds. Thus, in one aspect of the invention, a method for treating a disease or disorder selected from an autoimmune disease or disorder, asthma, an allergic disease or disorder, a metabolic disease or disorder, and cancer in a subject comprises administering to the subject a therapeutically effective amount of compound according to formula (I), stereoisomeric form, N-oxide, pharmaceutically acceptable salt, solvate, hydrate or pharmaceutical composition as described herein. See, e.g., L. A. Solt et al., "Action of RORs and their ligands in (patho) physiology," *Trends Endocrinol. Metab.* 2012, 23 (12): 619-627; M. S. Maddur et al., "Th17 cells: biology, pathogenesis of autoimmune and inflammatory diseases, and therapeutic strategies," *Am. J. Pathol.* 2012 July; 181(1):8-18; and A. M. Jetten, "Retinoid-related orphan receptors (RORs): critical roles in development, immunity, circadian rhythm, and cellular metabolism," *Nucl. Recept. Signal.* 2009; 7:e003, each of which is hereby incorporated herein by reference in its entirety, as well as the references discussed in the Background section. In certain embodiments, the autoimmune disease or disorder is selected from rheumatoid arthritis, ankylosing spondylitis, psoriasis and psoriatic arthritis, multiple sclerosis, inflammatory bowel diseases and lupus. In certain embodiments, the allergic disease or disorder is selected from allergic rhinitis and dermatitis. In certain embodiments, the metabolic disease or disorder is selected from obesity, obesity-induced insulin resistance and type II diabetes.

In certain embodiments, the disease or disorder is rheumatoid arthritis. See, e.g., L. A. Solt et al., referenced above, as well as the references discussed in the Background section.

In other embodiments, the disease or disorder is multiple sclerosis. See, e.g., L. Codarri et al., "RORγt drives production of the cytokine GM-CSF in helper T cells, which is essential for the effector phase of autoimmune neuroinflammation," *Nat. Immunol.*, 2011 June; 12(6):560-7, which is hereby incorporated herein by reference in its entirety, as well as the references discussed in the Background section.

In other embodiments, the disease or disorder is ankylosing spondylitis. See, e.g., E. Toussirot, "The IL23/Th17 pathway as a therapeutic target in chronic inflammatory diseases," *Inflamm. Allergy Drug Targets*, 2012 April; 11(2): 159-68, which is hereby incorporated herein by reference in its entirety, as well as the references discussed in the Background section.

In other embodiments, the disease or disorder is inflammatory bowel disease. See, e.g., M. Leppkes et al., "ROR-gamma-expressing Th17 cells induce murine chronic intestinal inflammation via redundant effects of IL-17A and IL-17F," *Gastroenterology*, 2009 January; 136(1):257-67, which is hereby incorporated herein by reference in its entirety, as well as the references discussed in the Background section.

In other embodiments, the disease or disorder is lupus. See, e.g., K. Yoh et al., "Overexpression of RORγt under control of the CD2 promoter induces polyclonal plasmacytosis and autoantibody production in transgenic mice," *Eur. J. Immunol.*, 2012 August; 42(8): 1999-2009, which is hereby incorporated herein by reference in its entirety, as well as the references discussed in the Background section.

In other embodiments, the disease or disorder is psoriasis. See, e.g., S. Pantelyushin et al., "RORγt+ innate lymphocytes and γδ T cells initiate psoriasiform plaque formation in mice," *J. Clin. Invest.*, 2012 Jun. 1; 122(6):2252-6; and S. P. Raychaudhuri, "Role of IL-17 in Psoriasis and Psoriatic Arthritis," Clin. Rev. Allergy Immunol., 2013; 44(2): 183-193, each of which is hereby incorporated herein by reference in its entirety, as well as the references discussed in the Background section.

In other embodiments, the disease or disorder is psoriatic arthritis. See, e.g., S. P. Raychaudhuri, referenced above, as well as the references discussed in the Background section.

In other embodiments, the disease or disorder is graft-vs.-host disease (GVHD). Y. Yu et al., "Prevention of GVHD while sparing GVL effect by targeting Th1 and Th17 transcription factor T-bet and RORγt in mice," *Blood,* 2011 Nov. 3; 118(18):5011-20, which is hereby incorporated herein by reference in its entirety, as well as the references discussed in the Background section.

In other embodiments, the disease or disorder is autoimmune uveitis. See, e.g., R. Horai et al., "Cytokines in autoimmune uveitis," *J. Interferon Cytokine Res.,* 2011 October; 31(10):733-44, which is hereby incorporated herein by reference in its entirety, as well as the references discussed in the Background section.

In other embodiments, the disease or disorder is obesity and/or insulin resistance. See, e.g., B. Meissburger et al., "Adipogenesis and insulin sensitivity in obesity are regulated by retinoid-related orphan receptor gamma," *EMBO Mol. Med.,* 2011 November; 3(11):637-51, which is hereby incorporated herein by reference in its entirety, as well as the references discussed in the Background section.

In other embodiments, the disease or disorder is melanoma. See, e.g., Purwar R, et al. Robust tumor immunity to melanoma mediated by interleukin-9-producing T cells. Nat. Med., 2012 July: 18:1248-53, which is hereby incorporated herein by reference in its entirety, as well as the references discussed in the Background section.

In certain aspects, the medical disorder being treated by use of the presently disclosed compounds can be, for example, an autoimmune disorder. In other embodiments, the disorder being treated by use of the presently disclosed compounds can be an inflammatory disorder. For example, in certain embodiments, the disorder is selected from arthritis, diabetes, multiple sclerosis, uveitis, rheumatoid arthritis, psoriasis, asthma, bronchitis, allergic rhinitis, chronic obstructive pulmonary disease, atherosclerosis, *H. pylori* infection and inflammatory bowel disease. In other embodiments, the disorder is selected from Crohn's disease, ulcerative colitis, sprue and food allergies. In other embodiments, the disorder is experimental autoimmune encephalomyelitis, imiquimod-induced psoriasis, colitis or allergic airway disease.

As used herein, the phrase "therapeutically effective amount" refers to the amount of active compound or pharmaceutical agent that elicits the biological or medicinal response that is being sought in a tissue, system, animal, individual or human by a researcher, veterinarian, medical doctor or other clinician.

In certain embodiments, a therapeutically effective amount can be an amount suitable for (1) preventing the disease; for example, preventing a disease, condition or disorder in an individual who may be predisposed to the disease, condition or disorder but does not yet experience or display the pathology or symptomatology of the disease; (2) inhibiting the disease; for example, inhibiting a disease, condition or disorder in an individual who is experiencing or displaying the pathology or symptomatology of the disease, condition or disorder; or (3) ameliorating the disease; for example, ameliorating a disease, condition or disorder in an individual who is experiencing or displaying the pathology or symptomatology of the disease, condition or disorder (i.e., reversing the pathology and/or symptomatology) such as decreasing the severity of disease.

As used here, the terms "treatment" and "treating" means (i) ameliorating the referenced disease state, for example, ameliorating a disease, condition or disorder in an individual who is experiencing or displaying the pathology or symptomatology of the disease, condition or disorder (i.e., reversing or improving the pathology and/or symptomatology) such as decreasing the severity of disease; (ii) eliciting the biological or medicinal response that is being sought in a tissue, system, animal, individual or human by a researcher, veterinarian, medical doctor or other clinician; or (iii) inhibiting the referenced disease state; for example, inhibiting a disease, condition or disorder in an individual who is experiencing or displaying the pathology or symptomatology of the disease, condition or disorder.

Methods of Preparation

The compounds of the present invention may be synthesized by many methods available to those skilled in the art of organic chemistry. General synthetic schemes for preparing compounds of the present invention are described below. These schemes are illustrative and are not meant to limit the possible techniques one skilled in the art may use to prepare the compounds disclosed herein. Different methods to prepare the compounds of the present invention will be evident to those skilled in the art. Examples of compounds of the present invention prepared by methods described in the general schemes are given in the Examples section set out hereinafter. Preparation of homochiral examples may be carried out by techniques known to one skilled in the art. For example, homochiral compounds may be prepared by separation of racemic products or diastereomers by chiral phase preparative HPLC. Alternatively, the example compounds may be prepared by methods known to give enantiomerically or diastereomerically enriched products.

The reactions and techniques described in this section are performed in solvents appropriate to the reagents and materials employed and are suitable for the transformations being effected. Also, in the description of the synthetic methods given below, it is to be understood that all proposed reaction conditions, including choice of solvent, reaction atmosphere, reaction temperature, duration of the experiment and work up procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents that are compatible with the reaction conditions will be readily apparent to one skilled in the art, with alternatives required when incompatible substituents are present. This will sometimes require a judgment to modify the order of the synthetic steps or to select one particular process scheme over another in order to obtain a desired compound of the invention. It will also be recognized that another major consideration in the planning of any synthetic route in this field is the judicious choice of a protecting group used for protection of reactive functional groups present in the compounds described in this invention. An authoritative account describing the many alternatives to the trained practitioner is Wuts and Greene, *Greene's Protective Groups in Organic Synthesis*, Fourth Edition, Wiley and Sons (2007).

Scheme 1 illustrates a method for the preparation of compounds 7. An appropriately functionalized carbonyl compound 1 (which can be purchased or synthesized using typical conditions; see, for example: *Eur. J. Med. Chem.* 2015, 90, 834; *Science of Synthesis* 2077, 31a, 1097; PCT Int. Appl. 2014/138484; *Bioorg. Med. Chem. Lett.* 2012, 22, 240; *Eur. J. Med. Chem.* 2013, 69, 490; or PCT Int. Appl. 2013/178322) may be reacted with an appropriate thiol in the presence of an acid such as HCl or TiCl$_4$ to afford a vinyl sulfide 2a, a thioketal 2b, or a mixture of 2a and 2b. Oxidation of sulfide 2a, thioketal 2b, or a mixture of 2a and 2b can be accomplished using a reagent such as m-chloroperoxybenzoic acid to afford sulfone 3. A nucleophile such as an amino alcohol 4 can then be added, yielding an alcohol 5. This compound could be converted to the corresponding methanesulfonate 6 using methanesulfonyl chloride and triethylamine, followed by treatment with a base such as potassium tert-butoxide, to give tricyclic amine 7.

SCHEME 1

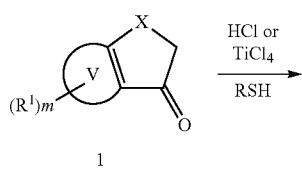

1

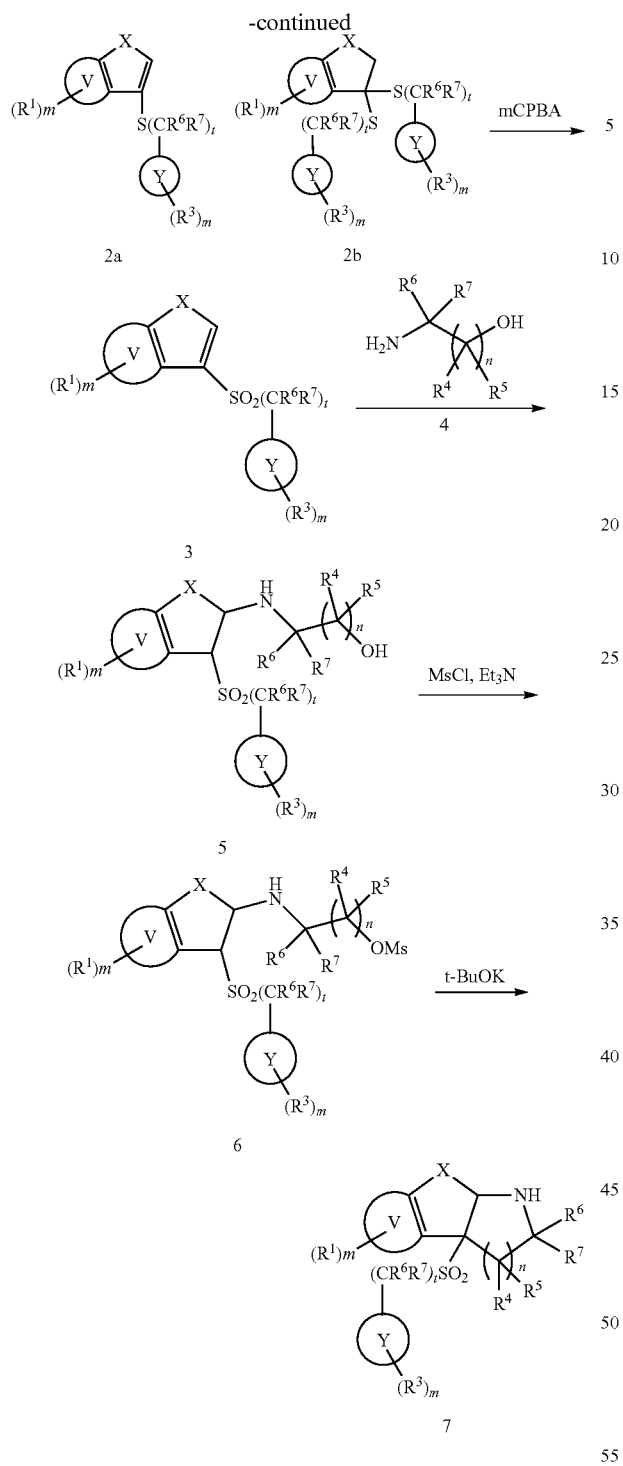

An alternative method for the preparation of compounds 7 is shown in Scheme 2. An appropriately substituted olefin 8 (which can be purchased, or prepared using typical methods; see for example US Pat. Appl. 2007/0155738 and US Pat. Appl. 2005/261310) can be converted to the epoxide 9, for example by treatment with a reagent such as m-chloroperoxybenzoic acid. The epoxide may be treated with a nucleophile such as a protected amino alcohol 10 (where P is, for example, tert-butyldimethylsilyl) to provide alcohol 11. Treatment of 11 with suitable reagents such as triphenylphosphine and diethyl azodicarboxylate can provide the substituted aziridine 12. Treatment of the aziridine with an appropriate thiol can give 13. Protection of the amino group with a suitable protecting group P' such as tert-butoxycarbonyl (Boc) or benzyloxycarbonyl (Cbz), followed by oxidation of the thiol with a reagent such as m-chloroperoxybenzoic acid, can provide the sulfone 14. Selective removal of the alcohol protecting group, followed by conversion to the corresponding methanesulfonate and treatment with a base such as potassium tert-butoxide (as in Scheme 1) can provide 15, which can be deprotected to provide the tricyclic amine 7.

SCHEME 2

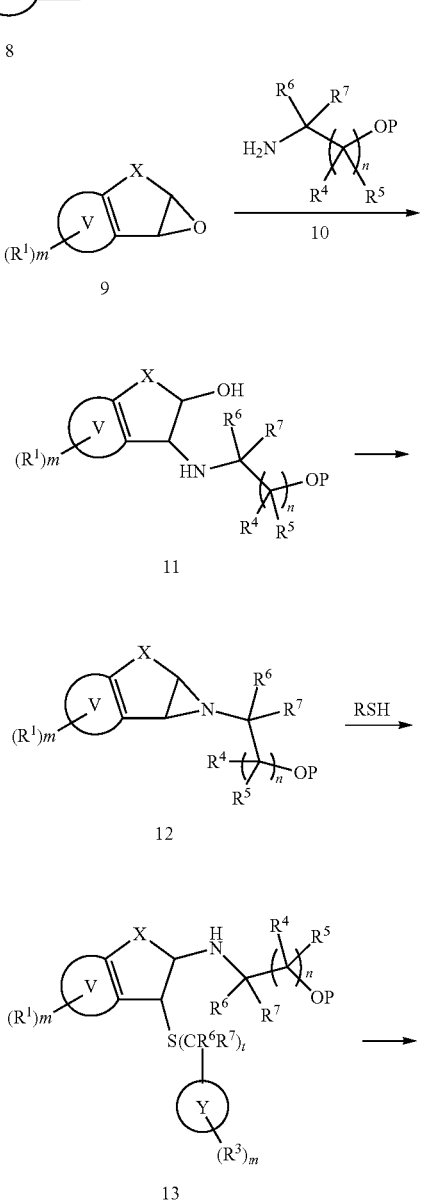

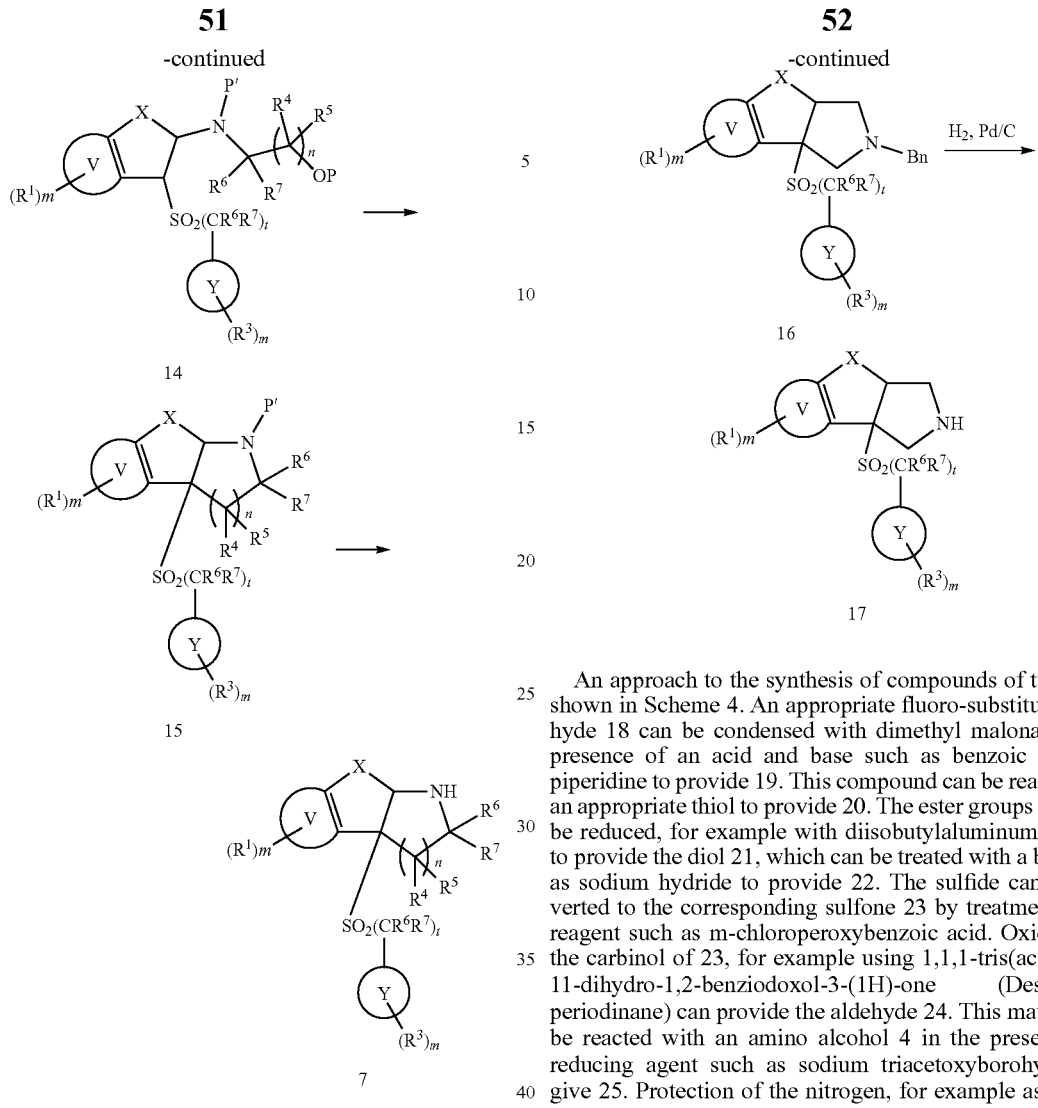

Scheme 3 illustrates an approach to the synthesis of compounds of type 17. Appropriately functionalized vinyl sulfone 3 may undergo cycloaddition reactions with a variety of reagents. For example, reaction with N-benzyl-1-methoxy-N-((trimethylsilyl)methyl)-methanamine in the presence of a catalytic amount of trifluoroacetic acid can provide pyrrolidine 16. Deprotection using hydrogen with catalytic palladium on carbon can give rise to pyrrolidine 17.

An approach to the synthesis of compounds of type 27 is shown in Scheme 4. An appropriate fluoro-substituted aldehyde 18 can be condensed with dimethyl malonate in the presence of an acid and base such as benzoic acid and piperidine to provide 19. This compound can be reacted with an appropriate thiol to provide 20. The ester groups of 20 can be reduced, for example with diisobutylaluminum hydride, to provide the diol 21, which can be treated with a base such as sodium hydride to provide 22. The sulfide can be converted to the corresponding sulfone 23 by treatment with a reagent such as m-chloroperoxybenzoic acid. Oxidation of the carbinol of 23, for example using 1,1,1-tris(acetyloxy)-11-dihydro-1,2-benziodoxol-3-(1H)-one (Dess-Martin periodinane) can provide the aldehyde 24. This material can be reacted with an amino alcohol 4 in the presence of a reducing agent such as sodium triacetoxyborohydride to give 25. Protection of the nitrogen, for example as the Boc or Cbz derivative, followed by conversion to the methanesulfonate and treatment with a base such as potassium tert-butoxide (as in Scheme 1) can provide the tricyclic compound 26. Deprotection of the amine can then provide 27.

SCHEME 3

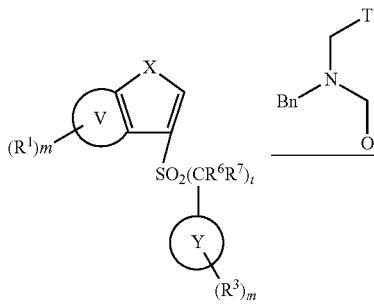

SCHEME 4

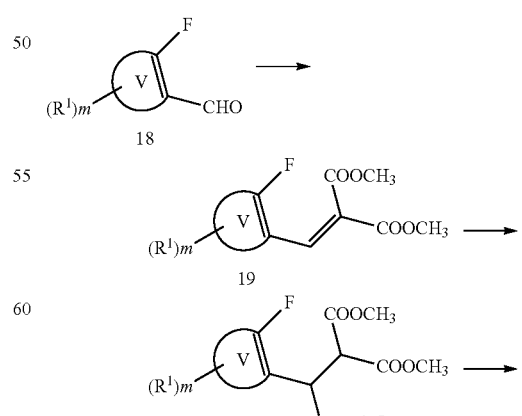

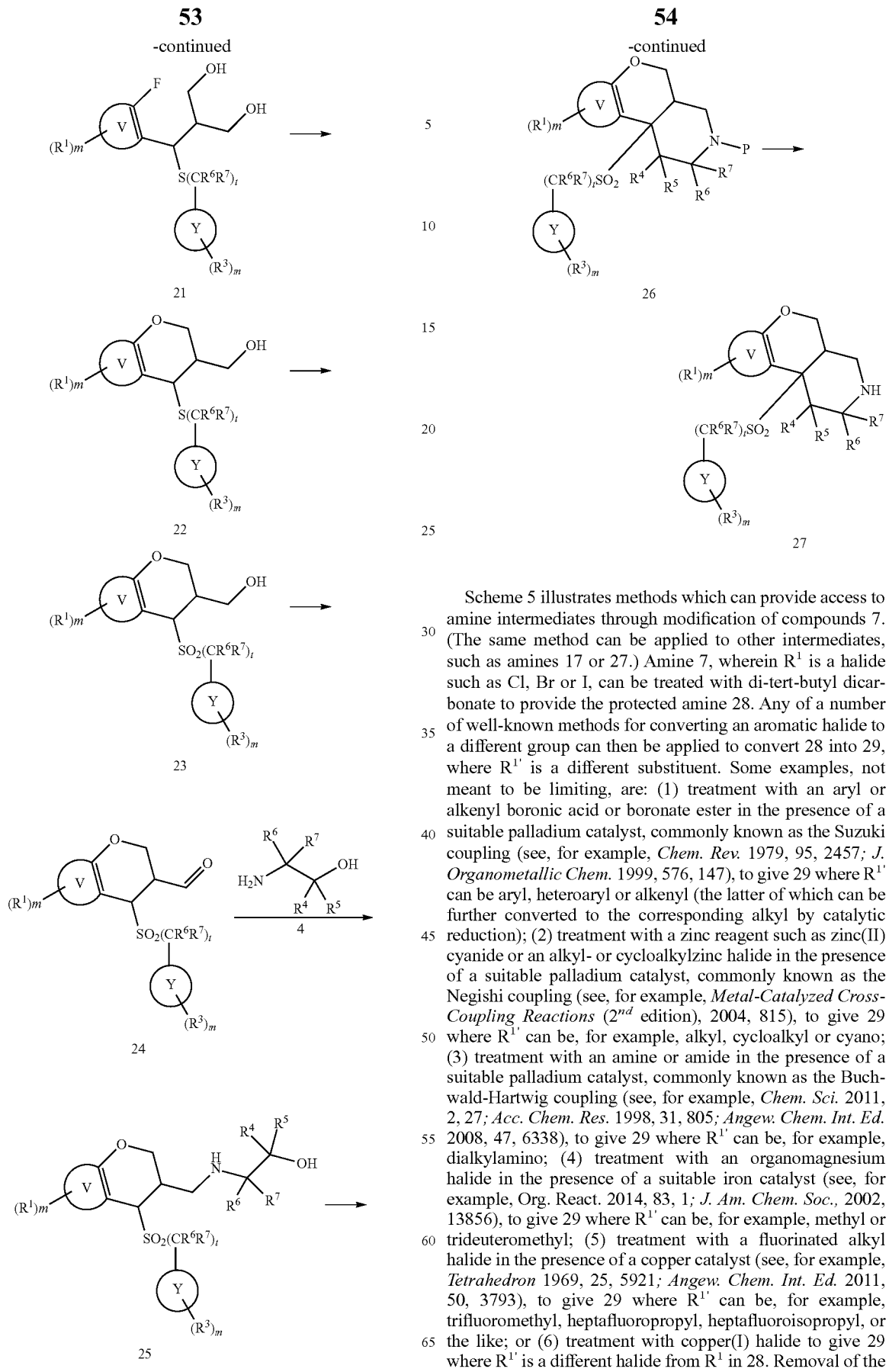

Scheme 5 illustrates methods which can provide access to amine intermediates through modification of compounds 7. (The same method can be applied to other intermediates, such as amines 17 or 27.) Amine 7, wherein $R^1$ is a halide such as Cl, Br or I, can be treated with di-tert-butyl dicarbonate to provide the protected amine 28. Any of a number of well-known methods for converting an aromatic halide to a different group can then be applied to convert 28 into 29, where $R^{1'}$ is a different substituent. Some examples, not meant to be limiting, are: (1) treatment with an aryl or alkenyl boronic acid or boronate ester in the presence of a suitable palladium catalyst, commonly known as the Suzuki coupling (see, for example, *Chem. Rev.* 1979, 95, 2457; *J. Organometallic Chem.* 1999, 576, 147), to give 29 where $R^{1'}$ can be aryl, heteroaryl or alkenyl (the latter of which can be further converted to the corresponding alkyl by catalytic reduction); (2) treatment with a zinc reagent such as zinc(II) cyanide or an alkyl- or cycloalkylzinc halide in the presence of a suitable palladium catalyst, commonly known as the Negishi coupling (see, for example, *Metal-Catalyzed Cross-Coupling Reactions* ($2^{nd}$ edition), 2004, 815), to give 29 where $R^{1'}$ can be, for example, alkyl, cycloalkyl or cyano; (3) treatment with an amine or amide in the presence of a suitable palladium catalyst, commonly known as the Buchwald-Hartwig coupling (see, for example, *Chem. Sci.* 2011, 2, 27; *Acc. Chem. Res.* 1998, 31, 805; *Angew. Chem. Int. Ed.* 2008, 47, 6338), to give 29 where $R^{1'}$ can be, for example, dialkylamino; (4) treatment with an organomagnesium halide in the presence of a suitable iron catalyst (see, for example, *Org. React.* 2014, 83, 1; *J. Am. Chem. Soc.*, 2002, 13856), to give 29 where $R^{1'}$ can be, for example, methyl or trideuteromethyl; (5) treatment with a fluorinated alkyl halide in the presence of a copper catalyst (see, for example, *Tetrahedron* 1969, 25, 5921; *Angew. Chem. Int. Ed.* 2011, 50, 3793), to give 29 where $R^{1'}$ can be, for example, trifluoromethyl, heptafluoropropyl, heptafluoroisopropyl, or the like; or (6) treatment with copper(I) halide to give 29 where $R^{1'}$ is a different halide from $R^1$ in 28. Removal of the Boc protecting group can be achieved by treatment with a strong acid such as HCl or trifluoroacetic acid. The same or similar methods can also be applied to a protected amine 30 (or a protected amine derived from amines 17 or 27) wherein $R^3$ is a halide such as Cl, Br or I to give the corresponding 31 where $R^{3'}$ is a different group, as described above.

SCHEME 5

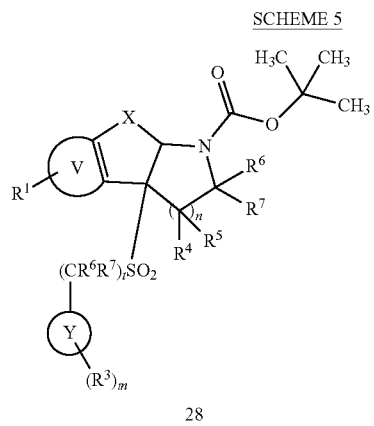

28

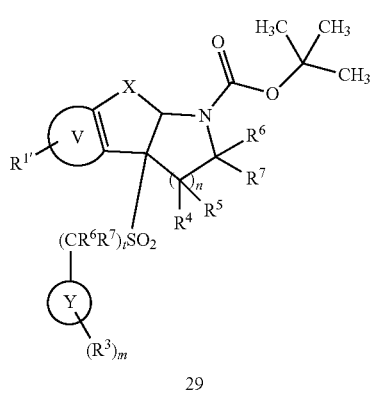

29

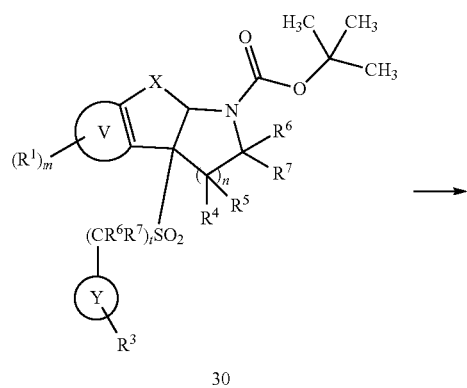

30

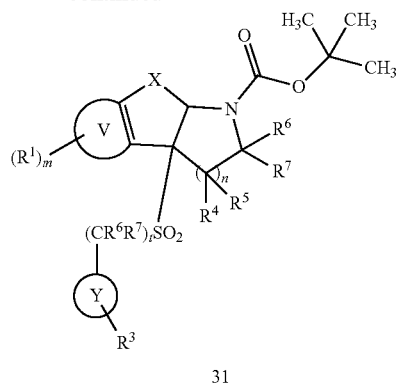

31

An alternative method for the conversion of a compound 28 where $R^1$ is Br or I to a compound 32 or 33 is shown in Scheme 6. Compound 28 can be treated with an organometallic reagent such as n-butyllithium, and then reacted with a carbonyl containing compound RC(=O)R' to provide alcohol 32. Optionally, alcohol 32 may be treated with a fluorinating agent such as (diethylamino)sulfur trifluoride, affording a fluorinated analog such as 33. Treatment of 32 or 33 with a strong acid such as HCl or trifluoroacetic acid would then remove the Boc protecting group.

SCHEME 6

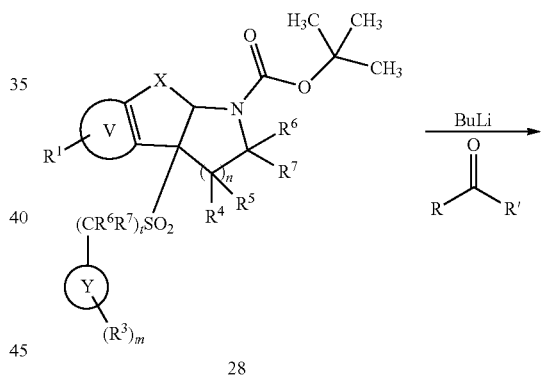

28

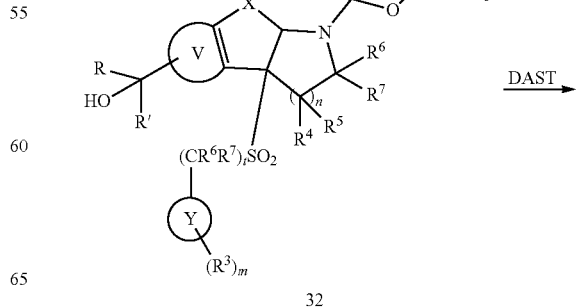

32

-continued

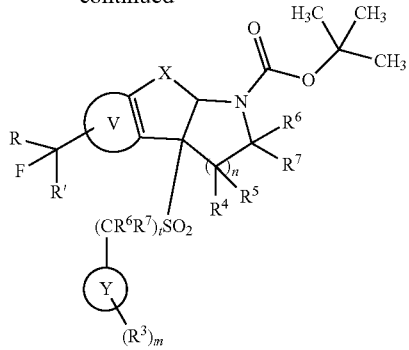

33

A variety of methods well known in the literature can be used for conversion of amines 7 to compounds of the present invention. (Such methods can also be used for similar conversions of amines 17 and 27 to compounds of the present invention.) Some examples are shown in Scheme 7. An amine 7 can be treated with an acid 34 (wherein P can be H, an alkyl or acyl group, or a protecting group such as Boc) in the presence of a suitable base and a coupling reagent such as (benzotriazol-1-yloxy)tris(dimethylamino)-phosphonium hexafluorophosphate (BOP), O-(7-azabenzo-triazol-1-yl)-1,1,3,3-tetramethyluronium hexafluorophosphate (HATU), benzotriazol-1-yl-oxytripyrrolidino-phosphonium hexafluorophosphate (PyBOP), or a combination of 1-hydroxy-benzotriazole (HOBT) and N-(3-dimethylaminopropyl)-N'-ethylcarbodiimide (EDC), to provide an amide 35. If P is a protecting group such as Boc, treatment with an appropriate reagent such as trifluoroacetic acid or hydrochloric acid can be used to remove the protecting group, giving an amide 35 wherein P is H. (Acids 34 can be prepared using a variety of methods known in the literature.)

Alternatively, an amine 7 can be treated with an acid 36, using methods described for the preparation of 35, to provide an amide 37. Amide 37 can be treated with an appropriate reagent such as sodium periodate to prepare the corresponding sulfoxide 38. The sulfoxide can be converted to the corresponding sulfoximine 35 (wherein P is H) using methods known in the literature, for example by treatment with ammonium carbamate and iodobenzene diacetate. (See, for example, *Angew. Chem. Int. Ed.* 2016, 55, 7203, and references cited therein.)

SCHEME 7

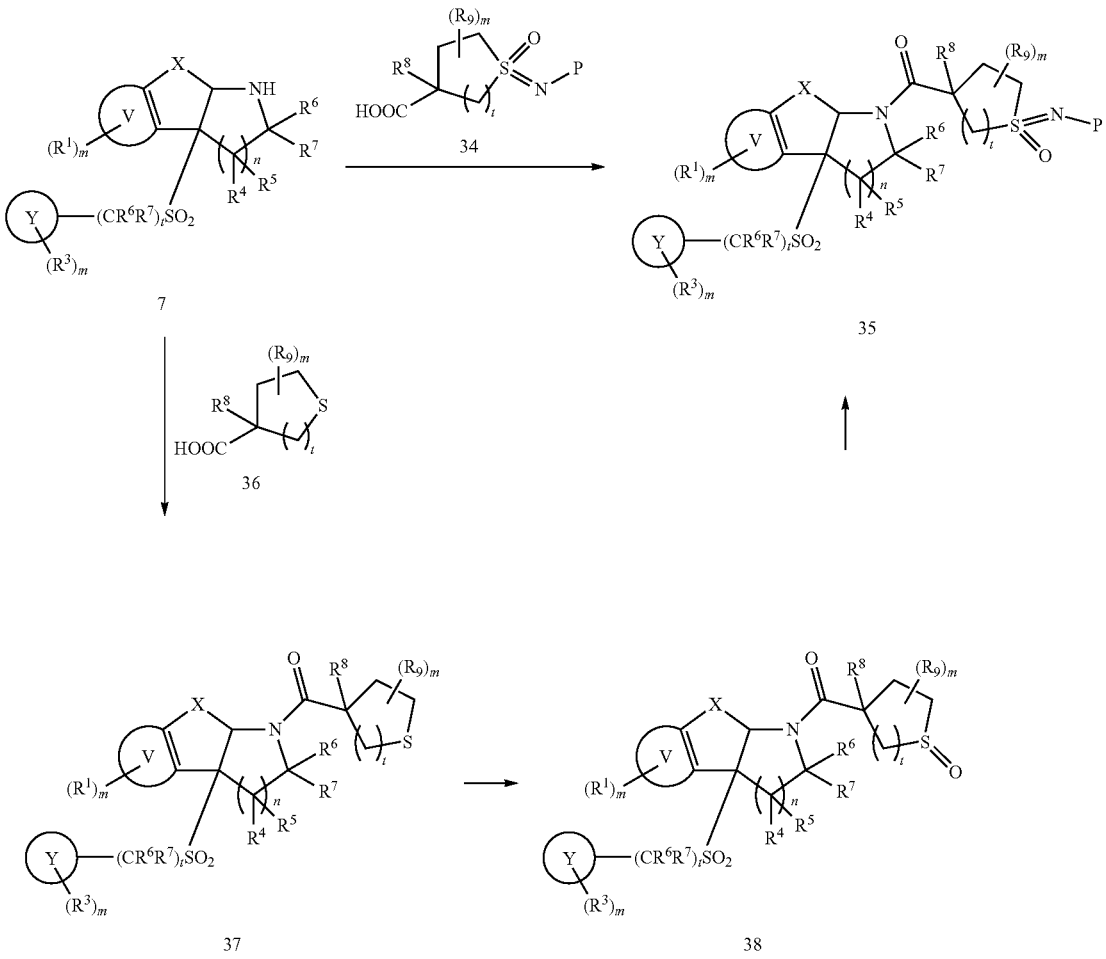

Methods for preparing certain compounds 40 and 41 of the present invention are shown in Scheme 8. A sulfoximine 39 can be treated with an acylating agent such as an acid anhydride RC(=O)OC(=O)R or an acid chloride RC(=O)Cl, in the presence of a suitable base such as pyridine, to provide an acylated compound 40. Alternatively, a sulfoximine 39 can be treated with an aldehyde such as formaldehyde (or the polymeric form paraformaldehyde) or acetaldehyde in the presence of suitable reagents such as trifluoroacetic acid and triethylsilane, as described in PCT Pat. Appl. 2004/002967, to provide an alkylated compound 41 (where R is methyl or ethyl, respectively).

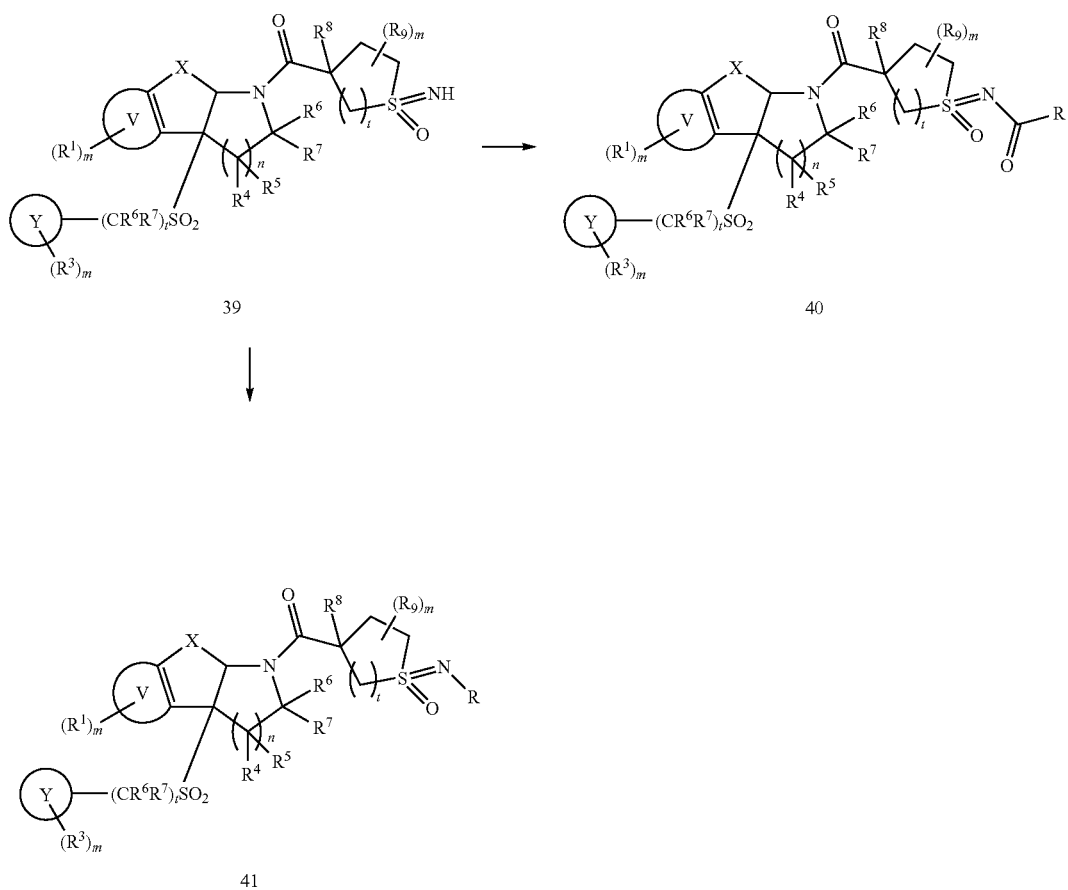

SCHEME 8

A method for preparing certain compounds 43 is shown in Scheme 9. An amine 42 can be treated with an aldehyde RCHO or a ketone RC(=O)R' in the presence of a reducing agent such as sodium triacetoxyborohydride or sodium cyanoborohydride to provide the alkylated amine 43. Alternatively, an amine 42 can be treated with an alkyl chloride, alkyl bromide, alkyl iodide or other activated alkyl derivative such as an alkyl methanesulfonate or alkyl trifluoromethanesulfonate, in the presence of a suitable base, to provide the alkylated amine 43. If $R^a$ in 43 is a protecting group such as Boc, it can be removed using standard methods and the resulting amine reacted as desired, for example as shown in Scheme 7.

SCHEME 9

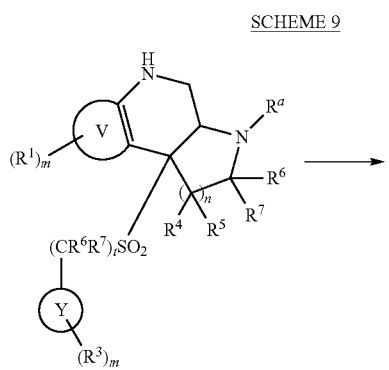

42

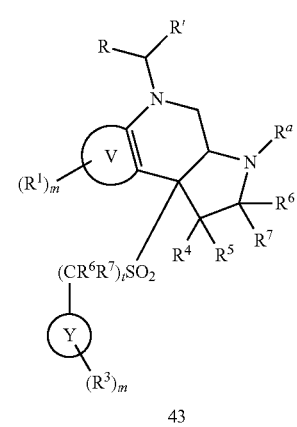

43

A variety of available methods may be used for conversion of intermediates or compounds of the invention to other intermediates or compounds of the invention. Some examples, well known to those skilled in the art of organic chemistry, include but are not limited to: conversion of a carboxylic acid ester to a carboxylic acid; conversion of a carboxylic acid to an amide; conversion of an amine to an amide, a urea, or a sulfonamide; alkylation or arylation of an amine; replacement of an aryl halide by an alkyl group, an aryl group or an amino group; and electrophilic substitution of an aromatic ring.

It will be appreciated by one skilled in the art of organic chemistry that various steps in a synthesis may be performed in an alternative sequence from that described in order to give a desired compound or compounds.

EXAMPLES

The following examples illustrate the particular and preferred embodiments of the present invention and do not limit the scope of the present invention. Chemical abbreviations and symbols as well as scientific abbreviations and symbols have their usual and customary meanings unless otherwise specified. Additional abbreviations employed in the Examples and elsewhere in this application are defined below. Common Intermediates are generally useful for the preparation of more than one Example and are identified sequentially by the Intermediate number and step in which they were prepared (e.g., Intermediate 1, Step A), or by the Intermediate number only where the compound is the title compound. Compounds of the Examples are identified by the Example number and step in which they were prepared (e.g., Example 1, Step A) if the compound is an intermediate, or by the Example number only where the compound is the title compound of the Example. In some instances alternative preparations of Intermediates or Examples are described. Frequently chemists skilled in the art of synthesis may devise alternative preparations which may be desirable based on one or more considerations such as shorter reaction time, less expensive starting materials, ease of operation or isolation, improved yield, suitability to catalysis, avoidance of toxic reagents, accessibility of specialized instrumentation, decreased number of linear steps, etc. The intent of describing alternative preparations is to further enable the preparation of the Examples of this invention. In some instances some functional groups in the outlined Examples and claims may be replaced by well known bioisosteric replacements known in the art, for example, replacement of a carboxylic acid group with a tetrazole or a phosphate moiety. Starting materials and intermediates for which no preparation is explicitly shown are available commercially, are known in the literature, or may be prepared by analogy to similar compounds which are known in the literature.

Drying of organic solutions to remove residual water was done by allowing to stand over anhydrous sodium sulfate, followed by decantation or filtration. Solvent removal was performed by concentration under reduced pressure. Column chromatography was generally performed with pre-packed silica gel cartridges using a CombiFlash® automated chromatography apparatus (Teledyne Isco), eluting with the solvent or solvent mixture indicated. Analytical and preparative high performance liquid chromatography (HPLC) were generally performed using a reverse phase column of a size appropriate to the quantity of material being separated, generally eluting with a gradient of increasing concentration of methanol or acetonitrile in water, also containing 0.05% or 0.1% trifluoroacetic acid or 10 mM ammonium acetate, at a rate of elution suitable to the column size and separation to be achieved. Chiral super-critical fluid chromatographic (SFC) separation of enantiomers or diastereomers was performed using conditions described for the individual cases. Mass spectral data were obtained by liquid chromatography mass spectroscopy (LCMS) using electrospray ionization.

Many Intermediates and Examples are homochiral (entirely or mostly a single enantiomer), but in some cases the absolute configuration has not been proven. In those cases, a text notation to the left of the structure will indicate that the compound is homochiral, and indicates whether the compound was obtained from (or is derived from an intermediate which was obtained from) the specified peak eluting during chiral SFC separation. However, in all cases, the stereochemistry within the tricyclic ring system is cis. Thus, for example, the structure 44 shown below indicates that, while the material is homochiral, the absolute stereochemistry of the material, which was derived from the second-eluting peak during SFC separation, is not known, but is either the absolute stereochemistry shown in 44a or that shown in 44b.

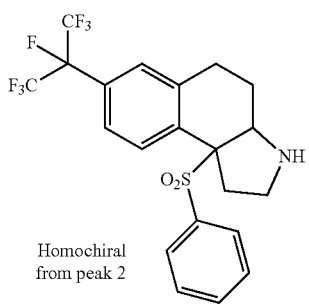

Homochiral
from peak 2

44

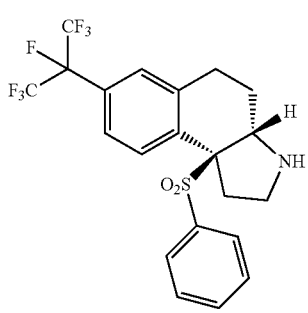

44a

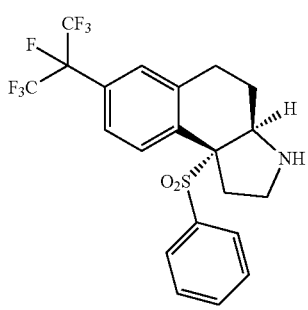

44b

In some cases, an Intermediate or Example is derived from combining a homochiral starting material with a non-homochiral or racemic starting material, yielding a mixture of two or more configurational isomers. In such cases, if the absolute stereochemistry of the homochiral starting material is not known, a text notation will indicate that the chiral centers of the tricyclic moiety are those of the homochiral tricyclic intermediate derived from the indicated peak eluting during chiral SFC separation (as above), while the non-homochiral asymmetric center or centers are indicated by a wavy line, for example as shown in structure 45 below.

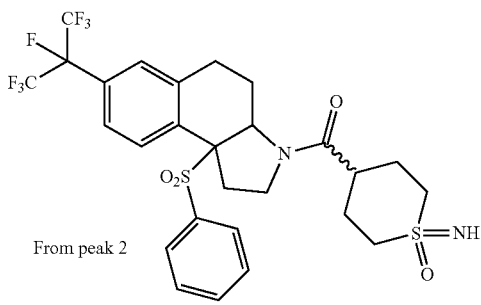

45

From peak 2

In some cases, a mixture of configurational isomers resulting from combining a homochiral starting material with a non-homochiral starting material has been separated by a method such as chiral SFC to give a homochiral product wherein the absolute stereochemistry at some or all of the asymmetric centers is not known. In such cases, the absolute configurations of any known chiral centers are shown explicitly, while a text notation will indicate the peak (from the separation of the diastereomeric mixture) from which the product was isolated. An example is shown in Structure 46 below, which indicates that the absolute configuration of the tricyclic moiety is known, while the product 46 is derived from peak 1 eluting during chiral separation of a mixture of configurational isomers.

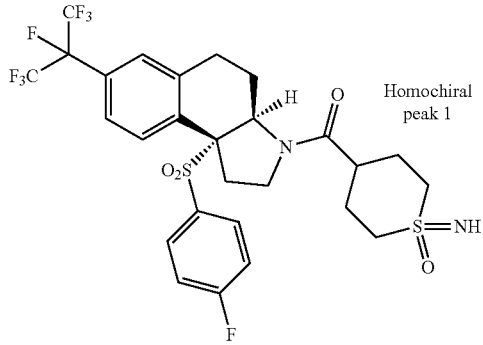

46

Homochiral peak 1

If the absolute configuration at an asymmetric center of an Intermediate or Example is known, or that asymmetric center is derived from a precursor whose absolute configuration is known, this is explicitly shown in the structure of the Intermediate or Example. If no absolute configuration is explicitly shown at an asymmetric center in a structure, and no text notation is present with the structure (as above), that chiral center is either racemic or of undefined stereochemistry.

Chemical names were determined using ChemBioDraw Ultra, version 14.0.0.126 (PerkinElmer Inc.). The following abbreviations are used:

| ABBREVIATION | NAME |
| --- | --- |
| BOP | (benzotriazol-1-yloxy)tris(dimethylamino)phosphonium hexafluorophosphate |
| $CDCl_3$ | deuterated chloroform |
| DAST | diethylaminosulfur trifluoride |
| DCM | dichloromethane |
| DIPEA | diisopropylethylamine |
| DMF | N,N-dimethylformamide |
| DMSO | dimethyl sulfoxide |
| $DMSO-d_6$ | deuterated dimethyl sulfoxide |
| $Et_3N$ | triethylamine |
| EtOAc | ethyl acetate |
| h | hours |
| HPLC | high performance liquid chromatography |
| LCMS | liquid chromatography-mass spectrometry |
| MeCN | acetonitrile |
| MeOH | methanol |
| mCPBA | meta-chloroperoxybenzoic acid |
| min | minutes |
| MsCl | methanesulfonyl chloride |
| rt | room temperature |
| SFC | super-critical fluid chromatography |
| TFA | trifluoroacetic acid |
| THF | tetrahydrofuran |
| $t_R$ | chromatographic retention time |

HPLC Methods

Method A: (Analytical)

Column: Acquity UPLC® BEH $C_{18}$ 2.1×50 mm, 1.7 μm (Waters Corp.); mobile phase A: water with 0.05% TFA; mobile phase B: MeCN with 0.05% TFA; temperature: 50° C.; flow rate 0.80 mL/min; gradient: 2-98% B over 1 min, then 0.5 min isocratic at 98% B.

Method B: (Analytical)

Column: Acquity UPLC® BEH $C_{18}$ 2.1×50 mm, 1.7 μm (Waters Corp.); mobile phase A: 5:95 MeCN-water with 10 mM ammonium acetate; mobile phase B: 95:5 MeCN-water with 10 mM ammonium acetate; temperature: 50° C.; flow rate 1.0 mL/min; gradient: 0-100% B over 3 min, then 0.75 min isocratic at 100% B.
Method C: (Analytical)

Column: Acquity UPLC® BEH $C_{18}$ 2.1×50 mm, 1.7 μm (Waters Corp.); mobile phase A: 5:95 MeCN-water with 0.1% TFA; mobile phase B: 95:5 MeCN-water with 0.1% TFA; temperature: 50° C.; flow rate 1.0 mL/min; gradient: 0-100% B over 3 min, then 0.75 min isocratic at 100% B.
Method D: (Preparative)

Column: XBridge™ $C_{18}$ 19×200 mm, 5 μm (Waters Corp.); mobile phase A: 5:95 MeCN-water with 0.1% TFA; mobile phase B: 95:5 MeCN-water with 0.1% TFA; flow rate 20 mL/min; gradient: increasing B, then isocratic.
Method E: (Preparative)

Column: XBridge™ $C_{18}$ 19×200 mm, 5 μm (Waters Corp.); mobile phase A: 5:95 MeCN-water with 10 mM ammonium acetate; mobile phase B: 95:5 MeCN-water with 10 mM ammonium acetate; flow rate 20 mL/min; gradient: increasing B, then isocratic.
Method F: (Preparative)

Column: Luna AXIA™ $C_{18}$ 30×100 mm, 5 μm (Phenomenex Co.); mobile phase A: water with 0.1% TFA; mobile phase B: MeCN with 0.1% TFA; flow rate 30 mL/min; gradient: increasing B, then isocratic.

Intermediate 1

4-((4-fluorophenyl)sulfonyl)-7-iodo-1,2-dihydronaphthalene

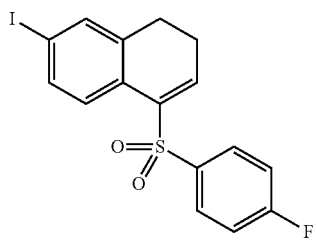 [SMILES: O=S(=O)(C1=CCCc2cc(I)ccc21)c1ccc(F)cc1]

A solution of 6-iodo-3,4-dihydronaphthalen-1(2H)-one (13.3 g, 48.9 mmol) and $TiCl_4$ (1 M in DCM, 48.9 mL, 48.9 mmol) in THF (326 mL) in an ice-water bath was treated with a solution of 4-fluorobenzenethiol (6.3 mL, 58.7 mmol) and $Et_3N$ (13.6 mL, 98 mmol) in THF (25 mL) at a rate such that the temperature remained below 10° C. The solution was stirred at rt for 60 min, then was treated with water (200 mL) and concentrated to remove the bulk of the organic solvents. The aqueous residue was extracted with diethyl ether (2×250 mL). The combined organic layers were dried and concentrated to provide crude (4-fluorophenyl)(6-iodo-3,4-dihydronaphthalen-1-yl)sulfane (20 g) as a mixture with the corresponding thioketal, which was used directly. HPLC $t_R$ 1.36 min (method A).

A solution of (4-fluorophenyl)(6-iodo-3,4-dihydronaphthalen-1-yl)sulfane and its thioketal (the mixture from the above reaction, 18.69 g) in DCM (978 mL) in an ice-water bath was treated portionwise with mCPBA (21.92 g, 98 mmol). The mixture was allowed to reach rt and was stirred for 1 h, when LCMS showed consumption of the starting material and 4-((4-fluorophenyl)sulfinyl)-7-iodo-1,2-dihydronaphthalene as the major product. Additional mCPBA (10.96 g, 48.9 mmol) was added at rt. The reaction was stirred for 30 min, when LCMS showed very little sulfoxide ($t_R$ 1.00 min, method B). The mixture was washed twice with saturated aqueous $NaHCO_3$, and the organic phase was dried and concentrated. The residue was purified by column chromatography, eluting with EtOAc-hexanes (gradient from 0-10%). The resulting material was dissolved in EtOAc and washed twice with saturated aqueous $NaHCO_3$. The organic phase was dried and concentrated to provide 4-((4-fluorophenyl)sulfonyl)-7-iodo-1,2-dihydronaphthalene as a white foamy solid (12 g, 59% yield over two steps). LCMS m/z 455.9 $(M+H+MeCN)^+$, HPLC $t_R$ 1.09 min (method A). $^1$H NMR (400 MHz, $CDCl_3$) δ 7.97-7.89 (m, 2H), 7.64 (d, J=8.8 Hz, 1H), 7.57-7.47 (m, 3H), 7.22-7.13 (m, 2H), 2.79-2.68 (m, 2H), 2.61-2.50 (m, 2H). $^{19}$F NMR (376 MHz, $CDCl_3$) δ −102.7 (s, 1F).

Alternative Procedure:

A solution of 6-iodo-3,4-dihydronaphthalen-1(2H)-one (5.0 g, 18.38 mmol), 4-fluorobenzenethiol (4.11 mL, 38.6 mmol) and absolute ethanol (20 mL) was cooled with an ice-water bath and bubbled with HCl gas until saturation was reached (observed by the formation of a white precipitate). The mixture was allowed to warm to rt and stirred overnight. The mixture was dissolved in ether (250 mL) and washed sequentially with water (2×125 mL), 0.5 M aqueous $Na_2CO_3$ (3×100 mL) and brine (100 mL). The organic layer was dried and concentrated to provide a solid (9.2 g) which was a mixture of thioketal and vinyl sulfide. The solid was dissolved in chloroform (150 mL) and cooled in an ice-water bath. A solution of mCPBA (35 g, 156 mmol) in DCM (200 mL) was washed with brine (50 mL), dried, filtered, and the filter cake was washed with DCM (50 mL). The combined filtrates were added dropwise in portions to the chloroform solution of the products from above until the reaction was completed as judged by LCMS (175 mL of the mCPBA solution was needed). The mixture was cooled in an ice bath, filtered to remove the insoluble material, and the filtrate was stirred with 10% aqueous $Na_2S_2O_3$ (120 mL) for 5 min. The organic phase was separated, washed sequentially with 10% aqueous $Na_2S_2O_3$ (2×120 mL), 10% aqueous $Na_2CO_3$ (3×200 mL) and brine (150 mL), dried and concentrated. The residue was purified by column chromatography on silica gel, eluting with EtOAc-hexanes (gradient from 0-20%) to give 4-((4-fluorophenyl)sulfonyl)-7-iodo-1,2-dihydronaphthalene (5.3 g, 70% yield) as a white foamy solid.

The Intermediates in Table 1 were prepared using the same methods or similar methods used to prepare Intermediate 1, by employing the appropriate ketone and substituted thiophenol.

TABLE 1
| Intermediate number | Structure | LCMS m/z observed | HPLC $t_R$ (min) | HPLC method |
|---|---|---|---|---|
| 2 | 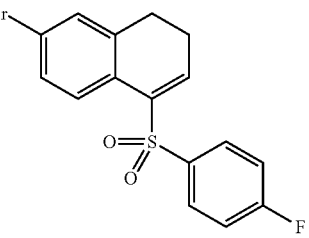 | 364.8 (M + H + MeCN)⁺ | 1.09 | A |
| 3 | 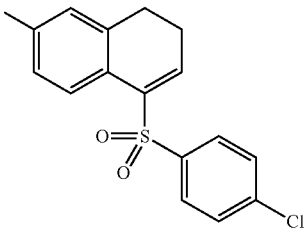 | 493.8 (M + Na + MeCN)⁺ | 1.13 | A |
| 4 | 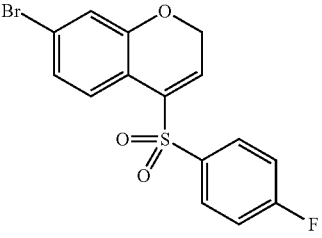 [SMILES: O=S(=O)(C1=CCOc2cc(Br)ccc21)c1ccc(F)cc1] | 410.0 (M + H + MeCN)⁺ | 1.08 | A |
| 5 | 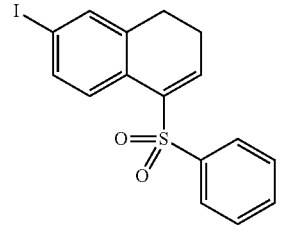 [SMILES: O=S(=O)(C1=CCCc2cc(I)ccc21)c1ccccc1] | 438.0 (M + H + MeCN)⁺ | 1.11 | A |
| 6 | 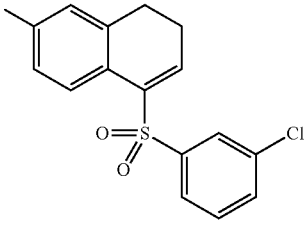 | 472.1 (M + H + MeCN)⁺ | 1.13 | A |
| 7 | 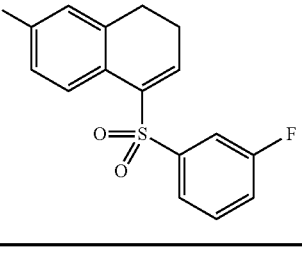 | 455.9 (M + H + MeCN)⁺ | 1.09 | A |

Intermediate 8

(3aR,9bR)-9b-((4-fluorophenyl)sulfonyl)-7-(perfluoropropan-2-yl)-2,3,3a,4,5,9b-hexahydro-1H-benzo[e]indole Hydrochloride

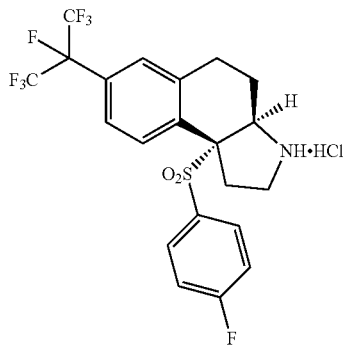

Step A: 2-((6-bromo-1-((4-fluorophenyl)sulfonyl)-1,2,3,4-tetrahydronaphthalen-2-yl)amino)ethan-1-ol

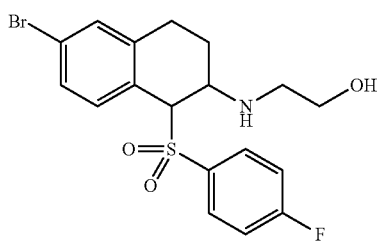 [SMILES: O=S(=O)(c1ccc(F)cc1)C1c2ccc(Br)cc2CCC1NCCO]

A solution of 7-bromo-4-((4-fluorophenyl)sulfonyl)-1,2-dihydronaphthalene (Intermediate 2; 5.7 g, 15.52 mmol) in THF (259 mL) in an ice-water bath was treated with 2-aminoethanol (13.42 mL, 233 mmol). The mixture was stirred at about 5° C. for 30 min, when LCMS showed complete consumption of the starting material. The mixture was concentrated and the resulting oil was dissolved in EtOAc (250 mL), washed with saturated aqueous NaHCO$_3$, then twice with brine, dried and concentrated. The residue was purified by column chromatography on silica gel, eluting with EtOAc, to provide 2-((6-bromo-1-((4-fluorophenyl)sulfonyl)-1,2,3,4-tetrahydronaphthalen-2-yl)amino)ethanol (2.8 g, 42% yield. LCMS m/z 427.8 (M+H)$^+$, HPLC $t_R$ 0.71 min (method A).

Step B: 2-((6-bromo-1-((4-fluorophenyl)sulfonyl)-1,2,3,4-tetrahydronaphthalen-2-yl)amino)ethyl methanesulfonate

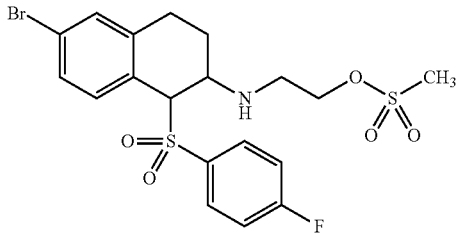 [SMILES: CS(=O)(=O)OCCNC1CCc2cc(Br)ccc2C1S(=O)(=O)c1ccc(F)cc1]

A solution of 2-((6-bromo-1-((4-fluorophenyl)sulfonyl)-1,2,3,4-tetrahydronaphthalen-2-yl)amino)ethanol (2.8 g, 6.54 mmol) in DCM (654 mL) was treated at rt with MsCl (0.611 mL, 7.84 mmol) followed by Et$_3$N (1.093 mL, 7.84 mmol). The mixture was stirred for 1 h, when LCMS showed complete consumption of the starting material. The mixture was washed with a 1:1 mixture of brine and water, and the organic layer was dried and concentrated to provide 2-((6-bromo-1-((4-fluorophenyl)sulfonyl)-1,2,3,4-tetrahydronaphthalen-2-yl)amino)ethyl methanesulfonate (2.9 g, 88% yield), used without further purification. LCMS m/z 505.9 (M+H)$^+$, HPLC $t_R$ 0.76 min (method A).

Step C: 7-bromo-9b-((4-fluorophenyl)sulfonyl)-2,3,3a,4,5,9b-hexahydro-1H-benzo[e]indole

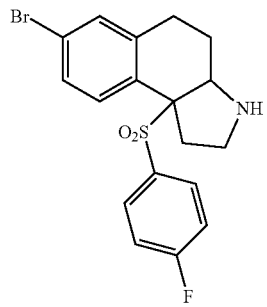 [SMILES: O=S(=O)(c1ccc(F)cc1)C12CCNC1CCc1cc(Br)ccc12]

A solution of 2-((6-bromo-1-((4-fluorophenyl)sulfonyl)-1,2,3,4-tetrahydronaphthalen-2-yl)amino)ethyl methanesulfonate (2.9 g, 5.73 mmol) in THF (286 mL) was treated portionwise with potassium tert-butoxide ((3.21 g, 28.6 mmol) at rt, such that the temperature of the reaction mixture did not exceed 25.5° C. The mixture was stirred for 1 h, when LCMS showed complete consumption of starting material. The mixture was treated with 100 mL of a 1:1 mixture of water and brine and partially concentrated. The aqueous residue was extracted with EtOAc (2×125 mL), and the combined organic layers were dried and concentrated to provide crude 7-bromo-9b-((4-fluorophenyl)sulfonyl)-2,3,3a,4,5,9b-hexahydro-1H-benzo[e]indole (2.1 g), used without further purification. LCMS m/z 409.9 (M+H)$^+$, HPLC $t_R$ 0.76 min (method A). $^1$H NMR (400 MHz, CDCl$_3$) δ 7.51-7.43 (m, 1H), 7.42-7.35 (m, 1H), 7.32-7.27 (m, 2H), 7.11 (s, 1H), 7.02 (t, J=8.78 Hz, 2H), 3.97 (dd, J=12.0, 6.0 Hz, 1H), 3.32 (dd, J=11.5, 4.0 Hz, 1H), 3.27-3.13 (m, 1H), 3.02 (d, J=12.0 Hz, 1H), 2.50-2.30 (m, 2H), 2.05-1.95 (m, 1H), 1.77-1.56 (m, 1H), 1.34-1.20 (m, 1H).

Step D: tert-butyl 7-bromo-9b-((4-fluorophenyl)
sulfonyl)-1,2,3a,4,5,9b-hexahydro-3H-benzo[e]in-
dole-3-carboxylate

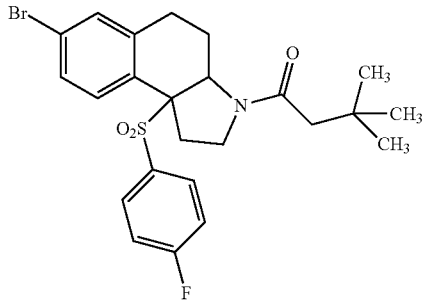 [SMILES: CC(C)(C)CC(=O)N1CCC2(S(=O)(=O)c3ccc(F)cc3)c3ccc(Br)cc3CCC12]

A solution of 7-bromo-9b-((4-fluorophenyl)sulfonyl)-2,3,3a,4,5,9b-hexahydro-1H-benzo[e]indole (2.1 g, 5.12 mmol) in DCM (50 mL) was treated with di-tert-butyl dicarbonate (1.426 mL, 6.14 mmol) and Et$_3$N (1.427 mL, 10.24 mmol). The mixture was stirred at rt for 1 h, when LCMS showed complete consumption of starting material. The mixture was diluted with DCM (100 mL) and washed sequentially with 1 M aqueous HCl and 1 M aqueous NaOH. The organic layer was dried and concentrated. The residue was purified by column chromatography on silica gel, eluting with EtOAc-hexanes, to afford tert-butyl 7-bromo-9b-((4-fluorophenyl)sulfonyl)-1,2,3a,4,5,9b-hexahydro-3H-benzo[e]indole-3-carboxylate (1.6 g, 61% yield for 3 steps). LCMS m/z 453.9 (M+H—C$_4$H$_8$)$^+$, HPLC t$_R$ 1.15 min (method A). $^1$H NMR (400 MHz, CDCl$_3$) δ 7.70-7.51 (m, 1H), 7.46-7.32 (m, 3H), 7.16-6.91 (m, 3H), 4.49-4.45 (m, 1H), 3.76-3.73 (m, 1H), 3.59-3.38 (m, 2H), 2.43-2.34 (m, 3H), 1.73 (t, J=14.8 Hz, 1H), 1.49 (s, 9H), 1.34-1.12 (m, 1H). $^{19}$F NMR (376 MHz) δ −102.6.

Step E: (3aS,9bS)-tert-butyl 7-bromo-9b-((4-fluoro-
phenyl)sulfonyl)-3a,4,5,9b-tetrahydro-1H-benzo[e]
indole-3-carboxylate and (3aR,9bR)-tert-butyl 9b-
((4-fluorophenyl)sulfonyl)-7-bromo-3a,4,5,9b-
tetrahydro-1H-benzo[e]indole-3-carboxylate Peak 1

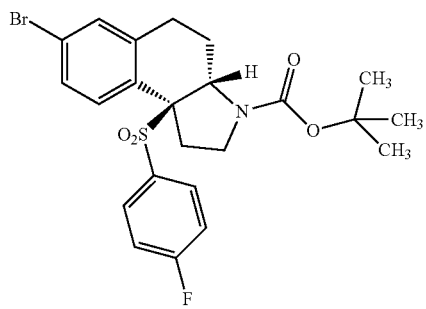

Peak 2

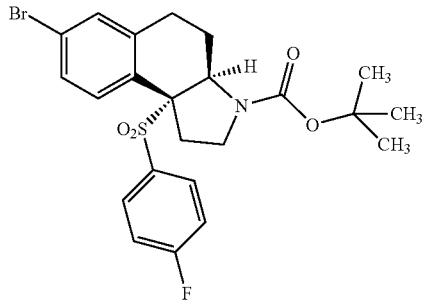

A sample of tert-butyl 9b-((4-fluorophenyl)sulfonyl)-7-bromo-3a,4,5,9b-tetrahydro-1H-benzo[e]indole-3-carboxylate (1.6 g, 3.13 mmol) was separated by chiral SFC using the following conditions: Column: Lux® Cellulose-4 (4.6× 250) mm, 5 μm (Phenomenex Inc.); column temperature 24.9° C.; CO$_2$ flow rate: 2.10 mL/min; co-solvent: 30% of 0.2% diethylamine in MeOH, flow rate 0.9 mL/min; injection volume: 10 mL. Peak 1 ((3aS,9bS)-tert-butyl 7-bromo-9b-((4-fluorophenyl)sulfonyl)-3a,4,5,9b-tetrahydro-1H-benzo[e]indole-3-carboxylate) was eluted with t$_R$ 2.79 min. Peak 2 ((3aR,9bR)-tert-butyl 9b-((4-fluorophenyl)sulfonyl)-7-bromo-3a,4,5,9b-tetrahydro-1H-benzo[e]indole-3-carboxylate, 0.7 g) was eluted with t$_R$ 3.92 min (100%). The absolute configurations of peaks 1 and 2 were determined based on single crystal X-ray analysis from the anomalous dispersion signal using the FLACK method. Analytical data for Peak 2: LCMS m/z 453.9 (M+H—C$_4$H$_8$)$^+$, HPLC t$_R$ 1.15 min (method A); $^1$H NMR (400 MHz, CDCl$_3$) δ 7.70-7.51 (m, 1H), 7.46-7.32 (m, 3H), 7.16-6.91 (m, 3H), 4.49-4.45 (m, 1H), 3.76-3.73 (m, 1H), 3.59-3.38 (m, 2H), 2.43-2.34 (m, 3H), 1.73 (t, J=14.8 Hz, 1H), 1.49 (s, 9H), 1.34-1.12 (m, 1H). $^{19}$F NMR (376 MHz) δ −102.6.

Step F: (3aR,9bR)-tert-butyl 9b-((4-fluorophenyl)
sulfonyl)-7-(1,1,1,3,3,3-hexafluoro-2-hydroxypro-
pan-2-yl)-3a,4,5,9b-tetrahydro-1H-benzo[e]indole-3-
carboxylate

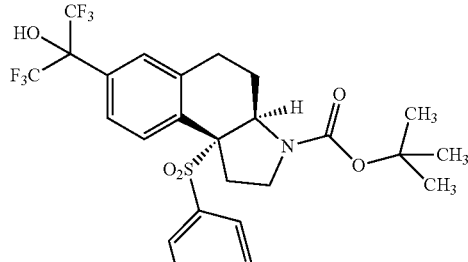

tert-Butyllithium (3 M in heptane, 376 μL, 0.940 mmol) was added dropwise to a stirred solution of (3aR,9bR)-tert-butyl 7-bromo-9b-((4-fluorophenyl)sulfonyl)-3a,4,5,9b-tetrahydro-1H-benzo[e]indole-3-carboxylate (240 mg, 0.470 mmol) (which had been dried by concentration from toluene three times) in diethyl ether (8.2 mL) under nitrogen in a dry ice acetone bath. The resulting brownish solution was stirred for 15 min at −78° C. Gaseous CF$_3$C(O)CF$_3$ (3.28 g, 19.73 mmol) was slowly added via a needle by placing the tip of the needle just above the cold solution to allow the gas to condense (about 2 min; the weight of reagent added was estimated by weighing the gas cylinder before and after the addition). The resulting mixture was stirred under nitrogen for 30 min at −78° C., then at rt for 30 min. The mixture was treated with saturated aqueous NH$_4$Cl (15 mL) and diluted with EtOAc (100 mL). The layers were separated and the aqueous layer was extracted with EtOAc (50 mL). The combined organic layers were dried and concentrated, and the residue was purified by column chromatography on silica gel, eluting with hexanes followed by a gradient to 30% EtOAc-hexanes, to provide (3aR,9bR)-tert-butyl 9b-((4-fluorophenyl)sulfonyl)-7-(1,1,1,3,3,3-hexafluoro-2-hydroxypropan-2-yl)-3a,4,5,9b-tetrahydro-1H-benzo[e]indole-3-carboxylate (200 mg, 71% yield, about 75% purity). LCMS m/z 541.8 (M+H—C$_4$H$_8$)$^+$, HPLC t$_R$ 1.08 min (method A). $^1$H NMR (400 MHz, CDCl$_3$) δ 7.75 (d, J=8.4 Hz, 1H), 7.61 (d, J=8.1 Hz, 1H), 7.41 (dd, J=8.3, 5.2 Hz, 2H), 7.38-7.32 (m, 1H), 7.04 (t, J=8.3 Hz, 2H), 4.55-4.38 (m, 1H), 3.81-3.66 (m, 1H), 3.57-3.32 (m, 2H), 2.52-2.29 (m, 3H), 1.74 (t, J=13.2 Hz, 1H), 1.52 (br. s., 9H). $^{19}$F NMR (376 MHz, CDCl$_3$) δ −102.5 (s, 1F), −75.5 (s, 6F).

Alternative Preparation of (3aR,9bR)-tert-butyl 9b-((4-fluorophenyl)sulfonyl)-7-(1,1,1,3,3,3-hexafluoro-2-hydroxypropan-2-yl)-3a,4,5,9b-tetrahydro-1H-benzo[e]indole-3-carboxylate The same procedure was used, but starting with (3aR,9bR)-tert-butyl 9b-((4-fluorophenyl)sulfonyl)-7-iodo-3a,4,5,9b-tetrahydro-1H-benzo[e]indole-3-carboxylate (prepared by following the procedures of Steps A through E above, but starting from Intermediate 1 instead of Intermediate 2; 1.1 g, 1.973 mmol) to provide (3aR,9bR)-tert-butyl 9b-((4-fluorophenyl)sulfonyl)-7-(1,1,1,3,3,3-hexafluoro-2-hydroxypropan-2-yl)-3a,4,5,9b-tetrahydro-1H-benzo[e]indole-3-carboxylate (0.7 g, 70% yield, about 80% purity).

Step G: (3aR,9bR)-tert-butyl 9b-((4-fluorophenyl)sulfonyl)-7-(perfluoropropan-2-yl)-3a,4,5,9b-tetrahydro-1H-benzo[e]indole-3-carboxylate

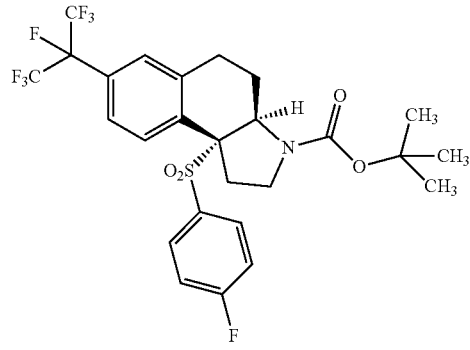 [SMILES: CC(C)(C)OC(=O)N1CC[C@@]2(S(=O)(=O)c3ccc(F)cc3)c3ccc(C(F)(C(F)(F)F)C(F)(F)F)cc3CC[C@@H]12]

DAST (2.92 mL, 22.09 mmol) was added to a stirred solution of (3aR,9bR)-tert-butyl 9b-((4-fluorophenyl)sulfonyl)-7-(1,1,1,3,3,3-hexafluoro-2-hydroxypropan-2-yl)-3a,4,5,9b-tetrahydro-1H-benzo[e]indole-3-carboxylate (1.1 g, 1.841 mmol) in 1,2-dichloroethane (18.41 mL) under N$_2$ at rt. The reaction vessel was sealed and heated with stirring at 60° C. After 15 h, LCMS showed only partial consumption of the starting material. Additional DAST (2.92 mL, 22.09 mmol) was added and the mixture was stirred at 60° C. for 4 h more. The mixture was cooled to rt, carefully quenched with MeOH (1 mL), diluted with EtOAc (160 mL) and washed with saturated aqueous NaHCO$_3$. The aqueous phase was separated and extracted with EtOAc (100 mL). The combined organic phases were washed with brine (50 mL), dried and concentrated. The residue was purified by column chromatography on silica gel, eluting with EtOAc-hexanes (gradient from 5-40%), to provide (3aR,9bR)-tert-butyl 9b-((4-fluorophenyl)sulfonyl)-7-(perfluoropropan-2-yl)-3a,4,5,9b-tetrahydro-1H-benzo[e]indole-3-carboxylate (800 mg, 72.5% yield). LCMS m/z 544.0 (M+H—C$_4$H$_8$)$^+$, HPLC t$_R$ 1.21 min (method A).

Alternative Preparation of (3aR,9bR)-tert-butyl 9b-((4-fluorophenyl)sulfonyl)-7-(perfluoropropan-2-yl)-3a,4,5,9b-tetrahydro-1H-benzo[e]indole-3-carboxylate Activated copper was prepared by adding zinc dust (24.57 g, 376 mmol) portionwise with stirring to a solution of copper(II) sulfate (45.09 g, 283 mmol) in water (250 mL) over 10 min. The mixture was stirred 10 min longer, then the supernatant was decanted from the red precipitate. This was washed twice with water by decantation, then was stirred with 1 M aqueous HCl (400 mL) for 2.5 h. The supernatant was decanted and the precipitate was washed with water by decantation until the pH of the supernatant was about 7. The solid was stored under water and an inert atmosphere (nitrogen or argon). For use the solid was washed twice by decantation with MeOH, then twice with diethyl ether, and dried under vacuum.

A mixture of activated copper (3.5 g, 55 mmol) and (3aR,9bR)-tert-butyl 9b-((4-fluorophenyl)sulfonyl)-7-iodo-3a,4,5,9b-tetrahydro-1H-benzo[e]indole-3-carboxylate (prepared by following the procedures of Steps A through E above, but starting from Intermediate 1 instead of Intermediate 2; 4 g, 7.2 mmol) in dry DMF (18 mL) was purged with nitrogen, treated with 1,1,1,2,3,3,3-heptafluoro-2-iodopropane (4.6 mL, 32 mmol) and heated at 120° C. in a sealed reaction vessel. After 4 h the mixture was cooled to rt, diluted with EtOAc and filtered through Celite. The filtrate was washed 4 times with brine, dried and concentrated. The residue was purified by column chromatography on silica, eluting with EtOAc-hexanes, to provide (3aR,9bR)-tert-butyl 9b-((4-fluorophenyl)sulfonyl)-7-(perfluoropropan-2-yl)-3a,4,5,9b-tetrahydro-1H-benzo[e]indole-3-carboxylate (3.6 g, 84% yield).

Step H: (3aR,9bR)-9b-((4-fluorophenyl)sulfonyl)-7-(perfluoropropan-2-yl)-2,3,3a,4,5,9b-hexahydro-1H-benzo[e]indole Hydrochloride

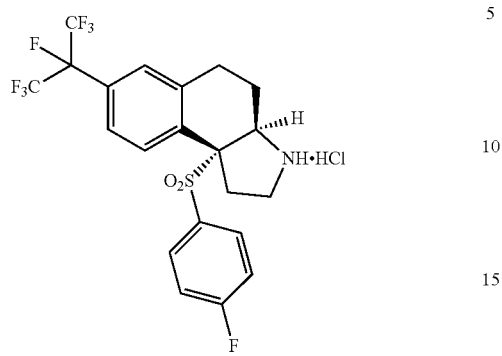

A solution of (3aR,9bR)-tert-butyl 9b-((4-fluorophenyl)sulfonyl)-7-(perfluoropropan-2-yl)-3a,4,5,9b-tetrahydro-1H-benzo[e]indole-3-carboxylate (250 mg, 0.417 mmol) in DCM (4.2 mL) was treated with HCl (4 M in 1,4-dioxane, 4.2 mL, 16.68 mmol). After 1 h at rt, the mixture was concentrated to provide (3aR,9bR)-9b-((4-fluorophenyl)sulfonyl)-7-(perfluoropropan-2-yl)-2,3,3a,4,5,9b-hexahydro-1H-benzo[e]indole, HCl (225 mg). LCMS m/z 500.0 (M+H)$^+$, HPLC $t_R$: 0.88 min (method A).

The Intermediates in Table 2 were prepared using procedures (or similar procedures) used in the preparation of Intermediate 8, starting from an appropriate vinylic sulfone.

TABLE 2

| Intermediate number | Structure | LCMS m/z observed | HPLC $t_R$ (min) | HPLC method |
|---|---|---|---|---|
| 9 | (structure shown) Homochiral from peak 2 | 516.0 (M + H)$^+$ | 0.94 | A |
| 10 | (structure shown) Homochiral from peak 2 | 502.1 (M + H)$^+$ | 0.84 | A |

TABLE 2-continued
| Intermediate number | Structure | LCMS m/z observed | HPLC $t_R$ (min) | HPLC method |
|---|---|---|---|---|
| 11 | 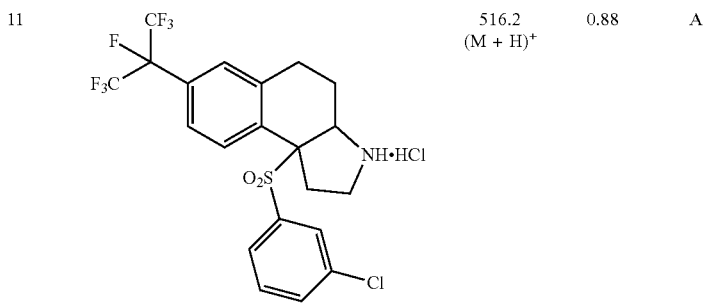 Homochiral from peak 2 | 516.2 (M + H)+ | 0.88 | A |
| 12 | 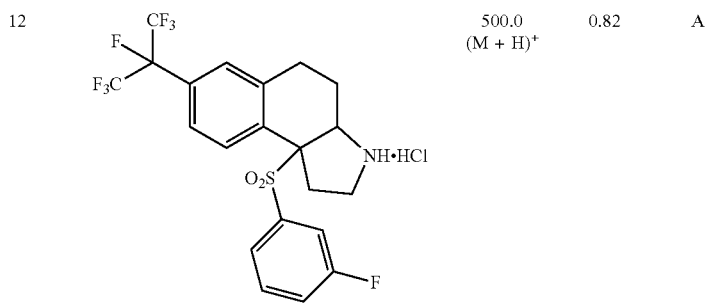 Homochiral from peak 2 | 500.0 (M + H)+ | 0.82 | A |
| 13 | 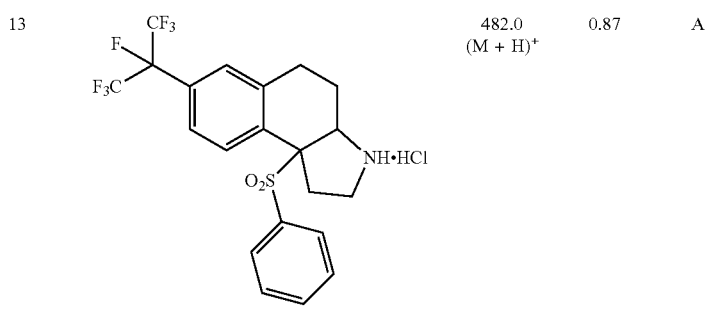 Homochiral from peak 2 | 482.0 (M + H)+ | 0.87 | A |

Intermediate 14

9b-((4-fluorophenyl)sulfonyl)-7-(perfluoropropan-2-yl)-2,3,3a,4,5,9b-hexahydro-1H-pyrrolo[2,3-c]quinoline Dihydrochloride

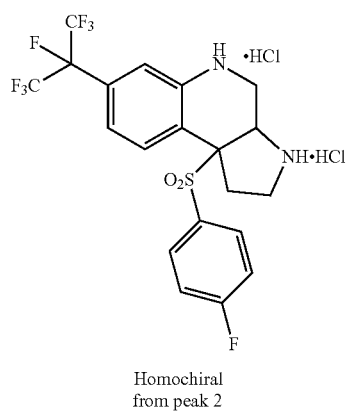

Homochiral
from peak 2

Step A: tert-butyl 7-bromo-4-((4-fluorophenyl)sulfonyl)quinoline-1(2H)-carboxylate

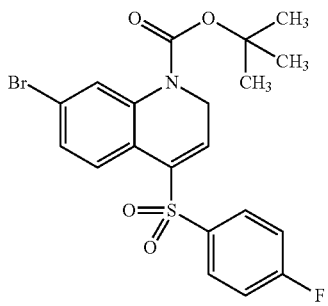 [SMILES: CC(C)(C)OC(=O)N1CC=C(S(=O)(=O)c2ccc(F)cc2)c2ccc(Br)cc21]

A solution of 7-bromo-2,3-dihydroquinolin-4(1H)-one (8 g, 35 mmol), 4-fluorobenzenethiol (7.9 mL, 74 mmol) and absolute ethanol (44 mL) was cooled with an ice-water bath. HCl gas was bubbled through the mixture until saturation was reached (as indicated by the formation of a white precipitate). The mixture was stirred on the ice-water bath for 1 h and at rt for 1 h more. The mixture was concentrated and the resulting oil was dissolved in DCM (250 mL) and washed with 1 M aqueous NaOH. The organic phase was dried and concentrated to give crude 7-bromo-4,4-bis((4-fluorophenyl)thio)-1,2,3,4-tetrahydroquinoline as a solid (16.4 g, 100% yield). HPLC $t_R$ 1.27 min (method A).

This material was dissolved in 1,4-dioxane (180 mL) and treated with 4-dimethylaminopyridine (13 g, 106 mmol) and di-tert-butyl dicarbonate (25 mL, 106 mmol). The mixture was stirred at rt for 16, then was diluted with EtOAc and washed twice with 1 M aqueous HCl. The organic phase was dried and concentrated to afford tert-butyl 7-bromo-4,4-bis((4-fluorophenyl)thio)-3,4-dihydroquinoline-1(2H)-carboxylate (20 g, 100% yield). HPLC $t_R$ 1.37 min (method A).

This material was dissolved in DCM (350 mL) and cooled with an ice-water bath. mCPBA (22 g, 172 mmol) was added and the mixture was stirred for 1 h. Additional mCPBA (22 g, 172 mmol) was added, and stirring was continued for 1 h more. The mixture was filtered to remove the insoluble material, and the filtrate was treated with 10% aqueous $Na_2S_2O_3$ (120 mL) and stirred for 5 min. The organic phase was separated, washed sequentially with 10% aqueous $Na_2S_2O_3$ (2×120 mL), 10% aqueous $Na_2CO_3$ (3×200 mL) and brine (150 mL), dried and concentrated to give crude tert-butyl 7-bromo-4-((4-fluorophenyl)sulfonyl)quinoline-1(2H)-carboxylate (17 g) which was used without further purification. LCMS m/z 468.0 (M+H+MeCN)$^+$, HPLC $t_R$ 1.16 min (method A).

Step B: tert-butyl 7-bromo-4-((4-fluorophenyl)sulfonyl)-3-((2-hydroxyethyl)amino)-3,4-dihydroquinoline-1(2H)-carboxylate

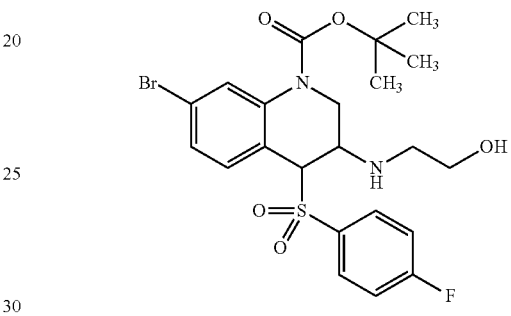

A solution of tert-butyl 7-bromo-4-((4-fluorophenyl)sulfonyl)quinoline-1(2H)-carboxylate (16.6 g, 35 mmol) in THF (700 mL) was stirred on an ice-water bath and treated with 2-aminoethanol (11 mL, 177 mmol). The mixture was stirred at about 5° C. for 30 min, then was concentrated. The resulting oil was dissolved in EtOAc (750 mL) and the solution washed three times with brine, dried and concentrated to provide tert-butyl 7-bromo-4-((4-fluorophenyl)sulfonyl)-3-((2-hydroxyethyl)amino)-3,4-dihydroquinoline-1(2H)-carboxylate (19.5 g) which was used without further purification. LCMS m/z 529.0 (M+H)$^+$, HPLC $t_R$ 0.89 min (method A).

Step C: tert-butyl 7-bromo-9b-((4-fluorophenyl)sulfonyl)-1,2,3,3a,4,9b-hexahydro-5H-pyrrolo[2,3-c]quinoline-5-carboxylate

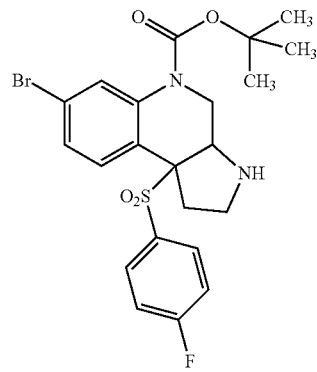 [SMILES: CC(C)(C)OC(=O)N1CC2NCCC2(S(=O)(=O)c2ccc(F)cc2)c2ccc(Br)cc21]

A solution of tert-butyl 7-bromo-4-((4-fluorophenyl)sulfonyl)-3-((2-hydroxyethyl)amino)-3,4-dihydroquinoline- 1(2H)-carboxylate (19 g, 35 mmol) in DCM (650 mL) was treated with MsCl (3.3 mL, 43 mmol), then with Et$_3$N (5.9 mL, 43 mmol) at rt. The mixture was stirred for 30 min, when LCMS showed complete conversion to the methanesulfonate derivative; LCMS m/z 607.0 (M+1)$^+$, HPLC t$_R$ 0.94 min (method A). The mixture was treated with a solution of potassium tert-butoxide (20 g, 180 mmol) in THF (150 mL) and stirred for 30 min. The mixture was then treated with a 1:1 mixture of water and saturated brine (100 mL) and diluted with EtOAc (1 L). The organic phase was separated and washed 3 times with brine, dried and concentrated to give crude tert-butyl 7-bromo-9b-((4-fluorophenyl)sulfonyl)-2,3,3a,4-tetrahydro-1H-pyrrolo[2,3-c]quinoline-5-carboxylate (19 g), used without further purification. LCMS m/z 511.0 (M+1)$^+$, HPLC t$_R$ 0.85 min (method A).

Step D: di-tert-butyl 7-bromo-9b-((4-fluorophenyl)sulfonyl)-1,3a,4,9b-tetrahydro-3H-pyrrolo[2,3-c]quinoline-3,5(2H)-dicarboxylate, Two Homochiral Enantiomers centrated. The residue was purified by column chromatography on silica gel, eluting with EtOAc-hexanes, to provide di-tert-butyl 7-bromo-9b-((4-fluorophenyl)sulfonyl)-1,3a,4,9b-tetrahydro-3H-pyrrolo[2,3-c]quinoline-3,5(2H)-dicarboxylate (7.6 g, 35% overall yield from 7-bromo-2,3-dihydroquinolin-4(1H)-one).

This material was separated by chiral SFC using the following conditions: Column: Chiralcel® OD-H 50×250 mm, 5 μm (Chiral Technologies Inc.); column temperature 35° C.; pressure 100 bars; mobile phase CO$_2$-MeOH (90:10); flow rate 300 mL/min; injection volume 0.9 mL. Peak 1 was eluted with t$_R$ 3.51 min. Peak 2 (2.6 g) was eluted with t$_R$ 4.01 min. LCMS m/z 454.9 (M+2H—CO$_2$C$_4$H$_9$—C$_4$H$_9$)$^+$, HPLC t$_R$ 1.22 min (method A).

Step E: di-tert-butyl 9b-((4-fluorophenyl)sulfonyl)-7-(perfluoropropan-2-yl)-1,3a,4,9b-tetrahydro-3H-pyrrolo[2,3-c]quinoline-3,5(2H)-dicarboxylate (Homochiral)

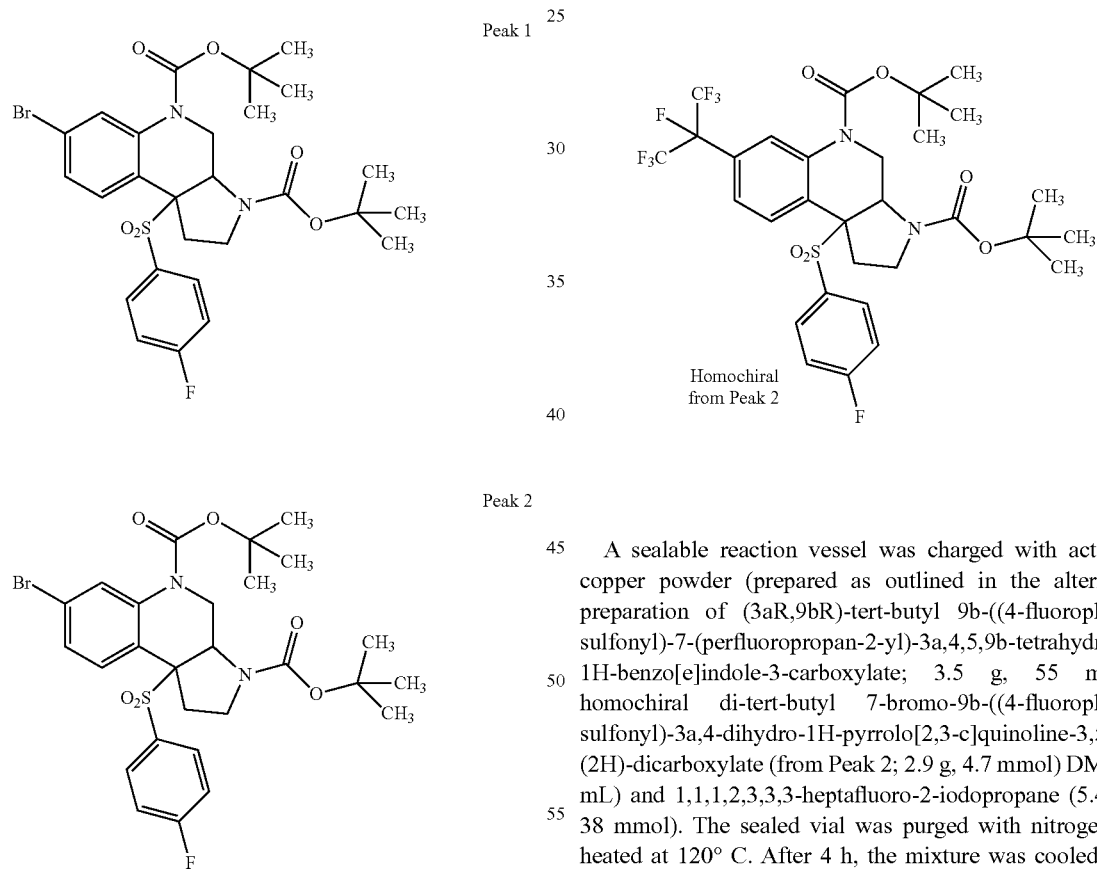

A solution of tert-butyl 7-bromo-9b-((4-fluorophenyl)sulfonyl)-2,3,3a,4-tetrahydro-1H-pyrrolo[2,3-c]quinoline-5-carboxylate (18 g, 35 mmol) in DCM (350 mL) was treated with di-tert-butyl dicarbonate (12 mL, 53 mmol) and diisopropylethylamine (18.5 mL, 106 mmol). The mixture was stirred at rt for 1 h, then was diluted with DCM (100 mL) and washed sequentially with 1 M aqueous HCl and 1 M aqueous NaOH. The organic phase was dried and con- A sealable reaction vessel was charged with activated copper powder (prepared as outlined in the alternative preparation of (3aR,9bR)-tert-butyl 9b-((4-fluorophenyl)sulfonyl)-7-(perfluoropropan-2-yl)-3a,4,5,9b-tetrahydro-1H-benzo[e]indole-3-carboxylate; 3.5 g, 55 mmol), homochiral di-tert-butyl 7-bromo-9b-((4-fluorophenyl)sulfonyl)-3a,4-dihydro-1H-pyrrolo[2,3-c]quinoline-3,5(2H)-dicarboxylate (from Peak 2; 2.9 g, 4.7 mmol) DMF (16 mL) and 1,1,1,2,3,3,3-heptafluoro-2-iodopropane (5.4 mL, 38 mmol). The sealed vial was purged with nitrogen and heated at 120° C. After 4 h, the mixture was cooled to rt, diluted with EtOAc and filtered through Celite. The filtrate was washed 4 times with brine, dried and concentrated. The residue was purified by column chromatography on silica gel, eluting with EtOAc-hexanes, to provide homochiral di-tert-butyl 9b-((4-fluorophenyl)sulfonyl)-7-(perfluoropropan-2-yl)-3a,4-dihydro-1H-pyrrolo[2,3-c]quinoline-3,5(2H)-dicarboxylate (712 mg, 22% yield) along with recovered starting material (1.1 g). LCMS m/z 545.0 (M+2H—CO$_2$C$_4$H$_9$—C$_4$H$_9$)$^+$, HPLC t$_R$ 1.27 min (method A).

Step F: 9b-((4-fluorophenyl)sulfonyl)-7-(perfluoropropan-2-yl)-2,3,3a,4,5,9b-hexahydro-1H-pyrrolo[2,3-c]quinoline Dihydrochloride

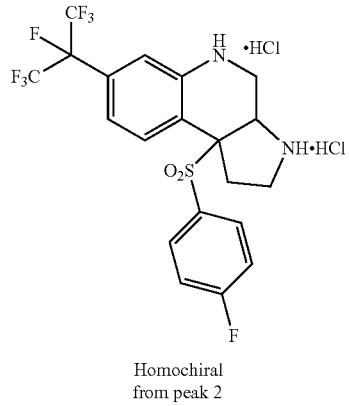

Homochiral
from peak 2

A solution of di-tert-butyl 9b-((4-fluorophenyl)sulfonyl)-7-(perfluoropropan-2-yl)-3a,4-dihydro-1H-pyrrolo[2,3-c]quinoline-3,5(2H)-dicarboxylate (from Peak 2; 358 mg, 0.511 mmol) in DCM (2.5 mL) was treated with HCl (4 M in 1,4-dioxane; 2.5 mL, 10 mmol). The mixture was allowed to stand at rt for 1 h, then was concentrated to provide 9b-((4-fluorophenyl)sulfonyl)-7-(perfluoropropan-2-yl)-2,3,3a,4,5,9b-hexahydro-1H-pyrrolo[2,3-c]quinoline dihydrochloride (290 mg, 99% yield). LCMS m/z 501.1 (M+1)$^+$, HPLC $t_R$ 0.89 min (method A). $^1$H NMR (500 MHz, DMSO-$d_6$) δ 7.52 (d, J=8.3 Hz, 1H), 7.44 (dd, J=8.3, 5.1 Hz, 2H), 7.26 (t, J=8.6 Hz, 2H), 6.85 (d, J=8.2 Hz, 1H), 6.74 (s, 1H), 6.27 (br. s., 1H), 3.77 (t, J=5.5 Hz, 1H), 3.13-3.05 (m, 1H), 3.01-2.91 (m, 1H), 2.91-2.74 (m, 3H), 2.55 (s, 1H), 2.46-2.32 (m, 1H). $^{19}$F NMR (376 MHz, DMSO-$d_6$) δ −104.9 (s, 1F), −77.3 (m, 1F), −77.0 (s, 6F).

Intermediate 15

1-iminohexahydro-1λ$^6$-thiopyran-4-carboxylic Acid 1-oxide, Mixture of Cis and Trans Isomers

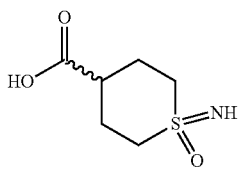 [SMILES: N=S1(=O)CCC(C(=O)O)CC1]

Step A: methyl tetrahydro-2H-thiopyran-4-carboxylate 1-Oxide, Mixture of Cis and Trans Isomers

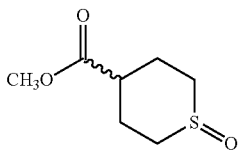

A solution of methyl tetrahydro-2H-thiopyran-4-carboxylate (2.00 g, 12.5 mmol) in MeOH (120 mL) was treated with a solution of sodium periodate (2.94 g, 13.7 mmol) in water (30 mL), and the resulting mixture was stirred at rt. After 18.5 h, the mixture was filtered and the collected solid was rinsed with MeOH. The filtrate was concentrated to remove most of the methanol, and the resulting aqueous phase was treated with solid NaCl and extracted 3 times with EtOAc. The combined organic phases were dried and concentrated to provide a mixture of cis and trans isomers of methyl tetrahydro-2H-thiopyran-4-carboxylate 1-oxide (948 mg, 43% yield). LCMS m/z 177.2 (M+H)$^+$, HPLC $t_R$ 0.58 min (Method A). $^1$H NMR (499 MHz, CDCl$_3$) δ 3.74 (2s, 3H), 3.11-2.98 (m, 2H), 2.80-2.72 (m, 1H), 2.71-2.47 (m, 4H), 2.09-1.93 (m, 2H). Additional methyl tetrahydro-2H-thiopyran-4-carboxylate 1-oxide (717 mg, 33% yield) was obtained by saturation of the aqueous phase with NaCl, followed by additional extraction with EtOAc (4 times), and drying and concentration of the combined organic phases.

Step B: methyl 1-iminohexahydro-1λ$^6$-thiopyran-4-carboxylate 1-oxide, Mixture of Cis and Trans Isomers

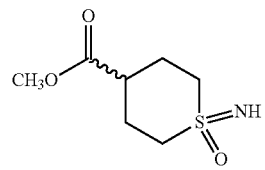

A mixture of methyl tetrahydro-2H-thiopyran-4-carboxylate 1-oxide (mixture of cis and trans isomers; 0.947 g, 5.37 mmol), ammonium carbamate (1.68 g, 21.5 mmol) and iodobenzene diacetate (5.19 g, 16.1 mmol) in MeOH (60 mL) was sonicated briefly and stirred vigorously at rt. After 2 h, additional ammonium carbamate (0.252 g, 3.22 mmol) and iodobenzene diacetate (0.779 g, 2.42 mmol) were added and stirring was continued for 90 min more. The mixture was concentrated to provide a mixture of a light yellow sludge and an immiscible colorless liquid. The mixture was washed twice with hexane by decantation and dried under vacuum. The residue was triturated and stirred in EtOAc, filtered, and the collected solid was washed with additional EtOAc. The filtrate was concentrated to provide a mixture of cis and trans isomers of methyl 1-iminohexahydro-1λ$^6$-thiopyran-4-carboxylate 1-oxide as a light yellow oil which gradually formed a pasty solid while drying under vacuum (1.37 g). This material, contaminated with byproducts derived from iodobenzene diacetate, was used without further purification. LCMS m/z 192.2 (M+H)$^+$, $t_R$ 0.47 min (Method A). $^1$H NMR (499 MHz, CDCl$_3$) δ 3.75 (2s, 3H), 3.28-3.15 (m, 2H), 3.13-3.01 (m, 2H), 2.73-2.60 (m, 1H), 2.46-2.30 (m, 4H.)

Step C: 1-iminohexahydro-1λ6-thiopyran-4-carboxylic Acid 1-oxide, Mixture of Cis and Trans Isomers

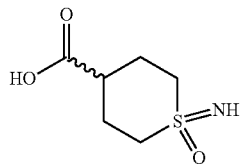 [SMILES: N=S1(=O)CCC(C(=O)O)CC1]

A solution of crude methyl 1-iminohexahydro-1λ6-thiopyran-4-carboxylate 1-oxide (mixture of cis and trans isomers; 0.60 g) in THF (18 mL) and MeOH (6 mL) was treated with a solution of LiOH monohydrate (0.277 g, 6.60 mmol) in water (6 mL) and stirred at rt. After 17 h, the mixture was treated with 1 M aqueous HCl (6.6 mL, resulting pH~3-4) and concentrated under vacuum. The gummy residue was suspended in benzene with a small amount of water and heated under a Dean-Stark trap at 100-110° C. for about 2 h, then the mixture was concentrated and dried under vacuum to provide a mixture of cis and trans isomers of 1-iminohexahydro-1λ6-thiopyran-4-carboxylic acid 1-oxide, mixed with LiCl, as a light orange glassy solid (928 mg) which was used without further purification, assuming about 60% purity. LCMS m/z 178.2 (M+H)+, $t_R$ 0.24-0.26 min (Method A).

Intermediate 16

1-((tert-butoxycarbonyl)imino)hexahydro-1λ6-thiopyran-4-carboxylic Acid 1-oxide, Mixture of Cis and Trans Isomers

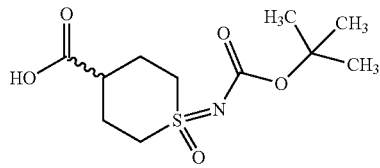 [SMILES: CC(C)(C)OC(=O)N=S1(=O)CCC(C(=O)O)CC1]

Step A: methyl 1-((tert-butoxycarbonyl)imino)hexahydro-1λ6-thiopyran-4-carboxylate 1-oxide, Mixture of Cis and Trans Isomers

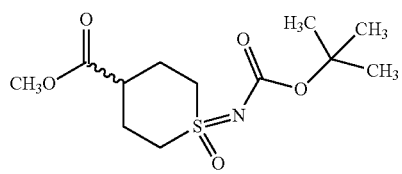

A solution of methyl 1-iminohexahydro-1λ6-thiopyran-4-carboxylate 1-oxide (mixture of cis and trans isomers, Intermediate 15 Step B; 1.29 g, 5.07 mmol) in THF (35 mL) was stirred under argon at rt and treated with sodium hydride (60% in mineral oil; 0.355 g, 8.88 mmol) causing a mild exotherm and gas evolution. The mixture was then treated with di-tert-butyl dicarbonate (3.05 g, 14.0 mmol) and stirred at rt. After 20.5 h, the mixture was treated with saturated aqueous NH4Cl and extracted 3 times with EtOAc. The combined organic phases were washed with saturated brine, dried and concentrated. The residue was subjected to column chromatography on silica gel (120 g), eluting with EOAc-hexanes (gradient from 0-100%), to provide a mixture of cis and trans isomers of methyl 1-((tert-butoxycarbonyl)imino)hexahydro-1λ6-thiopyran-4-carboxylate 1-oxide as a light yellow sticky solid (391 mg, 26% yield). LCMS m/z 292.2 (M+H)+, HPLC $t_R$ 0.74 min (Method A). 1H NMR (499 MHz, CDCl3) δ 3.77 (2s, 3H), 3.75-3.66 (m, 1H), 3.57-3.42 (m, 2H), 3.28 (ddd, J=13.7, 8.5, 4.7 Hz, 1H), 2.77-2.63 (m, 1H), 2.52-2.32 (m, 4H), 1.51 (2s, 9H).

Step B: 1-((tert-butoxycarbonyl)imino)hexahydro-1λ6-thiopyran-4-carboxylic Acid 1-oxide, Mixture of Cis and Trans Isomers

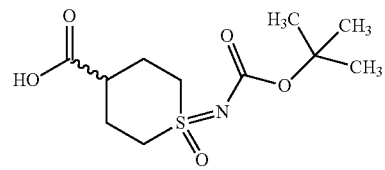 [SMILES: CC(C)(C)OC(=O)N=S1(=O)CCC(C(=O)O)CC1]

A solution of methyl 1-((tert-butoxycarbonyl)imino)hexahydro-1λ6-thiopyran-4-carboxylate 1-oxide (mixture of cis and trans isomers; 175 mg, 0.601 mmol) in THF (3 mL) and MeOH (1 mL) was treated with a solution of LiOH monohydrate (50.4 mg, 1.20 mmol) in water (1 mL) and the mixture was stirred at rt. After 21.5 h, the mixture was treated with 1 M aqueous HCl (1.2 mL) and concentrated under a nitrogen stream to remove the organic solvents. The resulting solid was collected by filtration, rinsed with water and dried under vacuum to provide a mixture of cis and trans isomers of 1-((tert-butoxycarbonyl)imino)hexahydro-1λ6-thiopyran-4-carboxylic acid 1-oxide as a white solid (66 mg, 40% yield). LCMS m/z 278.2 (M+H)+, HPLC $t_R$ 0.60 and 0.61 min (Method A). 1H NMR (499 MHz, CDCl3+1 drop of DMSO-d6) δ 3.78-3.61 (m, 1H), 3.60-3.40 (m, 2H), 3.30 (br dd, J=12.7, 6.0 Hz, 1H), 2.78-2.63 (m, 1H), 2.49-2.28 (m, 3H), 1.49 (2s, 9H); ratio of isomers about 43:57. Further concentration of the filtrate followed by collection of the resulting solid by filtration and drying under vacuum provided additional 1-((tert-butoxycarbonyl)imino)hexahydro-1λ6-thiopyran-4-carboxylic acid 1-oxide as a white solid (27 mg, 16%); ratio of isomers about 25:75 by NMR.

Intermediate 17 tetrahydro-2H-thiopyran-4-carboxylic Acid

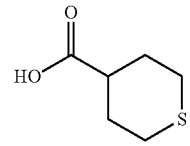

A solution of methyl tetrahydro-2H-thiopyran-4-carboxylate (2.00 g, 12.48 mmol) in THF (6 mL), MeOH (2 mL) and water (2 mL) was treated with LiOH monohydrate (1.048 g, 24.96 mmol) and the mixture was stirred at rt. After 17.5 h, the mixture was treated with 1 M aqueous HCl (2.2 mL). Most of the organic solvents were removed by stirring under a nitrogen stream, providing a thick white suspension. The precipitate was collected by filtration, washed with water and dried under vacuum to provide tetrahydro-2H-thiopyran-4-carboxylic acid as a white solid (1.563 g, 86% yield). $^1$H NMR (400 MHz, CDCl$_3$) δ 2.77-2.63 (m, 4H), 2.46 (tt, J=10.8, 3.4 Hz, 1H), 2.32-2.21 (m, 2H), 1.98-1.84 (m, 2H).

Intermediate 18

4-methyltetrahydro-2H-thiopyran-4-carboxylic Acid

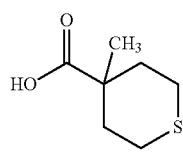

Step A: methyl 4-methyltetrahydro-2H-thiopyran-4-carboxylate

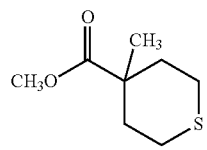

A mixture of lithium diisopropylamide (2 M in hexane-THF; 4.06 mL, 8.11 mmol) and THF (15 mL), stirred at −78° C. under argon, was treated dropwise with a solution of methyl tetrahydro-2H-thiopyran-4-carboxylate (1.00 g, 6.24 mmol) in THF (5 mL) over about 10 min. After stirring for 2 h at −78° C., the mixture was treated dropwise with iodomethane (0.51 mL, 8.11 mmol) over 2-3 min. The cooling bath was removed and the mixture was allowed to warm to rt and stirred overnight. After 21 h, the mixture was treated with saturated aqueous NH$_4$Cl and extracted 3 times with EtOAc. The combined organic phases were washed with saturated brine, dried and concentrated. The residue was subjected to column chromatography on silica gel (80 g), eluting with EtOAc-hexanes (gradient 0-15%), to provide methyl 4-methyltetrahydro-2H-thiopyran-4-carboxylate as a colorless liquid (899 mg, 83% yield). LCMS m/z 175.2 (M+H)$^+$, HPLC $t_R$ 0.82 min (Method A). $^1$H NMR (499 MHz, CDCl$_3$) δ 3.72 (s, 3H), 2.73-2.65 (m, 2H), 2.59-2.52 (m, 2H), 2.42-2.33 (m, 2H), 1.60 (ddd, J=13.8, 11.0, 3.2 Hz, 2H), 1.20 (s, 3H).

Step B: 4-methyltetrahydro-2H-thiopyran-4-carboxylic Acid

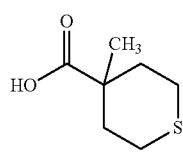

A solution of methyl 4-methyltetrahydro-2H-thiopyran-4-carboxylate (400 mg, 2.30 mmol) in THF (1.2 mL), MeOH (0.4 mL) and water (0.4 mL) was treated with LiOH monohydrate (193 mg, 4.59 mmol) and the mixture was stirred at rt. After 40 h, the mixture was treated with 1 M aqueous HCl (5 mL) and concentrated to remove most of the organic solvents. The resulting solid was collected by filtration, washed with water and dried under vacuum to provide 4-methyltetrahydro-2H-thiopyran-4-carboxylic acid as a white solid (176 mg). Additional 4-methyltetrahydro-2H-thiopyran-4-carboxylic acid (115 mg) was isolated by further concentration of the aqueous filtrate, for a total yield of 79%. LCMS m/z 161.2 (M+H)$^+$, HPLC $t_R$ 0.67 min (Method A). $^1$H NMR (499 MHz, CDCl$_3$) δ 2.82-2.72 (m, 2H), 2.62-2.53 (m, 2H), 2.43-2.34 (m, 2H), 1.64 (ddd, J=13.9, 11.0, 3.3 Hz, 2H), 1.27 (s, 3H).

Intermediate 19

4-hydroxytetrahydro-2H-thiopyran-4-carboxylic Acid

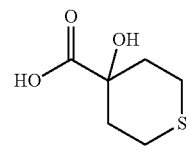

A solution of ethyl 4-hydroxytetrahydro-2H-thiopyran-4-carboxylate (prepared according to the procedures of PCT Pat. Appl. 2015/124541; 150 mg, 0.788 mmol) in THF (1.2 mL) and MeOH (0.4 mL) was treated with a solution of LiOH monohydrate (99 mg, 2.365 mmol) in water (0.4 mL) and the mixture was stirred at rt. After 3 h the mixture was concentrated and the aqueous residue was treated with 1 M aqueous HCl (2.5 mL). The resulting solution was concentrated under vacuum, and the residue was concentrated twice from toluene and dried under vacuum to provide a mixture of 4-hydroxytetrahydro-2H-thiopyran-4-carboxylic acid and LiCl (about 55:45 by weight) as a white solid (225 mg, 97% yield), used without further purification. LCMS m/z 161.2 (M−H)$^-$, HPLC $t_R$ 0.55-0.65 min (broad; method B). $^1$H NMR (499 MHz, DMSO-d$_6$) δ 3.01-4.10 (m, 1H), 2.79-2.93 (m, 2H), 2.37 (dt, J=13.5, 3.6 Hz, 2H), 1.87-1.97 (m, 2H), 1.78-1.87 (m, 2H).

Intermediate 20

4-cyanotetrahydro-2H-thiopyran-4-carboxylic Acid

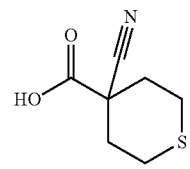

A solution of tert-butyl 4-cyanotetrahydro-2H-thiopyran-4-carboxylate (prepared according to the procedures of PCT Pat. Appl. 2013/134660; 1.00 g, 4.40 mmol) in DCM (5 mL) was treated with TFA (5 mL) and allowed to stand at rt. After 2 h, the mixture was concentrated, and the residue was concentrated twice from toluene and dried under vacuum to provide 4-cyanotetrahydro-2H-thiopyran-4-carboxylic acid as a tan gummy solid (812 mg, assumed 90% purity, 97% yield), used without further purification. LCMS m/z 170.2 (M−H)⁻, HPLC $t_R$ 0.29 min (method B). ¹H NMR (499 MHz, DMSO-d$_6$) δ 12.08-15.50 (m, 1H), 2.66-2.85 (m, 4H), 2.34 (dt, J=13.9, 2.9 Hz, 2H), 1.96-2.07 (m, 2H).

Example 1

(9b-((3-fluorophenyl)sulfonyl)-7-(perfluoropropan-2-yl)-1,2,3a,4,5,9b-hexahydro-3H-benzo[e]indol-3-yl)(1-imino-1-oxidohexahydro-1λ⁶-thiopyran-4-yl)methanone, Mixture of Cis and Trans Isomers

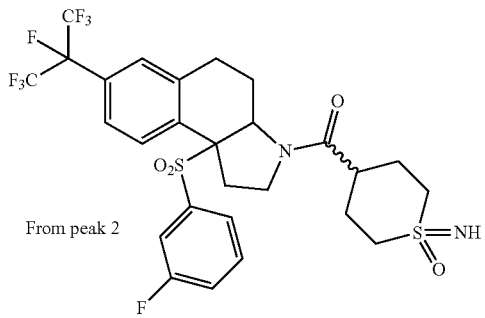 [SMILES: N=S1(=O)CCC(C(=O)N2CCC3(S(=O)(=O)c4cccc(F)c4)c4ccc(C(F)(C(F)(F)F)C(F)(F)F)cc4CCC23)CC1]

From peak 2

A solution of homochiral 9b-((3-fluorophenyl)sulfonyl)-7-(perfluoropropan-2-yl)-2,3,3a,4,5,9b-hexahydro-1H-benzo[e]indole hydrochloride (from peak 2, Intermediate 12; 30 mg, 0.056 mmol) and 1-iminohexahydro-1λ⁶-thiopyran-4-carboxylic acid 1-oxide (mixture of cis and trans isomers, Intermediate 15; 16.5 mg, 0.056 mmol) in DMF (0.8 mL) was treated with DIPEA (0.029 mL, 0.168 mmol) and BOP (49.5 mg, 0.112 mmol) and stirred at rt. After 15 h, the mixture was purified by preparative HPLC (Method E, gradient 45-90% B) to provide a mixture of cis and trans isomers of (9b-((3-fluorophenyl)sulfonyl)-7-(perfluoropropan-2-yl)-1,2,3a,4,5,9b-hexahydro-3H-benzo[e]indol-3-yl)(1-imino-1-oxidohexahydro-1λ⁶-thiopyran-4-yl)methanone (12 mg, 31% yield). LCMS m/z 659.4 (M+H)⁺, HPLC $t_R$ 1.89 min (Method B). ¹H NMR (500 MHz, DMSO-d$_6$) δ 7.84-7.98 (m, 1H), 7.67 (br d, J=7.93 Hz, 1H), 7.46-7.63 (m, 2H), 7.20-7.40 (m, 2H), 6.59-6.85 (m, 1H), 4.52-4.78 (m, 1H), 3.63-3.91 (m, 2H), 2.96-3.56 (m, 4H), 2.57-2.86 (m, 3H), 1.14-2.35 (m, 8H).

The Examples in Table 3 were prepared by following procedures used to prepare Example 1 or similar procedures, starting with an appropriate amine intermediate.

TABLE 3

| Ex. # | Structure | LCMS m/z observed | HPLC $t_R$ (min) | HPLC method |
|---|---|---|---|---|
| 2 | (structure shown; From peak 2) | 675.1, 677.1 (M + H)⁺ | 2.04 | B |
| 3 | (structure shown; From peak 2) | 640.9 (M + H)⁺ | 1.93 | B |

TABLE 3-continued

| Ex. # | Structure | LCMS m/z observed | HPLC $t_R$ (min) | HPLC method |
|---|---|---|---|---|
| 4 | (structure shown) From peak 2 | 661.2 (M + H)+ | 1.90 | B |
| 5 | (structure shown) From peak 2 | 675.0, 677.0 (M + H)+ | 2.06 | B |

Example 6

(9b-((4-fluorophenyl)sulfonyl)-7-(perfluoropropan-2-yl)-1,2,3,3a,4,5,9b-hexahydro-3H-pyrrolo[2,3-c]quinolin-3-yl)(1-imino-1-oxidohexahydro-1$\lambda^6$-thiopyran-4-yl)methanone, Mixture of Cis and Trans Isomers

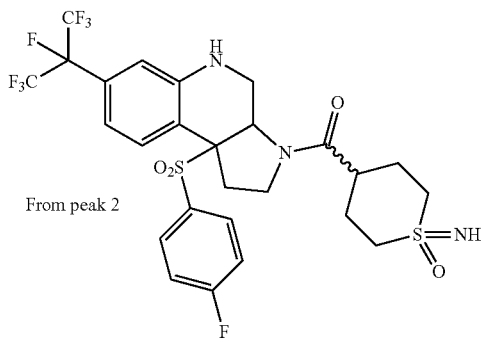 [SMILES: N=S1(=O)CCC(C(=O)N2CCC3(S(=O)(=O)c4ccc(F)cc4)c4ccc(C(F)(C(F)(F)F)C(F)(F)F)cc4NCC23)CC1]

From peak 2

Step A: tert-butyl (4-(9b-((4-fluorophenyl)sulfonyl)-7-(perfluoropropan-2-yl)-2,3,3a,4,5,9b-hexahydro-1H-pyrrolo[2,3-c]quinoline-3-carbonyl)-1-oxidotetrahydro-2H-1$\lambda^6$-thiopyran-1-ylidene)carbamate, Mixture of Cis and Trans Isomers

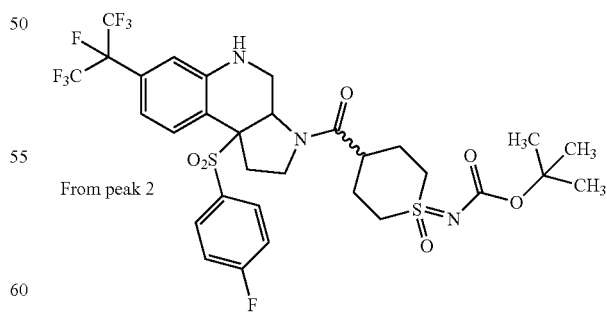

From peak 2

A solution of homochiral 9b-((4-fluorophenyl)sulfonyl)-7-(perfluoropropan-2-yl)-2,3,3a,4,5,9b-hexahydro-1H-pyrrolo[2,3-c]quinoline hydrochloride (from peak 2, Intermediate 14; 100 mg, 0.186 mmol) and 1-((tert-butoxycarbonyl)imino)hexahydro-1$\lambda^6$-thiopyran-4-carboxylic acid 1-oxide (mixture of cis and trans isomers, Intermediate 16; 51.7 mg, 0.186 mmol) in DMF (2 mL) was treated with DIPEA (0.098 mL, 0.559 mmol) and BOP (165 mg, 0.373 mmol) and stirred at rt. After 18.5 h, the mixture was diluted with water and extracted twice with EtOAc. The combined organic layers were washed sequentially with 1 M aqueous HCl, 10% aqueous LiCl and brine, dried and concentrated. The residue was subjected to column chromatography on silica gel (12 g), eluting with EtOAc-hexanes (gradient from 25-100%), to provide a mixture of cis and trans isomers of tert-butyl (4-(9b-((4-fluorophenyl)sulfonyl)-7-(perfluoropropan-2-yl)-2,3,3a,4,5,9b-hexahydro-1H-pyrrolo[2,3-c]quinoline-3-carbonyl)-1-oxidotetrahydro-2H-1$\lambda^6$-thiopyran-1-ylidene)carbamate as a tan glassy solid (116 mg, 82% yield). LCMS m/z 760.3 (M+H)$^+$, HPLC t$_R$ 1.04 min (Method A). $^1$H NMR (499 MHz, CDCl$_3$) δ 7.89 (d, J=8.52 Hz, 1H), 7.27 (td, J=4.45, 1.45 Hz, 2H), 7.10 (br d, J=8.52 Hz, 1H), 6.88-6.98 (m, 2H), 6.64 (s, 1H), 4.71-4.83 (m, 1H), 3.89-4.08 (m, 3H), 3.49-3.81 (m, 5H), 3.21-3.34 (m, 1H), 2.75-2.85 (m, 1H), 2.69 (dt, J=14.69, 9.63 Hz, 1H), 2.58 (td, J=10.77, 2.21 Hz, 1H), 2.35-2.52 (m, 3H), 2.21-2.35 (m, 1H), 1.53 (2s, 9H).

Step B: (9b-((4-fluorophenyl)sulfonyl)-7-(perfluoropropan-2-yl)-1,2,3a,4,5,9b-hexahydro-3H-pyrrolo[2,3-c]quinolin-3-yl)(1-imino-1-oxidohexahydro-1$\lambda^6$-thiopyran-4-yl)methanone, Mixture of Cis and Trans Isomers

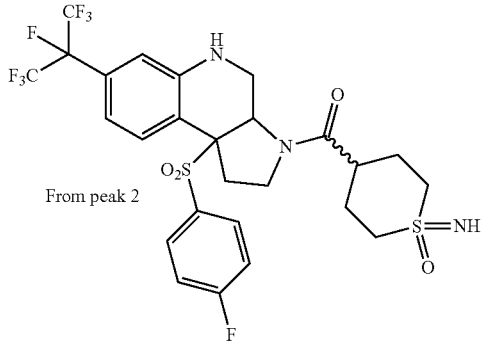 [SMILES: N=S1(=O)CCC(C(=O)N2CCC3(S(=O)(=O)c4ccc(F)cc4)c4ccc(C(F)(C(F)(F)F)C(F)(F)F)cc4NCC23)CC1]

From peak 2

A solution of a mixture of cis and trans isomers of tert-butyl (4-(9b-((4-fluorophenyl)sulfonyl)-7-(perfluoropropan-2-yl)-2,3,3a,4,5,9b-hexahydro-1H-pyrrolo[2,3-c]quinoline-3-carbonyl)-1-oxidotetrahydro-2H-1$\lambda^6$-thiopyran-1-ylidene)carbamate (25 mg, 0.033 mmol) in DCM (0.5 mL) was treated with HCl in dioxane (4 M; 0.5 mL, 2.00 mmol) and allowed to stand at rt. After 1 h, the mixture was concentrated. The residue was purified by preparative HPLC (Method D, gradient 30-70% B) to provide a mixture of cis and trans isomers of (9b-((4-fluorophenyl)sulfonyl)-7-(perfluoropropan-2-yl)-1,2,3a,4,5,9b-hexahydro-3H-pyrrolo[2,3-c]quinolin-3-yl)(1-imino-1-oxidohexahydro-1$\lambda^6$-thiopyran-4-yl)methanone (15 mg, 69% yield). LCMS m/z 660.4 (M+H)$^+$; HPLC t$_R$ 1.85 min (Method B). $^1$H NMR (500 MHz, DMSO-d$_6$) δ ppm 7.67-7.78 (m, 1H), 7.30 (br dd, J=8.7, 4.7 Hz, 2H), 7.12-7.24 (m, 2H), 6.97 (br d, J=8.2 Hz, 1H), 6.72-6.83 (m, 1H), 6.30 (br s, 1H), 4.53 (br dd, J=10.2, 5.3 Hz, 1H), 2.62-3.82 (m, 10H), 1.83-2.26 (m, 5H).

Example 7

((3aR,9bR)-9b-((4-fluorophenyl)sulfonyl)-7-(perfluoropropan-2-yl)-1,2,3a,4,5,9b-hexahydro-3H-benzo[e]indol-3-yl)(1-imino-1-oxidohexahydro-1$\lambda^6$-thiopyran-4-yl)methanone, Mixture of Cis and Trans Isomers

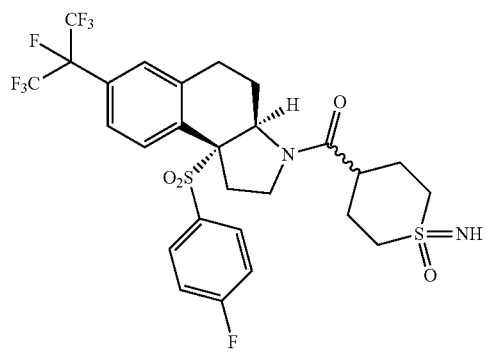 [SMILES: N=S1(=O)CCC(C(=O)N2CC[C@@]3(S(=O)(=O)c4ccc(F)cc4)c4ccc(C(F)(C(F)(F)F)C(F)(F)F)cc4CC[C@@H]23)CC1]

Step A: ((3aR,9bR)-9b-((4-fluorophenyl)sulfonyl)-7-(perfluoropropan-2-yl)-1,2,3a,4,5,9b-hexahydro-3H-benzo[e]indol-3-yl)(tetrahydro-2H-thiopyran-4-yl)methanone

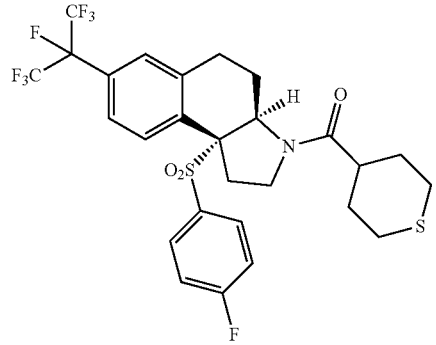 [SMILES: O=C(C1CCSCC1)N1CC[C@@]2(S(=O)(=O)c3ccc(F)cc3)c3ccc(C(F)(C(F)(F)F)C(F)(F)F)cc3CC[C@@H]12]

A solution of (3aR,9bR)-9b-((4-fluorophenyl)sulfonyl)-7-(perfluoropropan-2-yl)-2,3,3a,4,5,9b-hexahydro-1H-benzo[e]indole hydrochloride (Intermediate 8; 500 mg, 0.933 mmol) and tetrahydro-2H-thiopyran-4-carboxylic acid (Intermediate 17; 136 mg, 0.933 mmol) in DMF (5 mL) was treated with DIPEA (0.489 mL, 2.80 mmol) and BOP (825 mg, 1.87 mmol) and stirred at rt. After 18 h, the mixture was diluted with water and extracted twice with EtOAc. The combined organic layers were washed sequentially with 10% aqueous LiCl (twice), 1 M aqueous HCl, 1.5 M aqueous Na₂HPO₄ and brine, dried and concentrated. The residue was subjected to column chromatography on silica gel (40 g), eluting with EtOAc-hexanes (gradient from 5-60%), to provide ((3aR,9bR)-9b-((4-fluorophenyl)sulfonyl)-7-(perfluoropropan-2-yl)-1,2,3a,4,5,9b-hexahydro-3H-benzo[e]indol-3-yl)(tetrahydro-2H-thiopyran-4-yl)methanone as a pale orange solid (427 mg, 73% yield). LCMS m/z 628.2 (M+H)⁺, HPLC $t_R$ 1.11 min (Method A). ¹H NMR (400 MHz, CDCl₃) δ 7.99 (d, J=8.4 Hz, 1H), 7.58 (d, J=8.4 Hz, 1H), 7.27-7.21 (m, 2H), 7.17 (s, 1H), 6.98-6.88 (m, 2H), 4.73 (dd, J=12.0, 5.0 Hz, 1H), 4.02 (td, J=9.8, 8.1 Hz, 1H), 3.79 (td, J=9.6, 2.0 Hz, 1H), 3.68-3.57 (m, 1H), 2.84-2.67 (m, 4H), 2.67-2.55 (m, 2H), 2.54-2.40 (m, 2H), 2.31-2.19 (m, 1H), 2.13-1.92 (m, 3H), 1.87-1.73 (m, 1H), 1.19 (qd, J=12.6, 3.1 Hz, 1H).

Step B: ((3aR,9bR)-9b-((4-fluorophenyl)sulfonyl)-7-(perfluoropropan-2-yl)-1,2,3a,4,5,9b-hexahydro-3H-benzo[e]indol-3-yl)(1-oxidotetrahydro-2H-thiopyran-4-yl)methanone, Mixture of Cis and Trans Isomers

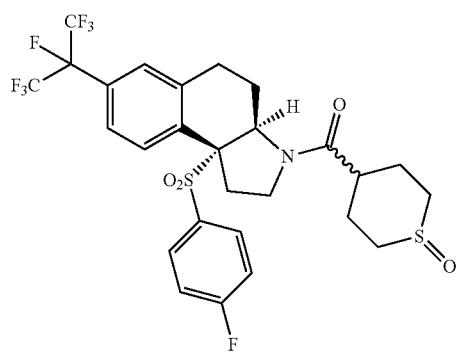 [SMILES: O=C(C1CCS(=O)CC1)N1CC[C@@]2(S(=O)(=O)c3ccc(F)cc3)c3ccc(C(F)(C(F)(F)F)C(F)(F)F)cc3CC[C@@H]12]

A mixture of ((3aR,9bR)-9b-((4-fluorophenyl)sulfonyl)-7-(perfluoropropan-2-yl)-1,2,3a,4,5,9b-hexahydro-3H-benzo[e]indol-3-yl)(tetrahydro-2H-thiopyran-4-yl)methanone (332 mg, 0.529 mmol) in MeOH (4.8 mL) was treated with a solution of sodium periodate (124 mg, 0.582 mmol) in water (1.2 mL), and the resulting suspension was stirred at rt. After 22.5 h, the mixture was diluted with water and extracted twice with EtOAc. The combined organic phases were washed with saturated brine, dried and concentrated to provide a mixture (about 60:40) of cis and trans isomers of ((3aR,9bR)-9b-((4-fluorophenyl)sulfonyl)-7-(perfluoropropan-2-yl)-1,2,3a,4,5,9b-hexahydro-3H-benzo[e]indol-3-yl)(1-oxidotetrahydro-2H-thiopyran-4-yl)methanone as an off-white solid (358 mg, >100% yield, containing about 5% by weight of residual solvents by NMR). LCMS m/z 644.2 (M+H)⁺, HPLC $t_R$ 0.98 min (Method A). ¹H NMR (400 MHz, CDCl₃) δ 8.03-7.96 (m, 1H), 7.59 (d, J=8.6 Hz, 1H), 7.27-7.20 (m, 2H), 7.18 (s, 1H), 6.99-6.89 (m, 2H), 4.75 (dd, J=12.1, 4.6 Hz, 1H), 4.12-3.99 (m, 1H), 3.88-3.77 (m, 1H), 3.71-3.61 (m, 1H), 3.47-3.18 (2m, 2H), 2.90-1.72 (m, 12H).

Step C: ((3aR,9bR)-9b-((4-fluorophenyl)sulfonyl)-7-(perfluoropropan-2-yl)-1,2,3a,4,5,9b-hexahydro-3H-benzo[e]indol-3-yl)(1-imino-1-oxidohexahydro-1λ⁶-thiopyran-4-yl)methanone, Mixture of Cis and Trans Isomers

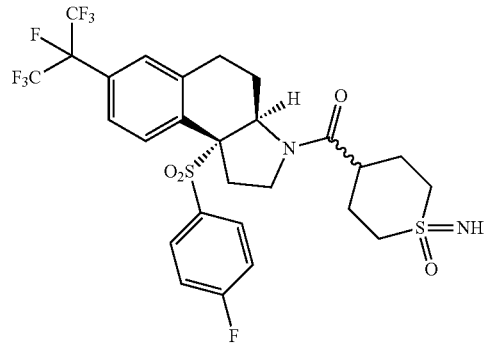 [SMILES: N=S1(=O)CCC(C(=O)N2CC[C@@]3(S(=O)(=O)c4ccc(F)cc4)c4ccc(C(F)(C(F)(F)F)C(F)(F)F)cc4CC[C@@H]23)CC1]

A mixture of ((3aR,9bR)-9b-((4-fluorophenyl)sulfonyl)-7-(perfluoropropan-2-yl)-1,2,3a,4,5,9b-hexahydro-3H-benzo[e]indol-3-yl)(1-oxidotetrahydro-2H-thiopyran-4-yl)methanone (mixture of cis and trans isomers; 343 mg, 0.533 mmol), ammonium carbamate (166 mg, 2.132 mmol) and iodobenzene diacetate (515 mg, 1.60 mmol) was treated with MeOH (7 mL), sonicated briefly, and stirred vigorously at rt. After 80 min, additional ammonium carbamate (166 mg, 2.132 mmol) and iodobenzene diacetate (77 mg, 0.240 mmol) were added and stirring was continued at rt. After 2.75 h more, the mixture was concentrated and the residue was partitioned between water and EtOAc. The aqueous phase was extracted again with EtOAc and the combined organic phases were washed with brine, dried and concentrated. The residue was subjected to column chromatography on silica gel (40 g), eluting with MeOH-DCM (gradient from 0-7.5%), to provide a mixture of cis and trans isomers of ((3aR,9bR)-9b-((4-fluorophenyl)sulfonyl)-7-(perfluoropropan-2-yl)-1,2,3a,4,5,9b-hexahydro-3H-benzo[e]indol-3-yl)(1-imino-1-oxidohexahydro-1λ⁶-thiopyran-4-yl)methanone as a white glassy solid (354 mg, 92% yield). LCMS m/z 659.1 (M+H)⁺, HPLC $t_R$ 0.88, 0.90 min (Method A). ¹H NMR (499 MHz, CDCl₃) δ 8.00 (d, J=8.5 Hz, 1H), 7.59 (d, J=8.4 Hz, 1H), 7.23 (ddd, J=8.8, 5.0, 1.9 Hz, 2H), 7.18 (s, 1H), 6.98-6.90 (m, 2H), 4.82-4.69 (m, 1H), 4.09-3.97 (m, 1H), 3.86-3.75 (m, 1H), 3.66 (ddd, J=14.6, 8.1, 1.8 Hz, 1H), 3.58-3.38 (m, 2H), 3.20-3.01 (m, 2H), 2.73 (qt, J=8.3, 3.9 Hz, 1H), 2.64 (dt, J=14.7, 9.9 Hz, 1H), 2.58-2.34 (m, 5H), 2.26 (ddd, J=14.4, 7.2, 3.2 Hz, 1H), 1.90-1.79 (m, 1H), 1.28-1.16 (m, 1H).

The Examples in Table 4 were prepared using procedures used to prepare Example 7 or similar procedures, using the appropriate acid and amine starting materials.

TABLE 4

| Ex. # | Structure | LCMS m/z observed | HPLC t_R (min) | HPLC method |
|---|---|---|---|---|
| 8 | 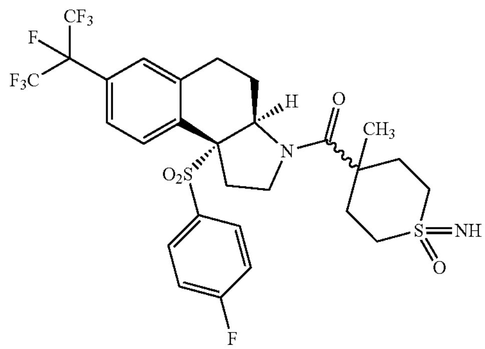 | 673.2 (M + H)+ | 0.96, 0.97 | A |
| 9 | 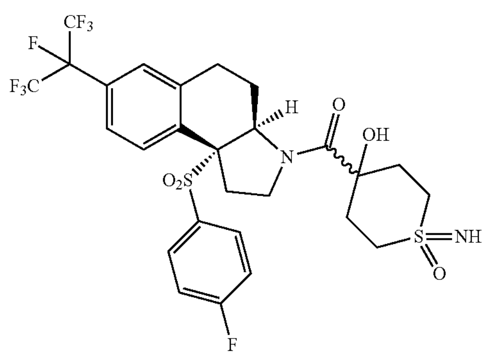 [SMILES: CC1(C(=O)N2CC[C@@]3(S(=O)(=O)c4ccc(F)cc4)c4ccc(C(F)(C(F)(F)F)C(F)(F)F)cc4CC[C@@H]23)CCS(=N)(=O)CC1] | 675.2 (M + H)+ | 0.87, 0.89 | A |
| 10 | 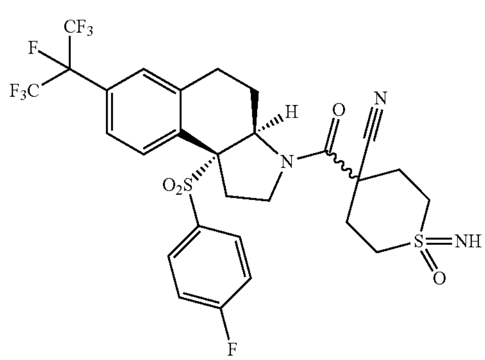 [SMILES: N#CC1(C(=O)N2CC[C@@]3(S(=O)(=O)c4ccc(F)cc4)c4ccc(C(F)(C(F)(F)F)C(F)(F)F)cc4CC[C@@H]23)CCS(=N)(=O)CC1] | 684.2 (M + H)+ | 0.97, 0.98 | A |

Examples 11 and 12

((3aR,9bR)-9b-((4-fluorophenyl)sulfonyl)-7-(perfluoropropan-2-yl)-1,2,3a,4,5,9b-hexahydro-3H-benzo[e]indol-3-yl)(1-imino-1-oxidohexahydro-1λ⁶-thiopyran-4-yl)methanone (Two Homochiral Stereoisomers)

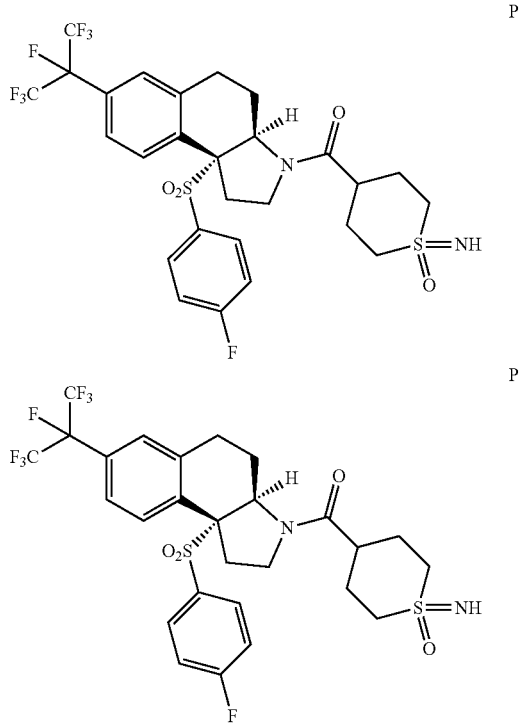

Peak 1

Peak 2

A sample of a mixture of cis and trans isomers of ((3aR,9bR)-9b-((4-fluorophenyl)sulfonyl)-7-(perfluoropropan-2-yl)-1,2,3a,4,5,9b-hexahydro-3H-benzo[e]indol-3-yl)(1-imino-1-oxidohexahydro-1λ⁶-thiopyran-4-yl)methanone (Example 8; 320 mg, 0.457 mmol) was separated by chiral SFC using the following conditions: Column: Lux® Cellulose-4 (3×250) mm, 5 μm (Phenomenex Inc.); column temperature 35° C.; CO$_2$ flow rate 120 mL/min; co-solvent 45% MeOH; flow rate 0.9 mL/min; injection volume 2 mL. Peak 1, eluting with $t_R$ 3.6 min, provided one homochiral stereoisomer of ((3aR,9bR)-9b-((4-fluorophenyl)sulfonyl)-7-(perfluoropropan-2-yl)-1,2,3a,4,5,9b-hexahydro-3H-benzo[e]indol-3-yl)(1-imino-1-oxidohexahydro-1λ⁶-thiopyran-4-yl)methanone as a white glassy solid (Example 11; 176 mg, 58% yield). LCMS m/z 659.1 (M+H)⁺, HPLC $t_R$ 0.91 min (Method A). ¹H NMR (499 MHz, CDCl$_3$) δ 7.99 (d, J=8.4 Hz, 1H), 7.59 (d, J=8.4 Hz, 1H), 7.26-7.20 (m, 2H), 7.18 (s, 1H), 6.94 (t, J=8.5 Hz, 2H), 4.76 (dd, J=12.1, 4.8 Hz, 1H), 4.11-3.98 (m, 1H), 3.81 (td, J=9.6, 2.1 Hz, 1H), 3.66 (ddd, J=14.6, 8.0, 1.8 Hz, 1H), 3.58-3.39 (m, 2H), 3.20-3.00 (m, 2H), 2.74 (tt, J=8.1, 3.9 Hz, 1H), 2.64 (dt, J=14.7, 9.8 Hz, 1H), 2.57-2.43 (m, 4H), 2.43-2.34 (m, 1H), 2.25 (ddd, J=10.7, 7.2, 3.3 Hz, 1H), 1.89-1.79 (m, 1H), 1.32-1.11 (m, 1H) [NH broad at about δ 1.8].

Peak 2, eluting with $t_R$ 6.5 min, provided the other homochiral stereoisomer of ((3aR,9bR)-9b-((4-fluorophenyl)sulfonyl)-7-(perfluoropropan-2-yl)-1,2,3a,4,5,9b-hexahydro-3H-benzo[e]indol-3-yl)(1-imino-1-oxidohexahydro-1λ⁶-thiopyran-4-yl)methanone as a white glassy solid (Example 12; 88 mg, 29% yield). LCMS m/z 659.2 (M+H)⁺, HPLC $t_R$ 0.92 min (Method A). ¹H NMR (499 MHz, CDCl$_3$) δ 8.00 (d, J=8.4 Hz, 1H), 7.59 (d, J=8.2 Hz, 1H), 7.27-7.20 (m, 2H), 7.18 (s, 1H), 6.95 (t, J=8.5 Hz, 2H), 4.76 (dd, J=12.2, 4.7 Hz, 1H), 4.09-3.99 (m, 1H), 3.81 (td, J=9.5, 2.1 Hz, 1H), 3.66 (ddd, J=14.6, 8.0, 1.8 Hz, 1H), 3.52 (br. s., 2H), 3.14-3.01 (m, 2H), 2.72 (tt, J=7.9, 3.9 Hz, 1H), 2.64 (dt, J=14.7, 9.8 Hz, 1H), 2.58-2.35 (m, 5H), 2.32-2.22 (m, 1H), 1.90-1.75 (m, 1H), 1.28-1.16 (m, 1H) [NH broad about δ 1.8].

The absolute configurations of the 1-imino-1-oxidohexahydro-1λ⁶-thiopyran-4-yl moieties of Examples 11 and 12 were not determined.

Example 13

((3aR,9bR)-9b-((4-fluorophenyl)sulfonyl)-7-(perfluoropropan-2-yl)-1,2,3a,4,5,9b-hexahydro-3H-benzo[e]indol-3-yl)(1-(methylimino)-1-oxidohexahydro-1λ⁶-thiopyran-4-yl)methanone (Single Homochiral Stereoisomer)

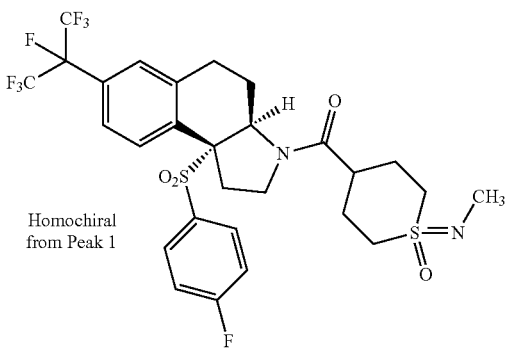 [SMILES: CN=S1(=O)CCC(C(=O)N2CC[C@@]3(S(=O)(=O)c4ccc(F)cc4)c4ccc(C(F)(C(F)(F)F)C(F)(F)F)cc4CC[C@@H]23)CC1]

Homochiral from Peak 1

A mixture of a single homochiral stereoisomer of ((3aR,9bR)-9b-((4-fluorophenyl)sulfonyl)-7-(perfluoropropan-2-yl)-1,2,3a,4,5,9b-hexahydro-3H-benzo[e]indol-3-yl)(1-imino-1-oxidohexahydro-1λ⁶-thiopyran-4-yl)methanone (Example 11, from SFC peak 1; 25 mg, 0.038 mmol) and paraformaldehyde (4.6 mg, 0.152 mmol) in MeCN (0.5 mL) was treated with TFA (0.012 mL, 0.152 mmol) and triethylsilane (0.018 mL, 0.114 mmol) and the mixture was stirred at rt. After 19.5 h, the mixture was purified by preparative HPLC (Method E, gradient 40-80% B) to provide a single homochiral stereoisomer of ((3aR,9bR)-9b-((4-fluorophenyl)sulfonyl)-7-(perfluoropropan-2-yl)-1,2,3a,4,5,9b-hexahydro-3H-benzo[e]indol-3-yl)(1-(methylimino)-1-oxidohexahydro-1λ⁶-thiopyran-4-yl)methanone (23.4 mg, 90% yield). LCMS m/z 673.4 (M+H)⁺, HPLC $t_R$ 1.99 min (Method B). ¹H NMR (500 MHz, DMSO-d$_6$) δ 7.93-7.81 (m, 1H), 7.64 (d, J=7.9 Hz, 1H), 7.36-7.29 (m, 3H), 7.28-7.19 (m, 2H), 4.71-4.53 (m, 1H), 3.84-2.97 (m, 11H), 2.85-2.55 (m, 4H), 2.34-1.76 (m, 5H). The absolute configuration of the 1-(methylimino)-1-oxidohexahydro-1λ⁶-thiopyran-4-yl moiety was not determined.

Example 14

((3aR,9bR)-9b-((4-fluorophenyl)sulfonyl)-7-(perfluoropropan-2-yl)-1,2,3a,4,5,9b-hexahydro-3H-benzo[e]indol-3-yl)(1-(methylimino)-1-oxidohexahydro-1λ⁶-thiopyran-4-yl)methanone (Single Homochiral Stereoisomer)

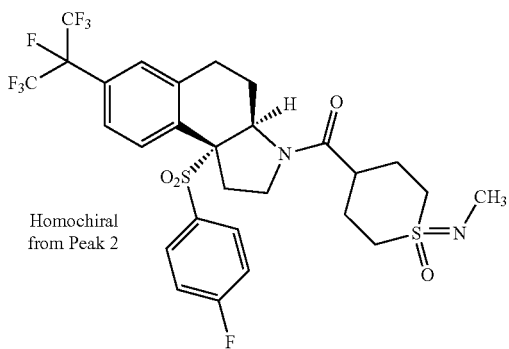 [SMILES: CN=S1(=O)CCC(C(=O)N2CC[C@@]3(S(=O)(=O)c4ccc(F)cc4)c4ccc(C(F)(C(F)(F)F)C(F)(F)F)cc4CC[C@@H]23)CC1]

Homochiral from Peak 2

Using the procedure of Example 13, a single homochiral stereoisomer of ((3aR,9bR)-9b-((4-fluorophenyl)sulfonyl)-7-(perfluoropropan-2-yl)-1,2,3a,4,5,9b-hexahydro-3H-benzo[e]indol-3-yl)(1-imino-1-oxidohexahydro-1λ⁶-thiopyran-4-yl)methanone (Example 12, from SFC peak 2) was converted into a single homochiral stereoisomer of ((3aR, 9bR)-9b-((4-fluorophenyl)sulfonyl)-7-(perfluoropropan-2-yl)-1,2,3a,4,5,9b-hexahydro-3H-benzo[e]indol-3-yl)(1-(methylimino)-1-oxidohexahydro-1λ⁶-thiopyran-4-yl)methanone in 67% yield. LCMS m/z 673.2 (M+H)⁺, HPLC $t_R$ 2.05 min (Method B). ¹H NMR (500 MHz, DMSO-$d_6$) δ 7.90-7.82 (m, 1H), 7.68-7.59 (m, 1H), 7.38-7.30 (m, 3H), 7.28-7.17 (m, 2H), 4.73-4.55 (m, 1H), 3.79-2.93 (m, 11H), 2.84-2.60 (m, 4H), 2.34-1.80 (m, 5H). The absolute configuration of the 1-(methylimino)-1-oxidohexahydro-1λ⁶-thiopyran-4-yl moiety was not determined.

Example 15

N-(4-((3aR,9bR)-9b-((4-fluorophenyl)sulfonyl)-7-(perfluoropropan-2-yl)-2,3,3a,4,5,9b-hexahydro-1H-benzo[e]indole-3-carbonyl)-1-oxidotetrahydro-2H-1λ⁶-thiopyran-1-ylidene)acetamide (Single Homochiral Stereoisomer)

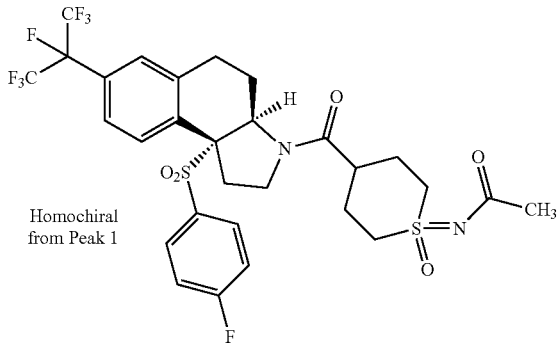 [SMILES: CC(=O)N=S1(=O)CCC(C(=O)N2CC[C@@]3(S(=O)(=O)c4ccc(F)cc4)c4ccc(C(F)(C(F)(F)F)C(F)(F)F)cc4CC[C@@H]23)CC1]

Homochiral from Peak 1

A solution of a single homochiral stereoisomer of ((3aR, 9bR)-9b-((4-fluorophenyl)sulfonyl)-7-(perfluoropropan-2-yl)-1,2,3a,4,5,9b-hexahydro-3H-benzo[e]indol-3-yl)(1-imino-1-oxidohexahydro-1λ⁶-thiopyran-4-yl)methanone (Example 11, from SFC peak 1; 25 mg, 0.038 mmol) in DCM (0.5 mL) was treated with pyridine (0.15 mL) and cooled on an ice-water bath. The solution was treated with acetic anhydride (11 μL, 0.114 mmol) and the mixture was stirred at rt. After 15.5 h, the mixture was purified by preparative HPLC (Method E, gradient 40-80% B) to provide a single homochiral stereoisomer of N-(4-((3aR,9bR)-9b-((4-fluorophenyl)sulfonyl)-7-(perfluoropropan-2-yl)-2,3,3a,4,5,9b-hexahydro-1H-benzo[e]indole-3-carbonyl)-1-oxidotetrahydro-2H-1λ⁶-thiopyran-1-ylidene)acetamide (20.9 mg, 79% yield). LCMS m/z 701.3 (M+H)⁺, HPLC $t_R$ 2.06 min (Method B). ¹H NMR (500 MHz, DMSO-$d_6$) δ 7.91-7.82 (m, 1H), 7.64 (d, J=7.4 Hz, 1H), 7.40-7.28 (m, 3H), 7.27-7.17 (m, 2H), 4.69-4.51 (m, 1H), 4.01-3.60 (m, 7H), 3.48-2.58 (m, 5H), 2.34-1.72 (m, 8H). The absolute configuration of the 1-(acetylimino)-1-oxidohexahydro-1λ⁶-thiopyran-4-yl moiety was not determined.

Example 16

N-(4-((3aR,9bR)-9b-((4-fluorophenyl)sulfonyl)-7-(perfluoropropan-2-yl)-2,3,3a,4,5,9b-hexahydro-1H-benzo[e]indole-3-carbonyl)-1-oxidotetrahydro-2H-1λ⁶-thiopyran-1-ylidene)acetamide (Single Homochiral Stereoisomer)

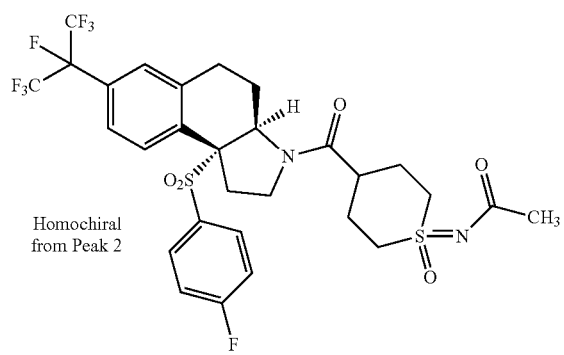 [SMILES: CC(=O)N=S1(=O)CCC(C(=O)N2CC[C@@]3(S(=O)(=O)c4ccc(F)cc4)c4ccc(C(F)(C(F)(F)F)C(F)(F)F)cc4CC[C@@H]23)CC1]

Homochiral from Peak 2

Using the procedure of Example 15, a single homochiral stereoisomer of ((3aR,9bR)-9b-((4-fluorophenyl)sulfonyl)-7-(perfluoropropan-2-yl)-1,2,3a,4,5,9b-hexahydro-3H-benzo[e]indol-3-yl)(1-imino-1-oxidohexahydro-1λ⁶-thiopyran-4-yl)methanone (Example 12, from SFC peak 2) was converted into a single homochiral stereoisomer of N-(4-((3aR,9bR)-9b-((4-fluorophenyl)sulfonyl)-7-(perfluoropropan-2-yl)-2,3,3a,4,5,9b-hexahydro-1H-benzo[e]indole-3-carbonyl)-1-oxidotetrahydro-2H-1λ⁶-thiopyran-1-ylidene)acetamide in 65% yield. LCMS m/z 701.5 (M+H)⁺, HPLC $t_R$ 2.05 min (Method B). ¹H NMR (500 MHz, DMSO-$d_6$) δ 7.92-7.83 (m, 1H), 7.64 (d, J=7.5 Hz, 1H), 7.38-7.29 (m, 3H), 7.28-7.19 (m, 2H), 4.71-4.54 (m, 1H), 3.84-3.13 (m, 7H), 2.98-2.55 (m, 3H), 2.35-1.99 (m, 5H), 1.99-1.92 (2s, 3H), 1.87 (t, J=14.0 Hz, 1H), 1.58-1.21 (m, 1H). The absolute configuration of the 1-(acetylimino)-1-oxidohexahydro-1λ⁶-thiopyran-4-yl moiety was not determined.

Example 17

9b-((4-fluorophenyl)sulfonyl)-5-methyl-7-(perfluoropropan-2-yl)-1,2,3a,4,5,9b-hexahydro-3H-pyrrolo[2,3-c]quinolin-3-yl)(1-imino-1-oxidohexahydro-1λ⁶-thiopyran-4-yl)methanone, Mixture of Cis and Trans Isomers

Examples 18 and 19

(4-fluoro-1-imino-1-oxidohexahydro-1λ⁶-thiopyran-4-yl)((3aR,9bR)-9b-((4-fluorophenyl)sulfonyl)-7-(perfluoropropan-2-yl)-1,2,3a,4,5,9b-hexahydro-3H-benzo[e]indol-3-yl)methanone (Two Homochiral Stereoisomers)

Peak 1

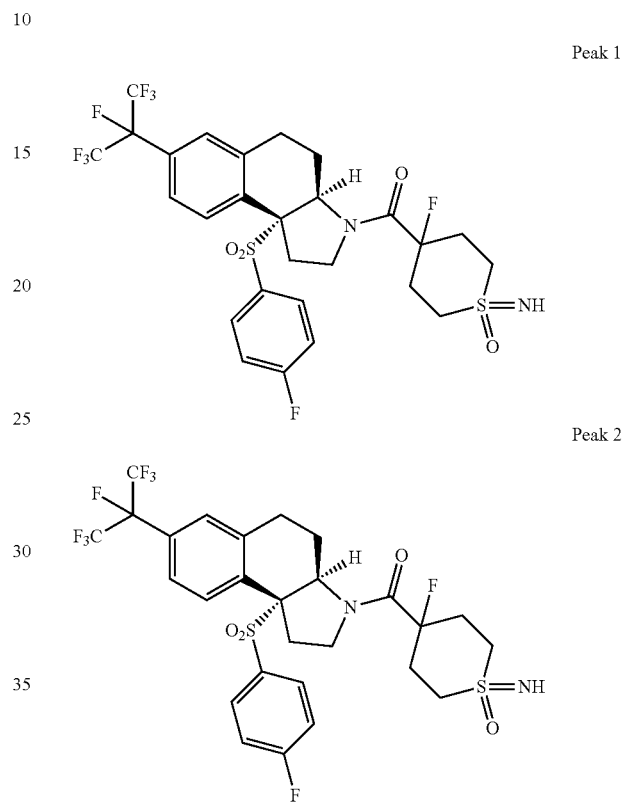

Peak 2

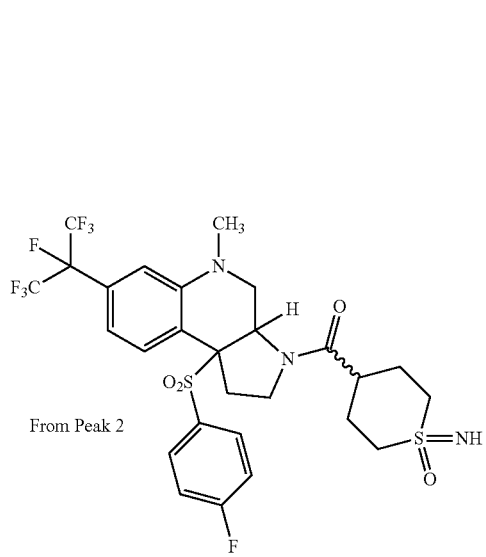 [SMILES: CN1CC2N(C(=O)C3CCS(=N)(=O)CC3)CCC2(S(=O)(=O)c2ccc(F)cc2)c2ccc(C(F)(C(F)(F)F)C(F)(F)F)cc21]

From Peak 2

A solution of tert-butyl (4-(9b-((4-fluorophenyl)sulfonyl)-7-(perfluoropropan-2-yl)-2,3,3a,4,5,9b-hexahydro-1H-pyrrolo[2,3-c]quinoline-3-carbonyl)-1-oxidotetrahydro-2H-thiopyran-1-ylidene)carbamate (Example 6; 88 mg, 0.116 mmol) in MeOH (1.25 mL) was treated with acetic acid (0.133 mL, 2.32 mmol), 30% aqueous formaldehyde (0.106 mL, 1.16 mmol) and sodium cyanoborohydride (72.8 mg, 1.16 mmol) and stirred at rt. After 2 h, additional formaldehyde (0.106 mL, 1.16 mmol) and sodium cyanoborohydride (72.8 mg, 1.16 mmol) were added and stirring was continued at rt for 4 days. The mixture was diluted with EtOAc, washed sequentially with 1 M aqueous HCl (twice), saturated aqueous NaHCO₃ and brine, dried and concentrated. The residue was dissolved in DCM (1 mL), treated with 4 M HCl in dioxane (1 mL), and allowed to stand at rt. After 80 min, the mixture was concentrated. The residue was purified by preparative HPLC (method E, gradient 40-80% B) to provide a mixture of cis and trans isomers of 9b-((4-fluorophenyl)sulfonyl)-7-(perfluoropropan-2-yl)-1,2,3a,4,5,9b-hexahydro-3H-pyrrolo[2,3-c]quinolin-3-yl)(1-imino-1-oxidohexahydro-1λ⁶-thiopyran-4-yl)methanone (53.6 mg, 67% yield). LCMS m/z 674.4 (M+H)⁺, HPLC $t_R$ 1.88, 1.92 min, ratio 57:43 (Method C). ¹H NMR (500 MHz, DMSO-d₆) δ ppm 7.72-7.82 (m, 1H), 7.26-7.39 (m, 2H), 7.15-7.25 (m, 2H), 7.10 (br d, J=8.2 Hz, 1H), 6.56-6.65 (m, 1H), 4.65-4.81 (m, 1H), 3.42-3.86 (m, 2H), 2.94-3.22 (m, 3H), 2.55-2.89 (m+s, 9H), 1.83-2.26 (m, 4H).

A solution of ((3aR)-9b-((4-fluorophenyl)sulfonyl)-7-(perfluoropropan-2-yl)-4,5-dihydro-1H-benzo[e]indol-3(2H,3aH,9bH)-yl)(4-hydroxy-1-imino-1-oxidotetrahydro-2H-thiopyran-4-yl)methanone (Example 9; 75 mg, 0.111 mmol) in DCM (2 mL) was stirred at rt under nitrogen and treated with DAST (0.059 mL, 0.445 mmol). The orange solution was stirred at rt for 15.75 h. The mixture was treated with saturated aqueous NaHCO₃ and extracted with DCM. The organic phase was dried and concentrated, and the residue was subjected to column chromatography on silica gel (12 g), eluting with MeOH-DCM (gradient from 0-10%), to provide a brown gum. This was purified further by preparative HPLC (Method F, gradient 20-100% B). Peak 1, eluting with $t_R$ 7.84 min, provided one homochiral stereoisomer of (4-fluoro-1-imino-1-oxidohexahydro-1λ⁶-thiopyran-4-yl)((3aR,9bR)-9b-((4-fluorophenyl)sulfonyl)-7-(perfluoropropan-2-yl)-1,2,3a,4,5,9b-hexahydro-3H-benzo[e]indol-3-yl)methanone (Example 18; 1.9 mg, 2.5% yield). LCMS m/z 677.2 (M+H)⁺, HPLC $t_R$ 0.95 min (Method A). ¹H NMR (499 MHz, CDCl₃) δ 8.02 (d, J=8.4 Hz, 1H), 7.60 (br d, J=8.2 Hz, 1H), 7.25 (br dd, J=8.5, 4.9 Hz, 2H), 7.20 (s, 1H), 6.96 (t, J=8.4 Hz, 2H), 4.88 (br dd, J=12.1, 4.5 Hz, 1H), 4.15-4.27 (m, 1H), 3.97-4.07 (m, 1H), 3.48-3.93 (m, 4H), 2.71-2.96 (m, 4H), 2.58-2.71 (m, 1H), 2.50-2.59 (m, 2H), 2.40-2.49 (m, 1H), 1.83-1.97 (m, 1H), 1.37-1.25 (m, 1H).

Peak 2, eluting with $t_R$ 8.07 min, provided the other homochiral stereoisomer of (4-fluoro-1-imino-1-oxidohexahydro-1λ⁶-thiopyran-4-yl)((3aR,9bR)-9b-((4-fluorophenyl)sulfonyl)-7-(perfluoropropan-2-yl)-1,2,3a,4,5,9b-hexahydro-3H-benzo[e]indol-3-yl)methanone (Example 19; 2.0 mg, 2.7% yield). LCMS m/z 677.1 (M+H)⁺, HPLC $t_R$ 0.96 min (Method A). ¹H NMR (499 MHz, CDCl₃) δ 8.02 (d, J=8.4 Hz, 1H), 7.60 (br d, J=8.1 Hz, 1H), 7.22-7.27 (m, 2H), 7.20 (s, 1H), 6.96 (t, J=8.4 Hz, 2H), 4.90 (dd, J=12.2, 4.9 Hz, 1H), 4.14-4.27 (m, 1H), 4.00-4.08 (m, 1H), 3.45-3.72 (m, 4H), 2.70-3.16 (m, 4H), 2.64 (dt, J=14.8, 9.8 Hz, 1H), 2.49-2.60 (m, 2H), 2.35-2.47 (m, 1H), 1.84-2.01 (m, 1H), 1.30-1.38 (m, 1H).

The absolute configurations of the 4-fluoro-1-imino-1-oxidohexahydro-1λ⁶-thiopyran-4-yl moieties of Examples 18 and 19 were not determined.

General RORγ Gal4 Reporter Assay

Inverse agonist activity of potential ligands to RORγ was measured by inhibition of luminescence in a Gal4-luciferase reporter assay in Jurkat cells.

Jurkat cells stably over-expressing the RORγ receptor, Jurkat pEx/Gal/hRORγ CLBD/HYG pG5luc/blast, were plated at a concentration of 10,000 cells/well in a 384-well solid white cell culture plate (Perkin Elmer #6007899) in assay buffer RPMI 1640 (Gibco 11875-085 1L) containing 0.1% BSA, 100×HEPES (Gibco 15360-080), 100 mM sodium pyruvate (Gibco 11360-040), 50 mg/mL Hygromycin B (Invitrogen 10687-010) and 10 mg/mL blasticidin (Invitrogen R210-01). 100 nL of test compound in a 3-fold serial dilution, with final concentrations ranging from 40 μM to 0.67 nM, were added to the cells which were then incubated overnight.

The following day, cells were lysed with 10 μL of Steady-Glo Luciferase Assay System (Promega Cat. No. EZ550), and analyzed immediately. IC₅₀ values were determined. The IC₅₀ value is defined as the concentration of test compound needed to reduce luciferase activity by 50% and is calculated using the four parameter logistic equation to fit the normalized data.

IC₅₀ values for compounds of the invention in the RORγ Gal4 assay are provided below.

| Ex. No. | RORγ Gal4 IC₅₀, μM |
|---------|---------------------|
| 1 | 0.040 |
| 2 | 0.057 |
| 3 | 0.056 |
| 4 | 0.246 |
| 5 | 0.058 |
| 6 | 0.051 |
| 7 | 0.028 |
| 8 | 0.034 |
| 9 | 0.014 |
| 10 | 0.048 |
| 11 | 0.039 |
| 12 | 0.056 |
| 13 | 0.026 |
| 14 | 0.040 |
| 15 | 0.049 |
| 16 | 0.077 |
| 17 | 0.021 |
| 18 | 0.052 |
| 19 | 0.060 |

What is claimed is:
1. The compound of the formula (I)

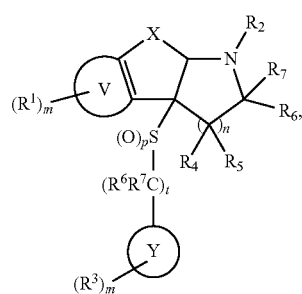

or a stereoisomer or pharmaceutically acceptable salt thereof, wherein

X is —CR⁴R⁵—, —(CR⁴R⁵)₂—, —OCR⁶R⁷—, —S(O)$_p$CR⁶R⁷— or —NR⁶CR⁶R⁷—;

V and Y are independently 5 or 6-membered aromatic or heteroaromatic rings;

R¹ is, independently at each occurrence, selected from hydrogen, CD₃, halo, OCF₃, CN, —O(C₁-C₆)alkyl, —O(C₁-C₆)alkyl-OH, -alkoxyalkoxy (e.g. —O—CH₂CH₂OCH₃), S(O)$_p$(C₁-C₆)alkyl, —S(O)$_p$(C₁-C₆)alkyl-OH, -thioalkoxyalkoxy (e.g. —SCH₂CH₂OCH₃), NR¹¹R¹¹, C₁₋₆ alkyl substituted with 0-3 R¹ᵃ, —(CR¹ᵇR¹ᶜ)$_r$-3-14 membered carbocycle substituted with 0-3 R¹ᵃ and —(CR¹ᵇR¹ᶜ)$_r$-5-10 membered heterocycle comprising carbon atoms and 1-4 heteroatoms selected from N, O, and S(O)$_p$ substituted with 0-3 R¹ᵃ;

R¹ᵃ is, independently at each occurrence, hydrogen, =O, halo, CF₃, OCF₃, CN, NO₂, —(CR¹ᵇR¹ᶜ)$_r$—OR$^b$, —(CR¹ᵇR¹ᶜ)$_r$—S(O)$_p$R$^b$, —(CR¹ᵇR¹ᶜ)$_r$—C(O)R$^b$, —(CR¹ᵇR¹ᶜ)$_r$—C(O)OR$^b$, —(CR¹ᵇR¹ᶜ)$_r$—OC(O)R$^b$, —(CR¹ᵇR¹ᶜ)$_r$—NR¹¹R¹¹, —(CR¹ᵇR¹ᶜ)$_r$—C(O)NR¹¹R¹¹, —(CR¹ᵇR¹ᶜ)$_r$—NR$^b$C(O)R$^c$, —(CR¹ᵇR¹ᶜ)$_r$—NR$^b$C(O)OR$^c$, —NR$^b$C(O)NR¹¹R¹¹, —S(O)$_p$NR¹¹R¹¹, —NR$^b$S(O)$_p$R$^c$, C₁₋₆ alkyl substituted with 0-3 R$^a$, C₁₋₆ haloalkyl, C₂₋₆ alkenyl substituted with 0-3 R$^a$, C₂₋₆ alkynyl substituted with 0-3 R$^a$, —(CR¹ᵇR¹ᶜ)$_r$-3-14 membered carbocycle substituted with 0-3 R$^a$, or —(CR¹ᵇR¹ᶜ)$_r$-5-7 membered heterocycle comprising carbon atoms and 1-4 heteroatoms selected from N, O, and S(O)$_p$ substituted with 0-3 R$^a$;

R¹ᵇ and R¹ᶜ are, independently at each occurrence, hydrogen, halogen or C₁₋₆ alkyl;

R² is

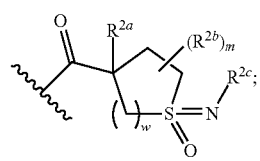

R²ᵃ and R²ᵇ are, independently at each occurrence, hydrogen, halo, OCF₃, CF₃, CHF₂, CN, NO₂, —(CR¹ᵇR¹ᶜ)$_r$—OR$^b$, —(CR¹ᵇR¹ᶜ)$_r$—S(O)$_p$R$^b$, —(CR¹ᵇR¹ᶜ)$_r$—C(O)R$^b$, —(CR¹ᵇR¹ᶜ)$_r$—C(O)OR$^b$, —(CR¹ᵇR¹ᶜ)$_r$—OC(O)R$^b$, —(CR¹ᵇR¹ᶜ)$_r$—NR¹¹R¹¹, —(CR¹ᵇR¹ᶜ)$_r$—C(O)NR¹¹R¹¹, —(CR¹ᵇR¹ᶜ)$_r$—NR$^b$C(O)R$^c$, —(CR¹ᵇR¹ᶜ)$_r$—NR$^b$C(O)OR$^c$, —NR$^b$C(O)

NR$^{11}$R$^{11}$, —S(O)$_p$NR$^{11}$R$^{11}$, —NR$^b$S(O)$_p$R$^c$, C$_{1-6}$ alkyl substituted with 0-3 R$^f$, C$_{1-6}$ haloalkyl, C$_{2-6}$ alkenyl substituted with 0-3 R$^e$, C$_{2-6}$ alkynyl substituted with 0-3 R$^e$, —(CR$^{1b}$R$^{1c}$)$_r$-3-14 membered carbocycle, or —(CR$^{1b}$R$^{1c}$)$_r$-5-7 membered heterocycle comprising carbon atoms and 1-4 heteroatoms selected from N, O, P(=O) and S(O)$_p$ substituted with 0-4 R$^f$;

R$^{2c}$ is hydrogen, C$_{1-6}$ alkyl substituted with 0-3 R$^f$, C$_{1-6}$ haloalkyl, —(CR$^{1b}$R$^{1c}$)$_r$—C(O)R$^b$, —(CR$^{1b}$R$^{1c}$)$_r$—C(O)OR$^b$, —(CR$^{1b}$R$^{1c}$)$_r$—C(O)NR$^{11}$R$^{11}$, —(CR$^{1b}$R$^{1c}$)$_r$-3-14 membered carbocycle, or —(CR$^{1b}$R$^{1c}$)$_r$-5-7 membered heterocycle comprising carbon atoms and 1-4 heteroatoms selected from N, O, P(=O) and S(O)$_p$ substituted with 0-4 R$^f$;

R$^3$ is, independently at each occurrence, selected from hydrogen, halo, N$_3$, CN, —(CR$^{1b}$R$^{1c}$)$_r$—OR$^{3b}$, —(CR$^{1b}$R$^{1c}$)$_r$—NR$^{11}$R$^{11}$, C$_{1-6}$ alkyl substituted with 0-3 R$^{3a}$, C$_{3-10}$ cycloalkyl substituted with 0-3 R$^{3a}$; and phenyl substituted with 0-3 R$^{3a}$, or 4-10 membered heterocycle containing 1-4 heteroatoms selected from N, O, and S(O)$_p$, substituted with 0-3 R$^{3a}$, or two R$^3$ located on adjacent carbon atoms link to form a 5-7 membered carbocycle or a 5-7 membered heterocycle comprising carbon atoms and 1-4 heteroatom selected from N, O and S(O)$_p$, both optionally substituted with 0-3 R$^{3a}$;

R$^{3a}$ is, independently at each occurrence, hydrogen, =O, halo, OCF$_3$, OCHF$_2$, CF$_3$, CHF$_2$, CN, NO$_2$, —(CR$^{1b}$R$^{1c}$)$_r$—OR$^b$, —(CR$^{1b}$R$^{1c}$)$_r$—S(O)$_p$R$^b$, —(CR$^{1b}$R$^{1c}$)$_r$—C(O)R$^b$, —(CR$^{1b}$R$^{1c}$)$_r$—C(O)OR$^b$, —(CR$^{1b}$R$^{1c}$)$_r$—OC(O)R$^b$, —(CR$^{1b}$R$^{1c}$)$_r$—NR$^{11}$R$^{11}$, —(CR$^{1b}$R$^{1c}$)$_r$—C(O)NR$^{11}$R$^{11}$, —(CR$^{1b}$R$^{1c}$)$_r$—NR$^b$C(O)R$^c$, —(CR$^{1b}$R$^{1c}$)$_r$—NR$^b$C(O)OR$^c$, —NR$^b$C(O)NR$^{11}$R$^{11}$, —S(O)$_p$NR$^{11}$R$^{11}$, —NR$^b$S(O)$_p$R$^c$, C$_{1-6}$ alkyl substituted with 0-3 R$^a$, C$_{2-6}$ alkenyl substituted with 0-3 R$^a$, C$_{2-6}$ alkynyl substituted with 0-3 R$^a$, C$_{1-6}$ haloalkyl, —(CR$^{1b}$R$^{1c}$)$_r$-3-14 membered carbocycle substituted with 0-3 R$^a$, or —(CR$^{1b}$R$^{1c}$)$_r$-5-10 membered heterocycle comprising carbon atoms and 1-4 heteroatoms selected from N, O, and S(O)$_p$ substituted with 0-3 R$^a$;

R$^{3b}$ is, independently at each occurrence, hydrogen, CF$_3$, —(CR$^{1b}$R$^{1c}$)$_q$OR$^b$, —(CR$^{1b}$R$^{1c}$)$_q$S(O)$_p$R$^b$, —(CR$^{1b}$R$^{1c}$)$_r$—C(O)R$^{3d}$, —(CR$^{1b}$R$^{1c}$)$_r$—C(O)OR$^b$, —(CR$^{1b}$R$^{1c}$)$_q$OC(O)R$^b$, —(CR$^{1b}$R$^{1c}$)$_q$NR$^{11}$R$^{11}$, —(CR$^{1b}$R$^{1c}$)$_q$C(O)NR$^{11}$R$^{11}$, —(CR$^{1b}$R$^{1c}$)$_q$NR$^b$C(O)R$^{3c}$, —(CR$^{1b}$R$^{1c}$)$_q$NR$^b$C(O)OR$^c$, —(CR$^{1b}$R$^{1c}$)$_q$NR$^b$C(O)N R$^{11}$R$^{11}$, —(CR$^{1b}$R$^{1c}$)$_q$S(O)$_2$N R$^{11}$R$^{11}$, —(CR$^{1b}$R$^{1c}$)$_q$NR$^b$S(O)$_2$R$^c$, C$_{1-6}$ alkyl substituted with 0-3 R$^a$, C$_{1-6}$ haloalkyl, —(CR$^{1b}$R$^{1c}$)$_r$-3-14 membered carbocycle substituted with 0-3 R$^a$, or —(CR$^{1b}$R$^{1c}$)$_r$-5-7 membered heterocycle comprising carbon atoms and 1-4 heteroatoms selected from N, O, and S(O), substituted with 0-3 R$^a$;

R$^{3c}$ and R$^{3d}$ are, independently at each occurrence, hydrogen or C$_{1-6}$ alkyl;

R$^4$ and R$^5$ are independently hydrogen, halo, C$_{1-6}$ alkyl or C$_{1-6}$ haloalkyl, or R$^4$ and R$^5$ together with the carbon atom to which they are attached form a 3- to 6-membered spirocarbocyclyl ring or a spiroheterocyclyl ring;

R$^6$ and R$^7$ are independently hydrogen, C(=O)C$_{1-4}$ alkyl, C(=O)OC$_{1-4}$ alkyl, C$_{1-6}$ alkyl or C$_{1-6}$ haloalkyl; or R$^6$ and R$^7$ taken together are =O;

R$^{11}$ is, independently at each occurrence, hydrogen, C$_{1-6}$ alkyl substituted with 0-3 R$^f$, CF$_3$, C$_{3-10}$ cycloalkyl substituted with 0-3 R$^f$, —(CR$^{1b}$R$^{1c}$)$_r$-phenyl substituted with 0-3 R$^d$, or —(CR$^{1b}$R$^{1c}$)$_r$-5-7 membered heterocycle comprising carbon atoms and 1-4 heteroatoms selected from N, O, P(=O) and S(O)$_p$ substituted with 0-4 R$^d$;

or one R$^{11}$ and a second R$^{11}$, both attached to the same nitrogen atom, combine to form a heterocycle comprising carbon atoms and 1-4 heteroatoms selected from N, O, P(=O) and S(O)$_p$ substituted with 0-4 R$^d$;

R$^a$ is, independently at each occurrence, hydrogen, =O, halo, OCF$_3$, CF$_3$, CHF$_2$, CN, NO$_2$, —(CR$^{1b}$R$^{1c}$)$_r$—OR$^b$, —(CR$^{1b}$R$^{1c}$)$_r$—S(O)$_p$R$^b$, —(CR$^{1b}$R$^{1c}$)$_r$—C(O)R$^b$, —(CR$^{1b}$R$^{1c}$)$_r$—C(O)OR$^b$, —(CR$^{1b}$R$^{1c}$)$_r$—OC(O)R$^b$, —(CR$^{1b}$R$^{1c}$)$_r$—NR$^{11}$R$^{11}$, —(CR$^{1b}$R$^{1c}$)$_r$—C(O)NR$^{11}$R$^{11}$, —(CR$^{1b}$R$^{1c}$)$_r$—NR$^b$C(O)R$^c$, —(CR$^{1b}$R$^{1c}$)$_r$—NR$^b$C(O)OR$^c$, —NR$^b$C(O)NR$^{11}$R$^{11}$, —S(O)$_p$NR$^{11}$R$^{11}$, —NR$^b$S(O)$_p$R$^c$, C$_{1-6}$ alkyl substituted with 0-3 R$^f$, C$_{1-6}$ haloalkyl, C$_{2-6}$ alkenyl substituted with 0-3 R$^e$, C$_{2-6}$ alkynyl substituted with 0-3 R$^e$, —(CR$^{1b}$R$^{1c}$)$_r$-3-14 membered carbocycle, or —(CR$^{1b}$R$^{1c}$)$_r$-5-7 membered heterocycle comprising carbon atoms and 1-4 heteroatoms selected from N, O, P(=O) and S(O)$_p$ substituted with 0-4 R$^f$;

R$^b$ is, independently at each occurrence, hydrogen, C$_{1-6}$ alkyl substituted with 0-3 R$^d$, C$_{1-6}$ haloalkyl, C$_{3-6}$ cycloalkyl substituted with 0-3 R$^d$, —(CR$^{1b}$R$^{1c}$)$_r$-5-7 membered heterocycle comprising carbon atoms and 1-4 heteroatoms selected from N, O, P(=O) and S(O)$_p$ substituted with 0-4 R$^f$, or —(CR$^{1b}$R$^{1c}$)$_r$-6-10 membered carbocycle substituted with 0-3 R$^d$;

R$^c$ is, independently at each occurrence, C$_{1-6}$ alkyl substituted with 0-3 R$^f$, —(CR$^{1b}$R$^{1c}$)$_r$—C$_{3-6}$ cycloalkyl substituted with 0-3 R$^f$, or —(CR$^{1b}$R$^{1c}$)$_r$-phenyl substituted with 0-3 R$^f$;

R$^d$ is, independently at each occurrence, hydrogen, =O, halo, OCF$_3$, CF$_3$, CN, NO$_2$, —OR$^e$, —(CR$^{1b}$R$^{1c}$)$_r$—C(O)R$^c$, —NR$^e$R$^e$, —NR$^e$C(O)OR$^c$, C(O)NR$^e$R$^e$, —NR$^e$C(O)R$^c$, CO$_2$H, CO$_2$R$^c$, —NR$^e$SO$_2$R$^c$, SO$_2$R$^c$, C$_{1-6}$ alkyl substituted with 0-3 R$^f$, C$_{3-6}$ cycloalkyl substituted with 0-3 R$^f$, —(CR$^{1b}$R$^{1c}$)$_r$-phenyl substituted with 0-3 R$^f$ or —(CR$^{1b}$R$^{1c}$)$_r$-5-7 membered heterocycle comprising carbon atoms and 1-4 heteroatoms selected from N, O, P(=O) and S(O)$_p$ substituted with 0-4 R$^f$;

R$^e$ is, independently at each occurrence, selected from hydrogen, C(O)NR$^f$R$^f$, C$_{1-6}$ alkyl, C$_{3-6}$ cycloalkyl, -5-7 membered heterocycle or —(CR$^{1b}$R$^{1c}$)$_r$-phenyl substituted with 0-3 R$^f$;

R$^f$ is, independently at each occurrence, hydrogen, =O, halo, CN, NH$_2$, NH(C$_{1-6}$ alkyl), N(C$_{1-6}$ alkyl)$_2$, SO$_2$(C$_{1-6}$ alkyl), CO$_2$H, CO$_2$(C$_{1-6}$ alkyl), OH, C$_{3-6}$ cycloalkyl, CF$_3$; O(C$_{1-6}$ alkyl); or an optionally substituted —(CR$^{1b}$R$^{1c}$)$_r$-5-10 membered heterocycle comprising carbon atoms and 1-4 heteroatoms selected from N, O, P(=O) and S(O)$_p$, phenyl or C$_{3-6}$ cycloalkyl, each group optionally substituted with halo, CN, CF$_3$, C$_{1-6}$ alkyl or O(C$_{1-6}$ alkyl);

m is 0, 1, 2 or 3 n is 0, 1 or 2;

p and q are, independently at each occurrence, 0, 1, or 2;

r is 0, 1, 2, 3, or 4;

t is 0 or 1; and w is 1, 2 or 3.

2. A compound according to claim 1 of formula Ia

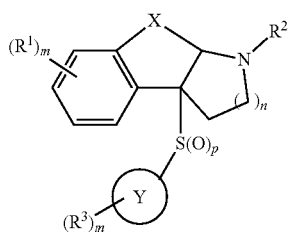

(Ia)

wherein
X is —CR$^4$R$^5$—, —(CR$^4$R$^5$)$_2$—, —OCR$^6$R$^7$—, —S(O)$_p$CR$^6$R$^7$— or —NR$^6$CR$^6$R$^7$—;
Y is a 5 or 6-membered aromatic or heteroaromatic ring;
R$^1$ is, independently at each occurrence, selected from hydrogen, CD$_3$, halo, C$_{1-6}$ alkyl substituted with 0-3 R$^{1a}$, —(CR$^{1b}$R$^{1c}$)$_r$-3-14 membered carbocycle substituted with 0-3 R$^{1a}$ and —(CR$^{1b}$R$^{1c}$)$_r$-5-10 membered heterocycle comprising carbon atoms and 1-4 heteroatoms selected from N, O, and S(O)$_p$ substituted with 0-3 R$^{1a}$;
R$^{1a}$ is, independently at each occurrence, hydrogen, =O, halo, CF$_3$, OCF$_3$, CN, NO$_2$, —(CR$^{1b}$R$^{1c}$)$_r$—OR$^b$, —(CR$^{1b}$R$^{1c}$)$_r$—S(O)$_p$R$^b$, —(CR$^{1b}$R$^{1c}$)$_r$—C(O)R$^b$, —(CR$^{1b}$R$^{1c}$)$_r$—C(O)OR$^b$, —(CR$^{1b}$R$^{1c}$)$_r$—OC(O)R$^b$, —(CR$^{1b}$R$^{1c}$)$_r$—NR$^{11}$R$^{11}$, —(CR$^{1b}$R$^{1c}$)$_r$—C(O)NR$^{11}$R$^{11}$, —(CR$^{1b}$R$^{1c}$)$_r$—NR$^b$C(O)R$^c$, —(CR$^{1b}$R$^{1c}$)$_r$—NR$^b$C(O)OR$^c$, —NR$^b$C(O)NR$^{11}$R$^{11}$, —S(O)$_p$NR$^{11}$R$^{11}$, —NR$^b$S(O)$_p$R$^c$, C$_{1-6}$ alkyl substituted with 0-3 R$^a$, C$_{1-6}$ haloalkyl, C$_{2-6}$ alkenyl substituted with 0-3 R$^a$, C$_{2-6}$ alkynyl substituted with 0-3 R$^a$, —(CR$^{1b}$R$^{1c}$)$_r$-3-14 membered carbocycle substituted with 0-3 R$^a$, or —(CR$^{1b}$R$^{1c}$)$_r$-5-7 membered heterocycle comprising carbon atoms and 1-4 heteroatoms selected from N, O, and S(O)$_p$ substituted with 0-3 R$^a$;
R$^{1b}$ and R$^{1c}$ are, independently at each occurrence, hydrogen, halogen or C$_{1-6}$ alkyl;
R$^2$ is

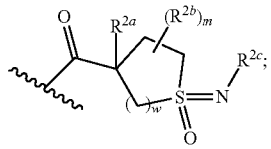

R$^{2a}$ and R$^{2b}$ are, independently at each occurrence, hydrogen, halo, OCF$_3$, CF$_3$, CHF$_2$, CN, NO$_2$, —(CR$^{1b}$R$^{1c}$)$_r$—OR$^b$, —(CR$^{1b}$R$^{1c}$)$_r$—S(O)$_p$R$^b$, —(CR$^{1b}$R$^{1c}$)$_r$—C(O)R$^b$, —(CR$^{1b}$R$^{1c}$)$_r$—C(O)OR$^b$, —(CR$^{1b}$R$^{1c}$)$_r$—OC(O)R$^b$, —(CR$^{1b}$R$^{1c}$)$_r$—NR$^{11}$R$^{11}$, —(CR$^{1b}$R$^{1c}$)$_r$—C(O)NR$^{11}$R$^{11}$, —(CR$^{1b}$R$^{1c}$)$_r$—NR$^b$C(O)R$^c$, —(CR$^{1b}$R$^{1c}$)$_r$—NR$^b$C(O)OR$^c$, —NR$^b$C(O)NR$^{11}$R$^{11}$, —S(O)$_p$NR$^{11}$R$^{11}$, —NR$^b$S(O)$_p$R$^c$, C$_{1-6}$ alkyl substituted with 0-3 R$^f$, C$_{1-6}$ haloalkyl, C$_{2-6}$ alkenyl substituted with 0-3 R$^e$, C$_{2-6}$ alkynyl substituted with 0-3 R$^e$, —(CR$^{1b}$R$^{1c}$)$_r$-3-14 membered carbocycle, or —(CR$^{1b}$R$^{1c}$)$_r$-5-7 membered heterocycle comprising carbon atoms and 1-4 heteroatoms selected from N, O, P(=O) and S(O)$_p$ substituted with 0-4 R$^f$;
R$^{2c}$ is hydrogen, C$_{1-6}$ alkyl substituted with 0-3 R$^f$, C$_{1-6}$ haloalkyl, —(CR$^{1b}$R$^{1c}$)$_r$—C(O)R$^b$, —(CR$^{1b}$R$^{1c}$)$_r$—C(O)OR$^b$, —(CR$^{1b}$R$^{1c}$)$_r$—C(O)NR$^{11}$R$^{11}$, —(CR$^{1b}$R$^{1c}$)$_r$-3-14 membered carbocycle, or —(CR$^{1b}$R$^{1c}$)$_r$-5-7 membered heterocycle comprising carbon atoms and 1-4 heteroatoms selected from N, O, P(=O) and S(O)$_p$ substituted with 0-4 R$^f$;
R$^3$ is, independently at each occurrence, selected from hydrogen, halo, N$_3$, CN, —(CR$^{1b}$R$^{1c}$)$_r$—OR$^{3b}$, —(CR$^{1b}$R$^{1c}$)$_r$—NR$^{11}$R$^{11}$, C$_{1-6}$ alkyl substituted with 0-3 R$^{3a}$, C$_{3-10}$ cycloalkyl substituted with 0-3 R$^{3a}$; and phenyl substituted with 0-3 R$^{3a}$, or 4-10 membered heterocycle containing 1-4 heteroatoms selected from N, O, and S(O)$_p$, substituted with 0-3 R$^{3a}$, or two R$^3$ located on adjacent carbon atoms link to form a 5-7 membered carbocycle or a 5-7 membered heterocycle comprising carbon atoms and 1-4 heteroatom selected from N, O and S(O)$_p$, both optionally substituted with 0-3 R$^{3a}$;
R$^{3a}$ is, independently at each occurrence, hydrogen, =O, halo, OCF$_3$, OCHF$_2$, CF$_3$, CHF$_2$, CN, NO$_2$, —(CR$^{1b}$R$^{1c}$)$_r$—OR$^b$, —(CR$^{1b}$R$^{1c}$)$_r$—S(O)$_p$R$^b$, —(CR$^{1b}$R$^{1c}$)$_r$—C(O)R$^b$, —(CR$^{1b}$R$^{1c}$)$_r$—C(O)OR$^b$, —(CR$^{1b}$R$^{1c}$)$_r$—OC(O)R$^b$, —(CR$^{1b}$R$^{1c}$)$_r$—NR$^{11}$R$^{11}$, —(CR$^{1b}$R$^{1c}$)$_r$—C(O)NR$^{11}$R$^{11}$, —(CR$^{1b}$R$^{1c}$)$_r$—NR$^b$C(O)R$^c$, —(CR$^{1b}$R$^{1c}$)$_r$—NR$^b$C(O)OR$^c$, —NR$^b$C(O)NR$^{11}$R$^{11}$, —S(O)$_p$NR$^{11}$R$^{11}$, —NR$^b$S(O)$_p$R$^c$, C$_{1-6}$ alkyl substituted with 0-3 R$^a$, C$_{2-6}$ alkenyl substituted with 0-3 R$^a$, C$_{2-6}$ alkynyl substituted with 0-3 R$^a$, C$_{1-6}$ haloalkyl, —(CR$^{1b}$R$^{1c}$)$_r$-3-14 membered carbocycle substituted with 0-3 R$^a$, or —(CR$^{1b}$R$^{1c}$)$_r$-5-10 membered heterocycle comprising carbon atoms and 1-4 heteroatoms selected from N, O, and S(O)$_p$ substituted with 0-3 R$^a$;
R$^{3b}$ is, independently at each occurrence, hydrogen, CF$_3$, —(CR$^{1b}$R$^{1c}$)$_q$OR$^b$, —(CR$^{1b}$R$^{1c}$)$_q$S(O)$_p$R$^b$, —(CR$^{1b}$R$^{1c}$)$_q$—C(O)R$^{3d}$, —(CR$^{1b}$R$^{1c}$)$_q$—C(O)OR$^b$, —(CR$^{1b}$R$^{1c}$)$_q$OC(O)R$^b$, —(CR$^{1b}$R$^{1c}$)$_q$NR$^{11}$R$^{11}$, —(CR$^{1b}$R$^{1c}$)$_q$—C(O)NR$^{11}$R$^{11}$, —(CR$^{1b}$R$^{1c}$)$_q$NR$^b$C(O)R$^{3c}$, —(CR$^{1b}$R$^{1c}$)$_q$NR$^b$C(O)OR$^c$, —(CR$^{1b}$R$^{1c}$)$_q$NR$^b$C(O)N R$^{11}$R$^{11}$, —(CR$^{1b}$R$^{1c}$)$_q$S(O)$_2$N R$^{11}$R$^{11}$, —(CR$^{1b}$R$^{1c}$)$_q$NR$^b$S(O)$_2$R$^c$, C$_{1-6}$ alkyl substituted with 0-3 R$^a$, C$_{1-6}$ haloalkyl, —(CR$^{1b}$R$^{1c}$)$_r$-3-14 membered carbocycle substituted with 0-3 R$^a$, or —(CR$^{1b}$R$^{1c}$)$_r$-5-7 membered heterocycle comprising carbon atoms and 1-4 heteroatoms selected from N, O, and S(O)$_p$ substituted with 0-3 R$^a$;
R$^{3c}$ and R$^{3d}$ are, independently at each occurrence, hydrogen or C$_{1-6}$ alkyl;
R$^4$ and R$^5$ are independently hydrogen, halo, C$_{1-6}$ alkyl or C$_{1-6}$ haloalkyl, or
R$^4$ and R$^5$ together with the carbon atom to which they are attached form a 3- to 6-membered spirocarbocyclyl ring or a spiroheterocyclyl ring;
R$^6$ and R$^7$ are independently hydrogen, C$_{1-6}$ alkyl or C$_{1-6}$ haloalkyl;
R$^{11}$ is, independently at each occurrence, hydrogen, C$_{1-6}$ alkyl substituted with 0-3 R$^f$, CF$_3$, C$_{3-10}$ cycloalkyl substituted with 0-3 R$^f$, —(CR$^{1b}$R$^{1c}$)$_r$-phenyl substituted with 0-3 R$^d$, or —(CR$^{1b}$R$^{1c}$)$_r$-5-7 membered heterocycle comprising carbon atoms and 1-4 heteroatoms selected from N, O, P(=O) and S(O)$_p$ substituted with 0-4 R$^d$;
or one R$^{11}$ and a second R$^{11}$, both attached to the same nitrogen atom, combine to form a heterocycle comprising carbon atoms and 1-4 heteroatoms selected from N, O, P(=O) and S(O)$_p$ substituted with 0-4 R$^d$;
R$^a$ is, independently at each occurrence, hydrogen, =O, halo, OCF$_3$, CF$_3$, CHF$_2$, CN, NO$_2$, —(CR$^{1b}$R$^{1c}$)$_r$—

OR$^b$, —(CR$^{1b}$R$^{1c}$)$_r$—S(O)$_p$R$^b$, —(CR$^{1b}$R$^{1c}$)$_r$—C(O) R$^b$, —(CR$^{1b}$R$^{1c}$)$_r$—C(O)OR$^b$, —(CR$^{1b}$R$^{1c}$)$_r$—OC(O) R$^b$, —(CR$^{1b}$R$^{1c}$)$_r$—NR$^{11}$R$^{11}$, —(CR$^{1b}$R$^{1c}$)$_r$—C(O) NR$^{11}$R$^{11}$, —(CR$^{1b}$R$^{1c}$)$_r$—NR$^b$C(O)R$^c$, —(CR$^{1b}$R$^{1c}$)$_r$—NR$^b$C(O)OR$^c$, —NR$^b$C(O)NR$^{11}$R$^{11}$, —S(O)$_p$NR$^{11}$R$^{11}$, —NR$^b$S(O)$_p$R$^c$, C$_{1-6}$ alkyl substituted with 0-3 R$^f$, C$_{1-6}$ haloalkyl, C$_{2-6}$ alkenyl substituted with 0-3 R$^e$, C$_{2-6}$ alkynyl substituted with 0-3 R$^e$, —(CR$^{1b}$R$^{1c}$)$_r$-3-14 membered carbocycle, or —(CR$^{1b}$R$^{1c}$)$_r$-5-7 membered heterocycle comprising carbon atoms and 1-4 heteroatoms selected from N, O, P(=O) and S(O)$_p$ substituted with 0-4 R$^f$;

R$^b$ is, independently at each occurrence, hydrogen, C$_{1-6}$ alkyl substituted with 0-3 R$^d$, C$_{1-6}$ haloalkyl, C$_{3-6}$ cycloalkyl substituted with 0-3 R$^d$, —(CR$^{1b}$R$^{1c}$)$_r$-5-7 membered heterocycle comprising carbon atoms and 1-4 heteroatoms selected from N, O, P(=O) and S(O)$_p$ substituted with 0-4 R$^f$, or —(CR$^{1b}$R$^{1c}$)$_r$-6-10 membered carbocycle substituted with 0-3 R$^d$;

R$^c$ is, independently at each occurrence, C$_{1-6}$ alkyl substituted with 0-3 R$^f$, —(CR$^{1b}$R$^{1c}$)$_r$—C$_{3-6}$ cycloalkyl substituted with 0-3 R$^f$, or —(CR$^{1b}$R$^{1c}$)$_r$-phenyl substituted with 0-3 R$^f$;

R$^d$ is, independently at each occurrence, hydrogen, =O, halo, OCF$_3$, CF$_3$, CN, NO$_2$, —OR$^e$, —(CR$^{1b}$R$^{1c}$)$_r$—C(O)R$^e$, —NR$^e$R$^e$, —NR$^e$C(O)OR$^e$, C(O)NR$^e$R$^e$, —NR$^e$C(O)R$^e$, CO$_2$H, CO$_2$R$^e$, —NR$^e$SO$_2$R$^e$, SO$_2$R$^e$, C$_{1-6}$ alkyl substituted with 0-3 R$^f$, C$_{3-6}$ cycloalkyl substituted with 0-3 R$^f$, —(CR$^{1b}$R$^{1c}$)$_r$-phenyl substituted with 0-3 R$^f$ or —(CR$^{1b}$R$^{1c}$)$_r$-5-7 membered heterocycle comprising carbon atoms and 1-4 heteroatoms selected from N, O, P(=O) and S(O)$_p$ substituted with 0-4 R$^f$;

R$^e$ is, independently at each occurrence, selected from hydrogen, C(O)NR$^f$R$^f$, C$_{1-6}$ alkyl, C$_{3-6}$ cycloalkyl, -5-7 membered heterocycle or —(CR$^{1b}$R$^{1c}$)$_r$-phenyl substituted with 0-3 R$^f$;

R$^f$ is, independently at each occurrence, hydrogen, =O, halo, CN, NH$_2$, NH(C$_{1-6}$ alkyl), N(C$_{1-6}$ alkyl)$_2$, SO$_2$(C$_{1-6}$ alkyl), CO$_2$H, CO$_2$(C$_{1-6}$ alkyl), OH, C$_{3-6}$ cycloalkyl, CF$_3$; O(C$_{1-6}$ alkyl); or an optionally substituted —(CR$^{1b}$R$^{1c}$)$_r$-5-10 membered heterocycle comprising carbon atoms and 1-4 heteroatoms selected from N, O, P(=O) and S(O)$_p$, phenyl or C$_{3-6}$ cycloalkyl, each group optionally substituted with halo, CN, CF$_3$, C$_{1-6}$ alkyl or O(C$_{1-6}$ alkyl);

m is 0, 1, 2 or 3
n is 0, 1 or 2;
p and q are, independently at each occurrence, 0, 1, or 2;
r is 0, 1, 2, 3, or 4; and
w is 1, 2 or 3;
or a stereoisomer or pharmaceutically-acceptable salt thereof.

3. A compound according to claim 2 of the formula

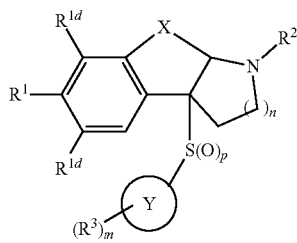

wherein
X is —CR$^4$R$^5$—, —(CR$^4$R$^5$)$_2$—, —OCR$^6$R$^7$—, —S(O)$_p$CR$^6$R$^7$— or —NR$^6$CR$^6$R$^7$—;
Y is a 5 or 6-membered aromatic or heteroaromatic ring;
R$^1$ is selected from halo, C$_{1-6}$ alkyl substituted with 0-3 R$^{1a}$, —(CR$^{1b}$R$^{1c}$)$_r$-3-14 membered carbocycle substituted with 0-3 R$^{1a}$ and —(CR$^{1b}$R$^{1c}$)$_r$-5-10 membered heterocycle comprising carbon atoms and 1-4 heteroatoms selected from N, O, and S(O)$_p$ substituted with 0-3 R$^{1a}$;
R$^{1a}$ is, independently at each occurrence, hydrogen, =O, halo, CF$_3$, OCF$_3$, CN, NO$_2$, —(CR$^{1b}$R$^{1c}$)$_r$—OR$^b$, —(CR$^{1b}$R$^{1c}$)$_r$—S(O)$_p$R$^b$, —(CR$^{1b}$R$^{1c}$)$_r$—C(O)R$^b$, —(CR$^{1b}$R$^{1c}$)$_r$—C(O)OR$^b$, —(CR$^{1b}$R$^{1c}$)$_r$—OC(O)R$^b$, —(CR$^{1b}$R$^{1c}$)$_r$—NR$^{11}$R$^{11}$, —(CR$^{1b}$R$^{1c}$)$_r$—C(O) NR$^{11}$R$^{11}$, —(CR$^{1b}$R$^{1c}$)$_r$—NR$^b$C(O)R$^c$, —(CR$^{1b}$R$^{1c}$)$_r$—NR$^b$C(O)OR$^c$, —NR$^b$C(O)NR$^{11}$R$^{11}$, —S(O)$_p$NR$^{11}$R$^{11}$, —NR$^b$S(O)$_p$R$^c$, C$_{1-6}$ alkyl substituted with 0-3 R$^a$, C$_{1-6}$ haloalkyl, C$_{2-6}$ alkenyl substituted with 0-3 R$^a$, C$_{2-6}$ alkynyl substituted with 0-3 R$^a$, —(CR$^{1b}$R$^{1c}$)$_r$-3-14 membered carbocycle substituted with 0-3 R$^a$, or —(CR$^{1b}$R$^{1c}$)$_r$-5-7 membered heterocycle comprising carbon atoms and 1-4 heteroatoms selected from N, O, and S(O)$_p$ substituted with 0-3 R$^a$;
R$^{1b}$ and R$^{1c}$ are, independently at each occurrence, hydrogen, halogen or C$_{1-6}$ alkyl;
R$^{1d}$ is, independently at each occurrence, hydrogen, CD$_3$, halo, CF$_3$, and C$_1$-C$_4$ alkyl;
R$^2$ is

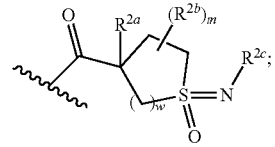

R$^{2a}$ and R$^{2b}$ are, independently at each occurrence, hydrogen, halo, OCF$_3$, CF$_3$, CHF$_2$, CN, NO$_2$, —(CR$^{1b}$R$^{1c}$)$_r$—OR$^b$, —(CR$^{1b}$R$^{1c}$)$_r$—S(O)$_p$R$^b$, —(CR$^{1b}$R$^{1c}$)$_r$—C(O)R$^b$, —(CR$^{1b}$R$^{1c}$)$_r$—C(O)OR$^b$, —(CR$^{1b}$R$^{1c}$)$_r$—OC(O)R$^b$, —(CR$^{1b}$R$^{1c}$)$_r$—NR$^{11}$R$^{11}$, —(CR$^{1b}$R$^{1c}$)$_r$—C(O)NR$^{11}$R$^{11}$, —(CR$^{1b}$R$^{1c}$)$_r$—NR$^b$C(O)R$^c$, —(CR$^{1b}$R$^{1c}$)$_r$—NR$^b$C(O)OR$^c$, —NR$^b$C(O)NR$^{11}$R$^{11}$, —S(O)$_p$NR$^{11}$R$^{11}$, —NR$^b$S(O)$_p$R$^c$, C$_{1-6}$ alkyl substituted with 0-3 R$^f$, C$_{1-6}$ haloalkyl, C$_{2-6}$ alkenyl substituted with 0-3 R$^e$, C$_{2-6}$ alkynyl substituted with 0-3 R$^e$, —(CR$^{1b}$R$^{1c}$)$_r$-3-14 membered carbocycle, or —(CR$^{1b}$R$^{1c}$)$_r$-5-7 membered heterocycle comprising carbon atoms and 1-4 heteroatoms selected from N, O, P(=O) and S(O)$_p$ substituted with 0-4 R$^f$;
R$^{2c}$ is hydrogen, C$_{1-6}$ alkyl substituted with 0-3 R$^f$, C$_{1-6}$ haloalkyl, —(CR$^{1b}$R$^{1c}$)$_r$—C(O)R$^b$, —(CR$^{1b}$R$^{1c}$)$_r$—C(O)OR$^b$, —(CR$^{1b}$R$^{1c}$)$_r$—C(O)NR$^{11}$R$^{11}$, —(CR$^{1b}$R$^{1c}$)$_r$-3-14 membered carbocycle, or —(CR$^{1b}$R$^{1c}$)$_r$-5-7 membered heterocycle comprising carbon atoms and 1-4 heteroatoms selected from N, O, P(=O) and S(O)$_p$ substituted with 0-4 R$^f$;
R$^3$ is, independently at each occurrence, selected from hydrogen, halo, N$_3$, CN, —(CR$^{1b}$R$^{1c}$)$_r$—OR$^{3b}$, —(CR$^{1b}$R$^{1c}$)$_r$—NR$^{11}$R$^{11}$, C$_{1-6}$ alkyl substituted with 0-3 R$^{3a}$, C$_{3-10}$ cycloalkyl substituted with 0-3 R$^{3a}$; and phenyl substituted with 0-3 R$^{3a}$, or 4-10 membered heterocycle containing 1-4 heteroatoms selected from N, O, and S(O)$_p$, substituted with 0-3 R$^{3a}$, or two R$^3$ located on adjacent carbon atoms link to form a 5-7 membered carbocycle or a 5-7 membered heterocycle comprising carbon atoms and 1-4 heteroatom selected from N, O and S(O)$_p$, both optionally substituted with 0-3 R$^{3a}$;

R$^{3a}$ is, independently at each occurrence, hydrogen, =O, halo, OCF$_3$, OCHF$_2$, CF$_3$, CHF$_2$, CN, NO$_2$, —(CR$^{1b}$R$^{1c}$)$_r$—OR$^b$, —(CR$^{1b}$R$^{1c}$)$_r$—S(O)$_p$R$^b$, —(CR$^{1b}$R$^{1c}$)$_r$—C(O)R$^b$, —(CR$^{1b}$R$^{1c}$)$_r$—C(O)OR$^b$, —(CR$^{1b}$R$^{1c}$)$_r$—OC(O)R$^b$, —(CR$^{1b}$R$^{1c}$)$_r$—NR$^{11}$R$^{11}$, —(CR$^{1b}$R$^{1c}$)$_r$—C(O)NR$^{11}$R$^{11}$, —(CR$^{1b}$R$^{1c}$)$_r$—NR$^b$C(O)R$^c$, —(CR$^{1b}$R$^{1c}$)$_r$—NR$^b$C(O)OR$^c$, —NR$^b$C(O)NR$^{11}$R$^{11}$, —S(O)$_p$NR$^{11}$R$^{11}$, —NR$^b$S(O)$_p$R$^c$, C$_{1-6}$ alkyl substituted with 0-3 R$^a$, C$_{2-6}$ alkenyl substituted with 0-3 R$^a$, C$_{2-6}$ alkynyl substituted with 0-3 R$^a$, C$_{1-6}$ haloalkyl, —(CR$^{1b}$R$^{1c}$)$_r$-3-14 membered carbocycle substituted with 0-3 R$^a$, or —(CR$^{1b}$R$^{1c}$)$_r$-5-10 membered heterocycle comprising carbon atoms and 1-4 heteroatoms selected from N, O, and S(O)$_p$ substituted with 0-3 R$^a$;

R$^{3b}$ is, independently at each occurrence, hydrogen, CF$_3$, —(CR$^{1b}$R$^{1c}$)$_q$OR$^b$, —(CR$^{1b}$R$^{1c}$)$_q$S(O)$_p$R$^b$, —(CR$^{1b}$R$^{1c}$)$_r$—C(O)R$^{3d}$, —(CR$^{1b}$R$^{1c}$)$_r$—C(O)OR$^b$, —(CR$^{1b}$R$^{1c}$)$_q$OC(O)R$^b$, —(CR$^{1b}$R$^{1c}$)$_q$NR$^{11}$R$^{11}$, —(CR$^{1b}$R$^{1c}$)$_q$C(O)NR$^{11}$R$^{11}$, —(CR$^{1b}$R$^{1c}$)$_q$NR$^b$C(O)R$^{3c}$, —(CR$^{1b}$R$^{1c}$)$_q$NR$^b$C(O)OR$^c$, —(CR$^{1b}$R$^{1c}$)$_q$NR$^b$C(O)NR$^{11}$R$^{11}$, —(CR$^{1b}$R$^{1c}$)$_q$S(O)$_2$NR$^{11}$R$^{11}$, —(CR$^{1b}$R$^{1c}$)$_q$NR$^b$S(O)R$^c$, C$_{1-6}$ alkyl substituted with 0-3 R$^a$, C$_{1-6}$ haloalkyl, —(CR$^{1b}$R$^{1c}$)$_r$-3-14 membered carbocycle substituted with 0-3 R$^a$, or —(CR$^{1b}$R$^{1c}$)$_r$-5-7 membered heterocycle comprising carbon atoms and 1-4 heteroatoms selected from N, O, and S(O)$_p$ substituted with 0-3 R$^a$;

R$^{3c}$ and R$^{3d}$ are, independently at each occurrence, hydrogen or C$_{1-6}$ alkyl;

R$^4$ and R$^5$ are independently hydrogen, halo, C$_{1-6}$ alkyl or C$_{1-6}$ haloalkyl, or R$^4$ and R$^5$ together with the carbon atom to which they are attached form a 3- to 6-membered spirocarbocyclyl ring or a spiroheterocyclyl ring;

R$^6$ and R$^7$ are independently hydrogen, C$_{1-6}$ alkyl or C$_{1-6}$ haloalkyl;

R$^{11}$ is, independently at each occurrence, hydrogen, C$_{1-6}$ alkyl substituted with 0-3 R$^f$, CF$_3$, C$_{3-10}$ cycloalkyl substituted with 0-3 R$^f$, —(CR$^{1b}$R$^{1c}$)$_r$-phenyl substituted with 0-3 R$^d$, or —(CR$^{1b}$R$^{1c}$)$_r$-5-7 membered heterocycle comprising carbon atoms and 1-4 heteroatoms selected from N, O, P(=O) and S(O)$_p$ substituted with 0-4 R$^d$;

or one R$^{11}$ and a second R$^{11}$, both attached to the same nitrogen atom, combine to form a heterocycle comprising carbon atoms and 1-4 heteroatoms selected from N, O, P(=O) and S(O)$_p$ substituted with 0-4 R$^d$;

R$^a$ is, independently at each occurrence, hydrogen, =O, halo, OCF$_3$, CF$_3$, CHF$_2$, CN, NO$_2$, —(CR$^{1b}$R$^{1c}$)$_r$—OR$^b$, —(CR$^{1b}$R$^{1c}$)$_r$—S(O)$_p$R$^b$, —(CR$^{1b}$R$^{1c}$)$_r$—C(O)R$^b$, —(CR$^{1b}$R$^{1c}$)$_r$—C(O)OR$^b$, —(CR$^{1b}$R$^{1c}$)$_r$—OC(O)R$^b$, —(CR$^{1b}$R$^{1c}$)$_r$—NR$^{11}$R$^{11}$, —(CR$^{1b}$R$^{1c}$)$_r$—C(O)NR$^{11}$R$^{11}$, —(CR$^{1b}$R$^{1c}$)$_r$—NR$^b$C(O)R$^c$, —(CR$^{1b}$R$^{1c}$)$_r$—NR$^b$C(O)OR$^c$, —NR$^b$C(O)NR$^{11}$R$^{11}$, —S(O)$_p$NR$^{11}$R$^{11}$, —NR$^b$S(O)$_p$R$^c$, C$_{1-6}$ alkyl substituted with 0-3 R$^f$, C$_{1-6}$ haloalkyl, C$_{2-6}$ alkenyl substituted with 0-3 R$^e$, C$_{2-6}$ alkynyl substituted with 0-3 R$^e$, —(CR$^{1b}$R$^{1c}$)$_r$-3-14 membered carbocycle, or —(CR$^{1b}$R$^{1c}$)$_r$-5-7 membered heterocycle comprising carbon atoms and 1-4 heteroatoms selected from N, O, P(=O) and S(O)$_p$ substituted with 0-4 R$^f$;

R$^b$ is, independently at each occurrence, hydrogen, C$_{1-6}$ alkyl substituted with 0-3 R$^d$, C$_{1-6}$ haloalkyl, C$_{3-6}$ cycloalkyl substituted with 0-3 R$^d$, —(CR$^{1b}$R$^{1c}$)$_r$-5-7 membered heterocycle comprising carbon atoms and 1-4 heteroatoms selected from N, O, P(=O) and S(O)$_p$ substituted with 0-4 R$^f$, or —(CR$^{1b}$R$^{1c}$)$_r$-6-10 membered carbocycle substituted with 0-3 R$^d$;

R$^c$ is, independently at each occurrence, C$_{1-6}$ alkyl substituted with 0-3 R$^f$, —(CR$^{1b}$R$^{1c}$)$_r$—C$_{3-6}$ cycloalkyl substituted with 0-3 R$^f$, or —(CR$^{1b}$R$^{1c}$)$_r$-phenyl substituted with 0-3 R$^f$;

R$^d$ is, independently at each occurrence, hydrogen, =O, halo, OCF$_3$, CF$_3$, CN, NO$_2$, —OR$^e$, —(CR$^{1b}$R$^{1c}$)$_r$—C(O)R$^c$, —NR$^e$R$^e$, —NR$^e$C(O)OR$^c$, C(O)NR$^e$R$^e$, —NR$^e$C(O)R$^c$, CO$_2$H, CO$_2$R$^c$, —NR$^e$SO$_2$R$^c$, SO$_2$R$^c$, C$_{1-6}$ alkyl substituted with 0-3 R$^f$, C$_{3-6}$ cycloalkyl substituted with 0-3 R$^f$, —(CR$^{1b}$R$^{1c}$)$_r$-phenyl substituted with 0-3 R$^f$ or —(CR$^{1b}$R$^{1c}$)$_r$-5-7 membered heterocycle comprising carbon atoms and 1-4 heteroatoms selected from N, O, P(=O) and S(O)$_p$ substituted with 0-4 R$^f$;

R$^e$ is, independently at each occurrence, selected from hydrogen, C(O)NR$^f$R$^f$, C$_{1-6}$ alkyl, C$_{3-6}$ cycloalkyl, -5-7 membered heterocycle or —(CR$^{1b}$R$^{1c}$)$_r$-phenyl substituted with 0-3 R$^f$;

R$^f$ is, independently at each occurrence, hydrogen, =O, halo, CN, NH$_2$, NH(C$_{1-6}$ alkyl), N(C$_{1-6}$ alkyl)$_2$, SO$_2$(C$_{1-6}$ alkyl), CO$_2$H, CO$_2$(C$_{1-6}$ alkyl), OH, C$_{3-6}$ cycloalkyl, CF$_3$; O(C$_{1-6}$ alkyl); or an optionally substituted —(CR$^{1b}$R$^{1c}$)$_r$-5-10 membered heterocycle comprising carbon atoms and 1-4 heteroatoms selected from N, O, P(=O) and S(O)$_p$, phenyl or C$_{3-6}$ cycloalkyl, each group optionally substituted with halo, CN, CF$_3$, C$_{1-6}$ alkyl or O(C$_{1-6}$ alkyl);

m is 0, 1, 2 or 3
n is 0, 1 or 2;
p and q are, independently at each occurrence, 0, 1, or 2;
r is 0, 1, 2, 3, or 4; and
w is 1, 2 or 3;

or a stereoisomer or pharmaceutically-acceptable salt thereof.

4. A compound according to claim 3 of the formula

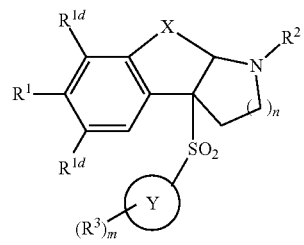

wherein

X is —CR$^4$R$^5$—, —(CR$^4$R$^5$)$_2$, —OCR$^6$R$^7$—, —S(O)$_p$CR$^6$R$^7$— or —NR$^6$CR$^6$R$^7$—;

Y is a 5 or 6-membered aromatic or heteroaromatic ring;

R$^1$ is selected from halo, C$_{1-6}$ alkyl substituted with 0-3 R$^{1a}$, —(CR$^{1b}$R$^{1c}$)$_r$-3-14 membered carbocycle substituted with 0-3 R$^{1a}$ and —(CR$^{1b}$R$^{1c}$)$_r$-5-10 membered heterocycle comprising carbon atoms and 1-4 heteroatoms selected from N, O, and S(O)$_p$ substituted with 0-3 R$^{1a}$;

R$^{1a}$ is, independently at each occurrence, hydrogen, =O, halo, CF$_3$, OCF$_3$, CN, NO$_2$, —(CR$^{1b}$R$^{1c}$)$_r$—OR$^b$, —(CR$^{1b}$R$^{1c}$)$_r$—S(O)$_p$R$^b$, —(CR$^{1b}$R$^{1c}$)$_r$—C(O)R$^b$, —(CR$^{1b}$R$^{1c}$)$_r$—C(O)OR$^b$, —(CR$^{1b}$R$^{1c}$)$_r$—OC(O)R$^b$, —(CR$^{1b}$R$^{1c}$)$_r$—NR$^{11}$R$^{11}$, —(CR$^{1b}$R$^{1c}$)$_r$—C(O)NR$^{11}$R$^{11}$, —(CR$^{1b}$R$^{1c}$)$_r$—NR$^b$C(O)R$^c$, —(CR$^{1b}$R$^{1c}$)$_r$—NR$^b$C(O)OR$^c$, —NR$^b$C(O)NR$^{11}$R$^{11}$, —S(O)$_p$NR$^{11}$R$^{11}$, —NR$^b$S(O)$_p$R$^c$, C$_{1-6}$ alkyl substituted with 0-3 R$^a$, C$_{1-6}$ haloalkyl, C$_{2-6}$ alkenyl substituted with 0-3 R$^a$, C$_{2-6}$ alkynyl substituted with 0-3 R$^a$, —(CR$^{1b}$R$^{1c}$)$_r$-3-14 membered carbocycle substituted with 0-3 R$^a$, or —(CR$^{1b}$R$^{1c}$)$_r$-5-7 membered heterocycle comprising carbon atoms and 1-4 heteroatoms selected from N, O, and S(O)$_p$ substituted with 0-3 R$^a$;

R$^{1b}$ and R$^{1c}$ are, independently at each occurrence, hydrogen, halogen or C$_{1-6}$ alkyl;

R$^{1d}$ is, independently at each occurrence, hydrogen, CD$_3$, halo, CF$_3$, and C$_1$-C$_4$ alkyl;

R$^2$ is

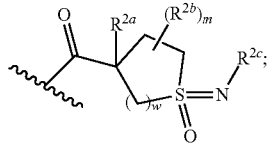

R$^{2a}$ and R$^{2b}$ are, independently at each occurrence, hydrogen, halo, OCF$_3$, CF$_3$, CHF$_2$, CN, NO$_2$, —(CR$^{1b}$R$^{1c}$)$_r$—OR$^b$, —(CR$^{1b}$R$^{1c}$)$_r$—S(O)$_p$R$^b$, —(CR$^{1b}$R$^{1c}$)$_r$—C(O)R$^b$, —(CR$^{1b}$R$^{1c}$)$_r$—C(O)OR$^b$, —(CR$^{1b}$R$^{1c}$)$_r$—OC(O)R$^b$, —(CR$^{1b}$R$^{1c}$)$_r$—NR$^{11}$R$^{11}$, —(CR$^{1b}$R$^{1c}$)$_r$—C(O)NR$^{11}$R$^{11}$, —(CR$^{1b}$R$^{1c}$)$_r$—NR$^b$C(O)R$^c$, —(CR$^{1b}$R$^{1c}$)$_r$—NR$^b$C(O)OR$^c$, —NR$^b$C(O)NR$^{11}$R$^{11}$, —S(O)$_p$NR$^{11}$R$^{11}$, —NR$^b$S(O)$_p$R$^c$, C$_{1-6}$ alkyl substituted with 0-3 R$^f$, C$_{1-6}$ haloalkyl, C$_{2-6}$ alkenyl substituted with 0-3 R$^e$, C$_{2-6}$ alkynyl substituted with 0-3 R$^e$, —(CR$^{1b}$R$^{1c}$)$_r$-3-14 membered carbocycle, or —(CR$^{1b}$R$^{1c}$)$_r$-5-7 membered heterocycle comprising carbon atoms and 1-4 heteroatoms selected from N, O, P(=O) and S(O)$_p$ substituted with 0-4 R$^f$;

R$^{2c}$ is hydrogen, C$_{1-6}$ alkyl substituted with 0-3 R$^f$, C$_{1-6}$ haloalkyl, —(CR$^{1b}$R$^{1c}$)$_r$—C(O)R$^b$, —(CR$^{1b}$R$^{1c}$)$_r$—C(O)OR$^b$, —(CR$^{1b}$R$^{1c}$)$_r$—C(O)NR$^{11}$R$^{11}$, —(CR$^{1b}$R$^{1c}$)$_r$-3-14 membered carbocycle, or —(CR$^{1b}$R$^{1c}$)$_r$-5-7 membered heterocycle comprising carbon atoms and 1-4 heteroatoms selected from N, O, P(=O) and S(O)$_p$ substituted with 0-4 R$^f$;

R$^3$ is, independently at each occurrence, selected from hydrogen, halo, N$_3$, CN, —(CR$^{1b}$R$^{1c}$)$_r$—OR$^{3b}$, —(CR$^{1b}$R$^{1c}$)$_r$—NR$^{11}$R$^{11}$, C$_{1-6}$ alkyl substituted with 0-3 R$^{3a}$, C$_{3-10}$ cycloalkyl substituted with 0-3 R$^{3a}$; and phenyl substituted with 0-3 R$^{3a}$, or 4-10 membered heterocycle containing 1-4 heteroatoms selected from N, O, and S(O)$_p$, substituted with 0-3 R$^{3a}$, or two R$^3$ located on adjacent carbon atoms link to form a 5-7 membered carbocycle or a 5-7 membered heterocycle comprising carbon atoms and 1-4 heteroatom selected from N, O and S(O)$_p$, both optionally substituted with 0-3 R$^{3a}$;

R$^{3a}$ is, independently at each occurrence, hydrogen, =O, halo, OCF$_3$, OCHF$_2$, CF$_3$, CHF$_2$, CN, NO$_2$, —(CR$^{1b}$R$^{1c}$)$_r$—OR$^b$, —(CR$^{1b}$R$^{1c}$)$_r$—S(O)$_p$R$^b$, —(CR$^{1b}$R$^{1c}$)$_r$—C(O)R$^b$, —(CR$^{1b}$R$^{1c}$)$_r$—C(O)OR$^b$, —(CR$^{1b}$R$^{1c}$)$_r$—OC(O)R$^b$, —(CR$^{1b}$R$^{1c}$)$_r$—NR$^{11}$R$^{11}$, —(CR$^{1b}$R$^{1c}$)$_r$—C(O)NR$^{11}$R$^{11}$, —(CR$^{1b}$R$^{1c}$)$_r$—NR$^b$C(O)R$^c$, —(CR$^{1b}$R$^{1c}$)$_r$—NR$^b$C(O)OR$^c$, —NR$^b$C(O)NR$^{11}$R$^{11}$, —S(O)$_p$NR$^{11}$R$^{11}$, —NR$^b$S(O)$_p$R$^c$, C$_{1-6}$ alkyl substituted with 0-3 R$^a$, C$_{2-6}$ alkenyl substituted with 0-3 R$^a$, C$_{2-6}$ alkynyl substituted with 0-3 R$^a$, C$_{1-6}$ haloalkyl, —(CR$^{1b}$R$^{1c}$)$_r$-3-14 membered carbocycle substituted with 0-3 R$^a$, or —(CR$^{1b}$R$^{1c}$)$_r$-5-10 membered heterocycle comprising carbon atoms and 1-4 heteroatoms selected from N, O, and S(O)$_p$ substituted with 0-3 R$^a$;

R$^{3b}$ is, independently at each occurrence, hydrogen, CF$_3$, —(CR$^{1b}$R$^{1c}$)$_q$OR$^b$, —(CR$^{1b}$R$^{1c}$)$_q$S(O)$_p$R$^b$, —(CR$^{1b}$R$^{1c}$)$_r$—C(O)R$^{3d}$, —(CR$^{1b}$R$^{1c}$)$_r$—C(O)OR$^b$, —(CR$^{1b}$R$^{1c}$)$_q$OC(O)R$^b$, —(CR$^{1b}$R$^{1c}$)$_q$NR$^{11}$R$^{11}$, —(CR$^{1b}$R$^{1c}$)$_r$—C(O)NR$^{11}$R$^{11}$, —(CR$^{1b}$R$^{1c}$)$_q$NR$^b$C(O)R$^{3c}$, —(CR$^{1b}$R$^{1c}$)$_q$NR$^b$C(O)OR$^c$, —(CR$^{1b}$R$^{1c}$)$_q$NR$^b$C(O)N R$^{11}$R$^{11}$, —(CR$^{1b}$R$^{1c}$)$_q$S(O)$_2$N R$^{11}$R$^{11}$, —(CR$^{1b}$R$^{1c}$)$_q$NR$^b$S(O)$_2$R$^c$, C$_{1-6}$ alkyl substituted with 0-3 R$^a$, C$_{1-6}$ haloalkyl, —(CR$^{1b}$R$^{1c}$)$_r$-3-14 membered carbocycle substituted with 0-3 R$^a$, or —(CR$^{1b}$R$^{1c}$)$_r$-5-7 membered heterocycle comprising carbon atoms and 1-4 heteroatoms selected from N, O, and S(O), substituted with 0-3 R$^a$;

R$^{3c}$ and R$^{3d}$ are, independently at each occurrence, hydrogen or C$_{1-6}$ alkyl;

R$^4$ and R$^5$ are independently hydrogen, halo, C$_{1-6}$ alkyl or C$_{1-6}$ haloalkyl, or R$^4$ and R$^5$ together with the carbon atom to which they are attached form a 3- to 6-membered spirocarbocyclyl ring or a spiroheterocyclyl ring;

R$^6$ and R$^7$ are independently hydrogen, C$_{1-6}$ alkyl or C$_{1-6}$ haloalkyl;

R$^{11}$ is, independently at each occurrence, hydrogen, C$_{1-6}$ alkyl substituted with 0-3 R$^f$, CF$_3$, C$_{3-10}$ cycloalkyl substituted with 0-3 R$^f$, —(CR$^{1b}$R$^{1c}$)$_r$-phenyl substituted with 0-3 R$^d$, or —(CR$^{1b}$R$^{1c}$)$_r$-5-7 membered heterocycle comprising carbon atoms and 1-4 heteroatoms selected from N, O, P(=O) and S(O)$_p$ substituted with 0-4 R$^d$;

or one R$^{11}$ and a second R$^{11}$, both attached to the same nitrogen atom, combine to form a heterocycle comprising carbon atoms and 1-4 heteroatoms selected from N, O, P(=O) and S(O)$_p$ substituted with 0-4 R$^d$;

R$^a$ is, independently at each occurrence, hydrogen, =O, halo, OCF$_3$, CF$_3$, CHF$_2$, CN, NO$_2$, —(CR$^{1b}$R$^{1c}$)$_r$—OR$^b$, —(CR$^{1b}$R$^{1c}$)$_r$—S(O)$_p$R$^b$, —(CR$^{1b}$R$^{1c}$)$_r$—C(O)R$^b$, —(CR$^{1b}$R$^{1c}$)$_r$—C(O)OR$^b$, —(CR$^{1b}$R$^{1c}$)$_r$—OC(O)R$^b$, —(CR$^{1b}$R$^{1c}$)$_r$—NR$^{11}$R$^{11}$, —(CR$^{1b}$R$^{1c}$)$_r$—C(O)NR$^{11}$R$^{11}$, —(CR$^{1b}$R$^{1c}$)$_r$—NR$^b$C(O)R$^c$, —(CR$^{1b}$R$^{1c}$)$_r$—NR$^b$C(O)OR$^c$, —NR$^b$C(O)NR$^{11}$R$^{11}$, —S(O)$_p$NR$^{11}$R$^{11}$, —NR$^b$S(O)$_p$R$^c$, C$_{1-6}$ alkyl substituted with 0-3 R$^f$, C$_{1-6}$ haloalkyl, C$_{2-6}$ alkenyl substituted with 0-3 R$^e$, C$_{2-6}$ alkynyl substituted with 0-3 R$^e$, —(CR$^{1b}$R$^{1c}$)$_r$-3-14 membered carbocycle, or —(CR$^{1b}$R$^{1c}$)$_r$-5-7 membered heterocycle comprising carbon atoms and 1-4 heteroatoms selected from N, O, P(=O) and S(O)$_p$ substituted with 0-4 R$^f$;

R$^b$ is, independently at each occurrence, hydrogen, C$_{1-6}$ alkyl substituted with 0-3 R$^d$, C$_{1-6}$ haloalkyl, C$_{3-6}$ cycloalkyl substituted with 0-3 R$^d$, —(CR$^{1b}$R$^{1c}$)$_r$-5-7 membered heterocycle comprising carbon atoms and 1-4 heteroatoms selected from N, O, P(=O) and S(O)$_p$ substituted with 0-4 R$^f$, or —(CR$^{1b}$R$^{1c}$)$_r$-6-10 membered carbocycle substituted with 0-3 R$^d$;

R$^c$ is, independently at each occurrence, C$_{1-6}$ alkyl substituted with 0-3 R$^f$, —(CR$^{1b}$R$^{1c}$)$_r$—C$_{3-6}$ cycloalkyl substituted with 0-3 R$^f$, or —(CR$^{1b}$R$^{1c}$)$_r$-phenyl substituted with 0-3 R$^f$;

R$^d$ is, independently at each occurrence, hydrogen, =O, halo, OCF$_3$, CF$_3$, CN, NO$_2$, —OR$^e$, —(CR$^{1b}$R$^{1c}$)$_r$—C (O)R$^c$, —NR$^e$R$^e$, —NR$^e$C(O)OR$^c$, C(O)NR$^e$R$^e$, —NR$^e$C(O)R$^c$, CO$_2$H, CO$_2$R$^c$, —NR$^e$SO$_2$R$^c$, SO$_2$R$^c$, C$_{1-6}$ alkyl substituted with 0-3 R$^f$, C$_{3-6}$ cycloalkyl substituted with 0-3 R$^f$, —(CR$^{1b}$R$^{1c}$)$_r$-phenyl substituted with 0-3 R$^f$ or —(CR$^{1b}$R$^{1c}$)$_r$-5-7 membered heterocycle comprising carbon atoms and 1-4 heteroatoms selected from N, O, P(=O) and S(O)$_p$ substituted with 0-4 R$^f$;

R$^e$ is, independently at each occurrence, selected from hydrogen, C(O)NR$^f$R$^f$, C$_{1-6}$ alkyl, C$_{3-6}$ cycloalkyl, -5-7 membered heterocycle or —(CR$^{1b}$R$^{1c}$)$_r$-phenyl substituted with 0-3 R$^f$;

R$^f$ is, independently at each occurrence, hydrogen, =O, halo, CN, NH$_2$, NH(C$_{1-6}$ alkyl), N(C$_{1-6}$ alkyl)$_2$, SO$_2$(C$_{1-6}$ alkyl), CO$_2$H, CO$_2$(C$_{1-6}$ alkyl), OH, C$_{3-6}$ cycloalkyl, CF$_3$; O(C$_{1-6}$ alkyl) or an optionally substituted —(CR$^{1b}$R$^{1c}$)$_r$-5-10 membered heterocycle comprising carbon atoms and 1-4 heteroatoms selected from N, O, P(=O) and S(O)$_p$, phenyl or C$_{3-6}$ cycloalkyl, each group optionally substituted with halo, CN, CF$_3$, C$_{1-6}$ alkyl or O(C$_{1-6}$ alkyl);

m is 0, 1, 2 or 3
n is 0, 1 or 2;
p and q are, independently at each occurrence, 0, 1, or 2;
r is 0, 1, 2, 3, or 4; and
w is 1, 2 or 3;
or a stereoisomer or pharmaceutically-acceptable salt thereof.

5. A compound according to claim 4 of the formula

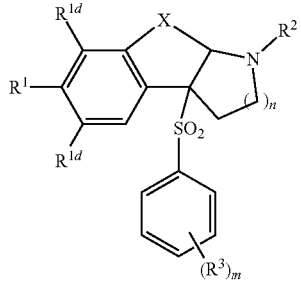

wherein
X is —CR$^4$R$^5$—, —(CR$^4$R$^5$)$_2$—, —OCR$^6$R$^7$—, —S(O)$_p$CR$^6$R$^7$— or —NR$^6$CR$^6$R$^7$—;

R$^1$ is selected from halo, C$_{1-6}$ alkyl substituted with 0-3 R$^{1a}$, —(CR$^{1b}$R$^{1c}$)$_r$-3-14 membered carbocycle substituted with 0-3 R$^{1a}$ and —(CR$^{1b}$R$^{1c}$)$_r$-5-10 membered heterocycle comprising carbon atoms and 1-4 heteroatoms selected from N, O, and S(O)$_p$ substituted with 0-3 R$^{1a}$;

R$^{1a}$ is, independently at each occurrence, hydrogen, =O, halo, CF$_3$, OCF$_3$, CN, NO$_2$, —(CR$^{1b}$R$^{1c}$)$_r$—OR$^b$, —(CR$^{1b}$R$^{1c}$)$_r$—S(O)$_p$R$^b$, —(CR$^{1b}$R$^{1c}$)$_r$—C(O)R$^b$, —(CR$^{1b}$R$^{1c}$)$_r$—C(O)OR$^b$, —(CR$^{1b}$R$^{1c}$)$_r$—OC(O)R$^b$, —(CR$^{1b}$R$^{1c}$)$_r$—NR$^{11}$R$^{11}$, —(CR$^{1b}$R$^{1c}$)$_r$—C(O)NR$^{11}$R$^{11}$, —(CR$^{1b}$R$^{1c}$)$_r$—NR$^b$C(O)R$^c$, —(CR$^{1b}$R$^{1c}$)$_r$—NR$^b$C(O)OR$^c$, —NR$^b$C(O)NR$^{11}$R$^{11}$, —S(O)$_p$NR$^{11}$R$^{11}$, —NR$^b$S(O)$_p$R$^c$, C$_{1-6}$ alkyl substituted with 0-3 R$^a$, C$_{1-6}$ haloalkyl, C$_{2-6}$ alkenyl substituted with 0-3 R$^a$, C$_{2-6}$ alkynyl substituted with 0-3 R$^a$, —(CR$^{1b}$R$^{1c}$)$_r$-3-14 membered carbocycle substituted with 0-3 R$^a$, or —(CR$^{1b}$R$^{1c}$)$_r$-5-7 membered heterocycle comprising carbon atoms and 1-4 heteroatoms selected from N, O, and S(O)$_p$ substituted with 0-3 R$^a$;

R$^{1b}$ and R$^{1c}$ are, independently at each occurrence, hydrogen, halogen or C$_{1-6}$ alkyl;

R$^{1d}$ is, independently at each occurrence, hydrogen, CD$_3$, halo, CF$_3$, and C$_1$-C$_4$ alkyl;

R$^2$ is

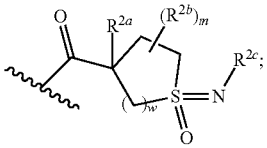

R$^{2a}$ and R$^{2b}$ are, independently at each occurrence, hydrogen, halo, OCF$_3$, CF$_3$, CHF$_2$, CN, NO$_2$, —(CR$^{1b}$R$^{1c}$)$_r$—OR$^b$, —(CR$^{1b}$R$^{1c}$)$_r$—S(O)$_p$R$^b$, —(CR$^{1b}$R$^{1c}$)$_r$—C(O)R$^b$, —(CR$^{1b}$R$^{1c}$)$_r$—C(O)OR$^b$, —(CR$^{1b}$R$^{1c}$)$_r$—OC(O)R$^b$, —(CR$^{1b}$R$^{1c}$)$_r$—NR$^{11}$R$^{11}$, —(CR$^{1b}$R$^{1c}$)$_r$—C(O)NR$^{11}$R$^{11}$, —(CR$^{1b}$R$^{1c}$)$_r$—NR$^b$C(O)R$^c$, —(CR$^{1b}$R$^{1c}$)$_r$—NR$^b$C(O)OR$^c$, —NR$^b$C(O)NR$^{11}$R$^{11}$, —S(O)$_p$NR$^{11}$R$^{11}$, —NR$^b$S(O)$_p$R$^c$, C$_{1-6}$ alkyl substituted with 0-3 R$^f$, C$_{1-6}$ haloalkyl, C$_{2-6}$ alkenyl substituted with 0-3 R$^e$, C$_{2-6}$ alkynyl substituted with 0-3 R$^e$, —(CR$^{1b}$R$^{1c}$)$_r$-3-14 membered carbocycle, or —(CR$^{1b}$R$^{1c}$)$_r$-5-7 membered heterocycle comprising carbon atoms and 1-4 heteroatoms selected from N, O, P(=O) and S(O)$_p$ substituted with 0-4 R$^f$;

R$^{2c}$ is hydrogen, C$_{1-6}$ alkyl substituted with 0-3 R$^f$, C$_{1-6}$ haloalkyl, —(CR$^{1b}$R$^{1c}$)$_r$—C(O)R$^b$, —(CR$^{1b}$R$^{1c}$)$_r$—C(O)OR$^b$, —(CR$^{1b}$R$^{1c}$)$_r$—C(O)NR$^{11}$R$^{11}$, —(CR$^{1b}$R$^{1c}$)$_r$-3-14 membered carbocycle, or —(CR$^{1b}$R$^{1c}$)$_r$-5-7 membered heterocycle comprising carbon atoms and 1-4 heteroatoms selected from N, O, P(=O) and S(O)$_p$ substituted with 0-4 R$^f$;

R$^3$ is, independently at each occurrence, selected from hydrogen, halo, N$_3$, CN, —(CR$^{1b}$R$^{1c}$)$_r$—OR$^{3b}$, —(CR$^{1b}$R$^{1c}$)$_r$—NR$^{11}$R$^{11}$, C$_{1-6}$ alkyl substituted with 0-3 R$^{3a}$, C$_{3-10}$ cycloalkyl substituted with 0-3 R$^{3a}$; and phenyl substituted with 0-3 R$^{3a}$, or 4-10 membered heterocycle containing 1-4 heteroatoms selected from N, O, and S(O)$_p$, substituted with 0-3 R$^{3a}$, or two R$^3$ located on adjacent carbon atoms link to form a 5-7 membered carbocycle or a 5-7 membered heterocycle comprising carbon atoms and 1-4 heteroatom selected from N, O and S(O)$_p$, both optionally substituted with 0-3 R$^{3a}$;

R$^{3a}$ is, independently at each occurrence, hydrogen, =O, halo, OCF$_3$, OCHF$_2$, CF$_3$, CHF$_2$, CN, NO$_2$, —(CR$^{1b}$R$^{1c}$)$_r$—OR$^b$, —(CR$^{1b}$R$^{1c}$)$_r$—S(O)$_p$R$^b$, —(CR$^{1b}$R$^{1c}$)$_r$—C(O)R$^b$, —(CR$^{1b}$R$^{1c}$)$_r$—C(O)OR$^b$, —(CR$^{1b}$R$^{1c}$)$_r$—OC(O)R$^b$, —(CR$^{1b}$R$^{1c}$)$_r$—NR$^{11}$R$^{11}$, —(CR$^{1b}$R$^{1c}$)$_r$—C(O)NR$^{11}$R$^{11}$, —(CR$^{1b}$R$^{1c}$)$_r$—NR$^b$C(O)R$^c$, —(CR$^{1b}$R$^{1c}$)$_r$—NR$^b$C(O)OR$^c$, —NR$^b$C(O)NR$^{11}$R$^{11}$, —S(O)$_p$NR$^{11}$R$^{11}$, —NR$^b$S(O)$_p$R$^c$, C$_{1-6}$ alkyl substituted with 0-3 R$^a$, C$_{2-6}$ alkenyl substituted with 0-3 R$^a$, C$_{2-6}$ alkynyl substituted with 0-3 R$^a$, C$_{1-6}$ haloalkyl, —(CR$^{1b}$R$^{1c}$)$_r$-3-14 membered carbocycle substituted with 0-3 R$^a$, or —(CR$^{1b}$R$^{1c}$)$_r$-5-10 membered heterocycle comprising carbon atoms and 1-4 heteroatoms selected from N, O, and S(O)$_p$ substituted with 0-3 R$^a$;

R$^{3b}$ is, independently at each occurrence, hydrogen, CF$_3$, —(CR$^{1b}$R$^{1c}$)$_q$OR$^b$, —(CR$^{1b}$R$^{1c}$)$_q$S(O)$_p$R$^b$, —(CR$^{1b}$R$^{1c}$)$_q$—C(O)R$^{3d}$, —(CR$^{1b}$R$^{1c}$)$_q$—C(O)OR$^b$, —(CR$^{1b}$R$^{1c}$)$_q$OC(O)R$^b$, —(CR$^{1b}$R$^{1c}$)$_q$NR$^{11}$R$^{11}$, —(CR$^{1b}$R$^{1c}$)$_q$—C(O)NR$^{11}$R$^{11}$, —(CR$^{1b}$R$^{1c}$)$_q$NR$^b$C(O)

R³ᶜ, —(CR¹ᵇR¹ᶜ)qNRᵇC(O)ORᶜ, —(CR¹ᵇR¹ᶜ)qNRᵇC(O)N R¹¹R¹¹, —(CR¹ᵇR¹ᶜ)qS(O)₂N R¹¹R¹¹, —(CR¹ᵇR¹ᶜ)qNRᵇS(O)₂Rᶜ, $C_{1-6}$ alkyl substituted with 0-3 Rᵃ, $C_{1-6}$ haloalkyl, —(CR¹ᵇR¹ᶜ)ᵣ-3-14 membered carbocycle substituted with 0-3 Rᵃ, or —(CR¹ᵇR¹ᶜ)ᵣ-5-7 membered heterocycle comprising carbon atoms and 1-4 heteroatoms selected from N, O, and S(O)ₚ substituted with 0-3 Rᵃ;

R³ᶜ and R³ᵈ are, independently at each occurrence, hydrogen or $C_{1-6}$ alkyl;

R⁴ and R⁵ are independently hydrogen, halo, $C_{1-6}$ alkyl or $C_{1-6}$ haloalkyl, or R⁴ and R⁵ together with the carbon atom to which they are attached form a 3- to 6-membered spirocarbocyclyl ring or a spiroheterocyclyl ring;

R⁶ and R⁷ are independently hydrogen, $C_{1-6}$ alkyl or $C_{1-6}$ haloalkyl;

R¹¹ is, independently at each occurrence, hydrogen, $C_{1-6}$ alkyl substituted with 0-3 Rᶠ, CF₃, $C_{3-10}$ cycloalkyl substituted with 0-3 Rᶠ, —(CR¹ᵇR¹ᶜ)ᵣ-phenyl substituted with 0-3 Rᵈ, or —(CR¹ᵇR¹ᶜ)ᵣ-5-7 membered heterocycle comprising carbon atoms and 1-4 heteroatoms selected from N, O, P(=O) and S(O)ₚ substituted with 0-4 Rᵈ;

or one R¹¹ and a second R¹¹, both attached to the same nitrogen atom, combine to form a heterocycle comprising carbon atoms and 1-4 heteroatoms selected from N, O, P(=O) and S(O)ₚ substituted with 0-4 Rᵈ;

Rᵃ is, independently at each occurrence, hydrogen, =O, halo, OCF₃, CF₃, CHF₂, CN, NO₂, —(CR¹ᵇR¹ᶜ)ᵣ—ORᵇ, —(CR¹ᵇR¹ᶜ)ᵣ—S(O)ₚRᵇ, —(CR¹ᵇR¹ᶜ)ᵣ—C(O)Rᵇ, —(CR¹ᵇR¹ᶜ)ᵣ—C(O)ORᵇ, —(CR¹ᵇR¹ᶜ)ᵣ—OC(O)Rᵇ, —(CR¹ᵇR¹ᶜ)ᵣ—NR¹¹R¹¹, —(CR¹ᵇR¹ᶜ)ᵣ—C(O)NR¹¹R¹¹, —(CR¹ᵇR¹ᶜ)ᵣ—NRᵇC(O)Rᶜ, —(CR¹ᵇR¹ᶜ)ᵣ—NRᵇC(O)ORᶜ, —NRᵇC(O)NR¹¹R¹¹, —S(O)ₚNR¹¹R¹¹, —NRᵇS(O)₂Rᶜ, $C_{1-6}$ alkyl substituted with 0-3 Rᶠ, $C_{1-6}$ haloalkyl, $C_{2-6}$ alkenyl substituted with 0-3 Rᵉ, $C_{2-6}$ alkynyl substituted with 0-3 Rᵉ, —(CR¹ᵇR¹ᶜ)ᵣ-3-14 membered carbocycle, or —(CR¹ᵇR¹ᶜ)ᵣ-5-7 membered heterocycle comprising carbon atoms and 1-4 heteroatoms selected from N, O, P(=O) and S(O)ₚ substituted with 0-4 Rᶠ;

Rᵇ is, independently at each occurrence, hydrogen, $C_{1-6}$ alkyl substituted with 0-3 Rᵈ, $C_{1-6}$ haloalkyl, $C_{3-6}$ cycloalkyl substituted with 0-3 Rᵈ, —(CR¹ᵇR¹ᶜ)ᵣ-5-7 membered heterocycle comprising carbon atoms and 1-4 heteroatoms selected from N, O, P(=O) and S(O)ₚ substituted with 0-4 Rᶠ, or —(CR¹ᵇR¹ᶜ)ᵣ-6-10 membered carbocycle substituted with 0-3 Rᵈ;

Rᶜ is, independently at each occurrence, $C_{1-6}$ alkyl substituted with 0-3 Rᶠ, —(CR¹ᵇR¹ᶜ)ᵣ—$C_{3-6}$ cycloalkyl substituted with 0-3 Rᶠ, or —(CR¹ᵇR¹ᶜ)ᵣ-phenyl substituted with 0-3 Rᶠ;

Rᵈ is, independently at each occurrence, hydrogen, =O, halo, OCF₃, CF₃, CN, NO₂, —ORᵉ, —(CR¹ᵇR¹ᶜ)ᵣ—C(O)Rᶜ, —NRᵉRᵉ, —NRᵉC(O)ORᶜ, C(O)NRᵉRᵉ, —NRᵉC(O)Rᶜ, CO₂H, CO₂Rᶜ, —NRᵉSO₂Rᶜ, SO₂Rᶜ, $C_{1-6}$ alkyl substituted with 0-3 Rᶠ, $C_{3-6}$ cycloalkyl substituted with 0-3 Rᶠ, —(CR¹ᵇR¹ᶜ)ᵣ-phenyl substituted with 0-3 Rᶠ or —(CR¹ᵇR¹ᶜ)ᵣ-5-7 membered heterocycle comprising carbon atoms and 1-4 heteroatoms selected from N, O, P(=O) and S(O)ₚ substituted with 0-4 Rᶠ;

Rᵉ is, independently at each occurrence, selected from hydrogen, C(O)NRᶠRᶠ, $C_{1-6}$ alkyl, $C_{3-6}$ cycloalkyl, -5-7 membered heterocycle or —(CR¹ᵇR¹ᶜ)ᵣ-phenyl substituted with 0-3 Rᶠ;

Rᶠ is, independently at each occurrence, hydrogen, =O, halo, CN, NH₂, NH($C_{1-6}$ alkyl), N($C_{1-6}$ alkyl)₂, SO₂($C_{1-6}$ alkyl), CO₂H, CO₂($C_{1-6}$ alkyl), OH, $C_{3-6}$ cycloalkyl, CF₃; O($C_{1-6}$ alkyl) or an optionally substituted —(CR¹ᵇR¹ᶜ)ᵣ-5-10 membered heterocycle comprising carbon atoms and 1-4 heteroatoms selected from N, O, P(=O) and S(O)ₚ, phenyl or $C_{3-6}$ cycloalkyl, each group optionally substituted with halo, CN, CF₃, $C_{1-6}$ alkyl or O($C_{1-6}$ alkyl);

m is 0, 1, 2 or 3 n is 0, 1 or 2;

p and q are, independently at each occurrence, 0, 1, or 2;

r is 0, 1, 2, 3, or 4; and w is 1, 2 or 3;

or a stereoisomer or pharmaceutically-acceptable salt thereof.

6. A compound according to claim 5 of the formula

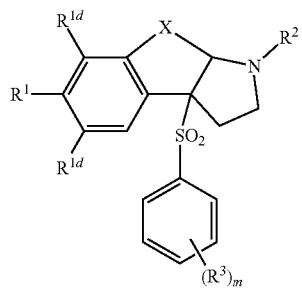

or a stereoisomer or pharmaceutically-acceptable salt thereof.

7. A compound according to claim 6 of the formula

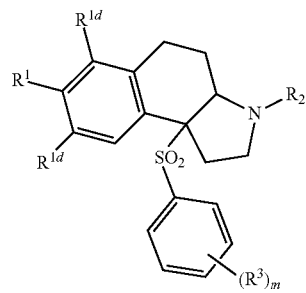

or a stereoisomer or pharmaceutically-acceptable salt thereof.

8. A compound according to claim 6 of the formula

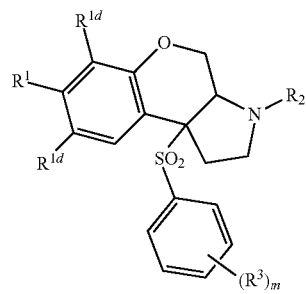

or a stereoisomer or pharmaceutically-acceptable salt thereof.

9. A compound according to claim 6 of the formula

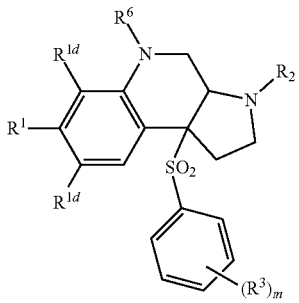

or a stereoisomer or pharmaceutically-acceptable salt thereof.

10. A compound according to claim 7 wherein
$R^1$ is halo, phenyl substituted with 0-3 $R^{1a}$, or $C_{1-6}$ alkyl substituted with 0-3 $R^{1a}$;
$R^{1a}$ is, independently at each occurrence, hydrogen, $CF_3$, halo, $C_{1-6}$ alkyl substituted with 0-3 $R^a$, $—(CR^{1b}R^{1c})_r—OR^b$, and $—(CR^{1b}R^{1c})_r$-phenyl substituted with 0-3 $R^a$,
$R^3$ is, independently at each occurrence, hydrogen, halo, $N_3$, CN, $OR^{3b}$, $—NH_2$, $NH(C_{1-6}$ alkyl), $N(C_{1-6}$ alkyl)$_2$, $C_{1-6}$ alkyl substituted with 0-3 $R^{3a}$ or $C_{3-10}$ cycloalkyl substituted with 0-3 $R^{3a}$;
$R^{3a}$ is, independently at each occurrence, hydrogen, =O, halo, $OCF_3$, $OCHF_2$, $CF_3$, $CHF_2$, CN, $NO_2$, $—(CR^{1b}R^{1c})_r—OR^b$, $—(CR^{1b}R^{1c})_r—S(O)_pR^b$, $—(CR^{1b}R^{1c})_r—C(O)R^b$, $—(CR^{1b}R^{1c})_r—C(O)OR^b$, $—(CR^{1b}R^{1c})_r—OC(O)R^b$, $—(CR^{1b}R^{1c})_r—NR^{11}R^{11}$, $—(CR^{1b}R^{1c})_r—C(O)NR^{11}R^{11}$, $—(CR^{1b}R^{1c})_r—NR^bC(O)R^c$, $—(CR^{1b}R^{1c})_r—NR^bC(O)OR^c$, $—NR^bC(O)NR^{11}R^{11}$, $—S(O)_pNR^{11}R^{11}$, $—NR^bS(O)_pR^c$, $C_{1-6}$ alkyl substituted with 0-3 $R^a$, $C_{2-6}$ alkenyl substituted with 0-3 $R^a$, $C_{2-6}$ alkynyl substituted with 0-3 $R^a$, $C_{1-6}$ haloalkyl, $—(CR^{1b}R^{1c})_r$-3-14 membered carbocycle substituted with 0-3 $R^a$, or $—(CR^{1b}R^{1c})_r$-5-10 membered heterocycle comprising carbon atoms and 1-4 heteroatoms selected from N, O, and $S(O)_p$ substituted with 0-3 $R^a$; and
$R^{3b}$ is, independently at each occurrence, hydrogen, $C_{1-6}$ alkyl substituted with 0-3 $R^a$ or phenyl substituted with 0-3 $R^a$;
or a stereoisomer or pharmaceutically-acceptable salt thereof.

11. A compound according to claim 8 wherein
$R^1$ is halo, phenyl substituted with 0-3 $R^{1a}$, or $C_{1-6}$ alkyl substituted with 0-3 $R^{1a}$;
$R^{1a}$ is, independently at each occurrence, hydrogen, $CF_3$, halo, $C_{1-6}$ alkyl substituted with 0-3 $R^a$, $—(CR^{1b}R^{1c})_r—OR^b$, and $—(CR^{1b}R^{1c})_r$-phenyl substituted with 0-3 $R^a$,
$R^3$ is, independently at each occurrence, hydrogen, halo, $N_3$, CN, $OR^{3b}$, $—NH_2$, $NH(C_{1-6}$ alkyl), $N(C_{1-6}$ alkyl)$_2$, $C_{1-6}$ alkyl substituted with 0-3 $R^{3a}$ or $C_{3-10}$ cycloalkyl substituted with 0-3 $R^{3a}$;
$R^{3a}$ is, independently at each occurrence, hydrogen, =O, halo, $OCF_3$, $OCHF_2$, $CF_3$, $CHF_2$, CN, $NO_2$, $—(CR^{1b}R^{1c})_r—OR^b$, $—(CR^{1b}R^{1c})_r—S(O)_pR^b$, $—(CR^{1b}R^{1c})_r—C(O)R^b$, $—(CR^{1b}R^{1c})_r—C(O)OR^b$, $—(CR^{1b}R^{1c})_r—OC(O)R^b$, $—(CR^{1b}R^{1c})_r—NR^{11}R^{11}$, $—(CR^{1b}R^{1c})_r—C(O)NR^{11}R^{11}$, $—(CR^{1b}R^{1c})_r—NR^bC(O)R^c$, $—(CR^{1b}R^{1c})_r—NR^bC(O)OR^c$, $—NR^bC(O)NR^{11}R^{11}$, $—S(O)_pNR^{11}R^{11}$, $—NR^bS(O)_pR^c$, $C_{1-6}$ alkyl substituted with 0-3 $R^a$, $C_{2-6}$ alkenyl substituted with 0-3 $R^a$, $C_{2-6}$ alkynyl substituted with 0-3 $R^a$, $C_{1-6}$ haloalkyl, $—(CR^{1b}R^{1c})_r$-3-14 membered carbocycle substituted with 0-3 $R^a$, or $—(CR^{1b}R^{1c})_r$-5-10 membered heterocycle comprising carbon atoms and 1-4 heteroatoms selected from N, O, and $S(O)_p$ substituted with 0-3 $R^a$; and
$R^{3b}$ is, independently at each occurrence, hydrogen, $C_{1-6}$ alkyl substituted with 0-3 $R^a$ or phenyl substituted with 0-3 $R^a$;
or a stereoisomer or pharmaceutically-acceptable salt thereof.

12. A compound according to claim 10 wherein
$R^1$ is $C_{1-6}$ alkyl substituted with 0-3 $R^{1a}$;
$R^{1a}$ is, independently at each occurrence, hydrogen, $CF_3$, halo or $C_{1-6}$ alkyl substituted with 0-3 $R^a$;
$R^3$ is hydrogen, halo, cyclopropyl or $C_{1-6}$ alkyl;
or a stereoisomer or pharmaceutically-acceptable salt thereof.

13. A compound according to claim 11 wherein
$R^1$ is $C_{1-6}$ alkyl substituted with 0-3 $R^{1a}$,
$R^{1a}$ is, independently at each occurrence, hydrogen, $CF_3$, halo or $C_{1-6}$ alkyl substituted with 0-3 $R^a$;
$R^3$ is hydrogen, halo, cyclopropyl or $C_{1-6}$ alkyl;
or a stereoisomer or pharmaceutically-acceptable salt thereof.

14. A compound according to claim 12 wherein
$R^1$ is

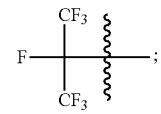

$R^3$ is F, Cl, cyclopropyl or methyl;
or a stereoisomer or pharmaceutically-acceptable salt thereof.

15. A compound according to claim 13 wherein
$R^1$ is

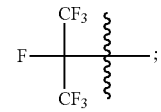

$R^3$ is F, Cl, cyclopropyl or methyl;
or a stereoisomer or pharmaceutically-acceptable salt thereof.

16. A compound according to claim 14 wherein
$R^2$ is:

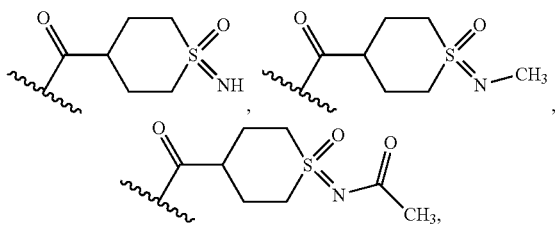

-continued

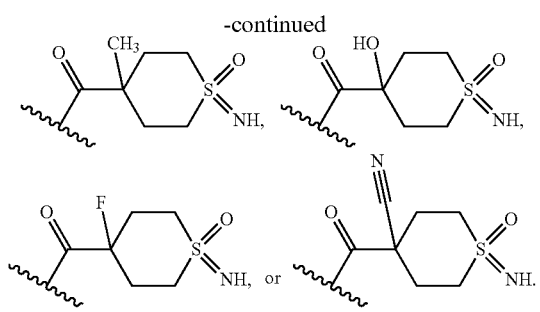

17. A compound according to claim 15 wherein R² is:

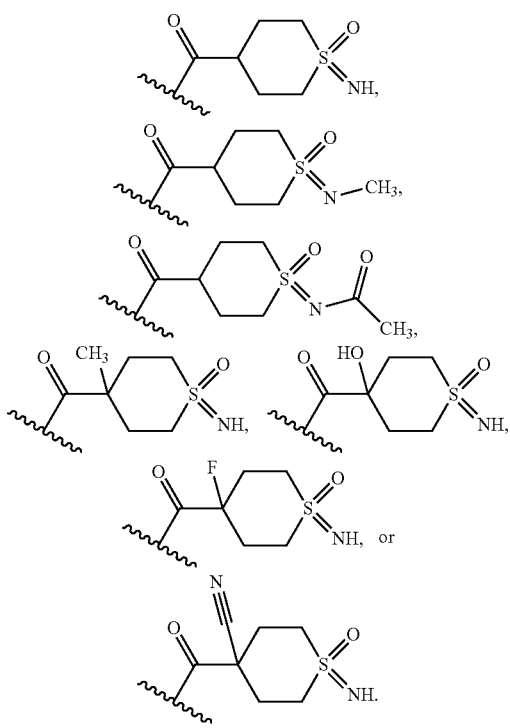

18. A compound selected from the following
(9b-((3-fluorophenyl)sulfonyl)-7-(perfluoropropan-2-yl)-1,2,3a,4,5,9b-hexahydro-3H-benzo[e]indol-3-yl)(1-imino-1-oxidohexahydro-1λ⁶-thiopyran-4-yl)methanone,
(9b-((3-chlorophenyl)sulfonyl)-7-(perfluoropropan-2-yl)-1,2,3a,4,5,9b-hexahydro-3H-benzo[e]indol-3-yl)(1-imino-1-oxidohexahydro-1λ⁶-thiopyran-4-yl)methanone,
(1-imino-1-oxidohexahydro-1λ⁶-thiopyran-4-yl)(7-(perfluoropropan-2-yl)-9b-(phenylsulfonyl)-1,2,3a,4,5,9b-hexahydro-3H-benzo[e]indol-3-yl)methanone,
(9b-((4-fluorophenyl)sulfonyl)-7-(perfluoropropan-2-yl)-1,3a,4,9b-tetrahydrochromeno[3,4-b]pyrrol-3 (2H)-yl)(1-imino-1-oxidohexahydro-1λ⁶-thiopyran-4-yl)methanone,
(9b-((4-chlorophenyl)sulfonyl)-7-(perfluoropropan-2-yl)-1,2,3a,4,5,9b-hexahydro-3H-benzo[e]indol-3-yl)(1-imino-1-oxidohexahydro-1λ⁶-thiopyran-4-yl)methanone,
(9b-((4-fluorophenyl)sulfonyl)-7-(perfluoropropan-2-yl)-1,2,3a,4,5,9b-hexahydro-3H-pyrrolo[2,3-c]quinolin-3-yl)(1-imino-1-oxidohexahydro-1λ⁶-thiopyran-4-yl)methanone,
((3 aR,9bR)-9b-((4-fluorophenyl)sulfonyl)-7-(perfluoropropan-2-yl)-1,2,3a,4,5,9b-hexahydro-3H-benzo[e]indol-3-yl)(1-imino-1-oxidohexahydro-1λ⁶-thiopyran-4-yl)methanone,
((3 aR,9bR)-9b-((4-fluorophenyl)sulfonyl)-7-(perfluoropropan-2-yl)-1,2,3a,4,5,9b-hexahydro-3H-benzo[e]indol-3-yl)(1-imino-4-methyl-1-oxidohexahydro-1λ⁶-thiopyran-4-yl)methanone,
((3 aR,9bR)-9b-((4-fluorophenyl)sulfonyl)-7-(perfluoropropan-2-yl)-1,2,3a,4,5,9b-hexahydro-3H-benzo[e]indol-3-yl)(4-hydroxy-1-imino-1-oxidohexahydro-1λ⁶-thiopyran-4-yl)methanone,
4-((3aR,9bR)-9b-((4-fluorophenyl)sulfonyl)-7-(perfluoropropan-2-yl)-2,3,3a,4,5,9b-hexahydro-1H-benzo[e]indole-3-carbonyl)-1-iminohexahydro-1λ⁶-thiopyran-4-carbonitrile 1-oxide,
((3 aR,9bR)-9b-((4-fluorophenyl)sulfonyl)-7-(perfluoropropan-2-yl)-1,2,3a,4,5,9b-hexahydro-3H-benzo[e]indol-3-yl)(1-imino-1-oxidohexahydro-1λ⁶-thiopyran-4-yl)methanone,
((3 aR,9bR)-9b-((4-fluorophenyl)sulfonyl)-7-(perfluoropropan-2-yl)-1,2,3a,4,5,9b-hexahydro-3H-benzo[e]indol-3-yl)(1-(methylimino)-1-oxidohexahydro-1λ⁶-thiopyran-4-yl)methanone,
((3 aR,9bR)-9b-((4-fluorophenyl)sulfonyl)-7-(perfluoropropan-2-yl)-1,2,3a,4,5,9b-hexahydro-3H-benzo[e]indol-3-yl)(1-(methylimino)-1-oxidohexahydro-1λ⁶-thiopyran-4-yl)methanone,
N-(4-43 aR,9bR)-9b-((4-fluorophenyl)sulfonyl)-7-(perfluoropropan-2-yl)-2,3,3a,4,5,9b-hexahydro-1H-benzo[e]indole-3-carbonyl)-1-oxidotetrahydro-2H-1λ⁶-thiopyran-1-ylidene)acetamide,
N-(4-43 aR,9bR)-9b-((4-fluorophenyl)sulfonyl)-7-(perfluoropropan-2-yl)-2,3,3a,4,5,9b-hexahydro-1H-benzo[e]indole-3-carbonyl)-1-oxidotetrahydro-2H-1λ⁶-thiopyran-1-ylidene)acetamide,
9b-((4-fluorophenyl)sulfonyl)-5-methyl-7-(perfluoropropan-2-yl)-1,2,3a,4,5,9b-hexahydro-3H-pyrrolo[2,3-c]quinolin-3-yl)(1-imino-1-oxidohexahydro-1λ⁶-thiopyran-4-yl)methanone,
(4-fluoro-1-imino-1-oxidohexahydro-1λ⁶-thiopyran-4-yl)((3aR,9bR)-9b-((4-fluorophenyl)sulfonyl)-7-(perfluoropropan-2-yl)-1,2,3a,4,5,9b-hexahydro-3H-benzo[e]indol-3-yl)methanone,
or a stereoisomer or pharmaceutically-acceptable salt thereof.

19. A pharmaceutical composition comprising one or more compounds according to claim 1 and a pharmaceutically acceptable carrier or diluent.

20. A method of treating a disease or disorder selected from psoriasis, rheumatoid arthritis, inflammatory bowel disease, Crohn's disease, ulcerative colitis, acute graft-versus-host disease, psoriatic arthritis, ankylosing spondylitis and multiple sclerosis, the method comprising administering to the subject a therapeutically-effective amount of a compound according to claim 1.

* * * * *